US011275079B2

(12) United States Patent
Boyden et al.

(10) Patent No.: US 11,275,079 B2
(45) Date of Patent: Mar. 15, 2022

(54) GENETICALLY ENCODED RED FLUORESCENT VOLTAGE SENSORS ENABLING MILLIVOLT-RESOLUTION AND HIGH-SPEED NEURAL VOLTAGE IMAGING

(71) Applicant: Massachusetts Institute of Technology, Cambridge, MA (US)

(72) Inventors: Edward Boyden, Chestnut Hill, MA (US); Kiryl Piatkevich, Quincy, MA (US); Eunjung Jung, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 343 days.

(21) Appl. No.: 16/026,551

(22) Filed: Jul. 3, 2018

(65) Prior Publication Data
US 2019/0004032 A1  Jan. 3, 2019

Related U.S. Application Data

(60) Provisional application No. 62/528,267, filed on Jul. 3, 2017.

(51) Int. Cl.
| | | |
|---|---|---|
| *A61K 38/00* | (2006.01) | |
| *G01N 33/50* | (2006.01) | |
| *C07K 14/435* | (2006.01) | |
| *G01N 21/17* | (2006.01) | |
| *C07K 14/705* | (2006.01) | |

(52) U.S. Cl.
CPC ..... *G01N 33/502* (2013.01); *C07K 14/43504* (2013.01); *C07K 14/705* (2013.01); *G01N 21/1717* (2013.01); *C07K 2319/60* (2013.01); *G01N 2021/1721* (2013.01)

(58) Field of Classification Search
None
See application file for complete search history.

(56) References Cited

U.S. PATENT DOCUMENTS

| | | | | |
|---|---|---|---|---|
| 10,220,092 | B2* | 3/2019 | Deisseroth | A61P 25/00 |
| 10,457,715 | B2* | 10/2019 | Cohen | G01N 33/566 |
| 2020/0025769 | A1* | 1/2020 | Schreiter | C12N 9/14 |

OTHER PUBLICATIONS

Jordan et al., "Transfecting mammalian cells: optimization of critical parameters affecting calcium-phosphate precipitate formation." Nucleic Acids Research (1996), vol. 24, No. 4, pp. 596-601.
Wang et al., "Evolving proteins in mammalian cells using somatic hypermutation." Nature Protocols (2006), vol. 1, No. 3, pp. 1346-1350.
Wyart et al., "Optogenetic dissection of a behavioral module in the vertebrate spinal cord." Nature (2009) 461(7262): pp. 407-410.
Yu et al., "A naturally monomeric infrared fluorescent protein for protein labeling in vivo." Nature Methods (2015), 6 pages.
Ahrens et al., "Brain-wide neuronal dynamics during motor adaptation in zebrafish." Nature (2013), 485(7399), pp. 417-477.
Ahrens et al., "Whole-brain functional imaging at cellular resolution using light-sheet microscopy." Nature Methods (2013), vol. 10, No. 5, pp. 413-424.
Ai et al., "Engineering and characterizing monomeric fluorescent proteins for live-cell imaging applications." Nature Protocols (2014), vol. 9, No. 4, pp. 910-928.
Bellini et al., "Structure of Bacteriophytochrome and Light-Stimulated Protomer Swapping with a Gene Repressor." Structure 20, pp. 1436-1446.
Bouchard et al., "Swept confocally-aligned planar excitation (SCAPE) microscopy for high speed volumetric imaging of behaving organisms." Nat. Photonics, (2015), 9(2), pp. 113-119.
Chen et al., "Ultra-sensitive fluorescent proteins for imaging neuronal activity." Nature (2013), 499(7458): pp. 295-300.
Chen et al., "High-Efficiency Transformation of Mammalian Cells by Plasmid DNA." Molecular and Cellular Biology (1987), vol. 7, No. 8, pp. 2745-2752.
Chow et al., "Synthetic Physiology: Strategies for Adapting Tools from Nature for Genetically Targeted Control of Fast Biological Processes." Methods in Enzymology (2011), vol. 497, 425-443.
Chow et al., "High-performance genetically targetable optical neural silencing by light-driven proton pumps." Nature (2010), 463(7277): pp. 98-102.
Chuong et al., "Noninvasive optical inhibition with a red-shifted microbial rhodopsin." Nat. Neurosci. (2014), 17(8):1123-1129, pp. 1-27.
Dell et al., "Sample Size Determination." ILAR Journal (2002) vol. 43, No. 4, pp. 207-213.
Drobizhev et al., "Two-photon absorption properties of fluorescent proteins." Nat. Methods (2011), 8(5): pp. 393-399.
Filonov et al., "Bright and Stable near infra-red fluorescent protein for in vivo imaging." Nat. Biotechnol. (2011), 29(8): 757-761, pp. 757-761.
Fisher et al. "Evaluating the biological relevance of putative enhancer using Tol2 transposon-mediated transgenesis in zebrafish" Nature Protocols (2006), vol. 1, No. 3, pp. 1297-1305.
Flytzanis et al., "Archaerhodopsin variants with enhanced voltage-sensitive fluorescence in mammalian and Caenorhabditis elegans neurons." Nature Communications (2014) 5:4894, pp. 1-9.
Friedrich et al., "Circuit Neuroscience in Zebrafish." Current Biology 20, (2010). pp. R371-R381.
Giraud et al., "Bacteriophytochrome controls photosystem synthesis in anoxygenic bacteria." Nature (2002), vol. 417, pp. 202-205.
Gong et al., "High-speed recording of neural spikes in awake mice and flies with a fluorescent voltage sensor." Science (2015), 350(6266): pp. 11361-1366.
Heiser William, C., "Optimizing Electroporation Conditions for the Transformation of Mammalian Cells." Methods in Molecular Biology (2000), vol. 130, pp. 117-134.

(Continued)

*Primary Examiner* — Satyanarayana R Gudibande
(74) *Attorney, Agent, or Firm* — Pierce Atwood LLP

(57) ABSTRACT

Voltage reporter molecules and compositions, and methods for detecting voltage and voltage change in cells are provided. Also provided are methods for delivery, expression, and use of the voltage reporter molecules in cells, tissues, and subjects.

15 Claims, 39 Drawing Sheets

Specification includes a Sequence Listing.

(56) References Cited

OTHER PUBLICATIONS

Hochbaum et al., "All-optical electrophysiology in mammalian neurons using engineered microbial rhodopsins." Nature Methods (2014), vol. 11, No. 8, pp. 825-840.
Jiang et al., "High Ca2+—phosphate transfection efficiency in low-density neuronal cultures." Nature Protocols (2006), vol. 1, No. 2, pp. 695-700.
Jordon et al., Transfection of adherent and suspended cells by calcium phophate. Methods 33 (2004), pp. 136-143.
Kimura et al., "V2a and V2b neurons are generated by the final divisions of pair-producing progenitors in the zebrafish spinal cord." Research Report (2008), Development 135, pp. 3001-3005.
Klapoetke et al., "Indepdendent Optical Excitation of Distinct Neural Populations." Nat. Methods (2014), 11(3): pp. 338-346.
Kornyei et al., "Cell sorting in a Petri dish controlled by computer vision." Scientific Reports (2013), 3:1088, 11 pages.
Kralj et al., "Optical recording of action potentials in mammalian neurons using a microbial rhodopsin." Nat. Methods (2012) 9(1): pp. 90-95.
Kutner et al., "Production, concentration and titration of pseudotyped HIV-1-based lentiviral ventors." Nature Protocols (2009), vol. 4, No. 4, pp. 495-505.
Kwan et al., "The To12kit: A Multisite Gateway-Based Construction Kit for Tol2 Transposon Transgenesis Constructs." Developmental Dynamics (2007), 236, pp. 3088-3099.
Lebkowski et al., "Transfected DNA is Mutated in Monkey, Mouse, and Human Cells." Molecular and Cellular Biology (1984), vol. 4. No. 10, pp. 1951-1960.
Lee et al., "Learning the parts of objects by non-negative matrix factorization." Nature (1999), vol. 401, pp. 788-791.
Lin et al., "Genetically encoded indicators of neuronal activity." Nat. Neurosic. (2016), 19(9): pp. 1142-1153.
Mahon, Mathew J., "Vectors bicistronically linking a gene of interest to the SV40 large T antigen in combination with the SV40 orgin of replication enhance transient protein expression and luciferase reporter activity." BioTechniques (2011) vol. 51: pp. 119-126.
Makarov et al., "Two-photon absorption standards in the 550-1600 nm excitation wavelength range." Optics Express (2008), vol. 16, No. 6, pp. 4029-4047.
McIsaac et al., "Directed evolution of a far-red fluorescent rhodopsin." PNAS (2014), vol. 111, No. 36, pp. 13034-13039.
Okazaki et al., "Affinity binding phenomena of DNA onto apatite crystals." Biomaterials 22 (2001), pp. 2459-2464.
Panier et al., "Fast functional imaging of multiple brain regions in intact zebrafish larvae using Selective Plane Illumination Microscopy." Frontiers in Neural Circuits (2013), vol. 7, Article 65, 11 pages.
Piatkevich et al., "Engineering of bacterial phytochromes for near-infrared imaging, sensing, and light-control in mammals." Che. Soc. Rev. (2013), 42, pp. 3441-3452.
Piatkevich et al., "Far-red light photoactivatable near-infrared fluorescent proteins engineered from a bacterial phytochrome" Nature Communications (2013), 4: 2153.
Prevedel et al., "Simultaneous whole-animal 3D-imaging of neuronal activity using light-field microscopy." Nat. Methods (2014), 11(7): pp. 727-739.
Pucihar et al., "Measuring the Induced Membrane Voltage with Di-8-ANEPPS." Journal of Visualized Experiments (2009), vol. 33, pp. 1-3.
Qin et al., "Systematic Comparison of Constitutive Promoters and the Doxycycline-Inducible Promoter." PLoS One (2010), vol. 5, Issue 5, pp. 1-4.
Reid et al., "Cotransformation and Gene Targeting in Mouse Embryonic Stem Cells." Molecular and Cellular Biology (1991), vol. 11, No. 5, pp. 2769-2777.
Renaud et al., "Studying cell behavior in whole zebrafish embryos by confocal live imaging: application to hematopoietic stem cells." Nature Protocols (2011), vol. 6, No. 12, pp. 1897-1904.
Shcherbakova et al., "Near-infrared fluorescent proteins for multicolor in vivo imaging." Nat. Methods (2013), 10(8), pp. 751-754.
Shcherbakova et al., "Bright monomeric near-infrared fluorescent proteins as tags and biosensors for multiscale imaging." Nature Communications (2016), 7:12405, 12 pages.
Stewart et al., "Zebrafish models for translational neuroscience research: from tank to bedside." Trends Neurosci. (2014), 37(5): pp. 264-278.
St-Pierre et al., "High-fidelity optical reporting of neuronal electrical activity with an ultrafast fluorescent voltage sensor." Nat. Neurosci. (2014), 17(6): pp. 884-889.
Subedi et al., "Adoption of the Q transcriptional regulatory system for zebrafish transgenesis." Methods 66, (2014), pp. 433-440.
Tsai et al., (2002) In: In Vivo Optical Imaging of Brain Function, Chapter: 6, Publisher: CRC Press, 113-171.
Wagner et al., "Non-additivity of molecule-surface van der Waals potential from force measurements." Nature Communications (2014), pp. 1-8.

\* cited by examiner

Fig 7A
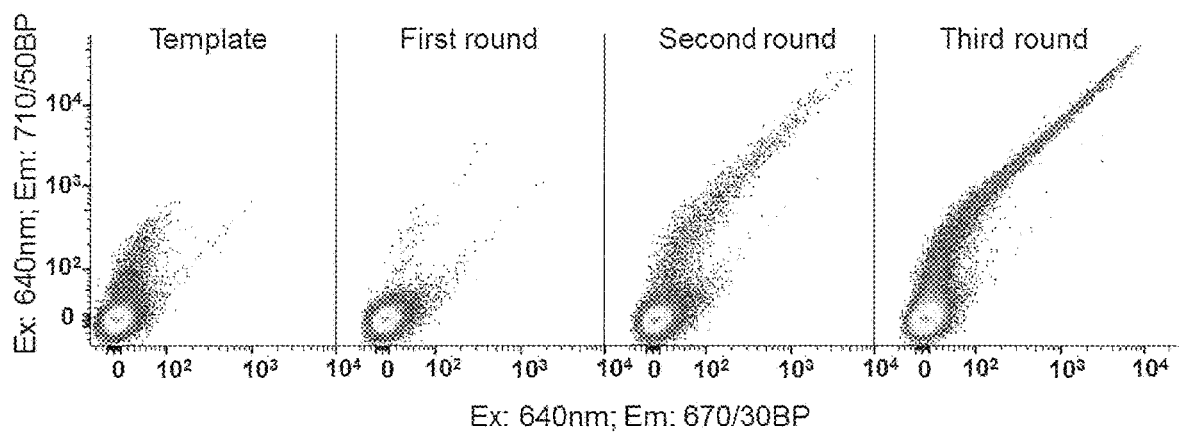
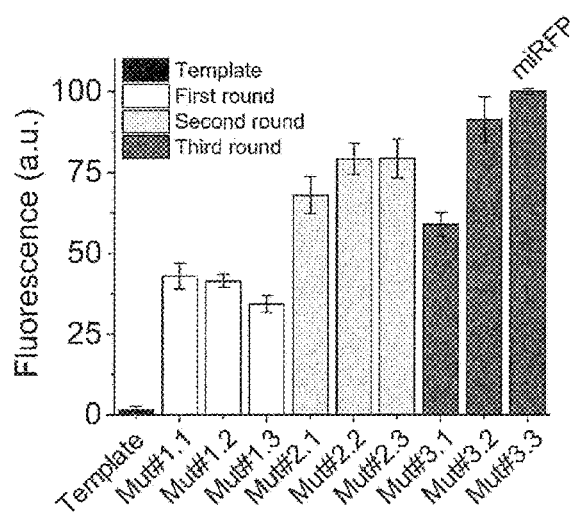
Fig 7B
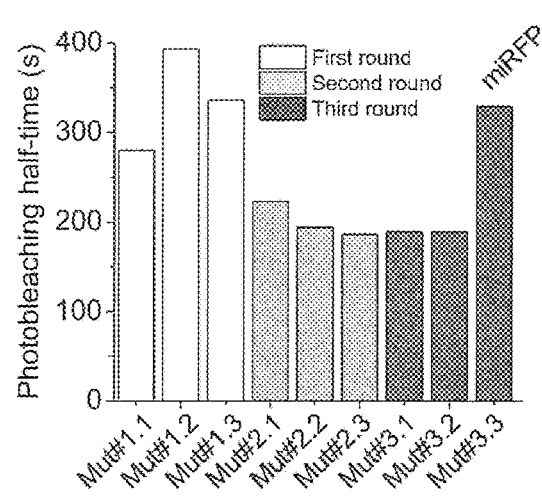
Fig 7C

Fig 8

```
                    10         20         30         40         50         60
                    |          |          |          |          |          |
RpBPhP1  MVAGHASGSPAFGTADLSNCEREEIHLAGSIQPHGALLVVSEPDHRIIQASANAAEFLNL
miRFP    MVAGHASGSPAFGTADLSNCEREEIHLAGSIQPHGLLVVSEPDHRIIQASANAAEFLNL 70         80         90        100        110        120
                    |          |          |          |          |          |
RpBPhP1  GSVLGVPLAEIDGDLLIKILPHLDPTAEGMPVAVRCRIGNPSTEYDGLMHRPPEGGLIIE
miRFP    GSVLGVPLAEIDGDLLIKILPHLDPTAEGMPVAVRCRIGNPSTEYDGLMHRPPEGGLIIE 130        140        150        160        170        180
                    |          |          |          |          |          |
RpBPhP1  LERAGPPIDLSGTLAPALERIRTAGSLRALCDDTALLFQQCTGYDRVMVYRFDEQGHGEV
miRFP    LERAGPPIDLSGTLAPALERIRTAGSLRALCDDTALLFQQCTGYDRVMVYRFDEQGHGEV 190        200        210        220        230        240
                    |         |**         |          |          |          |
RpBPhP1  FSERHVPGLESYFGNRYPSSDIPQMARRLYERQRVRVLVDVSYQPVPLEPRLSPLTGRDL
miRFP    FSERHVPGLESYFGNRYPSSDIPQMARRLYERQRVRVLVDVSYQPVPLEPRLSPLTGRDL 250        260        270        280        290        300
                    |    *     |          |         |*          |          |
RpBPhP1  DMSGCFLRSMSPTHLQTLKNMGVRATLVVSLVVGGKLWGLVACHHYLPRFIHFELRAICE
miRFP    DMSGCFLRSMSPHLQTLKNGVRATLVVSLVVGGKLWGLVCHHYLPRFIHFELRAICE

310
                    |
RpBPhP1  LLAEAIATRITAL
miRFP    LLAEAIATRITAL
```

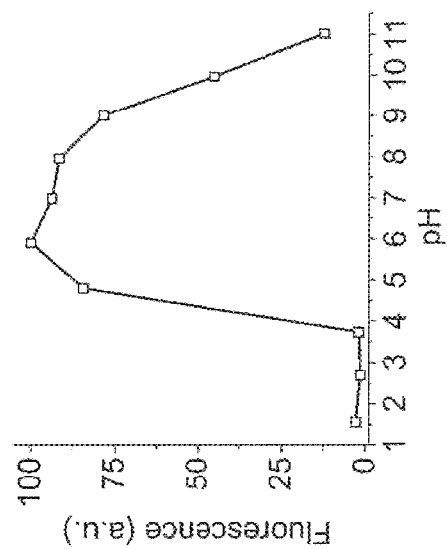
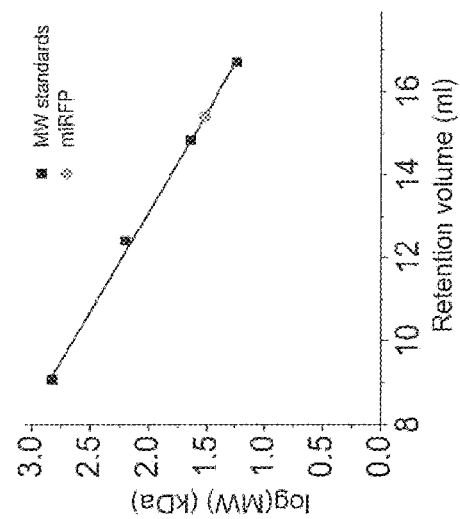
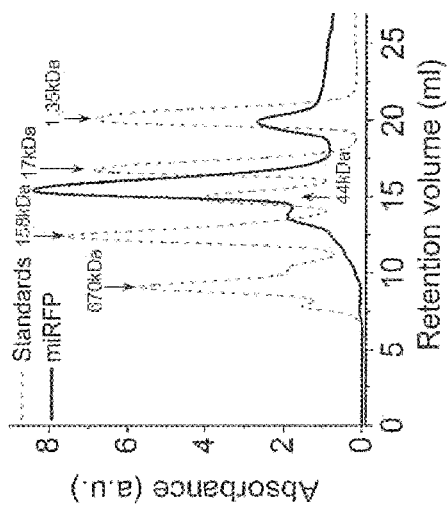

Fig 10A
Fig 10B
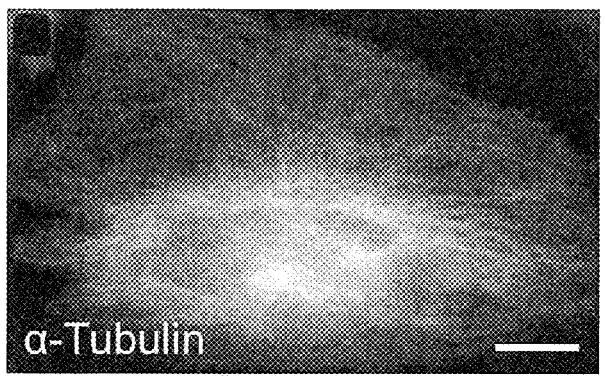
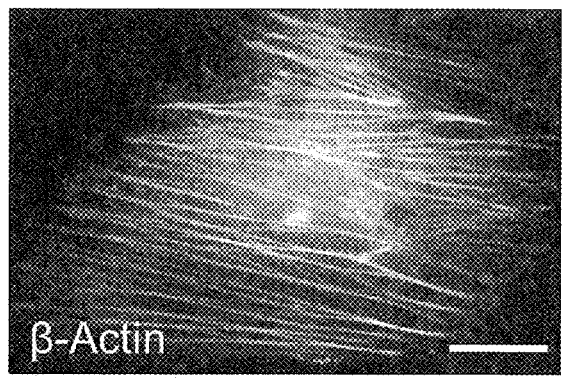
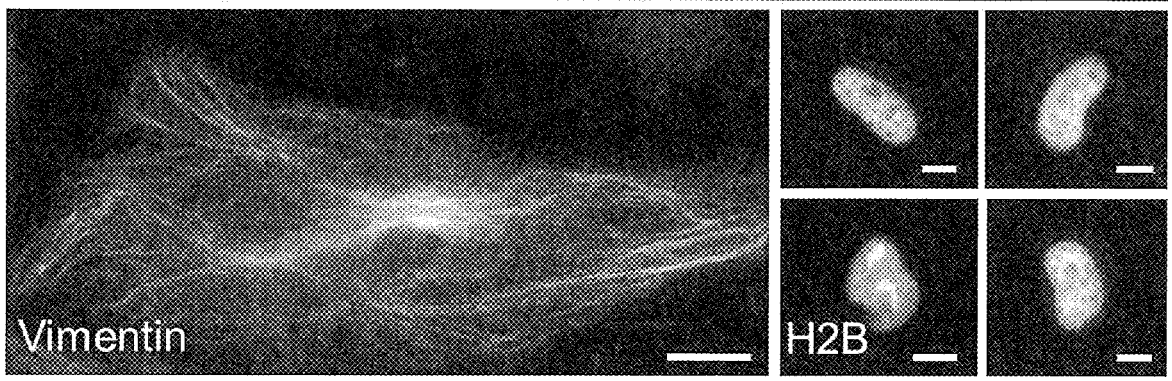
Fig 10C
Fig 10D

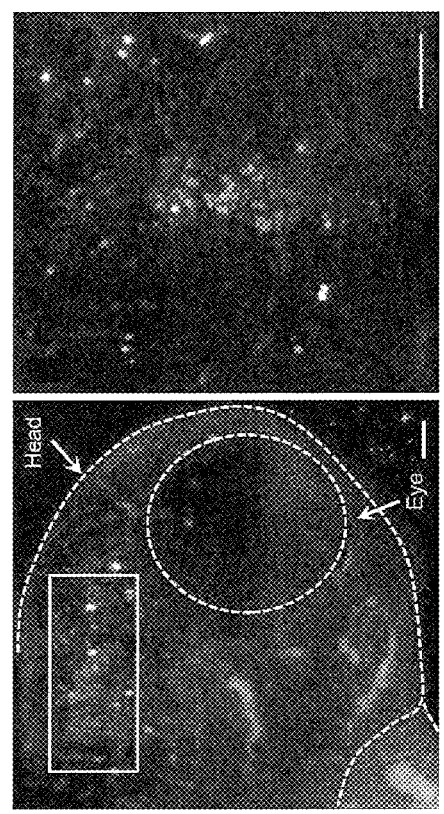
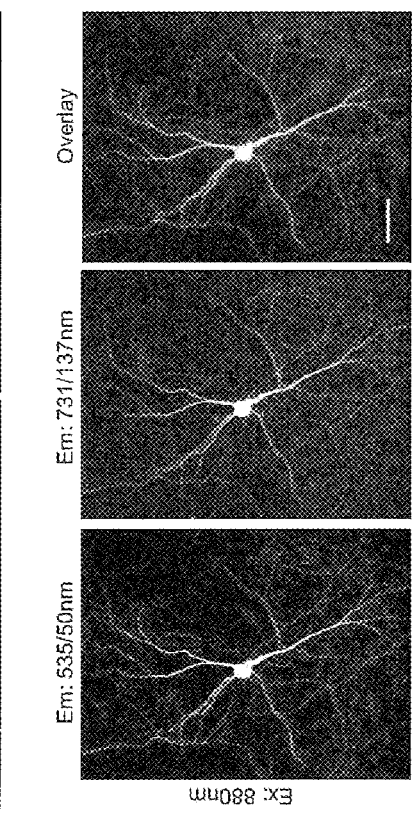
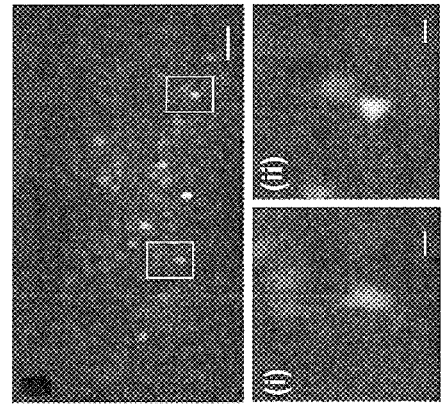
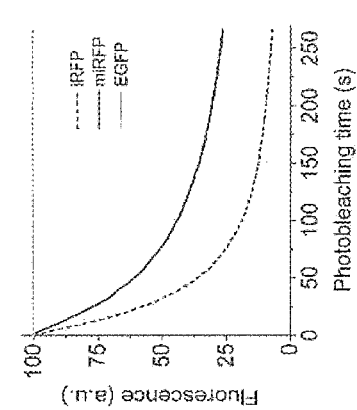
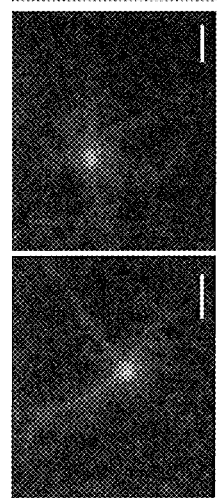
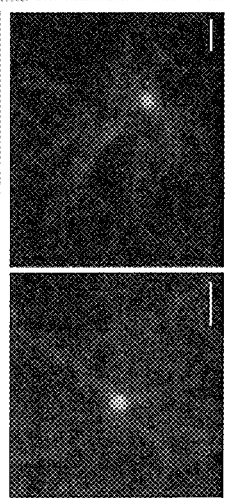
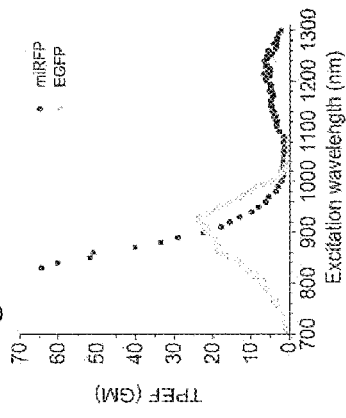

Figure 12

```
                    10         20         30         40         50         60
                    |          |          |          |          |          |
aR2          MDPIALQAGFDLLNDGRPETLWLGIGTLLMLIGTFYFIARGWGVTDKEAREYYAITILVP
Arch         MDPIALQAGYDLLGDGRPETLWLGIGTLLMLIGTFYF1VRGWGVTDKDAREYYAVTILVP
Archer1      MDPIALQAGYDLLGDGRPETLWLGIGTLLMLIGTFYF1VRGWGVTDKDAREYYAVTILVP
Arch-7       MDPIALQAGYDLLGDGRPETLWLGIGTLLMLIGTFYF1VRGWGVTDKDAREYYAVTILAL
QuasAr1      MDPIALQAGYDLLGDGRPETLWLGIGTLLMLIGTFYF1VRGWGVTDKDAREYYAVTILVS
QuasAr2      MVSIALQAGYDLLGDGRPETLWLGIGTLLMLIGTFYF1VRGWGVTDKDAREYYAVTILVS
QuasAr-I#3   MVSIALQAGYDLLGDGRPETLWLGIGTLLMLIGTFYFLVRGWGVTDKDAREYYAVEILVS
QuasAr-I#7   MVSIALQAGYDLLGDGRPETLWLGIGTLLMLIGTFYFLVRGWGVTDKDAREYYAVEILVS
QuasAr-I#14  MVSIALQAGYDLLGDGRPETLWLGIGTLLMLIGTFYFLVRGWGVTDRDAREYYAVEILVS
QuasAr-I#16  MVSIALQAGYDLLGDGRPETLWLGIGTLLMWIGTFYFLVRGWGVTDKDAREYYAVEILVS
QuasAr-I#22  MVSIALQAGYDLLGDGRPESLWLGIGTLLMLIGTFYFLVRAWGETDKDAREYYAVTILVS 70         80         90        100        110        120
                    |          |          |          |          |          |
aR2          GIASAAYLAMFFGIGVTEVELASGTVLDIYYARYADWLFTTPLLLLDLALLAKVDRVTIG
Arch         GIASAAYLSMFFGIG1TEVTVG-GEMLDIYYARYADWLFTTPLLLLDLALLAKVDRVTIG
Archer1      GIASAAYLSMFFGIG1TEVTVG-GEMLDIYYARYAEWLFCTPLLLLDLALLAKVDRVTIG
Arch-7       GIASAAYLSMFFGIG1TEVTVG-GEMLDIYYARYAEWLFCTPLLLLDLALLAKVDRVTIG
QuasAr1      GIASAAYLSMFFGIG1TEVSVG-GEMLDIYYARYAHWLFTTPLLLLHLALLAKVDRVTIG
QuasAr2      GIASAAYLSMFFGIG1TEVSVG-GEMLDIYYARYAQWLFTTPLLLLHLALLAKVDRVTIG
QuasAr-I#3   GIASAAYLSMFFGIGLTEVSVG-GEMLDIYYARYAHWLFTTPLLLLHLALLAKVDRVEIG
QuasAr-I#7   GIASAAYLSMFFGIGLTEVSVG-GEMLDIYEARYAHWLFTTPLLLLHLALLAKVDRVEIG
QuasAr-I#14  GIASAAYLSMFFGIGLTEVSVG-GEMLDIYYARYAHWLFTTPLLLLHLALLAKVDRVEIG
QuasAr-I#16  GIASAAYLSMFFGIGLTEVEVG-GEMLDIYYARYAHWLFTTPLLLLHLALLAKVDRVEIG
QuasAr-I#22  GIASAAYLSMFFGIGLTEVSVG-GEMLNIYYARYAQWLFTTPLLLLHLALLAKVDRVTIG 130        140        150        160        170        180
                    |          |          |          |          |          |
aR2          TLIGVDALMIVTGLIGALSKTPLARYTWWLFSTIAFLFVLYYLLTSLRSAAAKRSEEVRS
Arch         TLVGVDALMIVTGLIGALSHTAIARYSWWLFSTICMIVVLYFLATSLRSAAKERGPEVAS
Archer1      TLVGVDALMIVTGLIGALSHTAIARYSWWLFSTICMIVVLYFLATSLRSAAKERGPEVAS
Arch-7       TLVGVDALMIVTGLIGALSHTAIARYSWWLFSTICMIVVLYFLATSLRSAAKERGPEVAS
QuasAr1      TLVGVDALMIVTGLIGALSHTAIARYSWWLFSTICMIVVLYVLATSLRSAAKERGPEVAS
QuasAr2      TLVGVDALMIVTGLIGALSHTAIARYSWWLFSTICMIVVLYVLATSLRSAAKERGPEVAS
QuasAr-I#3   TLVGVDALMIVTGLIGALSHTAIARYSWWLFSTICMIVVLYVLATSLRSAAKERGPEVAS
QuasAr-I#7   TLVGVDALMIVTGLIGALSHTAIARYSWWLFSTICMIVVLYVLATSLRSAAKERGPEVAS
QuasAr-I#14  TLVGVDALMIVTGLIGALSHTAIARYSWWLFSTICMIVVLYVLATSLRSAAKERGPEVAS
QuasAr-I#16  TLVGVDALMIVTGLIGALSHTAIARYSWWLFSTICMIVVLYVLATSLRSAAKERGPEVAS
QuasAr-I#22  TLVGVDALMIVTGLIGELSHTAIARYSWWLFSTICMIVVLYVLATSLRSAAKERGPEVAS 190        200        210        220        230        240
                    |          |          |          |          |          |
aR2          TFNTLTALVAVLWTAYPILWIVGTEGAGVVGLGIETLAFMVLDVTAKVGFGFVLLRSRAI
Arch         TFNTLTALV1VLWTAYPILWIIGTEGAGVVGLGIETLLFMVLDVTAKVGFGFILLRSRAI
Archer1      TFNTLTALV1VLWTAYPILWIIGTEGAGVVGLGIETLLFMVLDVTAKVGFGFILLRSRAI
Arch-7       TFNTLTALV1VLWTAYSILWIIGTEGAGVVGLGIETLLFMVLSVTCKVGFGFILLRSRAI
QuasAr1      TFNTLTALV1VLWTAYPILWIIGTEGAGVVGLGIETLLFMVLDVTAKVGFGFILLRSRAI
QuasAr2      TFNTLTALV1VLWTAYPILWIIGTEGAGVVGLGIETLLFMVLDVTAKVGFGFILLRSRAI
QuasAr-I#3   TFNILTALVLVLWTAYPIEWIIGTEGAGVVGLGIETLLFMVLDVTAKVGFGFILLRSRAI
QuasAr-I#7   TFNILTALVLVLWTAYPIEWIIGTEGAGVVGLGIETLLFMVLDVTAKVGFGFILLRSRAE
QuasAr-I#14  TFNILTALVLVLWTAYPIEWIIGTEGAGVVGLGIETLLFMVLDVTAKVGFGFILLRSRAI
QuasAr-I#16  TFNILTALVLVLWTAYPIEWIIGTEGAGVVGLGIETLLFMVLDVTAKVGFGFILLRSRAI
QuasAr-I#22  TFNTLTALVLVLWTAYPILWIIGTEGAGVVGLGIETLLFMVLDVTAKVGFGFILLRSRAI
```

```
                              250
                               |
aR2           LGETEAPEPSAGADASAAD
Arch          LGDTEAPEPSAGADVSAAD
Archer1       LGDTEAPEPSAGADVSAAD
Arch-7        LGDTEAPEPSAGADVSAAD
QuasAr1       LGDTEAPEPSAGAD
QuasAr2       LGDTEAPEPSAGAD
QuasAr-I#3    LGDTEAPEPSAGAD
QuasAr-I#7    LGDTEAPEPSAGAD
QuasAr-I#14   LGDTEAPEPSAGAD
QuasAr-I#16   LGDTEAPEPSAGAD
QuasAr-I#22   LGDTEAPEPSAGAD
```

Figure 14

```
                        10        20        30        40        50        60
                        |         |         |         |         |         |
                                  *                             *         * *
aR2        MDPIALQAGFDLLNDGRPETLWLGIGTLLMLIGTFYFIARGWGVTDKEAREYYAITILVP
Arch       MDPIALQAGYDLLGDGRPETLWLGIGTLLMLIGTFYFLVRGWGVTDKDAREYYAVTILVP
Archer1    MDPIALQAGYDLLGDGRPETLWLGIGTLLMLIGTFYFLVRGWGVTDKDAREYYAVTILVP
QuasAr1    MDPIALQAGYDLLGDGRPETLWLGIGTLLMLIGTFYFLVRGWGVTDKDAREYYAVTILVS
QuasAr2    MVSIALQAGYDLLGDGRPETLWLGIGTLLMLIGTFYFLVRGWGVTDKDAREYYAVTILVS
Archon1    MVSIALQAGYDLLGDGRPESLWLGIGTLLMLIGTFYFLVRAWGSTDKDAREYYAVTILVS
Archon2    MVSIALQAGYDLLGDGRPETLWLGIGTLLMLIGTFYFLVRGWGVTDKDAREYYAVPILVS
Variant#3  MVSIALQAGYDLLGDGRPEILWLGIGTLLMLIGTFYFLVRGWGVTDKDAREYYAVTILVS
Variant#4  MVSIALQAGYDLLGDGRPEILWLGIGTLLMLIGTFYFLVRGWGVTDKDAREYYAVTILVS
Variant#5  MVSIALQAGYDLLGDGRPETLWLGIGTLLMLIGTFYFLVRGWGVTDKDAREYYAVPILVS
Variant#6  MVSIALQAGYDLLGDGRPETLWLGIGTLLMLIGTFYFVVRGWGVTDKDAREYYAVPILVC
Variant#7  MVSIALQAGYDLLGDGRPETLWLGIGTLLMLIGTFYFLVRGWGVTDRDAREYYAVPILVS 70        80        90       100       110       120
                        |         |         |         |         |         |
                                  *                   *         *         *
aR2        GIASAAYLAMFFGIGVTEVELASGTVLDIYYARYADWLFTTPLLLLDLALLAKVDRVTIG
Arch       GIASAAYLSMFFGIGlTEVTVG-GEMLDIYYARYADWLFTTPLLLLDLALLAKVDRVTIG
Archer1    GIASAAYLSMFFGIGlTEVTVG-GEMLDIYYARYAEWLFCTPLLLLDLALLAKVDRVTIG
QuasAr1    GIASAAYLSMFFGIGlTEVSVG-GEMLDIYYARYAHWLFTTPLLLHLALLAKVDRVTIG
QuasAr2    GIASAAYLSMFFGIGlTEVSVG-GEMLDIYYARYAQWLFTTPLLLHLALLAKVDRVTIG
Archon1    GIASAAYLSMFFGIGlTEVPVG-GEMLNIYYARYAQWLFTTPLLLHLALLAKVDRVTIG
Archon2    GIASAAYLSMFFGIGlTEVPVG-GEMLDIYYARYAHWLFSTPLLLLDLALLAKVDRVIIG
Variant#3  GIASAAYLSMFFGIGlTEVSVG-GEMLDIYYARYAEWLFCTPLLLLDLALLAKVDRVIIG
Variant#4  GIASAAYLSMFFGIGlTEVSVG-GEMLDIYYARYAEWLFCTPLLLLDLALLAKVDRVIIG
Variant#5  GIASAAYLSMFFGIGlTEVPVG-GEMLDIYYARYAHWLFTTPLLLHLALLAKVDRVIIG
Variant#6  GIASAAYLSMFFGIGlTEVPVG-GEMLDIYYARYAHWLFTTPLLLLDLALLAKVDRVTIG
Variant#7  GIASAAYLSMFFGIGlTEVSVG-GEMLDIYYARYAHWLFTTPLLLLDLALLAKVDRVTIG 130       140       150       160       170       180
                        |         |         |         |         |         |
aR2        TLIGVDALMIVTGLIGALSKTPLARYTWWLFSTIAFLFVLYYLLTSLRSAAAKRSEEVRS
Arch       TLVGVDALMIVTGLIGALSHTAIARYSWWLFSTICMIVVLYFLATSLRSAAKERGPEVAS
Archer1    TLVGVDALMIVTGLIGALSHTAIARYSWWLFSTICMIVVLYFLATSLRSAAKERGPEVAS
QuasAr1    TLVGVDALMIVTGLIGALSHTAIARYSWWLFSTICMIVVLYVLATSLRSAAKERGPEVAS
QuasAr2    TLVGVDALMIVTGLIGALSHTAIARYSWWLFSTICMIVVLYVLATSLRSAAKERGPEVAS
Archon1    TLVGVDALMIVTGLIGLSHTAIARYSWWLFSTICMIVVLYVLATSLRSAAKERGPEVAS
Archon2    TLVGVDALMIVTGLIGALSHTAIARYSWWLFSTICMIVVLYVLATSLRSAAKERGPEVAS
Variant#3  TLVGVDALMIVTGLIGALSHTAIARYSWWLFSTICMIVVLYVLATSLRSAAKERGPEVAS
Variant#4  TLVGVDALMIVTGLIGALSHTAIARYSWWLFSTICMIVVLYVLATSLRSAAKERGPEVAS
Variant#5  TLVGVDALMIVTGLIGALSHTAIARYSWWLFSTICMIVVLYVLATSLRSAAKERGPEVAS
Variant#6  TLVGVDALMIVTGLIGALSHTAIARYSWWLFSTICMIVVLYVLATSLRSAAKERGPEVAS
Variant#7  TLVGVDALMIVTGLIGALSPTAIARYSWWLFSTICMIVVLYVLATSLRSAAKERGPEVAS
```

Figure 14 (continued)

```
                    190       200       210       220       230       240
                     |         |         |         |         |         |
                     *         *                             ** *
aR2         TFNTLTALVAVLWTAYPILWIVGTEGAGVVGLGIETLAFMVLDVTAKVGFGFVLLRSRAI
Arch        TFNTLTALVLVLWTAYPILWIIGTEGAGVVGLGIETLLFMVLDVTAKVGFGFILLRSRAI
Archer1     TFNTLTALVLVLWTAYPILWIIGTEGAGVVGLGIETLLFMVLDVTAKVGFGFILLRSRAI
QuasAr1     TFNTLTALVLVLWTAYPILWIIGTEGAGVVGLGIETLLFMVLDVTAKVGFGFILLRSRAI
QuasAr2     TFNTLTALVLVLWTAYPILWIIGTEGAGVVGLGIETLLFMVLDVTAKVGFGFILLRSRAI
Archon1     TFNILTALVLVLWTAYPIIWIIGTEGAGVVGLGIETLLFMVLDVTAKVGFGFILLRSRAI
Archon2     TFNILTALVLVLWTAYPIIWIIGTEGAGVVGLGIETLLFMVLDVTGKVGFGFILLRSRAI
Variant#3   TFNILTALVLVLWTAYPIIWIIGTEGAGVVGLGIETLLFMVLDVTGKVGFGFILLRSRAI
Variant#4   TFNILTALVLVLWTAYPIIWIIGTEGAGVVGLGIETLLFMVLDVTAKVGFGFILLRSRAI
Variant#5   TFNILTALVLVLWTAYPIIWIIGTEGAGVVGLGIETLLFMVLDVTAKVGFGFILLRSRAI
Variant#6   TFNTLTALVLVLWTAYPIIWIIGTEGAGVVGLGIETLLFMVLDVTGKVGFGFILLRSRAI
Variant#7   TFNILTALVLVLWTAYPIIWIIGTEGAGVVGLGIETLLFMVLDVTGKVGFGFVLLRSRAI 250
                     |
aR2         LGETEAPEPSAGADASAAD
Arch        LGDTEAPEPSAGADVSAAD
Archer1     LGDTEAPEPSAGAD
QuasAr1     LGDTEAPEPSAGAD
QuasAr2     LGDTEAPEPSAGAD
Archon1     LQDTEAPEPSAGAD
Archon2     LGDTEAPEPSAGAD
Variant#3   LGDTEAPEPSAGAD
Variant#4   LGDTEAPEPSAGAD
Variant#5   LGDTEAPEPSAGAD
Variant#6   LGDTEAPEPSAGAD
Variant#7   LGDTEAPEPSAGAD
```

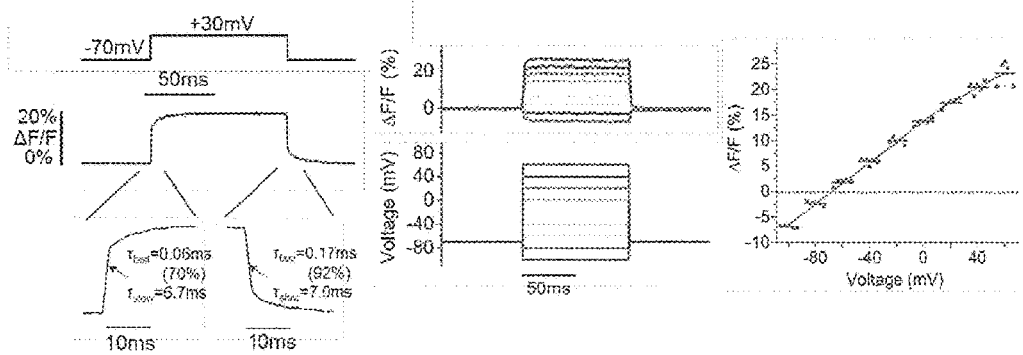
Fig 17A    Fig 17B    Fig 17C
Fig 17D 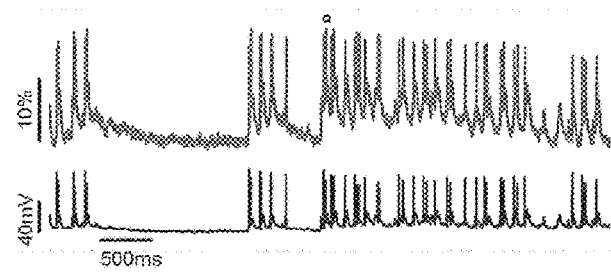    Fig 17E 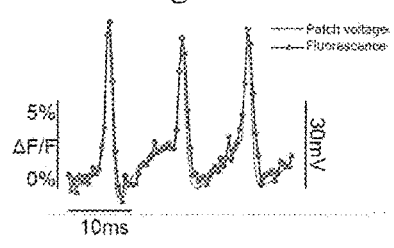
Fig 17F 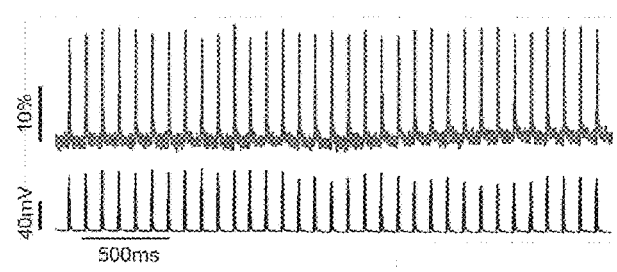    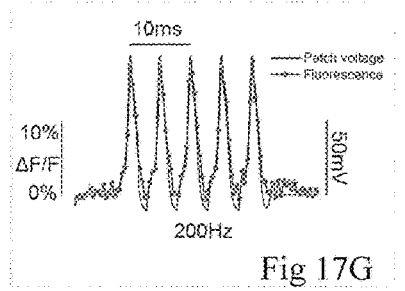
Fig 17G
Fig 17H 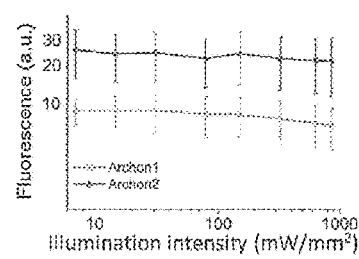    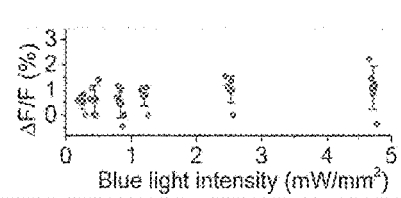
Fig 17I

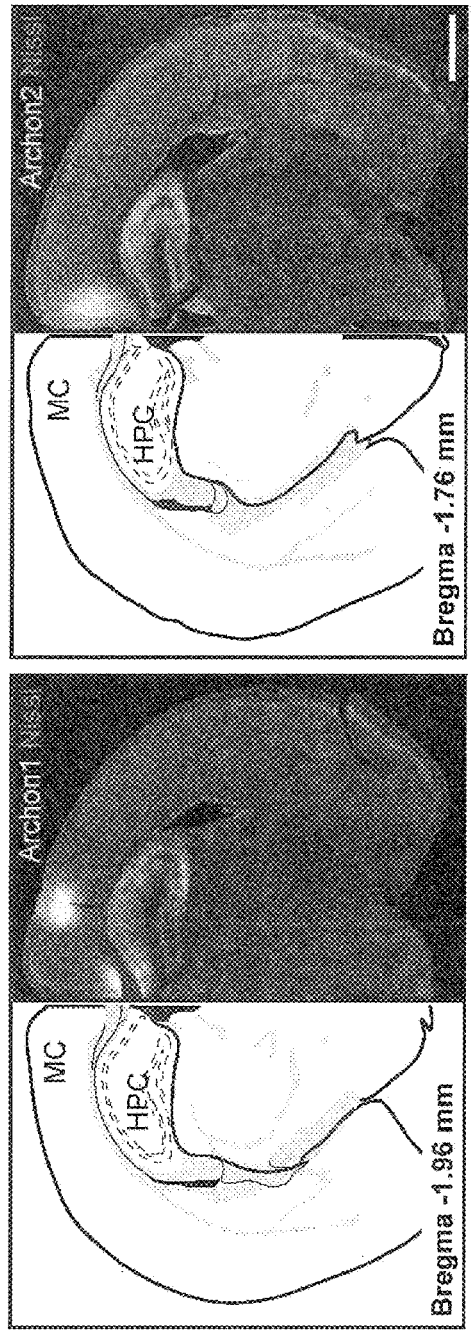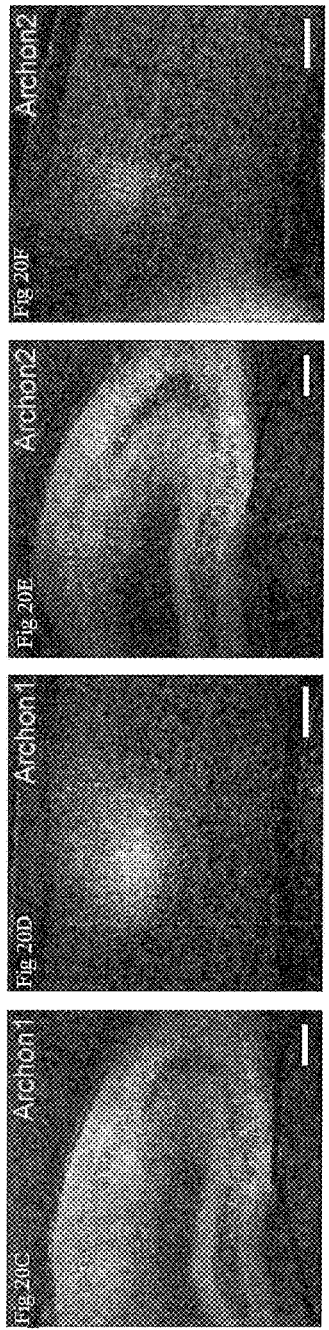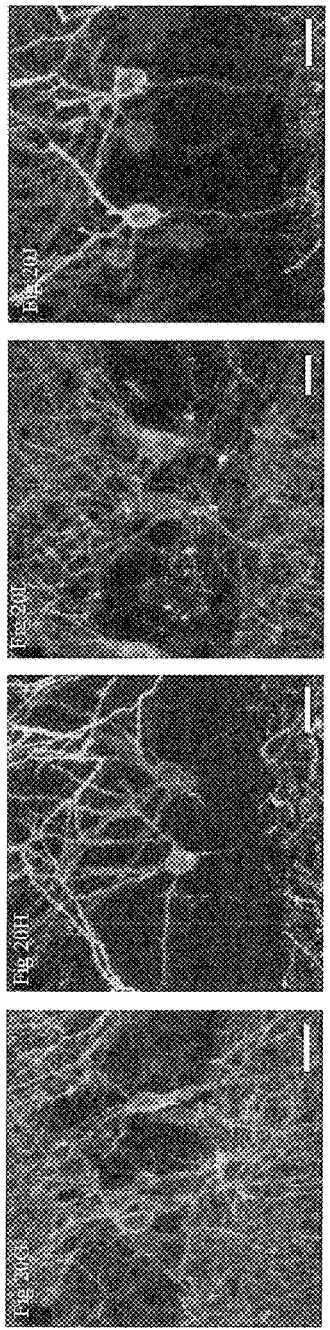

Fig 22A 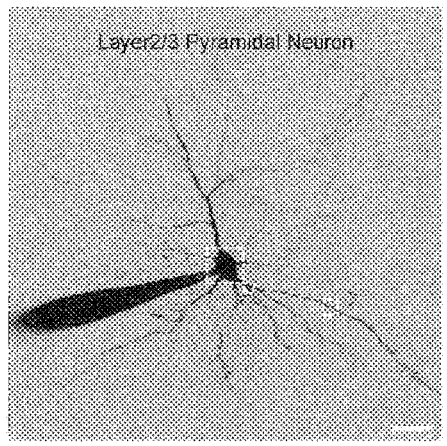 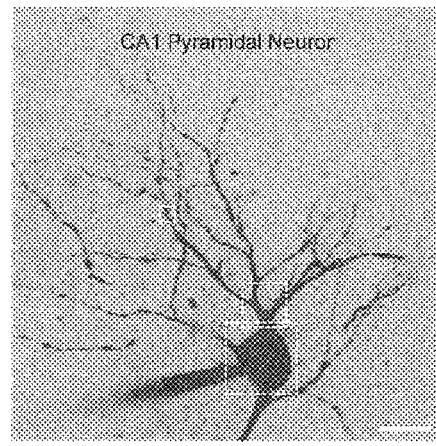 Fig 22B
Fig 22C 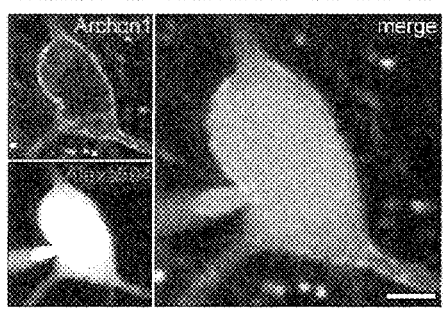 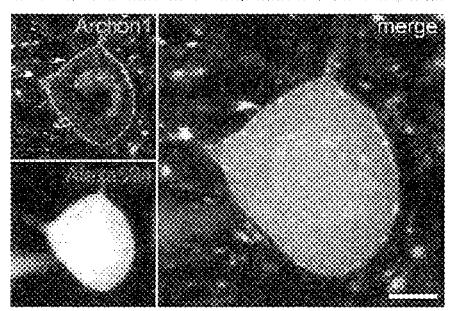 Fig 22D
Fig 22E 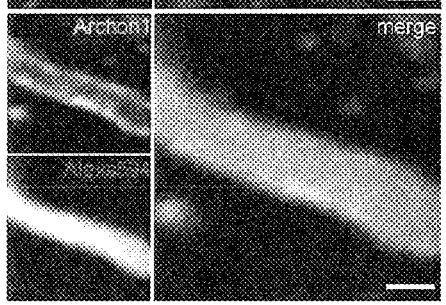 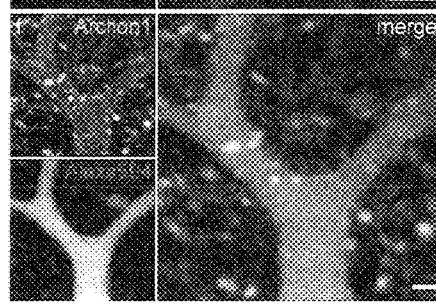 Fig 22F
Fig 22G 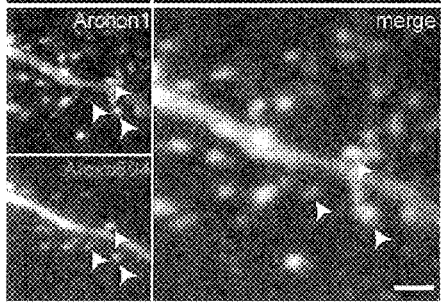 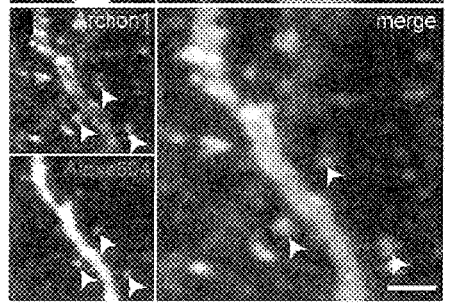 Fig 22H

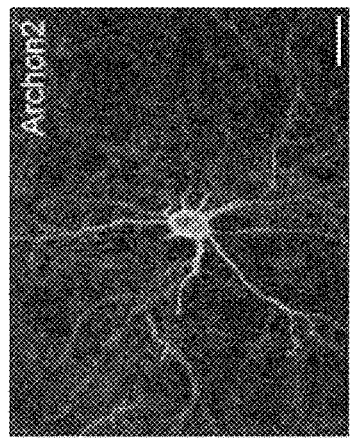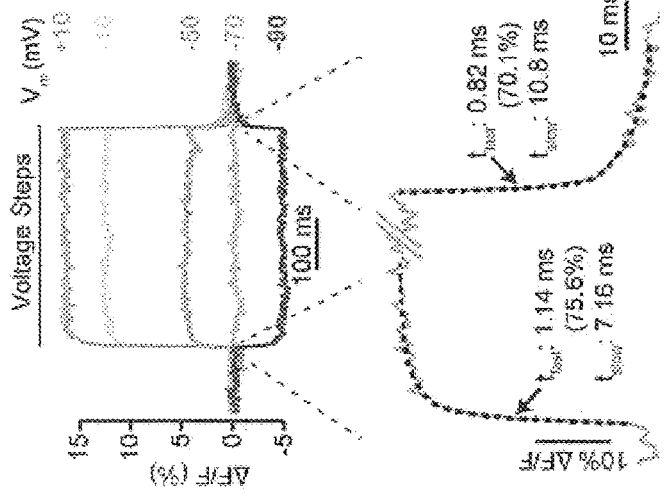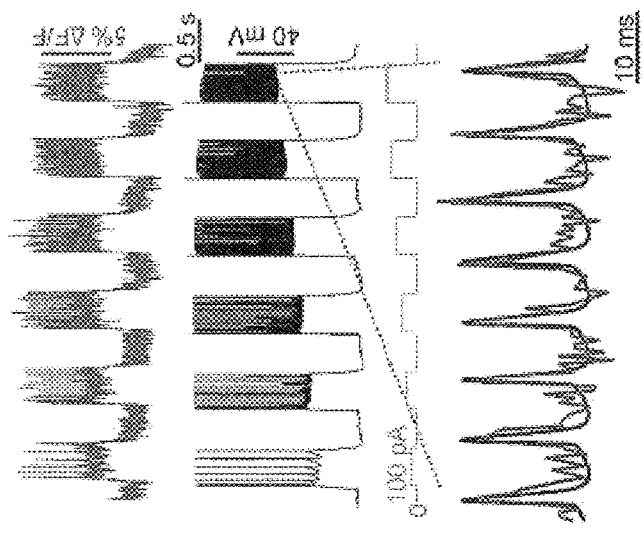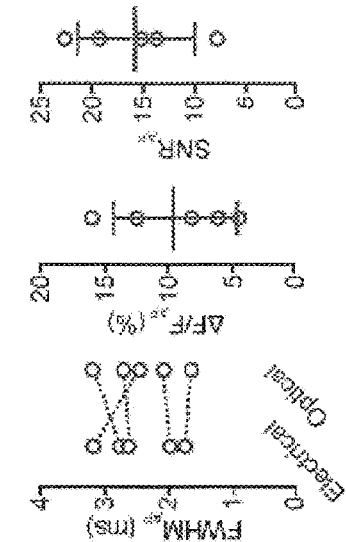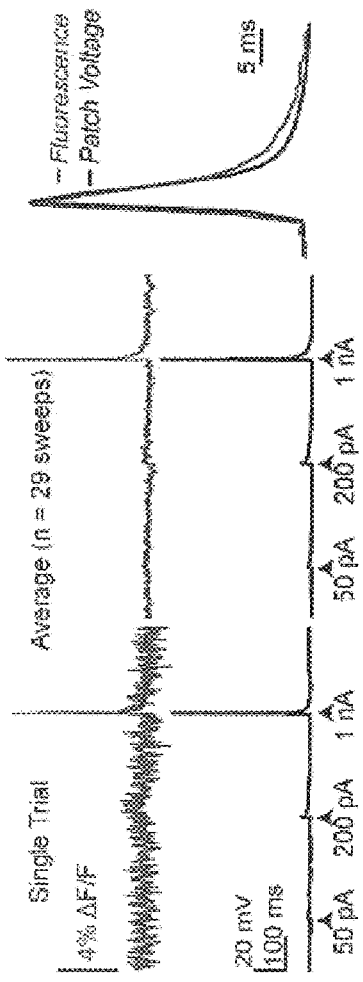

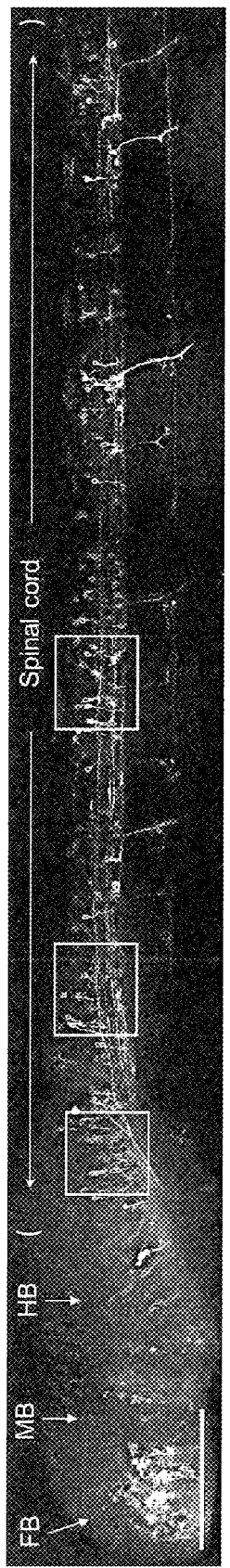
Fig 24A
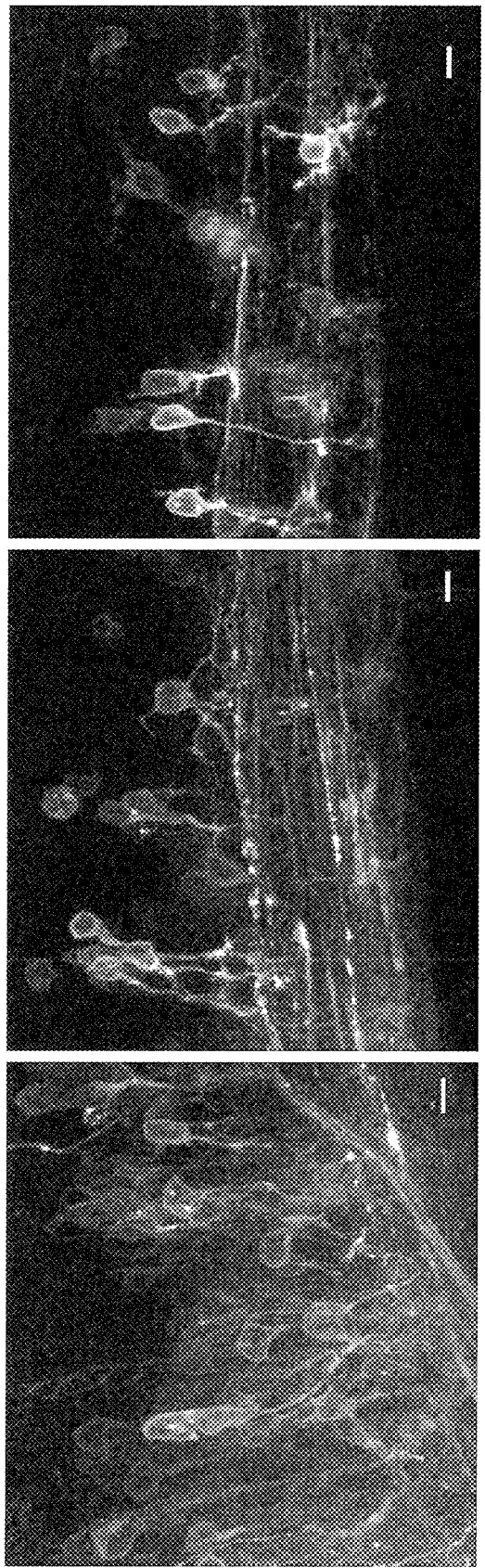
Fig 24B
Fig 24C
Fig 24D

Fig 26A
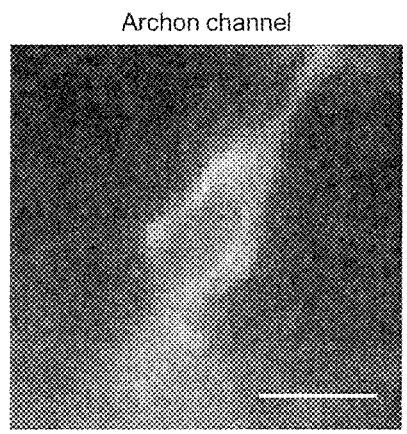
Fig 26B
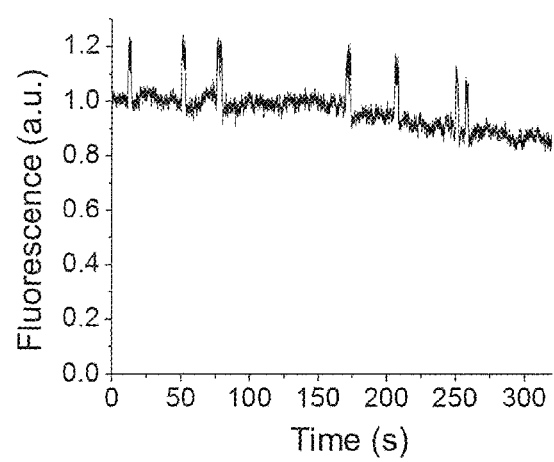
Fig 27A  Fig 27B  Fig. 27C
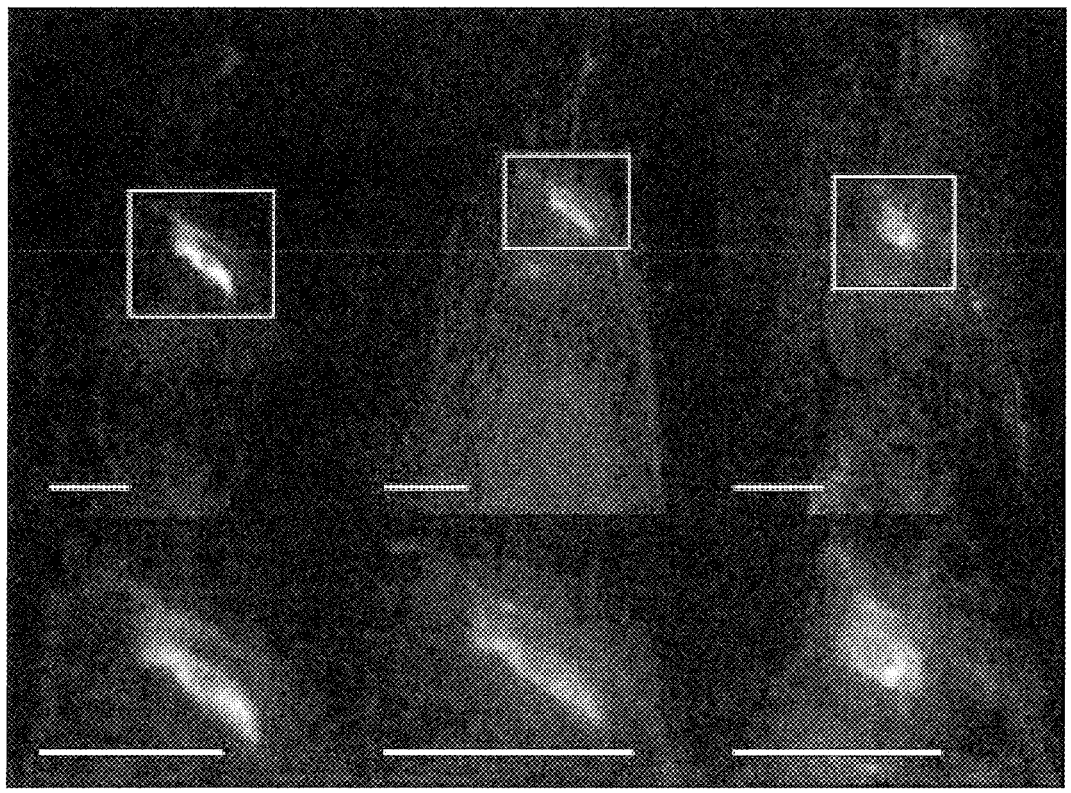
Fig 27D  Fig 27E  Fig 27F

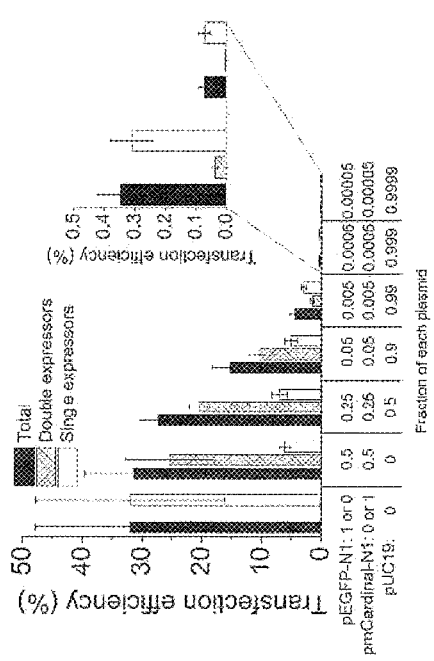
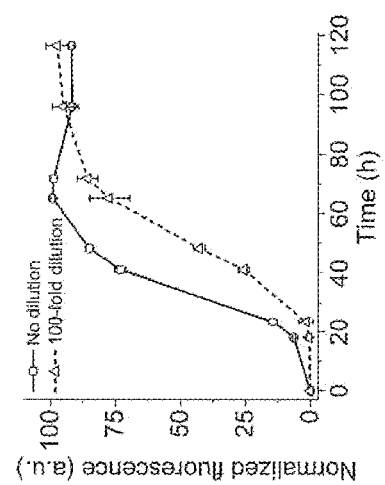
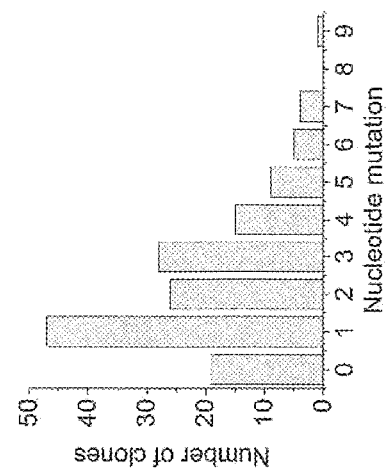
Fig 28A
Fig 28B
Fig 28C

Fig. 29A

| Sensor | Brightness[a] | ΔF/F (%) | | On kinetics (-70 to +30mV) | | | | Off kinetics (+30 to -70mV) | | | | Optical response linearity to voltage changes (-100 to +50mV)[b] | Bleaching rate/Conditions[c] | Photocurrents at excitation wavelength | | | Effect of blue illumination (450-500nm) used for optogenetic control | | | Sub-threshold voltage imaging (<10mV) | Voltage imaging at dendritic spine | Membrane localization (Supplementary Fig. 10 for representative images) | Ref. |
|---|---|---|---|---|---|---|---|---|---|---|---|---|---|---|---|---|---|---|---|---|---|---|---|
| | | Per 100mV (-70-+30mV) voltage step[b] | Per action potential (AP) | τfast (ms) | % of magnitude in τfast component[d] | τslow (ms) | | τfast (ms) | % of magnitude in τfast component[d] | τslow (ms) | | | | Steady-state photo-current[f] | Peak of transient photo-current[g] | | Photocurrent under blue light | | Sensor fluorescence change under blue light | | | | |
| | | | | | | | | | | | | | | | | | Steady-state photo-current[f] | Peak of transient photo-current[g] | | | | |
| QuasAr1 | No data available | No data available[h] | 21 (640nm, 3-5mW/mm²) | 0.05 in HEK cells (640nm, light intensity not specified,34°C) | 94 in HEK cells | 3.2 in HEK cells | | 0.07 in HEK cells | 88 in HEK cells | 1.9 in HEK cells | | Linear | No data available | 0pA averaged over 250ms (640nm, 3W/mm²), not broken down into steady state and transient photocurrents | | | 0pA averaged over 250ms (488nm, 5mW/mm²), not broken down into steady state and transient photocurrents | | 2% increase in red fluorescence with blue (488nm) light pulses at 5mW/mm² in HEK cells | No data available | No data available | | 3 |
| QuasAr2 | No data available | No data available[h] | 48 (640nm, 3-8W/mm²) | 0.3 in HEK cells (640nm, light intensity not specified, 34°C) | 62 in HEK cells | 3.2 in HEK cells | | 0.3 in HEK cells | 73 in HEK cells | 4.0 in HEK cells | | Linear | 0.05%/s (640nm, 3W/mm²) | 0pA averaged over 250ms (640nm, 5mW/mm²), not broken down into steady state and transient photocurrents | | | 0pA averaged over 250ms (488nm, 5mW/mm²), not broken down into steady state and transient photocurrents | | 2% increase in red fluorescence with blue (488nm) light pulses at 5mW/mm² in HEK cells | Detection of optically induced synaptic events | Voltage imaging at single dendritic spine during optically induced back-propagating action potential | Severe aggregation in soma and mild aggregation in processes | |
| | 100 ±66 (637nm, 800mW/mm²) | 39±13 (637nm, 800mW/mm²) | | 0.9 ±0.2 (637nm, 800mW/mm² 34°C) | 67 | 11.7 ±0.7 | | 1.6 ±0.3 | 76 | 20 ±6 | | | 0.05%/s (637nm, 2.2W/mm²) | | | | | | | | | | |
| Archer1 | 103 ±51 (637nm, 800mW/mm²) | 85 (655nm, 880mW/mm²) | 25-40 (655nm, 880mW/mm²) | No data available | | | | No data available | | | | Linear | No data available | +5pA (655sun, 880mW/m²) | First peak current of ~+30pA only at the beginning of light pulse with duration not specified; subsequent peak currents of ~30pA with duration not specified | | 70-180pA (~480nm, light intensity not specified) | 150-180pA (duration not specified) | No data available | No data available | No data available | Mild aggregation in soma and severe aggregation in processes | 4 |
| | | 34±8 (637nm, 800mW/mm²) | | 0.6 ±0.1 (637nm, 800mW/mm² 34°C) | 68 | 33 ±3 | | 1.1 ±0.3 | 77 | 87 ±4 | | | 0.07%/s (637nm, 2.2W/mm²) | | | | | | | | | | |
| Archon1 | 278 ±106 (637nm, 800mW/mm²) | 43±5 (637nm, 800mW/mm²) | 30±6 (637nm, 80-800mW/mm²) | 0.61 ±0.06 (637nm, 800mW/mm² 34°C) | 88 | 8.1 ±0.5 | | 1.1 ±0.2 | 88 | 13 ±3 | | Linear | 0.01%/s (637nm, 800mW/mm²) | 0pA in HEK cells (637nm, 800mW/m²) | First peak current of ~33pA only at the beginning of light pulse, with exponential decay lasting ~5ms, no | | 0pA in HEK cells (475/20 or 15 or 800mW/m²) | Peak currents of ~8pA only at the beginning of light pulse with exponential decay lasting for 10ms for the | 2% increase in red fluorescence with 475/20nm light pulses at 4.8mW/mm² | Detection of spontaneous events | No data available | Minimal aggregation in soma and no aggregation in processes | This work |

Fig. 29A continued

| | | | | | | | | | | | first and subsequent peaks in HEK cells | | | | |
|---|---|---|---|---|---|---|---|---|---|---|---|---|---|---|---|
| Archon2 | 801 ±407 (637nm, 800mW/mm²) | 19±2 (637nm, 80-800mW/mm²) | 18±2 (637nm, 80-800mW/mm²) | 0.06 ±0.01 (637nm, 800mW/mm², 34°C) | 70 | 6.7 ±0.4 | 0.17 ±0.01 | 92 | 7.0 ±0.5 | Linear | 0.03%/s (637nm, 0.8W/mm²) | 0pA in HEK cells (637nm, 800mW/mm²) | No peak currents in HEK cells | 0pA in HEK cells (470/20nm,15m W/mm²) | 1% increase in red fluorescence with 470/20nm light pulses at 4.8mW/mm² | Not tested | Voltage imaging at dendritic spines during spontaneous events | Mild aggregation in soma and no aggregation in processes |
| Ace2N-mNeon | -4 (steady state), -19 (peak)¹ (505nm, 15mW/mm²) | -12 (505nm, 15mW/mm²) | 0.36 in HEK cells (505nm, 15mW/mm², 22°C) | 74 in HEK cells | 4.2 in HEK cells | 0.42 in HEK cells | 64 in HEK cells | 5.2 in HEK cells | Nonlinear for steady state response; linear for peak fluorescence response | 0.7%/s (505nm, 15mW/mm²) | -0.2 ± 0.1 pA (505nm,15 mW/mm²) | Peak currents of ~-10pA and -+10pA at the beginning and the end of light pulse respectively with exponential decay lasting for ~200ns for each transient current; subsequent peak currents not specified | Same as the photocurrents measured under excitation wavelength; see data at left | Not applicable: blue light is used for voltage imaging | Detection of spontaneous events | No data available |
| Ace2N-4aa-mNeon | Steady-state fluorescence not specified, -9 (peak)¹ (505nm, 15mW/mm²) | -5 (505nm, 15mW/mm²) | 0.37 in HEK cells (505nm, 15mW/mm², 22°C) | 58 in HEK cells | 5.5 in HEK cells | 0.60 in HEK cells | 60 in HEK cells | 5.9 in HEK cells | No data available | 0.6%/s (505nm, 15mW/mm²) | No data available | | No data available | Not applicable: blue light is used for voltage imaging | No data available | |
| | -6 (475nm, 13mW/mm²)¹⁰ | -5±2 (475nm, 13mW/mm²)¹⁰ | 2.2 ±0.3 (475nm, 13mW/mm², 34°C)⁹ | 61 | 6.4 ±0.1 | 3.8 ±0.1 | 90 | 17.5 ±0.7 | | 0.13%/s (475nm, 13mW/mm²) | | | | | | | Mild aggregation in soma and no aggregation in processes |
| MacQ-mCitrine | -12 (505nm, 15mW/mm²) | -5 (505nm, 15mW/mm²) | 2.8 in HEK cells (505nm, 15mW/mm², 22°C) | 74 in HEK cells | 5.5 in HEK cells | 5.4 in HEK cells | 77 in HEK cells | 67 in HEK cells | Compressed dynamic range relative to linear (no additional changes >0mV) | 1.3%/s (505nm, 15mW/mm²) | -0.2 ± 0.2 pA (505nm, 15mW/mm²) | First peak current of -25pA only at the beginning of light pulse, with exponential decay lasting ~20ns; subsequent peak currents not specified | Same as the photocurrents measured under excitation wavelength; see data at left | Not applicable: blue light is used for voltage imaging | Detection of spontaneous events | No data available |
| ASAP1 | No data available⁶ | -6 (488nm, light intensity not specified) | 2.1 in HEK cells (488nm, 25-50mW/mm², 22°C) | 60 in HEK cells | 71.5 in HEK cells | 2.0 in HEK cells | 43 in HEK cells | 50.8 in HEK cells | Bi-exponential | 0.3%/s (470nm, 15mW/mm²) | No data available | | No data available | Not applicable: blue light is used for voltage imaging | Detection of spontaneous events | No data available |

Fig. 29B

| Tested organism | Voltage sensor | Tested area (cell type)/Promoter/Gene delivery | ΔF/F (%) per 100mV (-70-+30mV) voltage steps[a] | ΔF/F (%) per AP | Signal-to-noise ratio | Continuous recording duration (as shown in the study; not a fundamental parameter) | Ability to resolve temporally close (<50ms) spikes | Subthreshold voltage imaging | Voltage imaging at processes | Ref. |
|---|---|---|---|---|---|---|---|---|---|---|
| Organotypic brain slice | QuasAr2 | Hippocampus/ CaMKIIα/ biolistic gene delivery | No data available | 16 | 32[b] at 12W/mm², 1kHz | 10s | Resolved spikes evoked 10-20ms apart[c]. Higher frequency not reported. | Inhibitory potentials were presented but not quantified with electrophysiology | Single-trial voltage imaging of optically-induced events at proximal dendrites | 3 |
| Acute brain slice | Ace2N-mNeon | Visual cortex V1 /CMV-T7/rabies SAD-ΔG | No data available | ~9 | No data available | No data available | No data available | No data available | No data available | 5 |
| | MacQ-mCitrine | Neocortical pyramids & PV interneurons/ CAG/in utero electroporation | No data available | -2.5 in neocortical pyramids, -0.5 in PV interneurons | 6 in neocortical pyramids, 2 in PV interneurons[d] at 30mW/mm², 440Hz | 2s | No data available | No data available | No data available | 6 |
| | ASAP1 | Layer 5 cortical pyramidal neurons/ CAG/in utero electroporation | No data available | -6 | 5-10 at 8-50mW/mm², 400Hz | <1.5s | Unable to resolve spikes evoked 20ms apart. | Unable to resolve 30mV depolarization in 25Hz AP trains (2-5ms, 600-1,500pA current pulses) | No data available | 7 |
| | Archon1 | Motor cortex layer 2/3 pyramidal neurons/ CAG/in utero electroporation | 23.5±9.3 | 22.4±9.4 at 1.5W/mm², 22.2±10.2 at 15W/mm², both at 1kHz | 12±5 at 1.5W/mm², 21±11 at 15W/mm², both at 1kHz | 30s | Resolved spikes evoked 10ms apart. Higher frequency not tested. | Single trial recording of 5mV depolarization (by 2ms, 50-200pA current injections and synaptic inputs) | Not tested | This work |
| | Archon2 | Motor cortex layer 2/3 pyramidal neurons/ CAG/in utero electroporation | 18.8±8.3 | 9.4±2.1 at 15W/mm² | 16±3 at 15W/mm², 1kHz | 30s | Resolved spikes evoked 10ms apart. Higher frequency not tested | Single trial recording of 7mV depolarization (by 2ms, 50-200pA current injections and synaptic inputs) | Not tested | |
| In vivo C. elegans | Archer1 | AWC neuron /psr-2/ transgenic line | No data available | 0.4 | <5 at 880mW/mm², 250Hz | 40s | Not applicable | No data available | No data available | 4 |

Fig. 29B continued

| | Indicator | Expression | | | | | | | | Ref |
|---|---|---|---|---|---|---|---|---|---|---|
| In vivo Drosophila | Archon1 | AVA neuron rig-3/ transgenic line | No data available | 22±4 | 30±10 at 800mW/mm², 33Hz | 960s | Not applicable | No data available | Single-trial voltage imaging of spontaneous events in an axon | This work |
| | Ace2N-2aa-mNeon | Olfactory neurons /Gal4-UAS, Hsp70/ transgenic line | No data available | -2° | 10-15° at 20mW/mm²,1kHz | 3s | Resolved spikes evoked 10-20ms apart. Higher frequency not tested. | No data available | Single trial voltage imaging of stimulus-driven events at axon and dendrites | 5 |
| | ASAP2f | Various areas and cell types /various promoters/ transgenic line | No data available | (-5)-(-10) depending on cell types | No data available | 600s | No data available | No data available | Single-trial voltage imaging of stimulus-driven events at axon and dendrites | 12 |
| In vivo zebrafish | Archon1 | Random subset of neurons/ Gal4-UAS, β-actin/ transient expression | No data available | 33±6 | 16±10 at 2.2W/mm², 333Hz | 300s | Resolved spikes evoked 10ms apart. Higher frequency not tested. | Detection of subthreshold peaks | Single-trial voltage imaging of spontaneous events in an axon | This work |
| In vivo mouse | ACE2N-4aa-mNeon | Layer 2/3 visual cortical neurons/ CMV-T7/rabies SAD-ΔG | No data available | -3° | 5-10° at 25mW/mm²,1kHz | 30s | Resolved spikes evoked 10-20ms apart. Higher frequency not reported. | Detection of baseline fluctuation | Multi-trial voltage imaging of interrogated events at proximal dendrites (spike-triggered averages of 1900 spikes) | 5 |
| | MacQ-mCitrine | Purkinje neurons/ CAG/in utero electroporation | No data available | -1.5° | 5-10° at 10mW/mm²; 190Hz | <30s | No data available | No data available | No data available | 6 |

```
                              SEQUENCE LISTING

<160> NUMBER OF SEQ ID NOS: 27

<210> SEQ ID NO 1
  <211> LENGTH: 253
  <212> TYPE: PRT
  <213> ORGANISM: Artificial Sequence
  <220> FEATURE:
  <223> OTHER INFORMATION: Synthetic Polypeptide

<400> SEQUENCE: 1

Met Val Ser Ile Ala Leu Gln Ala Gly Tyr Asp Leu Leu Gly Asp Gly
  1               5                   10                  15

Arg Pro Glu Ser Leu Trp Leu Gly Ile Gly Thr Leu Leu Met Leu Ile
                  20                  25                  30

Gly Thr Phe Tyr Phe Leu Val Arg Ala Trp Gly Glu Thr Asp Lys Asp
              35                  40                  45

Ala Arg Glu Tyr Tyr Ala Val Thr Ile Leu Val Ser Gly Ile Ala Ser
          50                  55                  60

Ala Ala Tyr Leu Ser Met Phe Phe Gly Ile Gly Leu Thr Glu Val Pro
  65                  70                  75                  80

Val Gly Gly Glu Met Leu Asn Ile Tyr Tyr Ala Arg Tyr Ala Gln Trp
                  85                  90                  95

Leu Phe Thr Thr Pro Leu Leu Leu Leu His Leu Ala Leu Leu Ala Lys
                  100                 105                 110

Val Asp Arg Val Thr Ile Gly Thr Leu Val Gly Val Asp Ala Leu Met
                  115                 120                 125

Ile Val Thr Gly Leu Ile Gly Thr Leu Ser His Thr Ala Ile Ala Arg
              130                 135                 140

Tyr Ser Trp Trp Leu Phe Ser Thr Ile Cys Met Ile Val Val Leu Tyr
  145                 150                 155                 160

Val Leu Ala Thr Ser Leu Arg Ser Ala Ala Lys Glu Arg Gly Pro Glu
                  165                 170                 175

Val Ala Ser Thr Phe Asn Ile Leu Thr Ala Leu Val Leu Val Leu Trp
                  180                 185                 190

Thr Ala Tyr Pro Ile Ile Trp Ile Ile Gly Thr Glu Gly Ala Gly Val
              195                 200                 205

Val Gly Leu Gly Ile Glu Thr Leu Leu Phe Met Val Leu Asp Val Thr
          210                 215                 220

Ala Lys Val Gly Phe Gly Phe Ile Leu Leu Arg Ser Arg Ala Ile Leu
  225                 230                 235                 240

Gln Asp Thr Glu Ala Pro Glu Pro Ser Ala Gly Ala Asp
                  245                 250

<210> SEQ ID NO 2
  <211> LENGTH: 253
  <212> TYPE: PRT
  <213> ORGANISM: Artificial Sequence
  <220> FEATURE:
  <223> OTHER INFORMATION: Synthetic Polypeptide

<400> SEQUENCE: 2

Met Val Ser Ile Ala Leu Gln Ala Gly Tyr Asp Leu Leu Gly Asp Gly
```

```
1               5                   10                  15
Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
                35                  40                  45

Ala Arg Glu Tyr Tyr Ala Val Pro Ile Leu Val Ser Gly Ile Ala Ser
        50                  55                  60

Ala Ala Tyr Leu Ser Met Phe Phe Gly Ile Gly Leu Thr Glu Val Pro
65                  70                  75                  80

Val Gly Gly Glu Met Leu Asp Ile Tyr Tyr Ala Arg Tyr Ala His Trp
                85                  90                  95

Leu Phe Ser Thr Pro Leu Leu Leu Leu Asp Leu Ala Leu Leu Ala Lys
            100                 105                 110

Val Asp Arg Val Ile Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
            195                 200                 205

Val Gly Leu Gly Ile Glu Thr Leu Leu Phe Met Val Leu Asp Val Thr
        210                 215                 220

Cys Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 3
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 3

Met Val Ser Ile Ala Leu Gln Ala Gly Tyr Asp Leu Leu Gly Asp Gly
1               5                   10                  15

Arg Pro Glu Ile Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
                35                  40                  45

Ala Arg Glu Tyr Tyr Ala Val Thr Ile Leu Val Ser Gly Ile Ala Ser
        50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Glu Trp
                85                  90                  95

Leu Phe Cys Thr Pro Leu Leu Leu Leu Asp Leu Ala Leu Leu Ala Lys
            100                 105                 110

Val Asp Arg Val Ile Ile Gly Thr Leu Val Gly Val Asp Ala Leu Met
```

```
            115                 120                 125
Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Gly Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 4
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 4

Met Val Ser Ile Ala Leu Gln Ala Gly Tyr Asp Leu Leu Gly Asp Gly
1               5                   10                  15

Arg Pro Glu Ile Leu Trp Leu Gly Ile Gly Thr Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala Glu Trp
                85                  90                  95

Leu Phe Cys Thr Pro Leu Leu Leu Leu Asp Leu Ala Leu Leu Ala Lys
            100                 105                 110

Val Asp Arg Val Ile Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
```

```
                225                 230                 235                 240

Gly Asp Thr Glu Ala Pro Glu Pro Ser Ala Gly Ala Asp
                245                 250

<210> SEQ ID NO 5
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 5

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
                35                  40                  45

Ala Arg Glu Tyr Tyr Ala Val Pro Ile Leu Val Ser Gly Ile Ala Ser
        50                  55                  60

Ala Ala Tyr Leu Ser Met Phe Phe Gly Ile Gly Leu Thr Glu Val Pro
65                  70                  75                  80

Val Gly Gly Glu Met Leu Asp Ile Tyr Tyr Ala Arg Tyr Ala His Trp
                85                  90                  95

Leu Phe Thr Thr Pro Leu Leu Leu His Leu Ala Leu Leu Ala Lys
                100                 105                 110

Val Asp Arg Val Ile Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
                180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 6
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 6

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30
```

```
Gly Thr Phe Tyr Phe Val Val Arg Gly Trp Gly Val Thr Asp Lys Asp
            35                  40                  45

Ala Arg Glu Tyr Tyr Ala Val Pro Ile Leu Val Cys Gly Ile Ala Ser
 50                  55                  60

Ala Ala Tyr Leu Ser Met Phe Phe Gly Ile Gly Leu Thr Glu Val Pro
 65                  70                  75                  80

Val Gly Gly Glu Met Leu Asp Ile Tyr Tyr Ala Arg Tyr Ala His Trp
                    85                  90                  95

Leu Phe Thr Thr Pro Leu Leu Leu Leu Asp Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
                180                 185                 190

Thr Ala Tyr Pro Ile Ile Trp Ile Ile Gly Thr Glu Gly Ala Gly Val
                195                 200                 205

Val Gly Leu Gly Ile Glu Thr Leu Leu Phe Met Val Leu Asp Val Thr
            210                 215                 220

Cys Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 7
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 7

Met Val Ser Ile Ala Leu Gln Ala Gly Tyr Asp Leu Leu Gly Asp Gly
 1               5                  10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Arg Asp
            35                  40                  45

Ala Arg Glu Tyr Tyr Ala Val Pro Ile Leu Val Ser Gly Ile Ala Ser
 50                  55                  60

Ala Ala Tyr Leu Ser Met Phe Phe Gly Ile Gly Leu Thr Glu Val Ser
 65                  70                  75                  80

Val Gly Gly Glu Met Leu Asp Ile Tyr Tyr Ala Arg Tyr Ala His Trp
                    85                  90                  95

Leu Phe Thr Thr Pro Leu Leu Leu Leu Asp Leu Ala Leu Leu Ala Lys
                100                 105                 110

Val Asp Arg Val Thr Ile Gly Thr Leu Val Gly Val Asp Ala Leu Met
            115                 120                 125

Ile Val Thr Gly Leu Ile Gly Ala Leu Ser Pro Thr Ala Ile Ala Arg
130                 135                 140
```

```
Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Gly Lys Val Gly Phe Gly Phe Val Leu Leu Arg Ser Arg Ala Ile Leu
225                 230                 235                 240

Gly Asp Thr Glu Ala Pro Glu Pro Ser Ala Gly Ala Asp
                245                 250
```

<210> SEQ ID NO 8
<211> LENGTH: 259
<212> TYPE: PRT
<213> ORGANISM: Artificial Sequence
<220> FEATURE:
<223> OTHER INFORMATION: Synthetic Polypeptide

<400> SEQUENCE: 8

```
Met Asp Pro Ile Ala Leu Gln Ala Gly Phe Asp Leu Leu Asn Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Ile Ala Arg Gly Trp Gly Val Thr Asp Lys Glu
            35                  40                  45

Ala Arg Glu Tyr Tyr Ala Ile Thr Ile Leu Val Pro Gly Ile Ala Ser
        50                  55                  60

Ala Ala Tyr Leu Ala Met Phe Phe Gly Ile Gly Val Thr Glu Val Glu
65                  70                  75                  80

Leu Ala Ser Gly Thr Val Leu Asp Ile Tyr Tyr Ala Arg Tyr Ala Asp
                85                  90                  95

Trp Leu Phe Thr Thr Pro Leu Leu Leu Asp Leu Ala Leu Leu Ala
            100                 105                 110

Lys Val Asp Arg Val Thr Ile Gly Thr Leu Ile Gly Val Asp Ala Leu
        115                 120                 125

Met Ile Val Thr Gly Leu Ile Gly Ala Leu Ser Lys Thr Pro Leu Ala
130                 135                 140

Arg Tyr Thr Trp Trp Leu Phe Ser Thr Ile Ala Phe Leu Phe Val Leu
145                 150                 155                 160

Tyr Tyr Leu Leu Thr Ser Leu Arg Ser Ala Ala Lys Arg Ser Glu
                165                 170                 175

Glu Val Arg Ser Thr Phe Asn Thr Leu Thr Ala Leu Val Ala Val Leu
            180                 185                 190

Trp Thr Ala Tyr Pro Ile Leu Trp Ile Val Gly Thr Glu Gly Ala Gly
        195                 200                 205

Val Val Gly Leu Gly Ile Glu Thr Leu Ala Phe Met Val Leu Asp Val
    210                 215                 220

Thr Ala Lys Val Gly Phe Gly Phe Val Leu Leu Arg Ser Arg Ala Ile
225                 230                 235                 240

Leu Gly Glu Thr Glu Ala Pro Glu Pro Ser Ala Gly Ala Asp Ala Ser
                245                 250                 255
```

Ala Ala Asp

<210> SEQ ID NO 9
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 9

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 10
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 10

Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp

```
                35                  40                  45
Ala Arg Glu Tyr Tyr Ala Val Thr Ile Leu Val Pro Gly Ile Ala Ser
 50                  55                  60
Ala Ala Tyr Leu Ser Met Phe Phe Gly Ile Gly Leu Thr Glu Val Thr
 65                  70                  75                  80
Val Gly Gly Glu Met Leu Asp Ile Tyr Tyr Ala Arg Tyr Ala Glu Trp
                 85                  90                  95
Leu Phe Cys Thr Pro Leu Leu Leu Asp Leu Ala Leu Leu Ala Lys
                100                 105                 110
Val Asp Arg Val Thr Ile Gly Thr Leu Val Gly Val Asp Ala Leu Met
            115                 120                 125
Ile Val Thr Gly Leu Ile Gly Ala Leu Ser His Thr Ala Ile Ala Arg
        130                 135                 140
Tyr Ser Trp Trp Leu Phe Ser Thr Ile Cys Met Ile Val Val Leu Tyr
145                 150                 155                 160
Phe Leu Ala Thr Ser Leu Arg Ser Ala Ala Lys Glu Arg Gly Pro Glu
                165                 170                 175
Val Ala Ser Thr Phe Asn Thr Leu Thr Ala Leu Val Leu Val Leu Trp
            180                 185                 190
Thr Ala Tyr Pro Ile Leu Trp Ile Ile Gly Thr Glu Gly Ala Gly Val
        195                 200                 205
Val Gly Leu Gly Ile Glu Thr Leu Leu Phe Met Val Leu Asp Val Thr
    210                 215                 220
Ala Lys Val Gly Phe Gly Phe Ile Leu Leu Arg Ser Arg Ala Ile Leu
225                 230                 235                 240
Gly Asp Thr Glu Ala Pro Glu Pro Ser Ala Gly Ala Asp
                245                 250

<210> SEQ ID NO 11
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 11

Met Asp Pro Ile Ala Leu Gln Ala Gly Tyr Asp Leu Leu Gly Asp Gly
 1               5                  10                  15
Arg Pro Glu Thr Leu Trp Leu Gly Ile Gly Thr Leu Leu Met Leu Ile
                 20                  25                  30
Gly Thr Phe Tyr Phe Leu Val Arg Gly Trp Gly Val Thr Asp Lys Asp
             35                  40                  45
Ala Arg Glu Tyr Tyr Ala Val Thr Ile Leu Val Ser Gly Ile Ala Ser
 50                  55                  60
Ala Ala Tyr Leu Ser Met Phe Phe Gly Ile Gly Leu Thr Glu Val Ser
 65                  70                  75                  80
Val Gly Gly Glu Met Leu Asp Ile Tyr Tyr Ala Arg Tyr Ala His Trp
                 85                  90                  95
Leu Phe Thr Thr Pro Leu Leu Leu Leu His Leu Ala Leu Leu Ala Lys
                100                 105                 110
Val Asp Arg Val Thr Ile Gly Thr Leu Val Gly Val Asp Ala Leu Met
            115                 120                 125
Ile Val Thr Gly Leu Ile Gly Ala Leu Ser His Thr Ala Ile Ala Arg
        130                 135                 140
Tyr Ser Trp Trp Leu Phe Ser Thr Ile Cys Met Ile Val Val Leu Tyr
```

```
                 145                 150                 155                 160
Val Leu Ala Thr Ser Leu Arg Ser Ala Ala Lys Glu Arg Gly Pro Glu
                165                 170                 175
Val Ala Ser Thr Phe Asn Thr Leu Thr Ala Leu Val Leu Val Leu Trp
                180                 185                 190
Thr Ala Tyr Pro Ile Leu Trp Ile Ile Gly Thr Glu Gly Ala Gly Val
                195                 200                 205
Val Gly Leu Gly Ile Glu Thr Leu Leu Phe Met Val Leu Asp Val Thr
                210                 215                 220
Ala Lys Val Gly Phe Gly Phe Ile Leu Leu Arg Ser Arg Ala Ile Leu
225                 230                 235                 240
Gly Asp Thr Glu Ala Pro Glu Pro Ser Ala Gly Ala Asp
                245                 250

<210> SEQ ID NO 12
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 12

Met Val Ser Ile Ala Leu Gln Ala Gly Tyr Asp Leu Leu Gly Asp Gly
1               5                   10                  15
Arg Pro Glu Thr Leu Trp Leu Gly Ile Gly Thr Leu Leu Met Leu Ile
                20                  25                  30
Gly Thr Phe Tyr Phe Leu Val Arg Gly Trp Gly Val Thr Asp Lys Asp
                35                  40                  45
Ala Arg Glu Tyr Tyr Ala Val Thr Ile Leu Val Ser Gly Ile Ala Ser
            50                  55                  60
Ala Ala Tyr Leu Ser Met Phe Phe Gly Ile Gly Leu Thr Glu Val Ser
65              70                  75                  80
Val Gly Gly Glu Met Leu Asp Ile Tyr Tyr Ala Arg Tyr Ala Gln Trp
                85                  90                  95
Leu Phe Thr Thr Pro Leu Leu Leu His Leu Ala Leu Leu Ala Lys
                100                 105                 110
Val Asp Arg Val Thr Ile Gly Thr Leu Val Gly Val Asp Ala Leu Met
            115                 120                 125
Ile Val Thr Gly Leu Ile Gly Ala Leu Ser His Thr Ala Ile Ala Arg
        130                 135                 140
Tyr Ser Trp Trp Leu Phe Ser Thr Ile Cys Met Ile Val Val Leu Tyr
145                 150                 155                 160
Val Leu Ala Thr Ser Leu Arg Ser Ala Ala Lys Glu Arg Gly Pro Glu
                165                 170                 175
Val Ala Ser Thr Phe Asn Thr Leu Thr Ala Leu Val Leu Val Leu Trp
                180                 185                 190
Thr Ala Tyr Pro Ile Leu Trp Ile Ile Gly Thr Glu Gly Ala Gly Val
                195                 200                 205
Val Gly Leu Gly Ile Glu Thr Leu Leu Phe Met Val Leu Asp Val Thr
                210                 215                 220
Ala Lys Val Gly Phe Gly Phe Ile Leu Leu Arg Ser Arg Ala Ile Leu
225                 230                 235                 240
Gly Asp Thr Glu Ala Pro Glu Pro Ser Ala Gly Ala Asp Trp
                245                 250
```

<210> SEQ ID NO 13
<211> LENGTH: 258
<212> TYPE: PRT
<213> ORGANISM: Artificial Sequence
<220> FEATURE:
<223> OTHER INFORMATION: Synthetic Polypeptide

<400> SEQUENCE: 13

```
Met Asp Pro Ile Ala Leu Gln Ala Gly Tyr Asp Leu Gly Asp Gly
1               5                   10                  15

Arg Pro Glu Thr Leu Trp Leu Gly Ile Gly Thr Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Ala Leu Gly Ile Ala Ser
        50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Glu Trp
                85                  90                  95

Leu Phe Cys Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
            165                 170                 175

Val Ala Ser Thr Phe Asn Thr Leu Thr Ala Leu Val Leu Val Leu Trp
        180                 185                 190

Thr Ala Tyr Ser Ile Leu Trp Ile Ile Gly Thr Glu Gly Ala Gly Val
            195                 200                 205

Val Gly Leu Gly Ile Glu Thr Leu Leu Phe Met Val Leu Ser Val Thr
        210                 215                 220

Cys Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp
```

<210> SEQ ID NO 14
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 14

```
Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Pro Ile Leu Val Ser Gly Ile Ala Ser
```

```
                50                  55                  60
Ala Ala Tyr Leu Ser Met Phe Phe Gly Ile Gly Leu Thr Glu Val Ser
 65                  70                  75                  80

Val Gly Gly Glu Met Leu Asp Ile Tyr Tyr Ala Arg Tyr Ala His Trp
                 85                  90                  95

Leu Phe Thr Thr Pro Leu Leu Leu His Leu Ala Leu Leu Ala Lys
                100                 105                 110

Val Asp Arg Val Ile Ile Gly Thr Leu Val Gly Val Asp Ala Leu Met
                115                 120                 125

Ile Val Thr Gly Leu Ile Gly Ala Leu Ser His Thr Ala Ile Ala Arg
                130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
                180                 185                 190

Thr Ala Tyr Pro Ile Ile Trp Ile Ile Gly Thr Glu Gly Ala Gly Val
                195                 200                 205

Val Gly Leu Gly Ile Glu Thr Leu Leu Phe Met Val Leu Asp Val Thr
                210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 15
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 15

Met Val Ser Ile Ala Leu Gln Ala Gly Tyr Asp Leu Leu Gly Asp Gly
 1               5                  10                  15

Arg Pro Glu Thr Leu Trp Leu Gly Ile Gly Thr Leu Leu Met Leu Ile
                 20                  25                  30

Gly Thr Phe Tyr Phe Leu Val Arg Gly Trp Gly Val Thr Asp Lys Asp
                 35                  40                  45

Ala Arg Glu Tyr Tyr Ala Val Pro Ile Leu Val Ser Gly Ile Ala Ser
 50                  55                  60

Ala Ala Tyr Leu Ser Met Phe Phe Gly Ile Gly Leu Thr Glu Val Ser
 65                  70                  75                  80

Val Gly Gly Glu Met Leu Asp Ile Tyr Cys Ala Arg Tyr Ala His Trp
                 85                  90                  95

Leu Phe Thr Thr Pro Leu Leu Leu His Leu Ala Leu Leu Ala Lys
                100                 105                 110

Val Asp Arg Val Ile Ile Gly Thr Leu Val Gly Val Asp Ala Leu Met
                115                 120                 125

Ile Val Thr Gly Leu Ile Gly Ala Leu Ser His Thr Ala Ile Ala Arg
                130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
```

```
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Val Leu
225                 230                 235                 240

Gly Asp Thr Glu Ala Pro Glu Pro Ser Ala Gly Ala Asp
                245                 250

<210> SEQ ID NO 16
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 16

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Arg Asp
        35                  40                  45

Ala Arg Glu Tyr Tyr Ala Val Pro Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80

Val Gly Gly Glu Met Leu Asp Ile Tyr Tyr Ala Arg Tyr Ala His Trp
                85                  90                  95

Leu Phe Thr Thr Pro Leu Leu Leu His Leu Ala Leu Leu Ala Lys
            100                 105                 110

Val Asp Arg Val Ile Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
                245                 250

<210> SEQ ID NO 17
<211> LENGTH: 253
<212> TYPE: PRT
```

```
<213> ORGANISM: Artificial Sequence
<220> FEATURE:
<223> OTHER INFORMATION: Synthetic Polypeptide

<400> SEQUENCE: 17

Met Val Ser Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Val Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Pro Ile Leu Val Ser Gly Ile Ala Ser
    50                  55                  60

Ala Ala Tyr Leu Ser Met Phe Phe Gly Ile Gly Leu Thr Glu Val Pro
65                  70                  75                  80

Val Gly Gly Glu Met Leu Asp Ile Tyr Tyr Ala Arg Tyr Ala His Trp
                85                  90                  95

Leu Phe Thr Thr Pro Leu Leu Leu His Leu Ala Leu Ala Lys
            100                 105                 110

Val Asp Arg Val Ile Ile Gly Thr Leu Val Gly Val Asp Ala Leu Met
            115                 120                 125

Ile Val Thr Gly Leu Ile Gly Ala Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
                165                 170                 175

Val Ala Ser Thr Phe Asn Ile Leu Thr Ala Leu Val Leu Val Leu Trp
            180                 185                 190

Thr Ala Tyr Pro Ile Ile Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp
            245                 250

<210> SEQ ID NO 18
<211> LENGTH: 253
<212> TYPE: PRT
<213> ORGANISM: Artificial Sequence
<220> FEATURE:
<223> OTHER INFORMATION: Synthetic Polypeptide

<400> SEQUENCE: 18

Met Val Ser Ile Ala Leu Gln Ala Gly Tyr Asp Leu Leu Gly Asp Gly
1               5                   10                  15

Arg Pro Glu Ser Leu Trp Leu Gly Ile Gly Thr Leu Leu Met Leu Ile
            20                  25                  30

Gly Thr Phe Tyr Phe Leu Val Arg Ala Trp Gly Glu Thr Asp Lys Asp
        35                  40                  45

Ala Arg Glu Tyr Tyr Ala Val Thr Ile Leu Val Ser Gly Ile Ala Ser
    50                  55                  60

Ala Ala Tyr Leu Ser Met Phe Phe Gly Ile Gly Leu Thr Glu Val Ser
65                  70                  75                  80
```

Val Gly Gly Glu Met Leu Asn Ile Tyr Tyr Ala Arg Tyr Ala Gln Trp
            85                  90                  95

Leu Phe Thr Thr Pro Leu Leu Leu His Leu Ala Leu Leu Ala Lys
            100                 105                 110

Val Asp Arg Val Thr Ile Gly Thr Leu Val Gly Val Asp Ala Leu Met
            115                 120                 125

Ile Val Thr Gly Leu Ile Gly Thr Leu Ser His Thr Ala Ile Ala Arg
        130                 135                 140

Tyr Ser Trp Trp Leu Phe Ser Thr Ile Cys Met Ile Val Val Leu Tyr
145                 150                 155                 160

Val Leu Ala Thr Ser Leu Arg Ser Ala Ala Lys Glu Arg Gly Pro Glu
            165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
            195                 200                 205

Val Gly Leu Gly Ile Glu Thr Leu Leu Phe Met Val Leu Asp Val Thr
        210                 215                 220

Ala Lys Val Gly Phe Gly Phe Ile Leu Leu Arg Ser Arg Ala Ile Leu
225                 230                 235                 240

Gln Asp Thr Glu Ala Pro Glu Pro Ser Ala Gly Ala Asp
            245                 250

<210> SEQ ID NO 19
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 19
gtcccgtgca cgctgctcct gctgttggca gccgccctgg ctccgactca gacgcgggcc      60

<210> SEQ ID NO 20
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 20

Met Val Pro Cys Thr Leu Leu Leu Leu Ala Ala Ala Leu Ala Pro
1               5                   10                  15

Thr Gln Thr Arg Ala
            20

<210> SEQ ID NO 21
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 21
ttctgctacg agaatgaagt g                                                21

<210> SEQ ID NO 22
<211> LENGTH: 7
<212> TYPE: PRT
<213> ORGANISM: Artificial Sequence
<220> FEATURE:

<223> OTHER INFORMATION: Synthetic Polypeptide

<400> SEQUENCE: 22

Phe Cys Tyr Glu Asn Glu Val
1               5

<210> SEQ ID NO 23
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 23
aaatccagaa ttacttctga aggggagtat atccctctgg atcaaataga catcaatgtt    60

<210> SEQ ID NO 24
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 24

Lys Ser Arg Ile Thr Ser Glu Gly Glu Tyr Ile Pro Leu Asp Gln Ile
1               5                   10                  15

Asp Ile Asn Val
            20

<210> SEQ ID NO 25
<211> LENGTH: 96
<212> TYPE: DNA
<213> ORGANISM: Artificial Sequence
<220> FEATURE:
<223> OTHER INFORMATION: Synthetic Polynucleotide

<400> SEQUENCE: 25
gacagcaaag gttcgtcgca gaaagggtcc cgcctgctcc tgctgctggt ggtgtcaaat    60
ctactcttgt gccagggtgt ggtctccacc cccgtc                              96

<210> SEQ ID NO 26
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 26

Met Asp Ser Lys Gly Ser Ser Gln Lys Gly Ser Arg Leu Leu Leu Leu
1               5                   10                  15

Leu Val Val Ser Asn Leu Leu Leu Cys Gln Val Val Ser
            20                  25

<210> SEQ ID NO 27
<211> LENGTH: 32
<212> TYPE: PRT

```
<213> ORGANISM: Artificial Sequence
<220> FEATURE:
<223> OTHER INFORMATION: Synthetic Polypeptide

<400> SEQUENCE: 27

Asp Ser Lys Gly Ser Ser Gln Lys Gly Ser Arg Leu Leu Leu Leu Leu
1               5                   10                  15

Val Val Ser Asn Leu Leu Leu Cys Gln Gly Val Val Ser Thr Pro Val
            20                  25                  30
```

GENETICALLY ENCODED RED FLUORESCENT VOLTAGE SENSORS ENABLING MILLIVOLT-RESOLUTION AND HIGH-SPEED NEURAL VOLTAGE IMAGING

RELATED APPLICATIONS

This application claims benefit under 35 U.S.C. § 119(e) of U.S. Provisional application Ser. No. 62/528,267 filed Jul. 3, 2017, the disclosure of which is incorporated by reference herein in its entirety.

GOVERNMENT INTEREST

This invention was made with government support under grants 5-R01-DA029639-06 and 1-R01-GM104948 from the National Institutes of Health. The government has certain rights in the invention.

FIELD OF THE INVENTION

The invention, in some aspects, includes voltage reporter molecules and compositions, and includes methods for detecting voltage and voltage change in cells. The invention, in part, also relates to delivery, expression, and use of voltage reporter molecules in cells, tissues, and subjects.

BACKGROUND OF THE INVENTION

Despite much effort towards creating genetically encoded fluorescent voltage sensors, none have yet achieved widespread adoption. In general, opsin-based fluorescent reporters suffer from poor localization, whereas GFP-based fluorescent reporters exhibit small changes in fluorescence, photobleach rapidly, and spectrally overlap with optogenetic controllers. Many prior studies have aimed to create fully genetically encoded fluorescent indicators of membrane potential, but there remains a lack of effective tools for monitoring neural activity in defined cells or at defined points within cells such as neurons [Lin, M. Z. & Schnitzer, M. J. (2016) Nat. Neurosci 19, 1142-1153]. Prior voltage indicator molecules have lacked a complement of the following characteristics: (1) optimal localization to the plasma membrane, (2) bright signal, (3) high signal to noise ratio, (4) large and linear fluorescent changes in response to voltage fluctuations, (5) sufficiently rapid response to voltage changes to preserve the fidelity of spiking, (6) stable (i.e., non-photobleaching) fluorescence over timescales appropriate for conducting a biological experiment, (7) zero or minimal side effects, and (8) compatibility with optogenetic control of neural activity. Prior fluorescent voltage indicators might each possess a subset of these ideal properties, but to date molecules have not been developed in which all of these characteristics have been simultaneously optimized—at least in part because methods that select for one characteristic at times de-optimize other characteristics [Ai, H.-W., et al., (2014) Nat. Protoc. 9, 910-28], and also because the optimization had not been dome in mammalian cells in order to guarantee high performance in neurons [Chow, B. Y., et al., (2011) Methods Enzymol. 497, 425-443; Chen, T.-W. et al. (2013) Nature 499, 295-300].

There are two prior general classes of genetically encoded voltage reporters [Lin, M. Z. & Schnitzer, M. J. (2016) Nat. Neurosci 19, 1142-1153]—one utilizes the intrinsic fluorescence of microbial opsins (e.g., Archaerhodopsin-3 (Arch)-based fluorescent voltage reporters [Hochbaum, D. R. et al. (2014) Nat. Methods 1-34 doi:10.1038/nmeth.3000; Flytzanis, N. C. et al. (2014) Nat. Commun. 5, 4894]), to report neural activity, and the other couples a GFP-like fluorescent protein to another component (e.g., a voltage-sensitive phosphatase [St-Pierre, F. et al., (2014) Nat. Neurosci. 17, 884-9], or a non-fluorescent opsin [Wagner, M. J., et al., (2014) Nat. Commun. 5, 1-11; Gong, Y. et al. (2015) Scienc express 350, 1-11]). The fluorescent opsins have been relatively dim, and suffer from poor localization, and thus exhibit low signal-to-noise ratio. Previous GFP-like fluorescent protein-containing reporters have been brighter, but have to date exhibited small fractional changes in fluorescence, exhibit supramillisecond kinetics, and photobleach over timescales of a few minutes, and are incompatible with optogenetic control due to spectral overlap.

SUMMARY OF THE INVENTION

According to an aspect of the invention, voltage reporter polypeptides that include an amino acid sequence set forth as SEQ ID NO: 1 or a functional variant thereof, wherein the functional variant has at least 90% amino acid sequence identity to the corresponding region of SEQ ID NO: 1 and the amino acid sequence of the functional variant is not a sequence set forth as SEQ ID NO: 8, 9, 10, 11, 12, or 13, are provided. In some embodiments, the functional variant includes one or more amino acid substitutions, deletions, and insertions to the amino acid sequence set forth as SEQ ID NO: 1. In certain embodiments, the functional variant has at least 91%, 92%, 93%, 94%, 95%, 96%, 97%, 98%, 99%, and 100% amino acid sequence identity to the corresponding region of SEQ ID NO: 1. In some embodiments, the functional variant includes the amino acid sequence of SEQ ID NO: 1 (Archon1), having one or more modifications, wherein the amino acid sequence is not modified at 1, 2, 3, 4, 5, 6, 7, 8, 9, 10, 11, 12, or 13 of the amino acid positions corresponding to residues: 20, 41, 44, 60, 80, 88, 96, 107, 137, 162, 184, 199, and 242 of SEQ ID NO: 1. In some embodiments, the functional variant includes the amino acid sequence of SEQ ID NO: 1 (Archon1), having one or more modifications, wherein the amino acid sequence is not modified at 1, 2, 3, 4, 5, 6, 7, 8, 9, 10, 11, 12, or 13 of the amino acid positions corresponding to residues: 97, 129, 133, 149, 152, 153, 156, 193, 196, 197, 200, 223, and 227 of SEQ ID NO: 1. In certain embodiments, the modification includes one or more independently selected amino acid substitutions, deletions, and insertions. In some embodiments the voltage reporter polypeptide includes at least one of: (i) the amino acid in the position corresponding to residue 199 of SEQ ID NO: 1 is isoleucine (I); (ii) the amino acid in the position corresponding to residue 162 of SEQ ID NO: 1 is valine (V); and (iii) the amino acid in the position corresponding to residue 184 of SEQ ID NO: 1 is isoleucine (I). In certain embodiments the voltage reporter polypeptide includes at least one of (a) a lower level of photobleaching, (b) a higher level of reporting sensitivity, and (c) a higher plasma membrane localization specificity compared to a control level of the photobleaching, reporting sensitivity, and plasma membrane localization specificity, respectively, when expressed in a cell membrane that undergoes a voltage change under suitable conditions for the voltage reporter polypeptide to be activated. In some embodiments, the control levels of photobleaching, reporting sensitivity, and plasm membrane localization specificity comprise a level of the photobleaching, reporting sensitivity, and plasma membrane localization specificity of an Arch polypeptide having an amino acid sequence set forth as SEQ ID NO: 9 (Arch) expressed in a cell membrane that undergoes a voltage change under the suitable conditions for the voltage reporter polypeptide to be activated. In some embodiments the voltage reporter polypeptide, the amino acid sequence of the functional variant comprises the amino acid sequence set forth as SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); or SEQ ID NO: 7 (Variant #7). In certain embodiments, the amino acid sequence of the functional variant has 97%, 98%, 99%, or 100% identity to at least one of: SEQ ID NO: 1 (Archon1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); and SEQ ID NO: 7 (Variant #7). In some embodiments the voltage reporter polypeptide is expressed in a cell. In some embodiments, the cell is a vertebrate cell. In certain embodiments the cell is a mammalian cell. In some embodiments, the cell is a human cell. In some embodiments the voltage reporter polypeptide is expressed in a membrane. In certain embodiments, the cell is an excitable cell. In some embodiments the voltage reporter polypeptide includes a fluorescent component comprising a fluorescent reporter molecule. In certain embodiments, a voltage in the cell results in a detectable signal from the reporter molecule. In some embodiments, the detectable signal is a fluorescence. In some embodiments the voltage reporter polypeptide is part of a fusion protein.

According to another aspect of the invention, a fusion protein that includes an embodiment of any aforementioned aspect of a voltage reporter polypeptide is provided.

According to another aspect of the invention, a nucleic acid sequence that encodes an embodiment of any aforementioned aspect of a voltage reporter polypeptide is provided. In certain embodiments, the nucleic acid sequence is a mammalian codon-optimized DNA sequence.

According to another aspect of the invention, a vector that includes a nucleic acid sequence encoding an embodiment of any aforementioned aspect of a voltage reporter polypeptide is provided. In some embodiments, the vector includes a mammalian codon-optimized the nucleic acid sequence. In some embodiments, the nucleic acid sequence is operatively linked to a promoter sequence. In certain embodiments, the vector also includes one, two, or more nucleic acid signal sequences operatively linked to the nucleic acid sequence encoding the voltage reporter polypeptide. In some embodiments, the vector is a plasmid vector, a cosmid vector, a viral vector, or an artificial chromosome. In some embodiments, the vector is in a cell. In certain embodiments, the vector also includes a nucleic acid sequence encoding one or more of a trafficking polypeptide and a second fluorescent polypeptide.

According to another aspect of the invention a cell that includes an embodiment of any aforementioned aspect of a voltage reporter polypeptide is provided. In some embodiments, the cell is a vertebrate cell. In some embodiments the cell is a mammalian cell.

According to another aspect of the invention a cell that includes an embodiment of any aforementioned aspect of a vector is provided. In some embodiments, the cell is a vertebrate cell. In some embodiments the cell is a mammalian cell.

According to another aspect of the invention a cell that includes a nucleic acid encoding an embodiment of any aforementioned aspect of a voltage reporter polypeptide is provided. In some embodiments, the cell is a vertebrate cell. In some embodiments the cell is a mammalian cell.

According to another aspect of the invention, methods of determining voltage in a cell are provided, the methods including: a) monitoring a detectable signal of a voltage reporter polypeptide of an embodiment of any aforementioned aspect of voltage reporter polypeptide, that is expressed in a cell; and b) determining a voltage characteristic in the cell by detecting a detectable signal of the reporter molecule of the expressed voltage reporter polypeptide, where to the detectable signal indicates a voltage characteristic in the cell. In some embodiments, the detectable signal is a fluorescent signal. In some embodiments, the fluorescent signal is from a fluorescent component of the voltage reporter polypeptide. In certain embodiments, the expressed the voltage reporter polypeptide is positioned in a membrane of the cell. In some embodiments, the cell is one or more of: a vertebrate cell, a mammalian cell, a human cell, and an excitable cell. In some embodiments, of any of the aforementioned methods, the voltage characteristic is one or more of: presence of a voltage in the cell, an increase or decrease of voltage in the cell, and the level of voltage in the cell. In certain embodiments of any of the aforementioned methods, detecting the voltage includes one of more of detecting the presence of the voltage, detecting a change in the voltage, and detecting a level of the voltage. In some embodiments of any of the aforementioned methods, the change in voltage is an increase in voltage. In some embodiments of any of the aforementioned methods, the detected voltage comprises one or more of: an action potential in the cell, ion flux across a cell membrane of the cell, and proton flux across a cell membrane of the cell, an electrical pulse administered to the cell; and an electrical pulse administered to a second cell that has direct or indirect contact with the cell. In some embodiments of any of the aforementioned methods the cell is a neuronal cell, a nervous system cell, a cardiac cell, a circulatory system cell, a visual system cell, or an auditory system cell. In certain embodiments of any of the aforementioned methods the method also includes expressing the voltage reporter polypeptide in the cell. In some embodiments, the method also includes delivering into the cell a polynucleotide comprising a sequence encoding the voltage detecting polypeptide, wherein the expressed voltage detecting polypeptide is positioned in a membrane in the cell. In some embodiments of any of the aforementioned methods, the amino acid sequence of the voltage detecting polypeptide comprises the amino acid sequence set forth as SEQ ID NO: 1 (Archon 1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); or SEQ ID NO: 7 (Variant #7). In certain embodiments of any of the aforementioned methods, the amino acid sequence of the voltage reporter polypeptide has 97%, 98%, 99%, or 100% sequence identity to one or more of: SEQ ID NO: 1 (Archon1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); and SEQ ID NO: 7 (Variant #7). In some embodiments of any of the aforementioned methods, the monitoring includes imaging. In some embodiments of any of the aforementioned methods, the voltage reporter is contacted with a wavelength of light that excites a fluorescent component of the voltage reporter. In certain embodiments of any of the aforementioned methods, the method also includes contacting the voltage reporter with a pre-pulse of light.

According to another aspect of the invention, methods of identifying an effect of a test agent on a voltage in a cell are provided, the methods including: (a) contacting a first cell comprising the voltage reporter polypeptide of any embodiment of any aspect of the aforementioned voltage reporter polypeptide expressed in a membrane of the first cell, with a stimulus that results in voltage in the cell that is detectable by the voltage reporter polypeptide; (b) contacting the first cell or a cell in communication with the first cell with a test agent; (c) detecting at least one voltage characteristic in the first cell, by detecting a detectable signal of the reporter molecule of the expressed voltage reporter polypeptide, where the detectable signal indicates voltage in the first cell; and (d) comparing the at least one voltage characteristic detected in step (c) to the at least one voltage characteristic detected in a control cell, wherein a difference in the at least one voltage characteristic detected in the first cell compared to the at least one voltage detected in the control cell identifies an effect of the test agent on the voltage in the first cell. In some embodiments, the detectable signal is a fluorescent signal. In some embodiments, the expressed the voltage reporter polypeptide is positioned in a membrane of the first cell. In certain embodiments, the first cell is one or more of: a vertebrate cell, a mammalian cell, a human cell, and an excitable cell. In some embodiments, the voltage characteristic is one or more of: presence of a voltage in the first cell, an increase or decrease of voltage in the first cell, and the level of voltage in the first cell. In some embodiments, detecting the voltage characteristic comprises one of more of detecting the presence of the voltage, detecting a change in the voltage, and detecting a level of the voltage. In certain embodiments, the change in voltage is an increase in voltage. In some embodiments, the detected voltage comprises one or more of: an action potential in the first cell, ion flux across a cell membrane of the first cell, proton flux across a cell membrane of the first cell, an electrical pulse administered to the first cell; and an electrical pulse administered to the second cell that is in direct or indirect communication with the first cell. In some embodiments, the first cell is a neuronal cell, a nervous system cell, a cardiac cell, a circulatory system cell, a visual system cell, or an auditory system cell. In certain embodiments, the method also includes a step of expressing the voltage reporter polypeptide in the first cell. In some embodiments, expressing the voltage reporter polypeptide includes delivering into the first cell a polynucleotide comprising a sequence encoding the voltage detecting polypeptide, wherein the expressed voltage detecting polypeptide is positioned in a membrane in the first cell. In some embodiments, the amino acid sequence of the voltage detecting polypeptide comprises the amino acid sequence set forth as SEQ ID NO: 1 (Archon 1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); or SEQ ID NO: 7 (Variant #7). In some embodiments, the amino acid sequence of the voltage reporter polypeptide has 97%, 98%, 99%, or 100% sequence identity to one or more of: SEQ ID NO: 1 (Archon1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); and SEQ ID NO: 7 (Variant #7). In certain embodiments, the detecting includes imaging. In some embodiments, the voltage reporter is contacted with a wavelength of light that excites a fluorescent component of the voltage reporter. In some embodiments, the method also includes contacting the voltage reporter with a pre-pulse of light. In certain embodiments, the control cell comprises the voltage reporter polypeptide and is not contacted with the test agent. In some embodiments, the control cell includes the voltage reporter polypeptide and is not in communication with another cell not contacted with the test agent. In some embodiments, the test agent is a therapeutic compound, an electrical stimulus, a chemical compound, an inhibitory agent, or an excitatory agent.

According to another aspect of the invention, composition that include one or more of a: (i) an embodiment of any aforementioned aspect of a voltage reporter polypeptide; (ii) an embodiment of any aforementioned aspect of a fusion protein; (iii) an embodiment of any aforementioned aspect of an encoding polynucleotide sequence; and (iv) an embodiment of any aforementioned aspect of a vector. In certain embodiments, the composition also includes one or more of: a carrier agent, a delivery agent, and a detectable agent. In some embodiments, the composition is a pharmaceutically acceptable composition. In some embodiments, the carrier agent is a pharmaceutically acceptable carrier molecule. In certain embodiments, the composition is in a cell. In certain embodiments, the cell is one or more of a vertebrate cell, a mammalian cell, a human cell, and an excitable cell. In some embodiments, the amino acid sequence of the voltage detecting polypeptide includes the amino acid sequence set forth as SEQ ID NO: 1 (Archon 1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); or SEQ ID NO: 7 (Variant #7). In some embodiments, the amino acid sequence of the voltage reporter polypeptide has 97%, 98%, 99%, or 100% sequence identity to one or more of: SEQ ID NO: 1 (Archon1); SEQ ID NO: 2 (Archon2); SEQ ID NO: 3 (Variant #3); SEQ ID NO: 4 (Variant #4); SEQ ID NO: 5 (Variant #5); SEQ ID NO: 6 (Variant #6); and SEQ ID NO: 7 (Variant #7).

BRIEF DESCRIPTION OF THE DRAWINGS

FIG. 1A is a schematic diagram of a pipeline for multi-parameter directed evolution of proteins in mammalian cells using robotic cell picking. FIG. 1A (i) illustrates transfection of plasmids (rings) into cells (nuclei shown as ovals). FIG. 1A (ii) illustrates plasmid replication and protein (shown as cylinders) expression. FIG. 1A (iii) illustrates fluorescence-activating cell sorting (FACS) enrichment based on fluorescence with the black box shown as an example of a sort gate for positive cells. FIG. 1A (iv) illustrates culturing of collected cells. FIG. 1A (v-vii) illustrates multi-parameter screening of cells using wide-field fluorescence microscopy and robotic cell picking. FIG. 1A (v) illustrates examination of individual cells using a microscope. FIG. 1A (vi) illustrates image analysis. FIG. 1A (vii) illustrates isolation of selected cells via robotic cell picking. FIG. 1A (viii, ix) illustrates recovery of mutant genes from isolated cells using whole genome amplification (WGA). FIG. 1B is a graph showing absorbance (dotted line) and fluorescence (solid line) spectra of miRFP. FIG. 1C provides representative photomicrographic fluorescence images of HEK293T cells expressing mIFP and miRFP. Scale bar: 10 µm. Excitation ($\lambda$ex) 628/31BP (bandpass, used throughout; all wavelength numbers are in nm) from a LED at 62 mW/mm$^2$ and emission ($\lambda$em) 664 nm LP (longpass, used throughout) used for FIG. 1C-E. FIG. 1D is a graph showing mean fluorescence intensity of HEK293T cells transfected with mIFP and miRFP encoding plasmids (n=4 fields of view from independent transfections from the same culture passage; individual data points in black dots; *P=0.0286, Wilcoxon rank sum test; see Table 3 for full statistics for FIG. 1). Error bars, standard deviation. FIG. 1E is a graph showing photobleaching curves of mIFP and miRFP expressed in HEK293FT cells (n=8 cells from 1 transfected sample, each; *P<0.001, Wilcoxon rank sum test of photobleaching half times). FIG. 1F-I shows characterization of the template, Archon1 and Archon2 in HEK293T cells. FIG. 1F shows representative photomicrographic fluorescence images of HEK293T cells expressing the template, Archon1 and Archon2. Dynamic ranges for the images were normalized to facilitate visual comparison of localization between Archon1 and the template (see FIG. 1H for fluorescence brightness quantification). Scale bars, 5 μm. Imaging conditions: 62 mW/mm², λex=628/31BP (bandpass, used throughout) from an LED, λem=664 nm LP used in FIG. 1F-G. FIG. 1G is a graph showing relative membrane localization of these indicators in HEK293T cells, evaluated by computing the average difference in profile between opsins vs. co-expressed membrane-anchored YFP (n=15, 16, and 16 cells for Archon1, Archon2, and the template respectively, each from 2 independent transfections; *P<0.001, Kruskal-Wallis analysis of variance followed by post-hoc test via Steel's test with the template as control group). Box plots with notches are used throughout experimentation and examples provided herein, when n>6 as recommended by Krzywinski, M. & Altman, N. (2014) Nat. Methods 11, 119-120 (narrow part of notch, median; top and bottom of the notch, 95% confidence interval for the median; top and bottom horizontal lines, 25% and 75% percentiles for the data; whiskers extend to data points that are less than 1.5 times the interquartile range away from 25% and 75% percentiles). Transfection, culturing, and imaging conditions were as in FIG. 1F. FIG. 1H is a graph showing FACS mean fluorescence intensity, of sets of live HEK293T cells expressing these indicators (n=2 transfected samples, each; individual data points in black dots). Transfection, culturing, and FACS parameters (including light power) were the same across all indicators. FIG. 1I shows traces showing representative fluorescence changes for these indicators with a 100 mV voltage step, measured in HEK293T cells. Imaging conditions: λex=637 nm laser light, λem=664 nm LP, 800 mW/mm² used for the template and 80-800 mW/mm² used for Archons in FIG. 1I-J. The light intensity was adjusted to prevent signal saturation. FIG. 1J is a graph of population data of fluorescence changes, as in FIG. 1I, for these indicators (n=5, 6, and 4 cells for the template, Archon1, and Archon2, each from 2 independent transfections; individual data points in black dots; error bars, standard deviation; *P=0.0155 for Archon1 and *P=0.0374 for Archon2, Kruskal-Wallis analysis of variance followed by post-hoc Steel's test with the template as control group), taken in the steady state. Transfection, culturing, and imaging conditions were as in FIG. 1I.

FIG. 2A is a schematic diagram showing Archon-GFP vector design.

with the % indicating A/(A+B).

Figure 2A:
FIG. 2A-Q provides an embodiment of characterization of Archons in cultured cells.
Figure 2B:
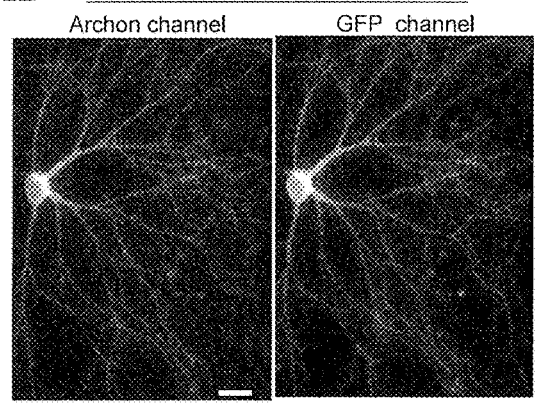
FIG. 2B provides representative photomicrographic fluorescent images of Archon1 (left, excitation (λex) at 637 nm laser light, emission (λem) at 664 nm LP) and GFP (right, λex=475/34BP from an LED and λem=527/50BP) channels in a cultured mouse hippocampal neuron. Scale bar: 10 μm.
Figure 2C:
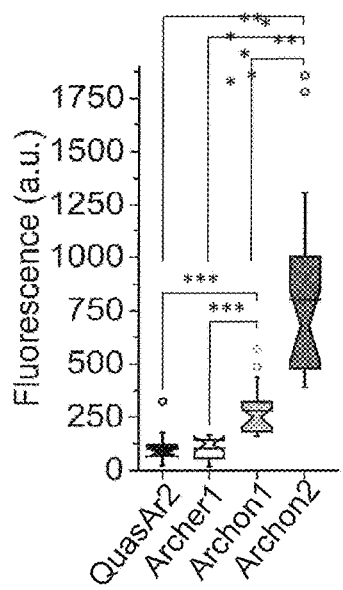
FIG. 2C is a graph showing relative fluorescence of QuasAr2, Archer1, Archon1, and Archon2 in cultured neurons (n=18, 16, 23, and 23 cells respectively, from 4 independent transfections each, from one culture; λex=637 nm laser light at 800 mW/mm² and λem=664 nm LP for FIG. 2C-M; ***P<0.001, Kruskal-Wallis analysis of variance followed by post-hoc Steel-Dwass test on each pair; see Table 3 for full statistics for FIG. 2). Box plots with notches are used (see caption for FIG. 1G for description). Open circles represent data points which are less than 25th percentile or greater than 75th percentile by more than 1.5 times the interquartile range.
Figure 2D:
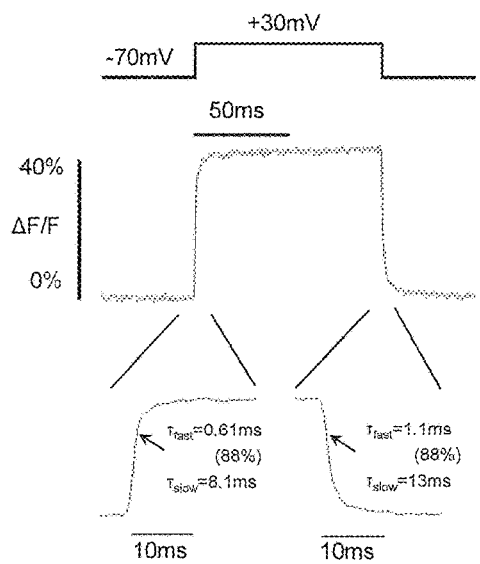
FIG. 2D provides a representative fluorescence response of Archon1 in a cultured neuron, to a 100 mV change delivered in voltage-clamp. $\tau_{fast}$ and $\tau_{slow}$ indicate time constants with the fluorescence trace fit according to $$\frac{\Delta F}{F}(t) = Ae^{-t/\tau_{fast}} + Be^{-t/\tau_{slow}}$$
Figure 2E:
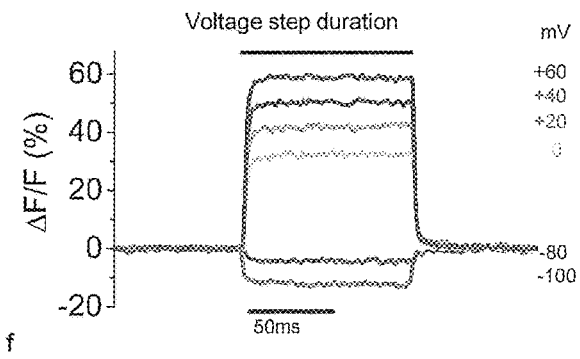

Image acquisition rate: 3.2 kHz. FIG. 2E shows representative fluorescence traces of Archon1 in response to a series of voltage steps in voltage-clamp mode. Image acquisition rate: 2.3 kHz.

Figure 1G:
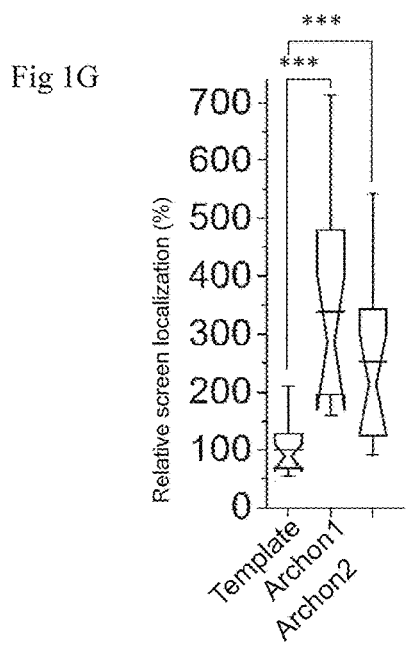
Figure 2F:
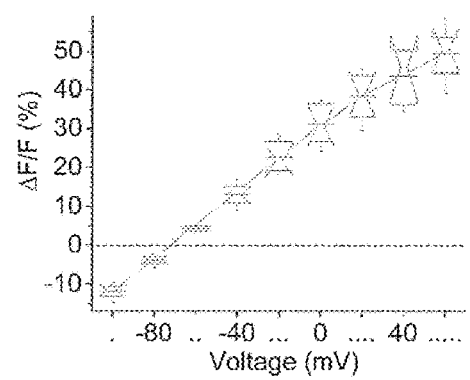
Figure 2G:
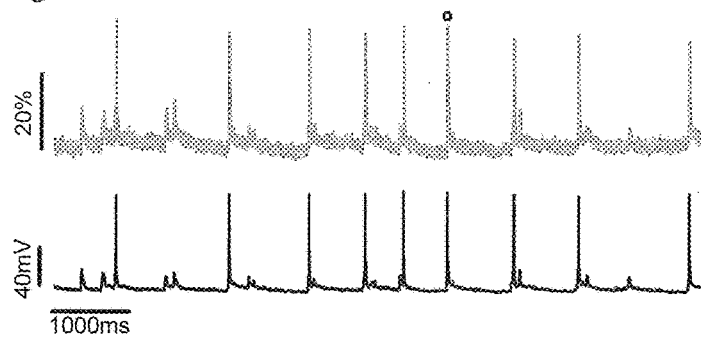
Figure 2H:
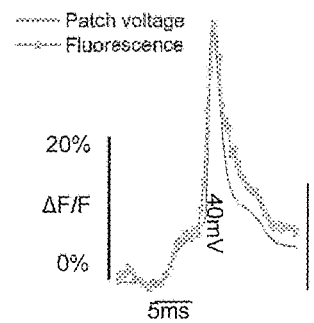
Figure 2I:
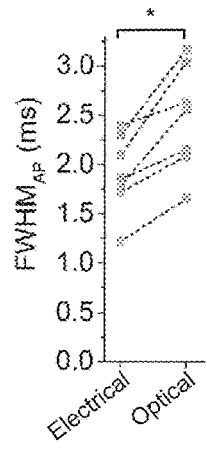
Figure 2J:
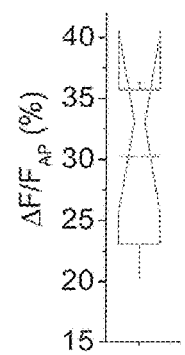
Figure 2K:
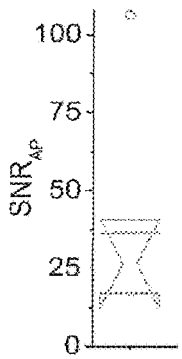
Figure 2L:
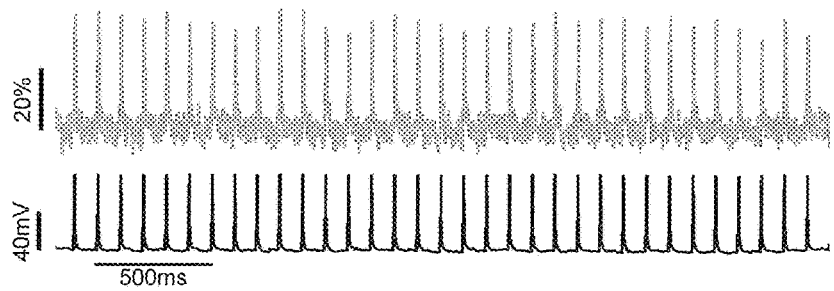
Figure 2M:
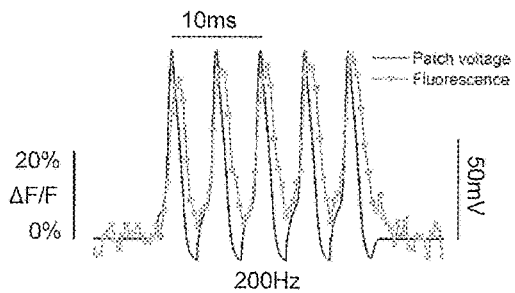
Figure 2N:
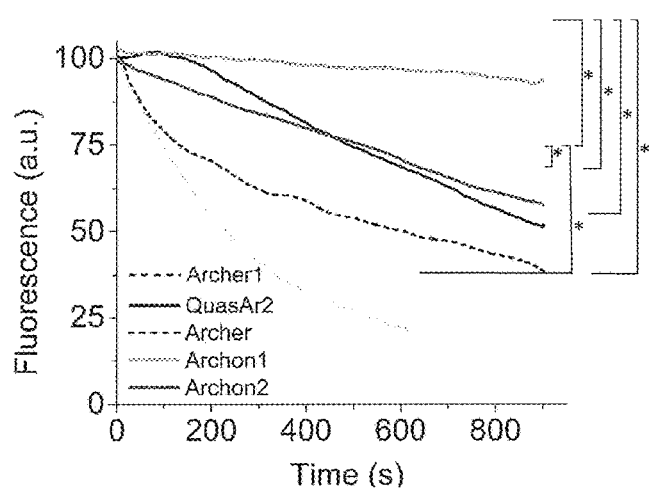
Figure 2O:
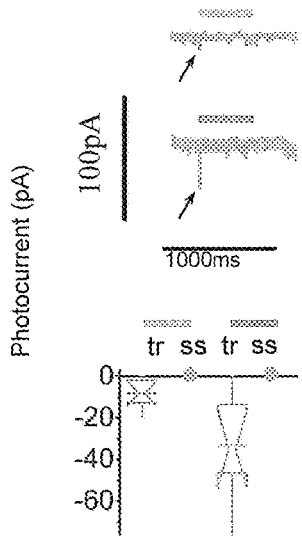
Figure 2P:
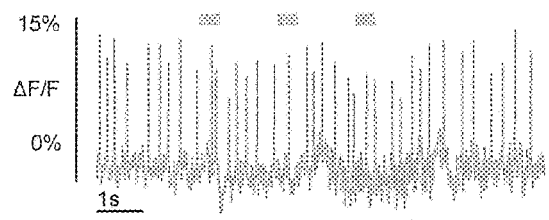
Figure 2Q:
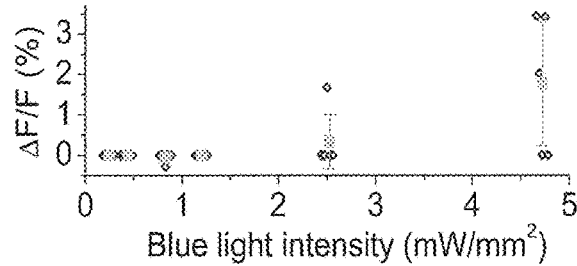

FIG. 2F is a graph showing population data corresponding to the experiment of e (n=8 neurons from 3 cultures). Box plots with notches (see above) are used. Data was normalized so that −70 mV was set to 0 ΔF/F. FIG. 2G shows a single-trial optical recording of Archon1 fluorescence responses (top trace) during spontaneous activity, and patching in current clamp (bottom trace) in a cultured hippocampal neuron. Peak marked with circle (○) is zoomed-in in FIG. 2H. Image acquisition rate: 2.3 kHz. FIG. 2H shows a zoomed-in view of peak marked with circle (○) in FIG. 2G. FIG. 2I-K shows quantification of electrical and optical full width at half maximum (FWHM; dashed lines connect data points from same neuron) FIG. 2I, ΔF/F FIG. 2J and SNR FIG. 2K, per action potential (AP) across all recordings (n=7 neurons from 5 cultures). In FIG. 2I, means are plotted for each cell; in FIG. 2J and FIG. 2K box plots with notches (see above) are used. In FIG. 2K, open circles represent data points which are less than 25th percentile or greater than 75th percentile by more than 1.5 times the interquartile range; *P=0.0156 for FIG. 2I, Wilcoxon signed-rank test. FIG. 2L shows a single-trial optical recording of Archon1 fluorescence responses (top trace) to a 10 Hz action potential train evoked by current injections (400 pA, 5 ms); patch voltage is shown in lower trace. Image acquisition rate: 2.3 kHz. FIG. 2M shows single-trial optical recording of Archon1 fluorescence response (line with dots) to a 200 Hz action potential-like voltage transient train (line without dots) in a voltage-clamped neuron. Image acquisition rate: 2.3 kHz. FIG. 2N provides photobleaching curves of Ace, QuasAr2, Archer1, Archon1 and Archon2 under continuous illumination (n=5, 7, 5, 9, and 7 neurons from 1, 1, 1, 2, and 2 cultures respectively; 475/34BP from an LED at 13 mW/mm² for Ace2N-4aa-mNeon, 637 nm laser light at 2.2 W/mm² for QuasAr2 and Archer1, 637 nm laser light at 800 mW/mm² for Archon1 and Archon2, light intensity was adjusted to have the same initial signal-to-noise ratio (SNR) of action potentials, e.g. 25±8, 26±12, 26±10, 26±10 and 28±7 for Quasar2, Archer1, Archon1, Archon2 and Ace2N-4aa-mNeon, n's are the same as used to obtain the photobleaching curves, image acquisition rate: 333 Hz for all constructs). *P<0.05, Kruskal-Wallis analysis of variance of bleaching time followed by post-hoc Steel-Dwass test on each pair). FIG. 2O (top two traces) provide representative trace of Archon1 photocurrent measured in HEK293T cells in response to 470/20 nm light from an LED (15 mW/mm², top trace with bar above) and 637 nm laser light (800 mW/mm², lower trace with bar above) illuminations. Arrows indicates transient photocurrents. FIG. 2O (bottom section) provides population data of transient (tr) and steady-state (ss) photocurrents in response to 470/20 nm light (left hand bar) and 637 nm (right hand bar) illumination as shown on top (n=8 cells for each from one and two cultures, respectively). Box plots with notches are used (see caption for FIG. 1G for description). FIG. 2P shows a representative fluorescence trace of Archon1 in a spiking neuron during blue illumination (blue illumination: 470/20 nm light from an LED, 500 ms, 0.5 Hz, at 4.8 mW/mm$^2$; red illumination: 637 nm laser light at 800 mW/mm$^2$). Image acquisition rate: 200 Hz. FIG. 2Q is graph of optical crosstalk of blue illumination into Archon1 fluorescence (diamonds) measured in cultured neurons expressing Archon1 (n=5 neurons from one culture), as in FIG. 2P (3-5 pulses for each illumination power), while holding red light power constant (as in FIG. 2P). Squares, mean; error bars, standard deviation.

Figure 3A:
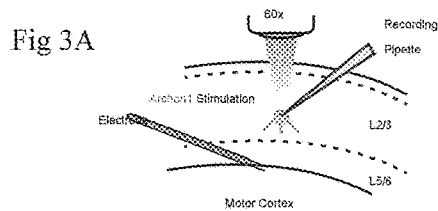
Figure 3B:
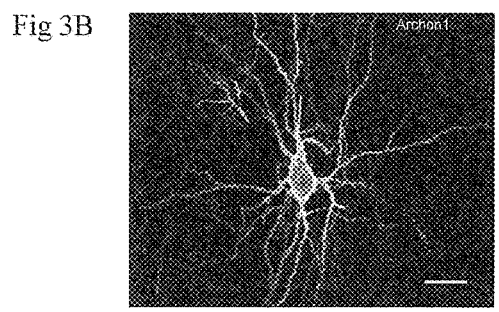
Figure 3C:
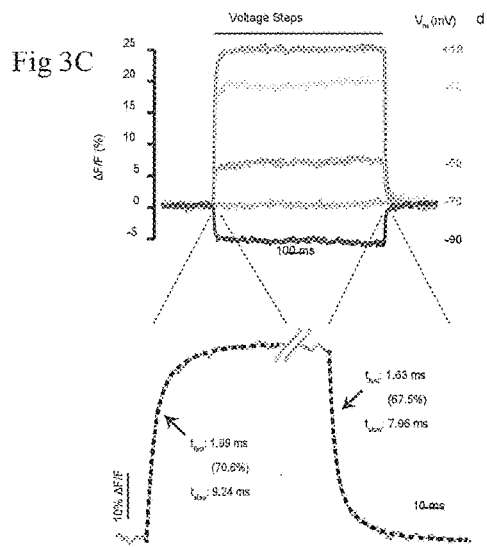
Figure 3D:
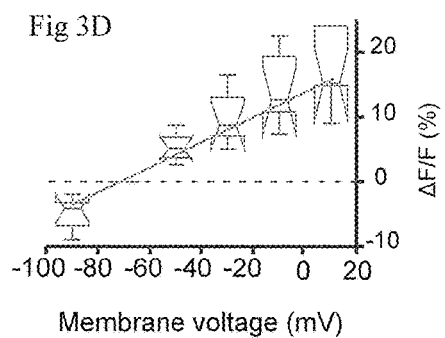
Figure 3E:
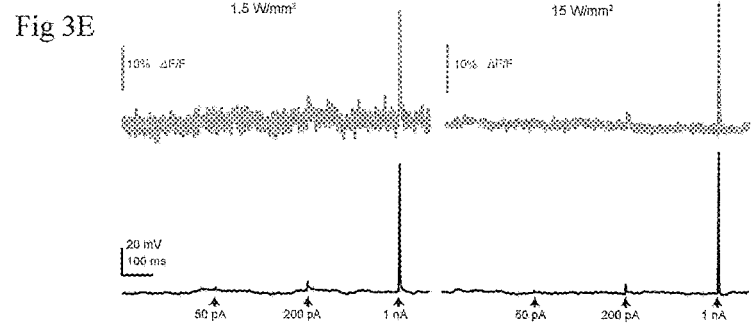
Figure 3F:
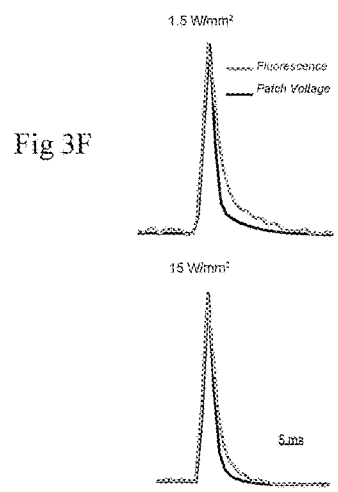
Figure 3G:
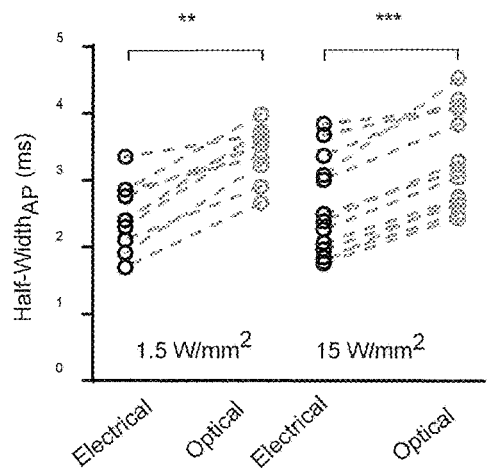
Figure 3H:
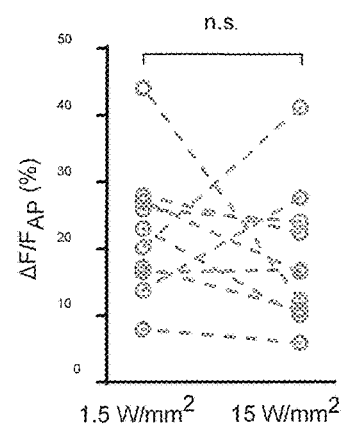
Figure 3I:
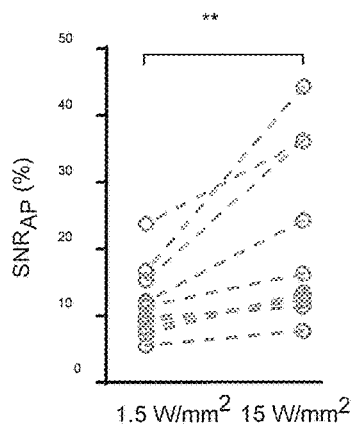
Figure 3J:
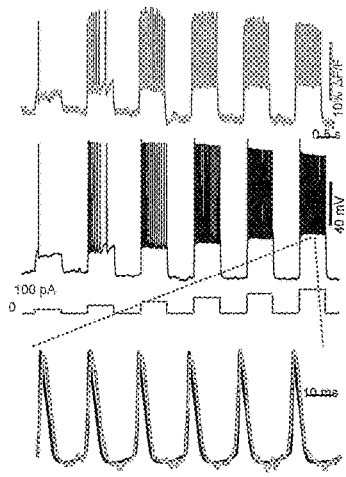
Figure 3K:
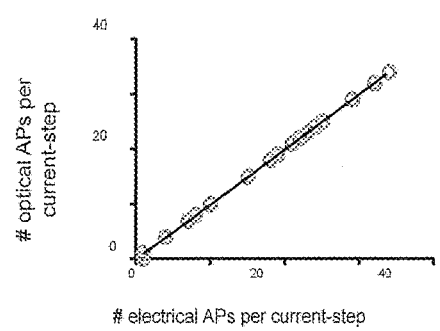
Figure 3L:
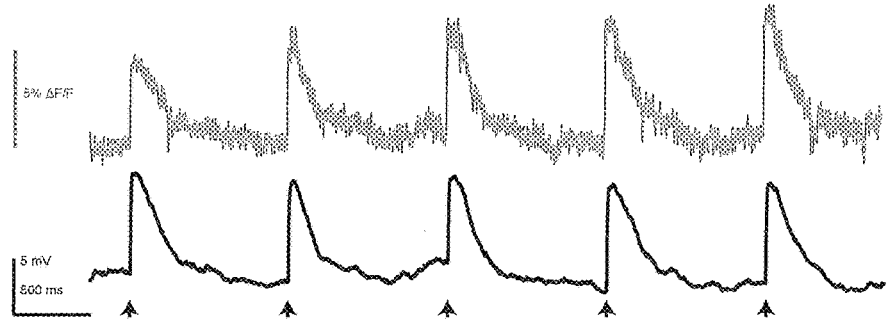
Figure 3M:
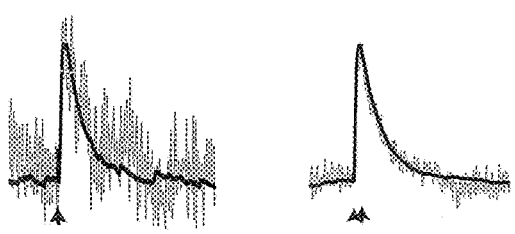
Figure 3N:
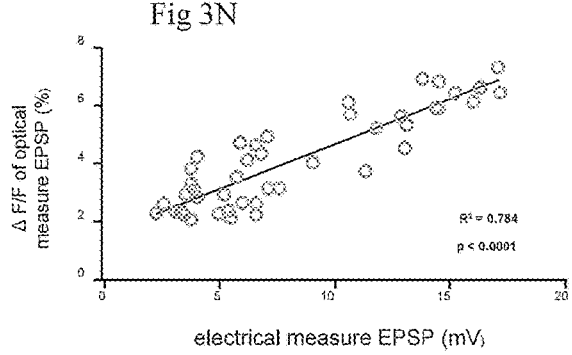

FIG. 3A-N shows millivolt-scale imaging of neural voltage in intact brain slices. FIG. 3A provides a schematic of experimental recording configuration. Archon1-expressing pyramidal neurons in layer (L) 2/3 of motor cortex were targeted by patch-clamp recording, and Archon fluorescence at the soma was imaged at 1 kHz. Excitation intensity was ~7 mW over the area of the soma (i.e., ~15 W/mm$^2$ at 637 nm, but 10× lower intensity, 1.5 W/mm$^2$ at 637 nm, was used in FIG. 3E-I for comparison to the high illumination condition). A bipolar stimulation electrode was in some experiments placed in L5 to trigger excitatory synaptic events in Archon1-expressing L2/3 pyramidal neurons. FIG. 3B is a representative photomicrographic image of Archon1 expressing neuron in L2/3 of mouse motor cortex. Scale bar: 25 µm. FIG. 3C shows representative traces of voltage imaging recordings for a series of hyper- and depolarizing voltage steps in voltage-clamp mode in a neuron expressing Archon1 (top). Rise and decay phases of the voltage step from −70 to +10 mV are shown on extended time scales (bottom image, solid line), overlaid with the fit to a double-exponential function to determine rise and decay kinetics (dotted line). Numbers are as in FIG. 2D. FIG. 3D is a graph showing population data corresponding to the experiment of FIG. 3C (n=7 neurons from 2 mice). Box plots with notches are used (see caption for FIG. 1G for description). Data was normalized so that −70 mV was set to 0 ∆F/F (and hence appears as a collapsed box). FIG. 3E shows simultaneous Archon fluorescence imaging (top trace) and whole-cell current-clamp patch recording (bottom trace) during injection of current pulses with increasing amplitude (50 pA, 200 pA, and 1 nA, 2 ms; arrows). Shown are 1-second long sweeps from Archon1 expressing cells first at 1.5 W/mm$^2$ (left) and then at 15 W/mm$^2$ (right) excitation light. Both imaging conditions, 1.5 W/mm$^2$ and 15 W/mm$^2$, were used in FIG. 3E-I. FIG. 3F provides traces showing overlay of averaged action potential current waveform (black) and fluorescent signal from Archon1 (grey), scaled to peak (from n=30 sweeps from one cell), and recorded at 1.5 W/mm$^2$ (top) and 15 W/mm$^2$ (bottom) excitation light. FIG. 3G-I provides graphs of quantification of electrical and optical full width at half maximum (FWHM; dashed lines connect data points from same neuron) FIG. 3G, ∆F/F FIG. 3H, and SNR FIG. 3I for action potentials, under 1.5 W/mm$^2$ and 15 W/mm$^2$ of excitation light; n=10 neurons from 6 mice; means are plotted for each cell; dashed lines connect data points from same neuron obtained at 1.5 W/mm$^2$ and 15 W/mm$^2$; Wilcoxon signed-rank test for FIG. 3G-I, P=0.002 and *P<0.001 for FIG. 3g, P>0.05 (not significant, n.s.) for FIG. 3H, **P=0.002 for FIG. 3I) see Table 3 for full statistics for FIG. 3. FIG. 3J provides a series of 500 ms current steps with increasing amplitudes (from 100 to 600 pA, in 100 pA increments; gray line) that were injected through the recording pipette, resulting in action potentials of varying frequency. Grey, imaged trace; black, simultaneous whole-cell patch-clamp in current clamp mode. FIG. 3K provides a graph of the number of optically detected APs vs. the number of electrically detected APs for every 500 ms-long current injection across all cells that underwent the experiment of FIG. 3J (n=22 steps from 5 neurons). FIG. 3L provides traces showing optical (top) and electrical (bottom) signals from electrically evoked excitatory postsynaptic potentials (EPSPs, with stimulation adjusted to yield 2-15 mV responses) for a single-trial. Arrows indicate times of stimulation (right; 5 stimuli at 1 Hz, followed by inter-trial intervals of >30 seconds). FIG. 3M provides overlays of optical (grey) and electrical (black) signals from EPSPs for a single-trial (left) and average of 35 consecutive events from one cell (right), performed in FIG. 3L. FIG. 3N is a graph of population data from individual EPSPs as in FIG. 3L across all cells (n=45 EPSPs from 4 neurons from 2 mice); straight line indicates fit with a linear regression (r2).

Figure 4A:
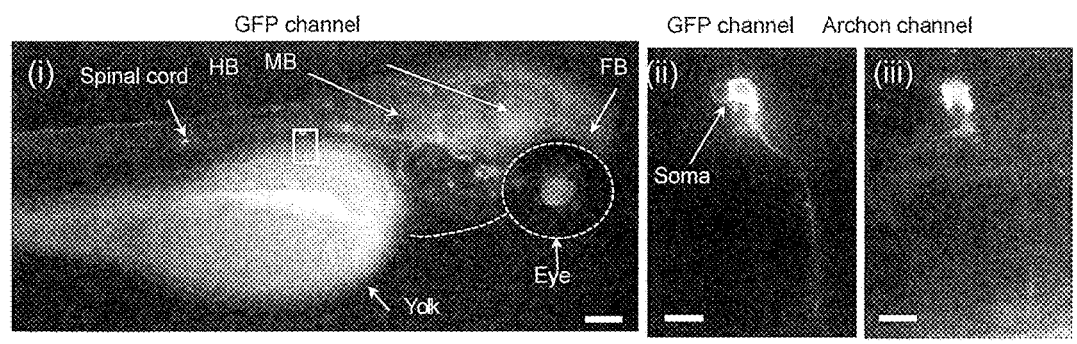
Figure 4B:
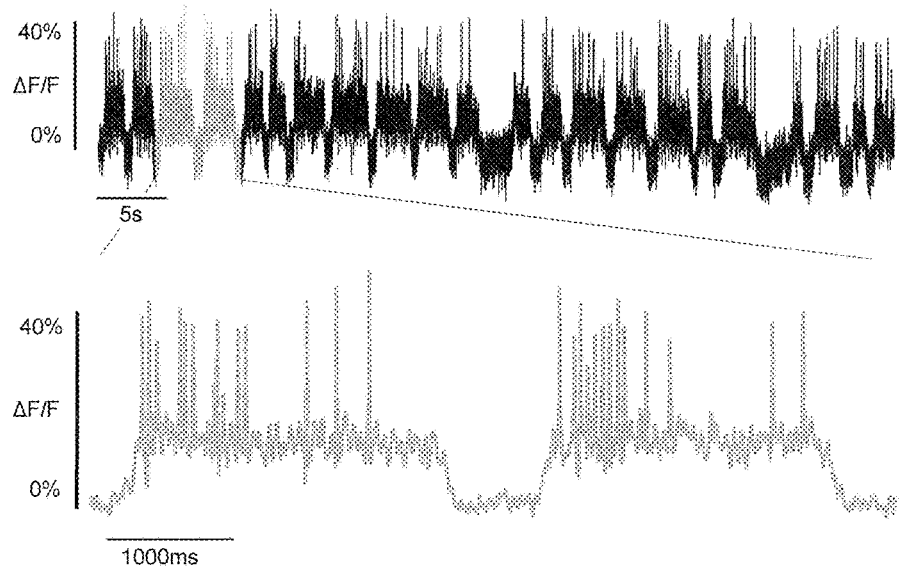
Figure 4C:
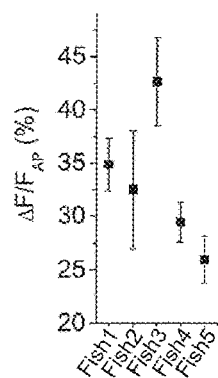
Figure 4D:
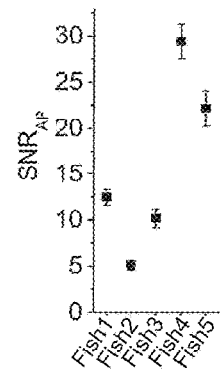
Figure 4E:
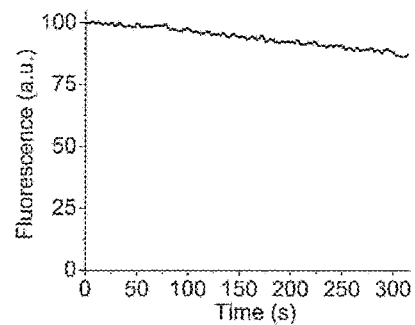
Figure 4F:
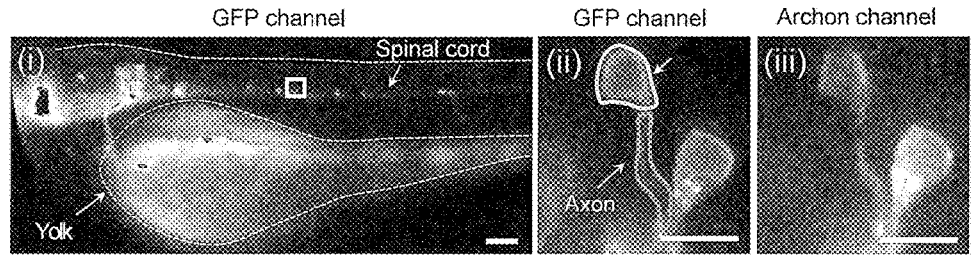
Figure 4G:
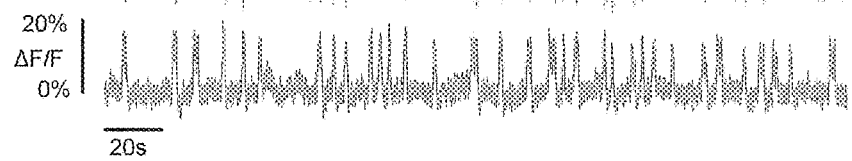

FIG. 4A-G shows results from voltage imaging of Archon1-expressing neurons in larval zebrafish. FIG. 4A(i) provides a photomicrographic image [excitation (λex) at 475/34BP from an LED, emission (λem) at 527/50BP, aka the GFP channel] of neurons expressing zebrafish codon-optimized fusion of Archon1 (or zArchon1 for short) with GFP in the spinal cord of a 4 day post fertilization (dpf) zebrafish larva immobilized in agarose under wide-field microscopy. A box (near center of field) indicates a neuron zoomed in in later panels. Scale bar: 100 µm; FB, forebrain; MB, midbrain; HB, hindbrain. FIG. 4A(ii) is a high magnification photomicrographic image of the neuron highlighted in the box of FIG. 4A(i) in the GFP channel. Scale bar: 10 µm. FIG. 4A(iii) is a photomicrographic image as in FIG. 4A(ii), but in the Archon (λex=637 nm laser light, λem=664 nm LP) channel. FIG. 4B (top) shows representative fluorescence trace of zArchon1 reporting spontaneous activity of the neuron shown in FIG. 4A. The trace was acquired at the soma of the neuron (λex=637 nm laser light at 2.2 W/mm$^2$, λem=664 nm LP, image acquisition rate: 500 Hz). FIG. 4B (bottom) shows the section of FIG. 4B (top) in grey, shown at an expanded time scale. FIG. 4C provides population data of fluorescence changes of zArchon1 during action potentials (APs; n=21, 4, 132, 71 and 58 action potentials for fish 1-5 respectively; plotted is mean and standard deviation). FIG. 4D shows population data of signal to noise ratios for the data that yielded results shown in FIG. 4C. FIG. 4E shows results of photobleaching of zArchon1 fluorescence measured in in vivo in zebrafish larvae (n=11 neurons in 6 fish) over 300 s of continuous illumination at 2.2 W/mm$^2$. FIG. 4F(i) provides a photomicrographic image (in the GFP channel) of neurons expressing zArchon1 in the spinal cord of a zebrafish larva at 4 dpf immobilized in agarose under wide-field microscopy. A box (upper center of field) indicates neurons zoomed-in in later panels. Part of the image was saturated (e.g., upper left) so that faint neural processes would be visible. Scale bar: 100 µm. FIG. 4F(ii) provides a high magnification photomicrographic image of the neurons highlighted in the box of FIG. 4F(i) in the GFP channel. Scale bar: 10 µm. Highlighted regions indicate the soma (circled) and the axon (circled and extending downward from soma) of the neuron of interest. FIG. 4F(iii) is a photomicrographic image, as in FIG. 4F(ii), but in the Archon channel. FIG. 4g shows representative fluorescence trace of zArchon1 reporting spontaneous activity at the soma and the axon of the neuron shown in FIG. 4F. The traces were acquired at the soma (top) and the axon (bottom) of the neuron (λex=637 nm laser light at 2.2 W/mm$^2$, λem=664 nm LP, image acquisition rate: 250 Hz).

Figure 5A:
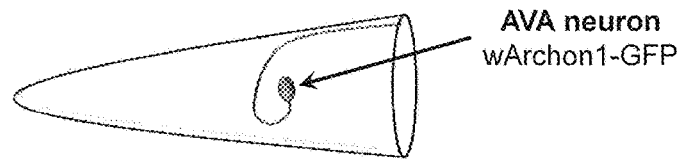
Figure 5B:
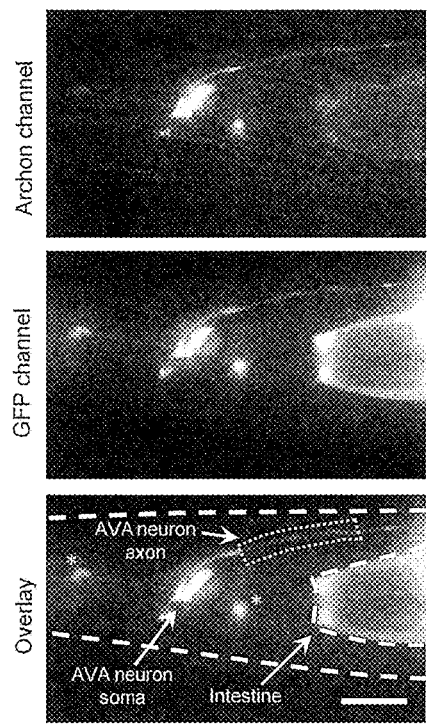
Figure 5C:
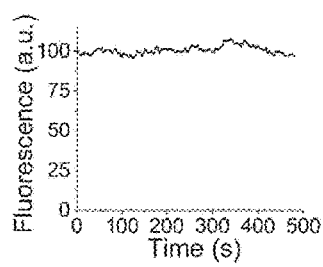
Figure 5D:
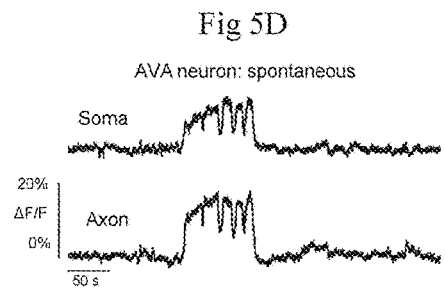
Figure 5E:
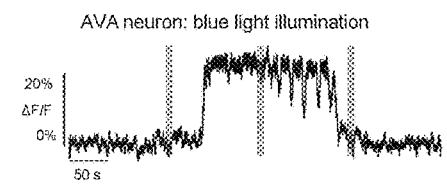
Figure 5F:
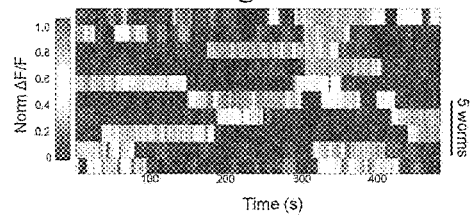
Figure 5G:
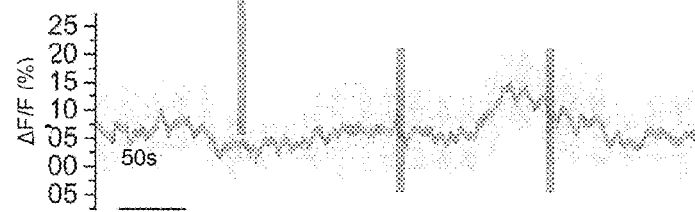
Figure 5H:
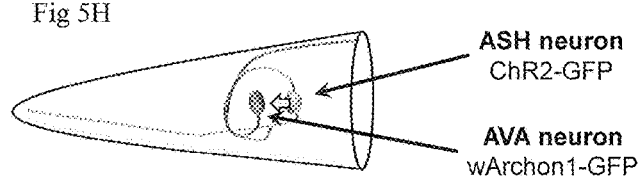
Figure 5I:
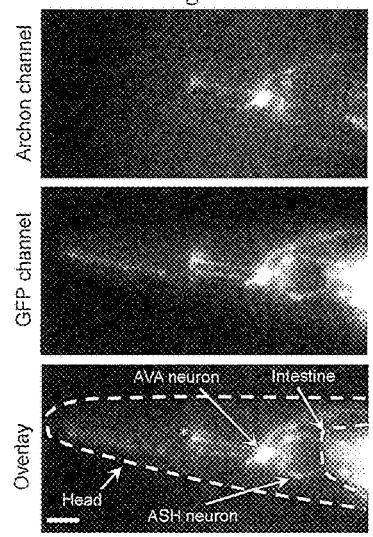
Figure 5J:
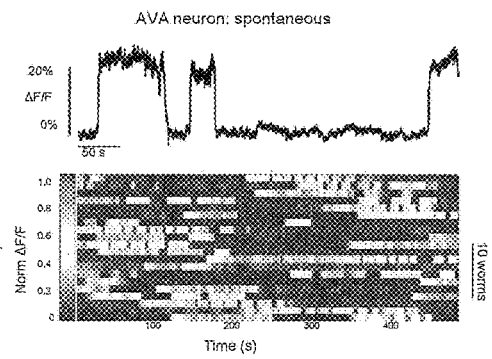
Figure 5K:
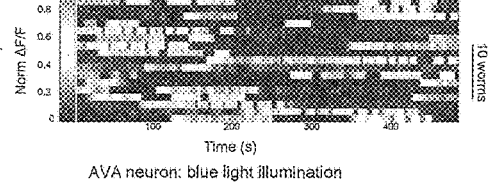
Figure 5L:
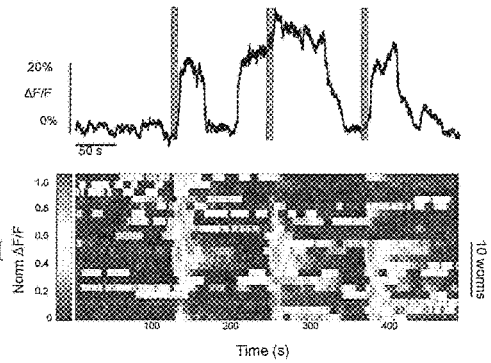
Figure 5M:
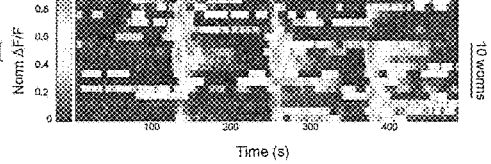
Figure 5N:
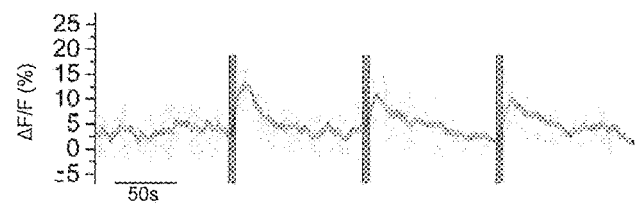

FIG. 5A-N shows results from embodiments of all-optical electrophysiology in *C. elegans*. FIG. 5A provides a schematic of AVA neuron expressing *C. elegans* codon-optimized fusion of Archon1 (or wArchon1 for short) with GFP (grey) in the head of *C. elegans*. FIG. 5B provides photomicrographic fluorescence images of *C. elegans* head expressing wArchon1-GFP under control of the rig-3 promoter. Shown is fluorescence in an AVA neuron (top, Archon channel (excitation (λex) at 637 nm laser light, emission (λem) at 664 nm LP); middle, GFP channel (λex=475/34BP from an LED and λem=527/50BP); bottom, overlay), as well as in pharyngeal neurons that also express under control of the rig-3 promoter (asterisks). AVA neuron soma and axon are indicated. Scale bar: 10 μm. FIG. 5C provides a photobleaching curve of wArchon1 expressed in AVA neurons under continuous 637 nm excitation illumination (n=10 cells from 10 worms, λex=637 nm laser light at 800 mW/mm², λem=664 nm LP). FIG. 5D shows representative fluorescence traces of wArchon1 reporting spontaneous activity in soma (top) and axon (bottom) of an AVA neuron. Imaging conditions (λex=637 nm laser light at 800 mW/mm², λem=664 nm LP; image acquisition rate: 33 Hz) used throughout the figure for Archon imaging. FIG. 5E provides a representative trace of wArchon1 fluorescence in soma of an AVA neuron under three pulses of blue light illumination (0.2 mW/mm², λex=475/34BP from an LED, 6 s; three vertical bars). FIG. 5F shows results of individual traces of wArchon1 fluorescence in AVA neurons under blue light illumination (n=10 neurons in 10 worms). FIG. 5G provides averaged wArchon1 fluorescence changes for traces presented in panel FIG. 5F. Shaded area is standard deviation. FIG. 5H provides a schematic of AVA neuron expressing wArchon1-GFP and ASH neuron expressing ChR2-GFP, in the head of *C. elegans*. An arrow from the ASH to AVA neuron indicates synaptic connection from ASH onto AVA. FIG. 5I provides fluorescence photomicroscopic images of the *C. elegans* head expressing wArchon1-GFP in an AVA neuron (under rig-3 promoter) and ChR2-GFP (under sra-6 promoter) in the ASH neuron (top panel: Archon channel; middle panel: GFP channel; bottom panel is overlay of top and middle panels), as well as pharyngeal neurons that express wArchon1-GFP under control of the rig-3 promoter (asterisks). Scale bar: 20 μm. FIG. 5J provides a representative trace of wArchon1 fluorescence reporting spontaneous activity in the soma of an AVA neuron. FIG. 5K shows individual traces of wArchon1 fluorescence reporting spontaneous activity in an AVA neuron (n=20 neurons in 20 worms). FIG. 5L provides a representative trace of wArchon1 fluorescence in soma of an AVA neuron under three pulses of blue light stimulation (0.2 mW/mm², λex=475/34BP light from an LED, 6 s; three vertical bars). FIG. 5M shows individual traces of wArchon1 fluorescence in an AVA neuron under blue light illumination (n=20 neurons in 20 worms). FIG. 5N shows averaged wArchon1 fluorescence changes for traces presented in panel FIG. 5M. Shaded area is standard deviation.

Figure 6:
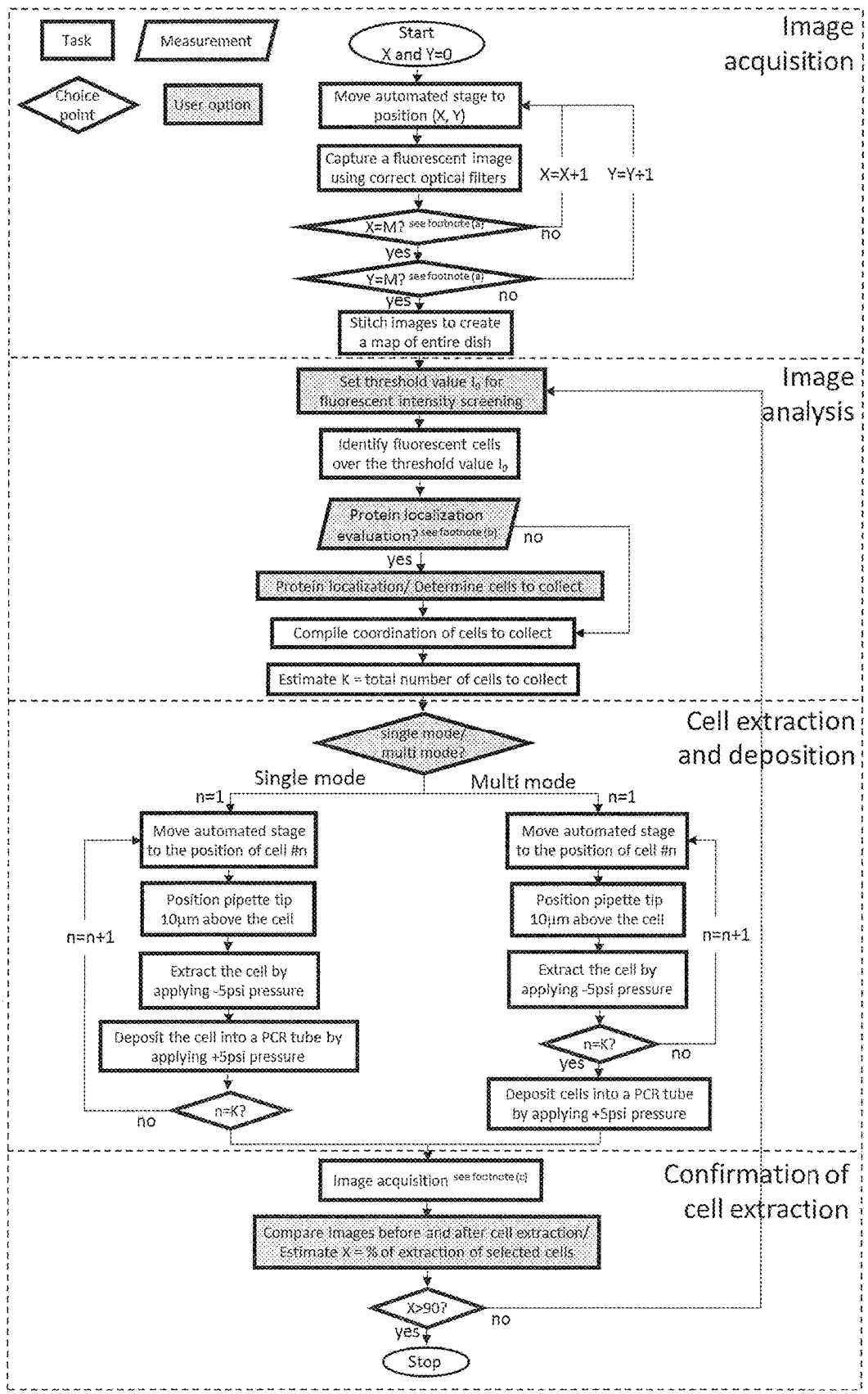

FIG. 6 provides a flowchart illustrating an embodiment of workflow of robotic cell picking based upon microscopy-derived imaging parameters. The cell picking process based upon microscopy-derived imaging parameters consists of image acquisition, image analysis, cell extraction and deposition using automated micropipette, and confirmation of cell extraction. The CellSorter hardware1 was installed on the inverted epi-fluorescent microscope (Nikon Eclipse Ti) equipped with an automated stage (Ludl). M was 12 when a 3 cm cell culture dish (Falcon) was imaged using a 10× objective lens and an sCMOS camera (Zyla 5.5, Andor). Protein localization evaluation was performed on voltage sensor variants with brightness exceeding a threshold value IO. In this study, the evaluation was manually conducted by examining whether voltage sensor fluorescent signals exclusively came from plasma membranes or not. Later Matlab code was developed to automate the protein localization evaluation by comparing fluorescent signals of membrane localized GFPs to those of protein(s) of interest. Image acquisition was repeated in the same way as described in the first part of the flowchart.

FIG. 7A-C illustrates embodiment of directed molecular evolution of monomeric near-infrared FPs in HEK293T cells using FACS and robotic cell picking with microscopy image-based criteria. FIG. 7A provides FACS dot-plots representing near-infrared fluorescence of HEK293T cells expressing the RpBphP1 PAS-GAF template ("Template") and gene libraries generated in first ("First round"), second ("Second round") and third ("Third round") round of directed molecular evolution (see Table 1 for details). FIG. 7B is a graph showing mean near-infrared fluorescence intensity of HEK293T cells expressing template protein (black bar) and individual clones selected in first (bars 1-3 to right of template bar), second (bars 4-6 to right of template bar) and third (bars 7-9 to right of template bar) rounds of directed molecular evolution (n=2 transfected samples from the same passage culture each). Compared to the template, the mutants found in first round had various combinations of the N19D; A28V; D72G; R97C; S102P; A149D; F181Y; D201V,M,L; I202V; D241Y; I253T; Y257F, M; M261L; and A282I,V substitutions. Compared to the template, the mutants found in second round had various combinations of the A11D; L17P; N19D; D72G; V92T; R97C; A149V,D; F181Y; R184I; D201V,L; I202V; D241H, Y; Y257F; M261L; and A282I,V,C substitutions. Compared to the template, the mutants found in third round had various combinations of the A11D; L17P; N19D; A36T; D44G; A93T; A149V; F181Y; R184I; D201V,L; I202V; I253T; Y257F; and A282I,V substitutions. The Mut #3.3 clone was named miRFP and selected for further characterization. Error bars, standard deviation. Imaging conditions are the same as in FIG. 1D. FIG. 7C provides a graph showing mean photobleaching half-time of individual clones selected in first round (bars 1-3 counted from left), second round (bars 4-6 counted from left), and third round (bars 7-9 counted from left) of directed molecular evolution measured in live HEK293T cells, measured for 3-5 cells per construct (shown are raw data, not normalized for photonic dosage). Imaging conditions are the same as in FIG. 1E.

FIG. 8 shows alignment of amino acid sequences of the RpBPhP1 PAS-GAF domains and miRFP (SEQ ID NO: 23). The residues surrounding the chromophore (within 4.0 Å) are highlighted in cyan. Mutations resulting in the conversion of parental RpBphP1 (SEQ ID NO: 22) into the miRFP variant are highlighted and include amino acids at positions 11, 17, 19, 36, 181, 184, 187, 201, 202, 253, 257, and 282 of SEQ ID NO: 22. The β-sheet-forming regions and α-helixes are shaded and denoted with arrows and ribbons, respectively. Amino acid positions selected for site-directed mutagenesis are marked with asterisks.

FIG. 9A-C provides graphs illustrating an embodiment of in vitro characterization of miRFP oligomeric state and fluorescence pH stability. FIG. 9A is a graph showing size exclusion chromatography of miRFP at a concentration of 4 mg/ml (solid line), and indicated molecular weight (MW) standards (dashed line). Apparent molecular weight of miRFP was ~33.6 kDa calculated at its major peak, and ~75.8 kDa calculated at its minor peak. The ratio of dimer to sum of dimer and monomer, estimated as the ratio of corresponding peak areas, was ~4%. FIG. 9B is size exclusion chromatography calibration plot showing the relative retention volumes of protein molecular weight standards (squares; Gel Filtration Standard, Bio-Rad) and miRFP (circle) at its major peak. FIG. 9C is a graph showing equilibrium pH dependence of miRFP fluorescence.

FIG. 10A-D provides wide-field fluorescence photomicrographic imaging of miRFP fusion proteins in live HeLa cells. Wide-field fluorescence images of live HeLa cells transfected with FIG. 10A miRFP-α-Tubulin, FIG. 10B miRFP-β-Actin, FIG. 10C miRFP-Vimentin, and FIG. 10D miRFP-Histone 2B (H2B). Scale bars, 10 µm.

FIG. 11A-J provides images and graphs illustrating expression of miRFP in primary cultured mouse hippocampal neurons, mouse brain and zebrafish larvae and characterization of two-photon properties of miRFP. FIG. 11A-D shows photomicrographic fluorescence images of primary cultured mouse hippocampal neurons expressing miRFP at FIG. 11A, B 15 days and FIG. 11 C, D 24 days in vitro (DIV). Scale bars, 50 µm. FIG. 11E provides photomicrographic fluorescence images of coronal sections of mouse brain with neurons expressing miRFP under Syn promoter. Scale bar, 50 µm. FIG. 11E (i, ii) provide magnified views of the neurons in the boxed regions of upper panel of FIG. 11E. Scale bars, 10 µm. Expression of miRFP was targeted by in utero electroporation (IUE; embryonic day (E) 15.5). FIG. 11F-G provides photomicrographic images showing an overview of transient expression of miRFP in zebrafish larva. miRFP was expressed in zebrafish larvae without co-injection of heme oxygenase-1 mRNA. FIG. 11F provides a lateral view of the brain of a zebrafish larva at 4 dpf imaged on a light sheet microscope (Zeiss Lightsheet Z.1). FIG. 11G provides magnified top view of the brain area selected in the box shown in FIG. 11F. Scale bars, 50 µm. FIG. 11H shows a graph illustrating two-photon excited fluorescence (TPEF) measured for miRFP (black circles) and EGFP (grey circles). GM, Goeppert-Mayer units. FIG. 11I provides raw photobleaching curves for iRFP (n=9 neurons from 2 cultures; dashed line), miRFP (n=6 neurons from 2 cultures; solid black line) and EGFP (n=6 neurons from 2 cultures; grey solid line) expressed in live cultured primary mouse neurons measured under two photon excitation at 880 nm and 4.05 mW of total power. FIG. 11J provides two-photon photomicrographic fluorescence images of cultured neuron co-expressing EGFP (left) and miRFP (middle) under 880 nm excitation (right, overlay). Scale bar, 10 µm.

Figure 12:
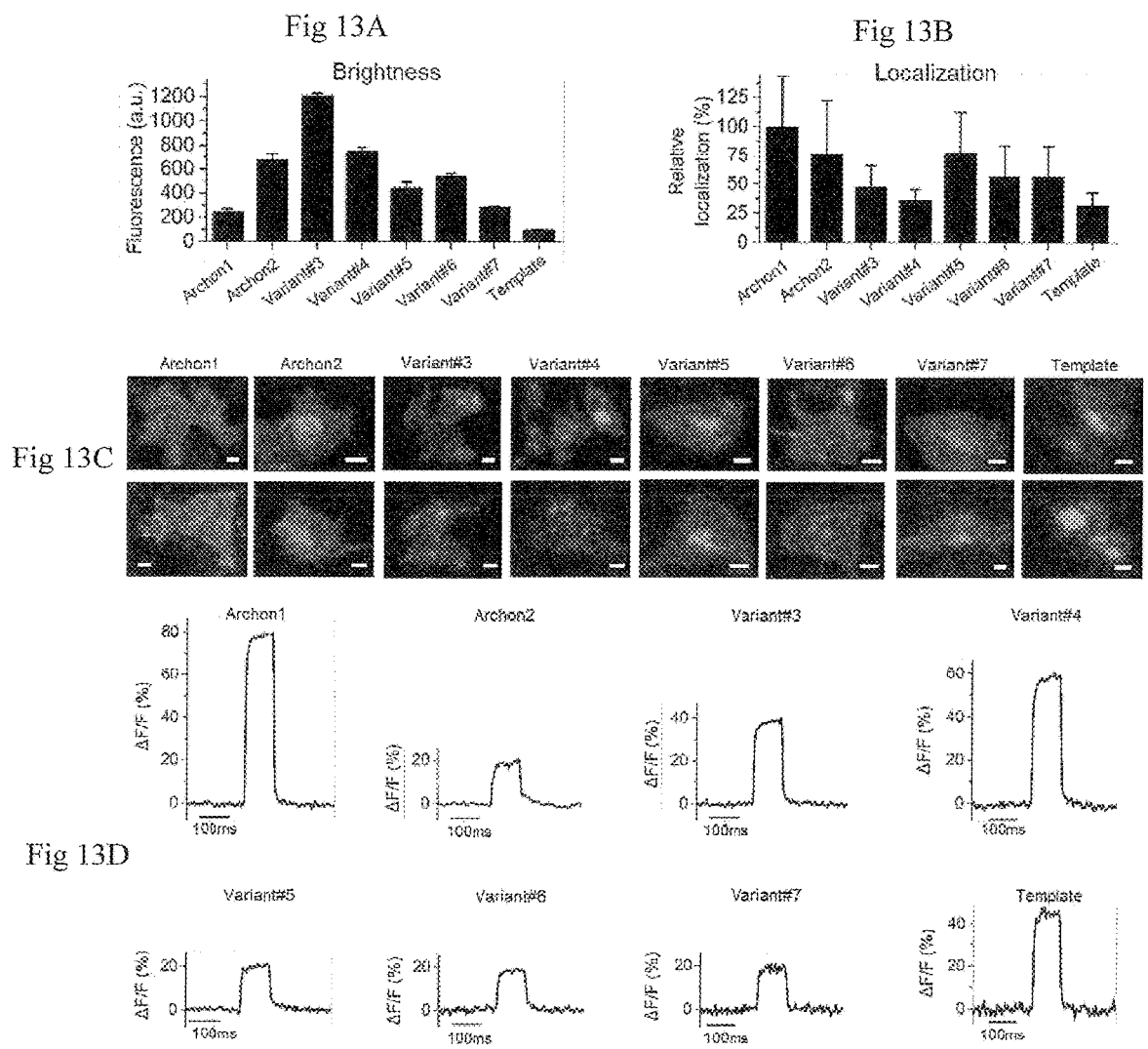
Figure 15A:
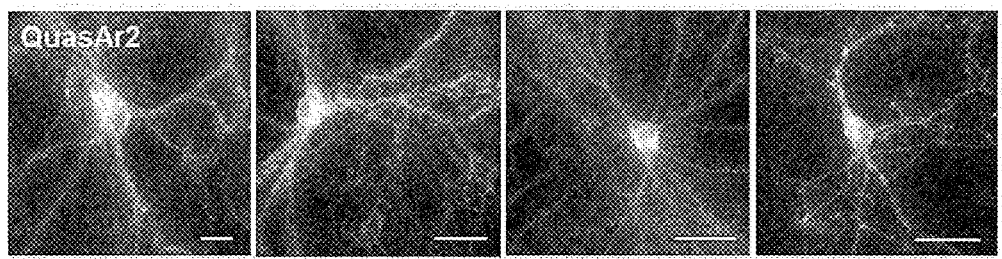
Figure 15B:
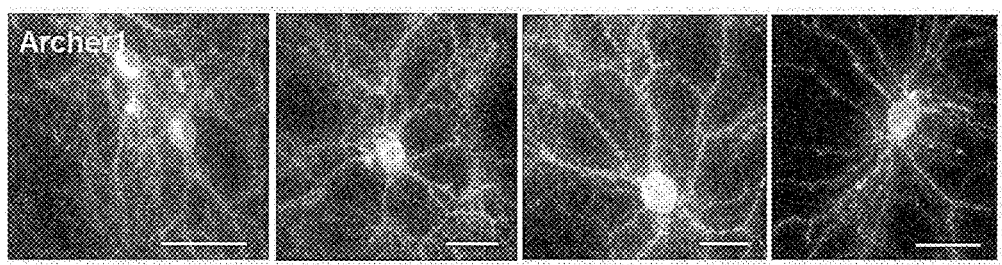
Figure 15C:
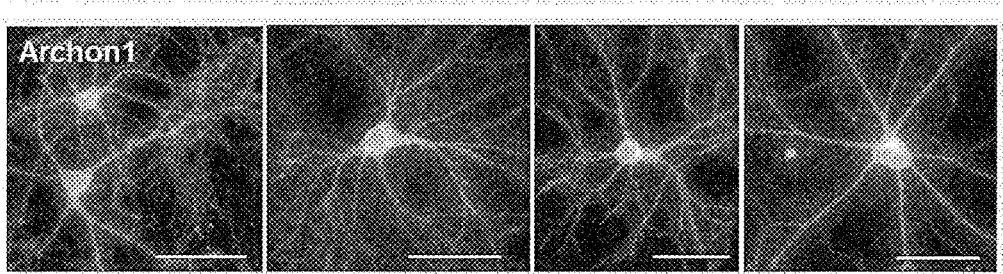
Figure 15D:
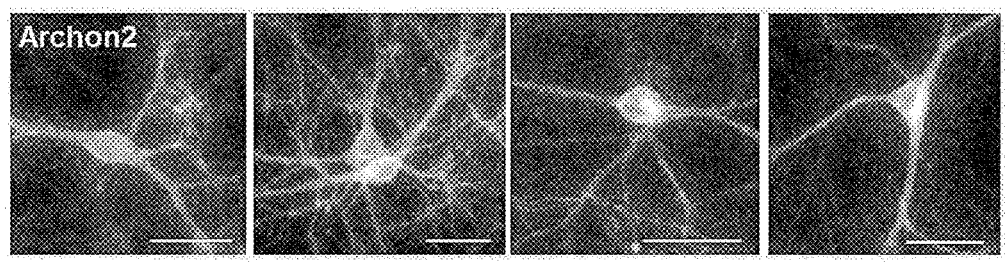
Figure 15E:
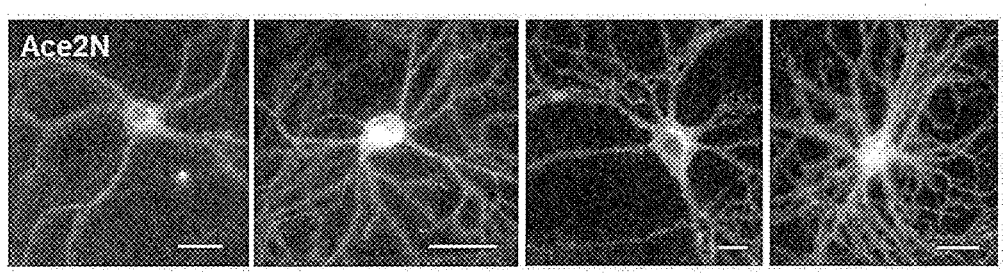

FIG. 12 shows alignment of amino acid sequences of Archaerhodopsin-2 (aR2; SEQ ID NO: 8), Archaerhodopsin-3 (Arch, SEQ ID NO: 9), Archer1 (SEQ ID NO: 10), Arch-7 (SEQ ID NO: 13), QuasAr1 (SEQ ID NO: 11), QuasAr2 (SEQ ID NO: 12) and voltage sensor variants selected in the first round of directed molecular evolution. Amino acid numbering follows that of aR2. The chromophore-surrounding residues (within 4.0 Å) are at positions corresponding to amino acid numbers: 94, 97, 100, 101, 129, 133, 149, 152, 153, 156, 193, 196, 197, 200, 223, and 227. Mutations resulting in the conversion of the parental Arch into Archer1, Arch-7, QuasAr1, and QuasAr2 variants are at: amino acids 96 and 100 for Archer1; amino acids 59, 60, 96, 100, 197, 223, and 226 for Arch-7; amino acids 60, 80, 96, 107, and 162 for QuasAr1; amino acids 60, 80, 96, 107, and 162 for QuasAr2. Mutations introduced during the first round of directed molecular evolution are shown in dark shading in FIG. 12. The β-sheet-forming regions and α-helixes are lightly shaded and denoted with arrows and ribbons, respectively. The voltage sensor variants shown are: QuasAr-I #3 (SEQ ID NO: 14); QuasAr-I #7 (SEQ ID NO: 15); QuasAr-I #14 (SEQ ID NO: 16); QuasAr-I #16 (SEQ ID NO: 17); and QuasAr-I #22 (SEQ ID NO: 18). The alignments show amino acid variations between the sequences shown.

FIG. 13A-D shows characterization of selected Archon variants in comparison to their parental protein in HEK293T cells. FIG. 13A provides a bar graph showing relative fluorescence brightness of selected Archon variants compared to the template (fluorescence brightness was measured using flow cytometry as in FIG. 1H, 2 independent transfections per construct were used for flow cytometry analysis; transfection, culturing, and FACS parameters including light power were the same across all indicators). Error bars, standard deviation. FIG. 13B is a bar graph of relative membrane localization of Archon variants compared to the template. Membrane localization analysis and imaging conditions were the same as in FIG. 1G. (n=15, 16, 12, 8, 9, 11, 5, 16 cells for Archon1, Archon2, Variant #3, Variant #4, Variant #5, Variant #6, Variant #7, and the template, from one culture each, respectively). Error bars, standard deviation.

FIG. 13C provides representative photomicrographic fluorescence images of HEK293T cells expressing Archon variants. Imaging conditions same as in FIG. 1F. Dynamic range for all images was normalized to facilitate visual comparison across selected variants (see panel FIG. 13D for fluorescence brightness quantification). Scale bar, 5 µm. FIG. 13D includes representative fluorescence traces of Archon variants in response to 100 mV changes in membrane voltage (from −70 to +30 mV). Traces were recorded as in FIG. 1J.

FIG. 14 shows alignment of amino acid sequences of Archaerhodopsin-2 (aR2, SEQ ID NO: 8), Archaerhodopsin-3 (Arch, SEQ ID NO: 9), Archer1 (SEQ ID NO: 10), QuasAr1 (SEQ ID NO: 11), QuasAr2 (SEQ ID NO: 12), and voltage sensor variants selected in the second round of directed molecular evolution. Amino acid numbering follows that of aR2. The chromophore-surrounding residues (within 4.0 Å) are present at amino acid positions: 60, 94, 97, 100, 101, 129, 133, 149, 152, 153, 156, 193, 196, 197, 200, 223, and 227. Mutations resulting in the conversion of the parental Arch into Archer1, QuasAr1, and QuasAr2 variants are at: amino acids 96 and 100 in Archer1; amino acids 60, 80, 96, 107, and 162 in QuasAr1; amino acids 60, 80, 96, 107, and 162 in QuasAr2. Mutations introduced during the first round of directed molecular evolution are shown in dark shading in FIG. 14. The β-sheet-forming regions and α-helixes are shaded and denoted with arrows and ribbons, respectively. Amino acid positions selected for site-directed mutagenesis are marked with asterisks. The voltage sensor variants shown are: Variant #3 [(SEQ ID NO: 3), also referred to herein as Var #3]; Variant #4 [(SEQ ID NO: 4), also referred to herein as Var #4]; Variant #5 [(SEQ ID NO: 5), also referred to herein as Var #5]; Variant #6 [(SEQ ID NO: 6), also referred to herein as Var #6]; and Variant #7 [(SEQ ID NO: 7), also referred to herein as Var #7] and the alignments show amino acid variations between the sequences shown.

FIG. 15A-E provides photomicrographic images of cultured primary hippocampal mouse neurons expressing selected voltage sensors. Representative images of cultured hippocampal mouse neurons (12-15 DIV) expressing QuasAr2-mOrange (FIG. 15A, imaged via mOrange2 fluorescence: λex=586/20BP from an LED and λem=628/32BP); Archer1-EGFP (FIG. 15B), Archon1-EGFP (FIG. 15C), Archon2-EGFP (FIG. 15D), the last three were imaged via EGFP fluorescence using λex=474/23BP from an LED and λem=527/50BP); Ace2N (FIG. 15E, imaged via mNeon-Green fluorescence using λex=474/23BP from an LED and λem=527/50BP; from the top). Scale bars, 20 μm.

Figures 16A, 16B:
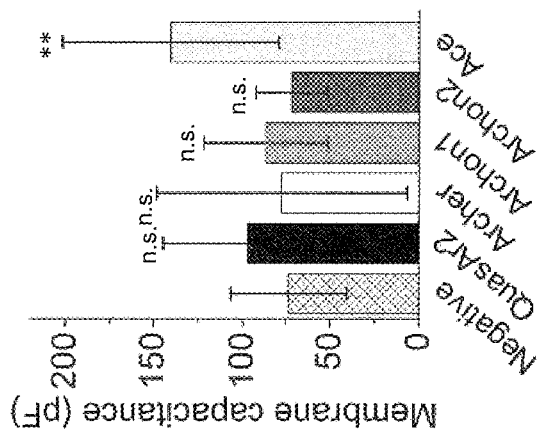
Figure 16C:
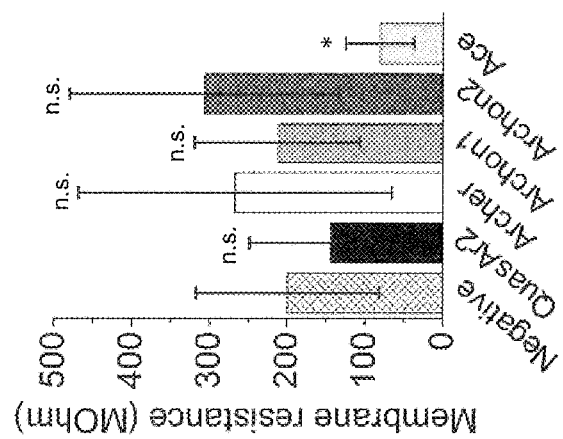

FIG. 16A-C provides bar graphs illustrating membrane properties of cultured primary hippocampal mouse neurons expressing selected voltage sensors. Cultured hippocampal neurons expressing QuasAr2 (n=11 cells from two cultures), Archer1 (n=9 cells from two cultures), Archon1 (n=20 cells from four cultures), Archon2 (n=14 cells from for cultures), and Ace2N4aa-mNeon (Ace, n=17 cells from single culture) were patched to compare membrane properties. Neurons were transfected by calcium phosphate transfection except the negative control (non-transfected neurons, n=10 cells from two cultures). FIG. 16A shows membrane resistance. P>0.05, not significant (n.s.), throughout this panel; *P=0.0136 compared to negative control; Kruskal-Wallis analysis followed by post-hoc Steel's test with negative as control group throughout this panel; see Table 3 for full statistics for FIG. 16A-C. Error bars, standard deviation. FIG. 16B shows membrane capacitance. **P=0.0077 compared to negative control. Error bars, standard deviation. FIG. 16C shows resting potential. *P=0.0483 compared to negative control. Error bars, standard deviation.

FIG. 17A-I shows results from characterization of Archon2 in cultured primary hippocampal mouse neurons. FIG. 17A shows a representative fluorescence response of Archon2 in a cultured neuron, to a 100 mV change delivered in voltage-clamp. Excitation (λex) at 637 nm laser light, 800 mW/mm$^2$ and emission (λem) at 664 nm LP for FIG. 17A-G. Image acquisition rate: 3.2 kHz. Archon2 exhibited 19±2% of ΔF/F (mean±standard deviation; n=9 cells from 4 cultures) for a 100 mV deflection. $\tau_{fast}$ and $\tau_{slow}$ indicate time constants with the fluorescence trace fit according to $$\frac{\Delta F}{F}(t) = Ae^{-t/\tau fast} + Be^{-t/\tau slow},$$

with the with the % indicating A/(A+B) (n=8 neurons from 2 cultures). FIG. 17B shows representative fluorescence traces of Archon2 in response to a series of voltage steps in voltage-clamp mode. Image acquisition rate: 2.3 kHz.

FIG. 17C is a graph showing population data corresponding to the experiment of FIG. 17B (n=5 neurons from 3 cultures). Error bars, standard deviation. FIG. 17D provides traces of single-trial optical recording of Archon2 fluorescence responses (top trace) during spontaneous activity, and patching in current clamp (bottom trace) in a cultured hippocampal neuron. Peaks marked with circle (○) are zoomed-in in FIG. 17E. Image acquisition rate: 2.3 kHz. FIG. 17H provides zoomed-in view of peaks marked with circle (○) in FIG. 17E. FIG. 17F shows a single-trial optical recording of Archon2 fluorescence responses (top) to a 10 Hz action potential train evoked by current injections (400 pA, 5 ms); patch voltage is shown in lower trace. Image acquisition rate: 2.3 kHz. FIG. 17G shows a single-trial optical recording of Archon2 fluorescence response to a 200 Hz action potential-like voltage transient train (black) in a voltage-clamped neuron. Image acquisition rate: 2.3 kHz. FIG. 17H is a graph of Fluorescence of Archon1 (top) and Archon2 (bottom) as a function of illumination (n=5 neurons from one culture, each). λex=637 nm laser light, λem=664 nm LP. Error bars: standard deviation. FIG. 17I shows optical crosstalk of blue illumination into Archon2 fluorescence (diamonds) measured in cultured neurons expressing Archon2 (n=5 neurons from one culture), as in FIG. 2L (3-5 pulses for each illumination power). Circles, mean; error bars, standard deviation.

Figure 18C:
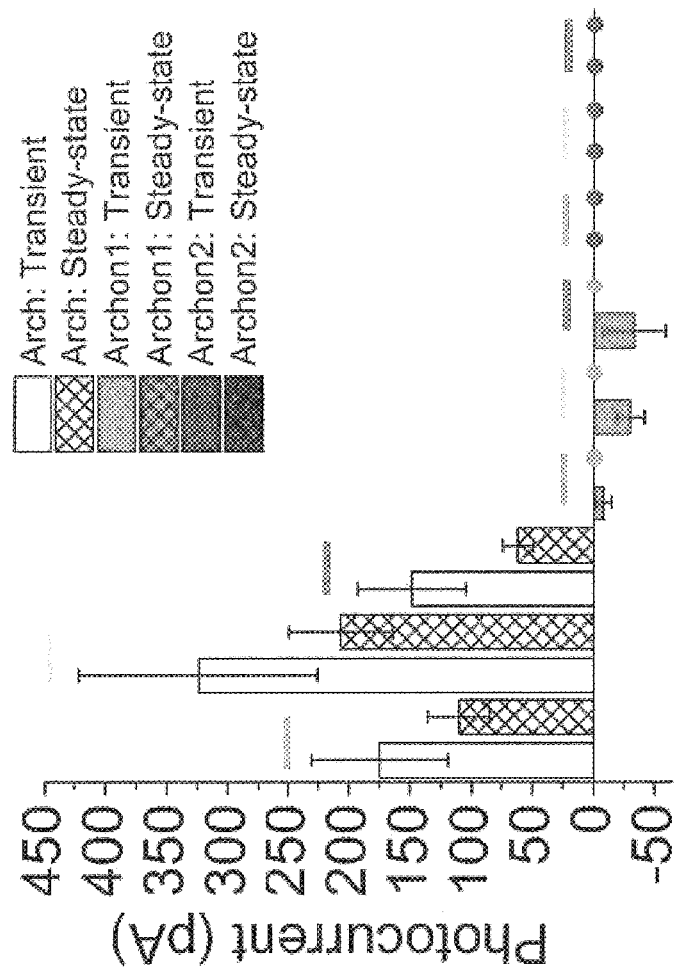
Figure 18A:
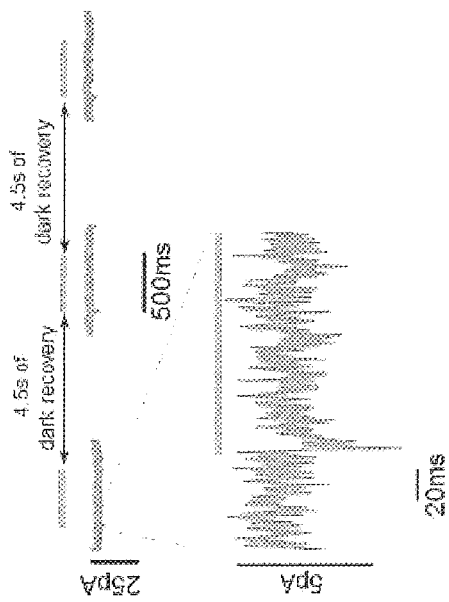
Figure 18B:

FIG. 18A-C shows traces and graphic illustrations from photocurrent measurements for Archon1, Archon2, and Arch in HEK293FT cells. FIG. 18A provides a representative trace (top) of Archon1 photocurrent measured in HEK293FT cells in response to 470/20BP illuminations from an LED (15 mW/mm$^2$, three horizontal bars above three traces shown). Three pulses of blue light were applied with 4.5 second-long dark recovery periods. The lower trace and single bar provide a zoomed-in view of the first peak of transient photocurrent of the top trace. FIG. 18B presents representative trace as in FIG. 18A but with 637 nm laser illumination (800 mW/mm$^2$, bars). FIG. 18C is a bar graph of population data for transient (open columns) and steady-state (crosshatched columns) photocurrents in response to 470/20BP light from an LED [shown left to right as 1-9 horizontal bars] (15 mW/mm$^2$, bars 1, 4, and 7; n=5, 8, 4 cells from one, two and one cultures for Arch, Archon1 and Archon2, respectively), 550/20BP light from an LED (26 mW/mm$^2$, bars 2, 5, and 8; n=5, 4, 4 cells from one culture each for Arch, Archon1 and Archon2, respectively), 631/28BP (24 mW/mm$^2$, bar 3; n=5 cells from one culture for Arch) and 637 nm laser light (800 mW/mm$^2$, bars 6 and 9; n=8 and 3 cells from one culture each for Archon1 and Archon2, respectively) illumination. Circle corresponds to zero detected photocurrent. Error bars, standard deviation.

Figure 19A:
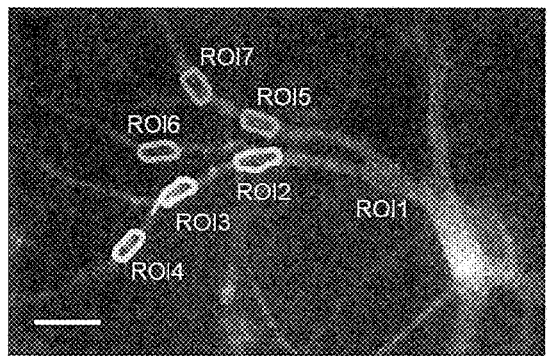
Figure 19B:
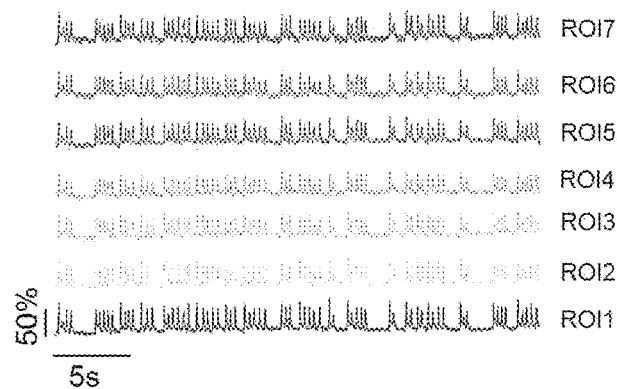
Figure 19C:
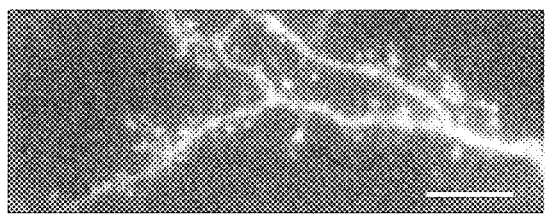
Figure 19D:
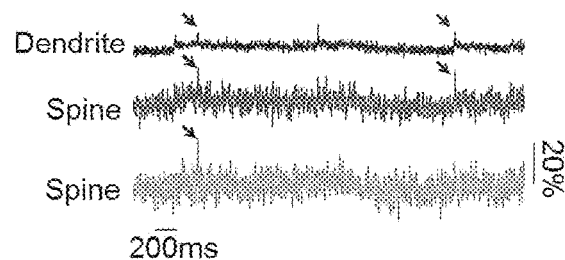
Figure 19E:
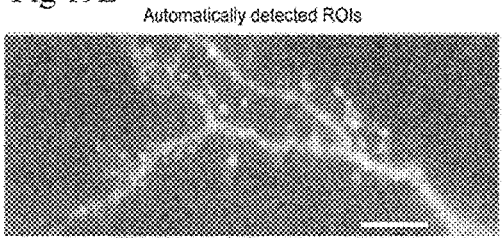
Figure 19F:
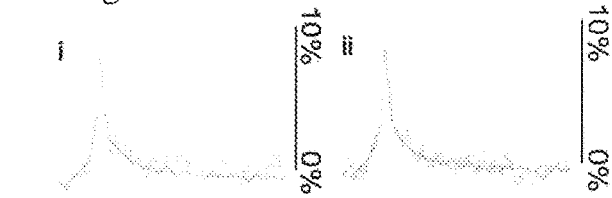
Figure 19G:
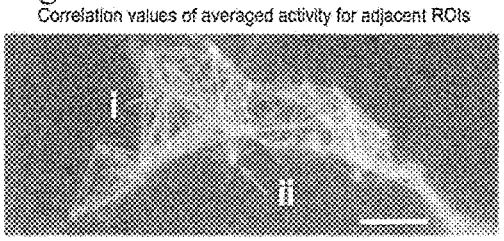
Figure 19H:
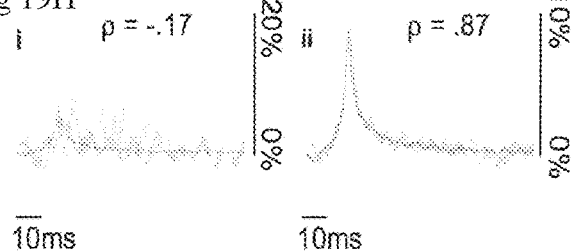

FIG. 19A-H provides from dendritic voltage imaging in cultured primary hippocampal mouse neurons. FIG. 19A is a photomicrograhic fluorescence image of a cultured neuron expressing Archon1. Excitation at 637 nm laser light, 800 mW/mm$^2$, emission at 664 nm LP, image acquisition rate: 381 Hz for FIG. 19A, B. FIG. 19B provides fluorescence traces from single-trial optical recordings of action potentials analyzed for the matched dendritic regions of interest (ROIs) outlined in FIG. 19A. FIG. 19C provides a fluorescence photomicrographic image of dendrites of a cultured neuron expressing Archon1. Arrows indicate dendritic spines referred to later in the figure. FIG. 19D provides fluorescence traces from single-trial optical recordings analyzed for the individual spines indicated with matched arrows in FIG. 19C. Excitation at 637 nm laser light, 800 mW/mm$^2$, emission at 664 nm LP, image acquisition rate: 555 Hz for FIG. 19C-11, Black trace acquired from dendritic shaft proximal to the indicated spines, FIG. 19E results from the computational method for identifying ROIs classifies pixels as either noise or signal via a rank-2 non-negative matrix factorization (NMF) on the power spectral density of each pixel trace. The signal or noise classification for all pixels is based on a human expert choosing a single example pixel that corresponds to clear Archon2 signal. Shown (dots) are the pixels determined to be Archon2 signal by the NMF algorithm and clustered into ROIs via connected components (ROIs of less than 6 pixels are excluded, see Examples Section for details of analysis and MATLAB code), and overlaid on a fluorescence image of the same dendrite shown in FIG. 19C. FIG. 19F provides an overlay of averaged waveforms of fluorescence signal for peak events (n=131 peaks exhibiting over 5% ΔF/F, the selected time window per waveform starts 18 ms before peak and includes 72 ms after peak). The black trace is the averaged waveform from the sum of all ROIs in FIG. 19E and included as reference in FIG. 19F(i) and (ii) and again in FIG. 19H(i) and (ii). Two representative ROIs from dendritic spines, top arrow (i, light grey trace) and lower arrow (ii, dark grey trace), are overlaid with average waveform across all ROIs (black trace) to show difference between a single dendritic spine waveform and total dendritic waveform. The standard error of the mean is drawn around each averaged trace. FIG. 19G shows image of pearson correlation coefficients, p, calculated between pairs of averaged fluorescence traces from each ROE such as those shown in FIG. 19F, visualized by drawing lines for positive (p>0) correlation and lines for negative (p<0) correlation. The thickness of each line is proportional to the magnitude of correlation value and for clarity of presentation, only ROI pairs within 16 µm of each other are visualized. FIG. 19H shows pairs of averaged spike waveforms identified with matched arrows in FIG. 19G are overlaid to demonstrate a negatively correlated pair of ROIs FIG. 19H(i) and a highly correlated pair of ROIs FIG. 19H(ii). Scale bars, 20 µm.

FIG. 20A-J provides images showing expression of Archons in mouse brain slice. Archon1-EGFP or Archon2-EGFP were expressed in mouse brain by IUE at E15.5 and observed at P20-P30. FIG. 20A-F provides epi-fluorescence images from coronal sections of Archon1-EGFP (FIG. 20A, C, D) and Archon2-EGFP (FIG. 20B, E, F) expression (EGFP channel shown in light regions; Nissl staining is shown in darker areas; (Archon fluorescence does not survive formaldehyde fixation). FIG. 20A-B shows a whole brain overview from the hemisphere targeted by IUE (right panel), and the corresponding brain atlas section (adapted from Paxinos, G. & Franklin, K. B. J. The mouse brain in stereotaxic coordinates. Academic Press 2nd, (2004), relative to bregma (left panel). Targeting hippocampus (HPC) by IUE at E15.5 resulted also in sparse expression of L2/3 pyramidal neurons in motor cortex (MC) of the same hemisphere (negative pole electrode), and recordings were obtained from pyramidal neurons in MC. FIG. 20C-F provides higher magnification from the same images showing expression of Archon1-EGFP (FIG. 20C-D) and Archon2-EGFP (FIG. 20E-F) in HPC (FIG. 20C, E) and MC (FIG. 20D, F). Note the sparser expression of Archons in MC, allowing better optical isolation of individual cells. FIG. 20G-J shows confocal images of Archon1-EGFP (FIG. 20G, H) and Archon2-EGFP (FIG. 20I, J)-expressing pyramidal neurons (FIG. 20G, I) and dentate gyrus granule cells (FIG. 20h, J) in hippocampus. Scale bars, 1 mm (FIG. 20A, B), 200 µm (FIG. 20C-F), and 25 µm (FIG. 20G-J).

Figure 21C:
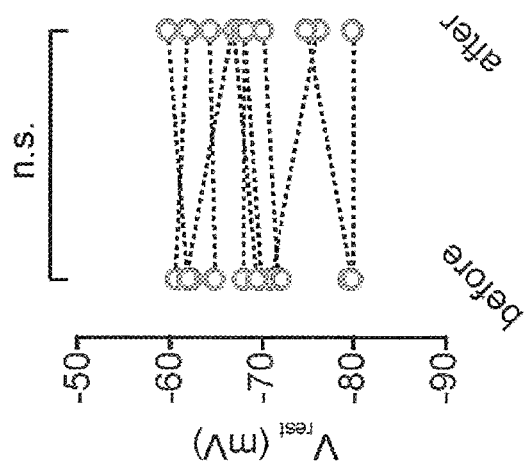
Figure 21B:
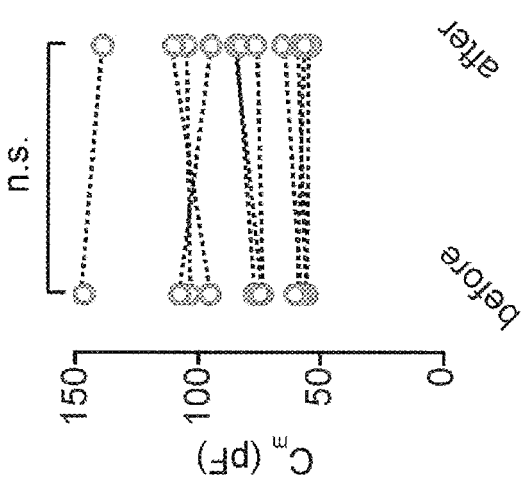
Figure 21A:
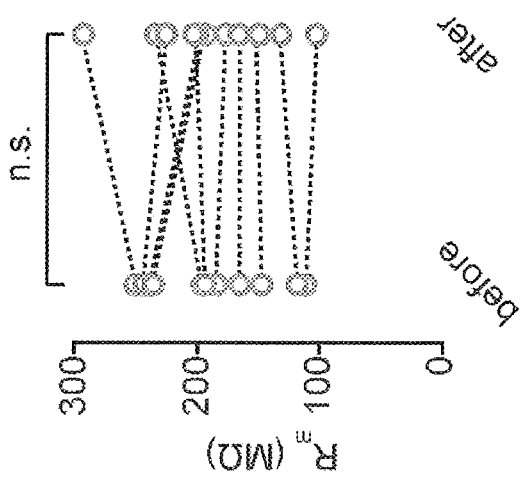

FIG. 21A-C illustrates membrane properties of neurons in mouse brain slice under red light illumination. Quantification of membrane resistance Rm (FIG. 21A), membrane capacitance Cm (FIG. 21B), and resting potential $V_{rest}$ (FIG. 21C) from Archon1-expressing pyramidal neurons in L2/3 mouse brain slice before and after the illumination ($\lambda$ex=637 nm laser light at 15 W/mm²; accumulative illumination duration ranged from 30 to 200 seconds per cell; n=11 neurons from 6 mice). Dashed lines connect data points from same neuron. No obvious change in membrane properties was noticed (P>0.05, not significant (n.s.), throughout this figure; Wilcoxon rank sum test).

FIG. 22A-H shows membrane localization of Archon1 in mouse brain slice. Two-photon images of pyramidal neurons in cortex L2/3 (left) and hippocampus CA1 (right) expressing Archon1-EGFP in acute brain slices; shown is the EGFP channel (see FIG. 20 for details). FIG. 22A-B provides low-magnification overview of cells filled though the recording pipette with Alexa Fluor 594. Images represent maximum projections of z-stacks; boxes indicate regions shown below at higher magnification from individual z-planes. FIG. 22C-F images show result of studies in which Archon1-EGFP (light puncta and regions) was enriched at the cell surface, both at the soma (FIG. 22C-D) and in spiny, proximal dendrites (FIG. 22E-F). In contrast, soluble Alexa Fluor 594 (Alexa594, solid internal regions) filled the cell homogenously. FIG. 22G-H images show results indicating that Archon1-EGFP was also readily detected at spine-heads in more distal dendrites (arrowheads). Scale bars are 25 µm (FIG. 22A-B), 5 µm (FIG. 22C-D), and 2 µm (FIG. 22E-H).

FIG. 23A-I illustrates results from voltage imaging of Archon2 in mouse brain slice. Archon2 expressing pyramidal neurons in L2/3 of motor cortex were targeted by patch clamp recordings, and Archon fluorescence at the soma was imaged simultaneously with an EMCCD camera at 1 kHz. Excitation intensity was ~7 mW over the area of the soma (i.e., ~15 W/mm² at 637 nm. FIG. 23A is a representative image of Archon2-EGFP expression in L2/3 pyramidal neurons. Scale bar: 25 µm. FIG. 23B provides representative traces of voltage imaging recordings for a series of hyper- and depolarizing voltage steps in voltage-clamp mode in a neuron expressing Archon2 (top). Rise and decay phases of the voltage step from −70 to +10 mV are shown on extended time scales (bottom, solid line), overlaid with the fit to a double-exponential function to determine rise and decay kinetics (black dotted line). Numbers are as in FIG. 7D. FIG. 23C is a graph showing population data corresponding to the experiment of FIG. 23B (n=3 neurons from 1 mouse; individual data points in grey dots). Open circles: mean; error bars: standard deviation. FIG. 23D shows results obtained when a series of 500 ms current steps with increasing amplitudes (from 100 to 600 pA in 100 pA steps; gray line) were injected through the recording pipette, resulting in action potentials of varying frequency. FIG. 23E shows simultaneous Archon2 fluorescence imaging (top trace) and whole-cell current-clamp patch recording (bottom trace) during injection of current pulses with increasing amplitude (50 pA, 200 pA, and 1 nA, 2 ms; arrows). Shown are 1-second long sweeps from Archon2 expressing cells, from both single trials (left) and averaged over 29 sweeps from the same cell (right). FIG. 23F shows overlay of averaged action potential current waveform (black) and fluorescent signal from Archon2 (blue), scaled to peak (from n=29 sweeps from one cell). FIG. 23G-I show quantification of electrical and optical full width at half maximum (FWHM; dashed lines connect data points from same neuron) (FIG. 23G), ΔF/F (FIG. 23H), and SNR (FIG. 23I) across all recordings (n=5 neurons from 2 mice), for action potentials. In FIG. 23G-I open circles represent individual neurons; in FIG. 23H-I bars indicated mean±standard derivation.

FIG. 24A-D provides photomicrograhic images of membrane localization of zArchon1 in larval zebrafish. Top frame (FIG. 24A) provides fluorescence image (GFP channel: excitation ($\lambda$ex) at 465 nm laser light, emission ($\lambda$em) at 527/50BP) of neurons expressing zArchon1-EGFP in the spinal cord of a zebrafish larva at 3 days post fertilization (dpf), acquired using spinning disk confocal microscopy (Nikon Ti equipped with X-Light V2Tp Confocal Imager). Boxes indicate neurons zoomed-in in the bottom panels (FIG. 24B-D). Scale bar: 125 FB, forebrain; MB, midbrain; HB, hindbrain. Bottom row shows, left (FIG. 24B); center (FIG. 24C); to right (FIG. 24D): high magnification images of the neurons highlighted in the boxes in the top panel, also in the GFP channel. Scale bar: 5 µm.

Figure 25A:
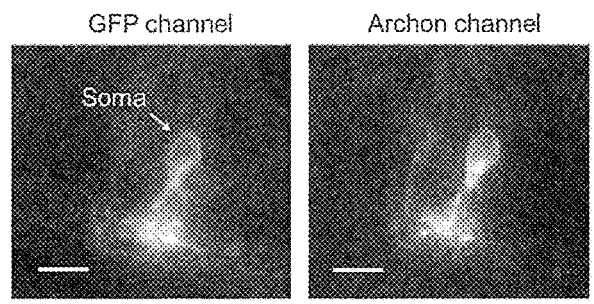
Figure 25B:
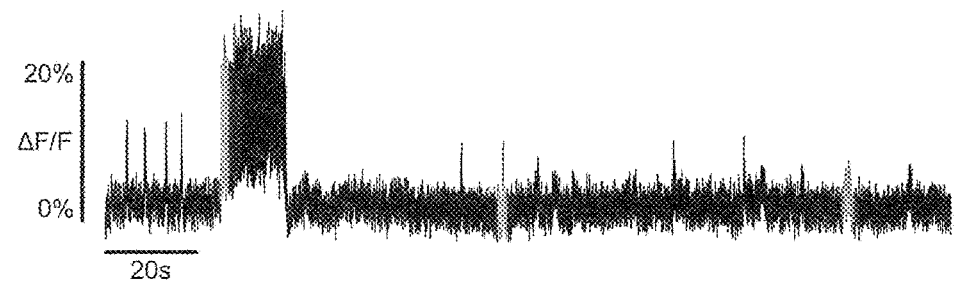
Figure 25C:
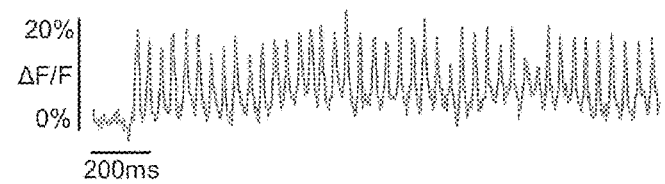
Figure 25D:
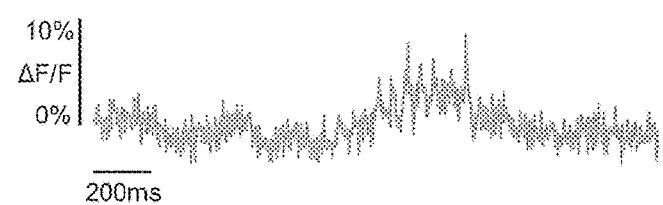
Figure 25E:
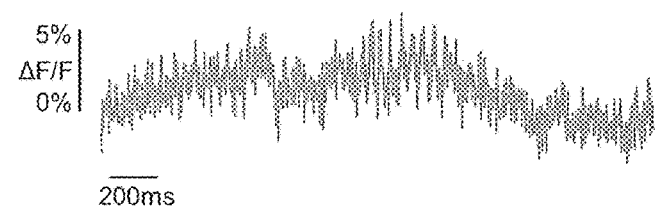

FIG. 25A-E shows result from subthreshold voltage imaging of zArchon1 in larval zebrafish. FIG. 25A provides an image of a neuron expressing zArchon1-EGFP in the spinal cord of a zebrafish larva at 4 days post fertilization (dpf) immobilized in agarose under wide-field microscopy in the GFP channel (left; excitation ($\lambda$ex) at 474/23BP from an LED, emission (λem) at 527/50BP) and the Archon channel (right; λex=637 nm laser light, λem=664 nm LP). Scale bar: 10 FIG. 25B provides a representative fluorescence trace of zArchon1-EGFP reporting spontaneous activity of the neuron shown in FIG. 25A. The trace was acquired at the soma of the neuron (λex=637 nm at 2.2 W/mm$^2$, λem=664 nm LP, image acquisition rate: 333 Hz). FIG. 25C-E show expanded views of the sections of FIG. 25B (FIG. 25 C shows expanded time scale of left-most grey region in FIG. 25B; FIG. 25D shows expanded time scale of middle grey region in FIG. 25B; and FIG. 25E shows expanded time scale of right-most grey region in FIG. 25B.

FIG. 26A-B shows a photomicrographic image and a graph illustrating photostability of zArchon1 in larval zebrafish. FIG. 26A is an image [excitation (λex) at 637 nm laser light, emission (λem) at 664 nm LP, the Archon channel] of a neuron expressing zArchon1 in a zebrafish larva at 4 days post fertilization (dpf) immobilized in agarose under wide-field microscopy. Scale bar: 10 FIG. 26B shows a representative fluorescence trace of zArchon1 reporting spontaneous activity of the neuron shown in FIG. 26A. The trace was acquired at the soma of the neuron over 300 seconds of continuous illumination (λex=637 nm laser light at 2.2 W/mm$^2$, λem=664 nm LP; image acquisition rate: 25 Hz).

FIG. 27A-F provides photomicrographic images showing membrane localization of wArchon1 in *C. elegans*. FIG. 27A-F provides representative fluorescence images of *C. elegans* expressing wArchon1 in AVA neurons. FIG. 27D-F provides magnified views of the AVA neuron somas in the boxed regions of FIG. 27A-C, respectively. The fluorescence images were acquired using 637 nm laser light excitation and a 664 nm LP emission filter. Scale bars, 20 µm.

FIG. 28A-C provides graphs illustrating optimization of calcium phosphate transfection conditions for expression of gene libraries in HEK293T cells. FIG. 28A is a bar graph showing transfection efficiency of a series of DNA mixtures containing pEGFP-N1, pmCardinal-N1 and pUC19 plasmids in ratios 1:0:0, 0:1:0, 0.5:0.5:0, 0.25:0.25:0.5, 0.05: 0.05:0.9, 0.005:0.005:0.99, 0.0005:0.0005:0.999, and 0.00005:0.00005:0.9999, respectively, upon delivery into HEK293T cells using calcium phosphate protocol. The plot represents transfection efficiency (percentage of FP-expressing cells; black bars, "Total"), including cells expressing both FPs (cross hatched bars, "Double expressors") and just one FP (either EGFP or mCardinal; open bars, "Single expressors"; n=6 transfected samples from two cultures). FIG. 28B is a graph showing kinetics of EGFP expression in HEK293T cells upon calcium phosphate transfection of pEGFP-N1 plasmid with no dilution (open circles, solid line; n=4 transfected samples from the same culture passage) and 100-fold dilution with pUC19 plasmid (open triangles, dashed line; n=4 transfected samples from the same culture passage). The 0 time point corresponds to time of the transfection performed. FIG. 28C is a bar graph showing distribution of nucleotide mutation counts in the gene of the RpBphP1 PAS-GAF domains recovered from HEK293T cells transfected with the gene library using our calcium phosphate transfection protocol (see Results section in Examples section for additional detail).

FIG. 29A-B provides details of genetically encoded voltage sensors. FIG. 29A provides information on certain characteristics of genetically encoded fluorescence voltage sensors. FIG. 29A includes reference letters [a]-[n] which are described below. Voltage sensors tested in brain tissues (organotypic or acute brain slice) and live animals with single cell resolution are included (unless they were shown to be exceeded in specifications by a more recent reporter [St-Pierre, F. et al. (2014) Nat. Neurosci. 17, 884-91; Tsutsui, H. et al. (2013) J Physiol 591, 4427-4437; Akemann, W. et al. (2012) J Neurophysiol 108, 2323-2337; and Zou, P. et al. (2014) Nat. Commun. 5, 4625] Quasar1 was also included. Sensors highlighted in red and green are based on opsins (excitation at ~640 nm for QuasAr2, 655 nm for Archer1 and 637 nm for Archon1 and Archon2) and GFP-like proteins (excitation at 488-505 nm), respectively. Data from references and this study were measured in neuronal culture if not specified. Some data from references were estimated from plots/traces in papers. Data highlighted in grey were obtained in this study. Numbers shown for measurements from this study are mean±standard deviation. In this study, ΔF/F and on/off kinetics were measured in neuronal cultures at 32° C. (n=11, 8, 10, 9, 17 neurons for QuasAr2, Archer1, Archon1, Archon2 and Ace2N-4aa-mNeon, respectively). [a] Brightness of red voltage sensors expressed in neurons were expressed as a percentage relative to QuasAr2 (i.e., 100%=QuasAr2; n=18, 16, 23, 23 neurons for QuasAr2, Archer1, Archon1 and Archon2, respectively; imaging condition, $\lambda_{ex}$=637 nm at 800 mW/mm$^2$ and $\lambda_{em}$=664 nm LP for all constructs). [b] Values represent fluorescence change between baseline fluorescence at−70 mV and steady-state fluorescence at +30 mV during 100 mV voltage step. [c] Imaging condition described in $\tau_{fast}$ section used throughout the measurement of on and off kinetics of each sensors. [d] In this study, voltage kinetics was evaluated by bi-exponential fitting, $F(t)=A\times(C\times exp(-t/\tau_{fast})+(1-C)\times exp(-t/\tau_{slow}))$, where C represent % of magnitude in $\tau_{fast}$ component. [e] Light intensity used for bleaching tests in this study was adjusted to have the same initial signal-to-noise ratio (SNR) of action potentials (25±8, 26±12, 26±10, 26±10 and 28±7 for Quasar2, Archer1, Archon1, Archon2 and Ace2N-4aa-mNeon, respectively; n's are as in FIG. 2N); see Methods section in Examples for hardware configuration used for these experiments for each construct. [f] Steady state value is the photocurrent during the time when the first derivative of photocurrent with respect to time reaches zero immediately after the time point of the transient peak value. [g] Transient peak value is the maximum of absolute photocurrent at the start and/or the end of illumination. [h] Data for 100 mV voltage step was acquired only in HEK cells in the original manuscript. [i] Subsequent peak currents were measured in the reference$_4$ by applying repetitive pulses of light with same intensity separated by dark recovery periods of a few seconds. Duration of peak currents was not shown in the paper. [j] Light intensity was adjusted to prevent signal saturation. ΔF/F did not depend on light intensity. [k] Subsequent peak currents were measured in this study by applying repetitive pulses of light with same intensity separated by dark recovery periods of a few seconds. [1] The difference in steady-state and peak fluorescence changes relative baseline for Ace2N-mNeon and Ace2N-4aa-mNeon are due to hysteric behavior in response to a voltage step. [m] 475 nm illumination efficiently excited green fluorescence of mNeonGreen$_{11}$ in the Ace2N-4aa-mNeon fusion protein allowing to achieve similar signal-to-noise ratio for action potentials imaging as for other voltage sensors tested in this study (see above). [n] Photobleaching rate of Ace2N-4aa-mNeonGreen measured in this study was slower than that reported in the original publication most likely due to slightly blue shifted excitation wavelength used for imaging (475 nm vs 505 nm) [Gong, Y. et al. (2015) Science 350(6266):1361-6].

FIG. 29B provides information on certain genetically encoded fluorescence voltage sensors in brain tissues and live animals. Sensors from FIG. 29A, excluding Quasar1 because it was not used in intact brain tissues, and including ASAP2f which had been used in *Drosophila* but not extensively characterized in culture. Sensors highlighted with red and green are based on opsins (excitation at ~637 nm) and GFP-like proteins (excitation at 488-505 nm), respectively. Some data from references was estimated from plots/traces in the papers. Data highlighted with grey was obtained in this study. Numbers shown for our measurements are mean±standard deviation. [a] Values represent fluorescence change between baseline fluorescence at −70 mV and steady-state fluorescence at +30 mV during 100 mV voltage step. [b] Method to calculate SNR was not specified in the paper. [c] Estimated from traces presented in the corresponding paper. [d] SNR defined as $\Delta F/F \times \sqrt{\overline{F}}$ where $\overline{F}$ is a pixel's mean baseline fluorescence emission rate.

Brief Description of Certain of the Sequences

SEQ ID NO: 1 is amino acid sequence of Archon1
MVSIALQAGYDLLGDGRPESLWLGIGTLLMLIGTFYFLVRAWGETDKDAR
EYYAVTILVSGIASAAYLSMFFGIGlTEVPVGGEMLNIYYARYAQWLFTT
PLLLLHLALLAKVDRVTIGTLVGVDALMIVTGLIGTLSHTAIARYSWWLF
STICMIVVLYVLATSLRSAAKERGPEVASTFNILTALVLVLWTAYPIIWI
IGTEGAGVVGLGIETLLFMVLDVTAKVGFGFILLRSRAILQDTEAPEPSA
GAD.

SEQ ID NO 2 is amino acid sequence of Archon2
MVSIALQAGYDLLGDGRPETLWLGIGTLLMLIGTFYFLVRGWGVTDKDAR
EYYAVPILVSGIASAAYLSMFFGIGlTEVPVGGEMLDIYYARYAHWLFST
PLLLLLDLALLAKVDRVIIGTLVGVDALMIVTGLIGALSHTAIARYSWWLF
STICMIVVLYVLATSLRSAAKERGPEVASTFNILTALVLVLWTAYPIIWI
IGTEGAGVVGLGIETLLFMVLDVTCKVGFGFILLRSRAILGDTEAPEPSA
GAD.

SEQ ID NO: 3 is amino acid sequence of Variant#3
also referred to herein as Var#3
MVSIALQAGYDLLGDGRPEILWLGIGTLLMLIGTFYFLVRGWGVTDKDAR
EYYAVTILVSGIASAAYLSMFFGIGlTEVSVGGEMLDIYYARYAEWLFCT
PLLLLLDLALLAKVDRVIIGTLVGVDALMIVTGLIGALSHTAIARYSWWLF
STICMIVVLYVLATSLRSAAKERGPEVASTFNILTALVLVLWTAYPIIWI
IGTEGAGVVGLGIETLLFMVLDVTGKVGFGFILLRSRAILGDTEAPEPSA
GAD.

SEQ ID NO: 4 is amino acid sequence of Variant#4
also referred to herein as Var#4
MVSIALQAGYDLLGDGRPEILWLGIGTLLMLIGTFYFLVRGWGVTDKDAR
EYYAVTILVSGLASAAYLSMFFGIGlTEVSVGGEMLDIYYARYAEWLFCT
PLLLLLDLALLAKVDRVIIGTLVGVDALMIVTGLIGALSHTAIARYSWWLF
STICMIVVLYVLATSLRSAAKERGPEVASTFNILTALVLVLWTAYPIIWI
IGTEGAGVVGLGIETLLFMVLDVTAKVGFGFILLRSRAILGDTEAPEPSA
GAD.

SEQ ID NO: 5 is amino acid sequence of Variant#5
also referred to herein as Var#5
MVSIALQAGYDLLGDGRPETLWLGIGTLLMLIGTFYFLVVRGWGVTDKDA
REYYAVPILVSGIASAAYLSMFFGIGlTEVPVGGEMLDIYYARYAHWLFT
TPLLLLHLALLAKVDRVIIGTLVGVDALMIVTGLIGALSHTAIARYSWWL
FSTICMIVVLYVLATSLRSAAKERGPEVASTFNILTALVLVLWTAYPIIW
IIGTEGAGVVGLGIETLLFMVLDVTAKVGFGFILLRSRAILGDTEAPEPS
AGAD.

SEQ ID NO: 6 is amino acid sequence of Variant#6
also referred to herein as Var#6
MVSIALQAGYDLLGDGRPETLWLGIGTLLMLIGTFYFVVRGWGVTDKDAR
EYYAVPILVCGIASAAYLSMFFGIGlTEVPVGGEMLDIYYARYAHWLFTT
PLLLLLDLALLAKVDRVTIGTLVGVDALMIVTGLIGALSHTAIARYSWWLF
STICMIVVLYVLATSLRSAAKERGPEVASTFNTLTALVLVLWTAYPIIWI
IGTEGAGVVGLGIETLLFMVLDVTCKVGFGFILLRSRAILGDTEAPEPSA
GAD.

Brief Description of Certain of the Sequences

SEQ ID NO: 7 is amino acid sequence of Variant#7
also referred to herein as Var#7
MVSIALQAGYDLLGDGRPETLWLGIGTLLMLIGTFYFLVRGWGVTDRDAS
GIASAAYLSMFFGIGITEVSVGGEMLDIYYARYAHWLFTTPLLLLDLALL
AKVDRVTIGREYYAVPILVTLVGVDALMIVTGLIGALSPTAIARYSWWLF
STICMIVVLYVLATSLRSAAKERGPEVASTFNILTALVLVLWTAYPIIWI
IGTEGAGVVGLGIETLLFMVLDVTGKVGFGFVLLRSRAILGDTEAPEPSA
GAD.

SEQ ID NO: 8 is amino acid sequence of aR2
MDPIALQAGFDLLNDGRPETLWLGIGTLLMLIGTFYFIARGWGVTDKEAR
EYYAITILVPGIASAAYLAMFFGIGVTEVELASGTVLDIYYARYADWLFT
TPLLLLLDLALLAKVDRVTIGTLIGVDALMIVTGLIGALSKTPLARYTWWL
FSTIAFLFVLYYLLTSLRSAAAKRSEEVRSTFNTLTALVAVLWTAYPILW
IVGTEGAGVVGLGIETLAFMVLDVTAKVGFGFVLLRSRAILGETEAPEPS
AGADASAAD.

SEQ ID NO: 9 is amino acid sequence of Arch
MDPIALQAGYDLLGDGRPETLWLGIGTLLMLIGTFYFLVRGWGVTDKDAR
EYYAVTILVPGIASAAYLSMFFGIGITEVTVGGEMLDIYYARYADWLFTT
PLLLLLDLALLAKVDRVTIGTLVGVDALMIVTGLIGALSIITAIARYSWWL
FSTICMIVVLYFLATSLRSAAKERGPEVASTFNTLTALVLVLWTAYPILW
IIGTEGAGVVGLGIETLLFMVLDVTAKVGFGFILLRSRAILGDTEAPEPS
AGADVSAAD.

SEQ ID NO: 10 is amino acid sequence of Archer1
MDPIALQAGYDLLGDGRPETLWLGIGTLLMLIGTFYFLVRGWGVTDKDAR
EYYAVTILVPGIASAAYLSMFFGIGITEVTVGGEMLDIYYARYAEWLFCT
PLLLLLDLALLAKVDRVTIGTLVGVDALMIVTGLIGALSHTAIARYSWWLF
STICMIVVLYFLATSLRSAAKERGPEVASTFNTLTALVLVLWTAYPFLWI
IGTEGAGVVGLGIETLLFMVLDVTAKVGFGFILLRSRAILGDTEAPEPSA
GAD.

SEQ ID NO: 11 is amino acid sequence of QuasAr1
MDPIALQAGYDLLGDGRPETLWLGIGTLLMLIGTFYFLVRGWGVTDKDAR
EYYAVTILVSGIASAAYLSMFFGIGITEVSVGGEMLDIYYARYAFIWLFT
TPLLLLHLALLAKVDRVTIGTLVGVDALMIVTGLIGALSHTAIARYSWWL
FSTICMIVVLYVLATSLRSAAKERGPEVASTFNTLTALVLVLWTAYPILW
IIGTEGAGVVGLGIETLLFMVLDVTAKVGFGFILLRSRAILGDTEAPEPS
AGAD.

SEQ ID NO: 12 is amino acid sequence of QuasAr2
MVSIALQAGYDLLGDGRPETLWLGIGTLLMLIGTFYFLVRGWGVTDKDAR
EYYAVTILVSGIASAAYLSMFFGIGITEVSVGGEMLDIYYARYAQWLFTT
PLLLLHLALLAKVDRVTIGTLVGVDALMIVTGLIGALSHTAIARYSVVWL
FSTICMIVVLYVLATSLRSAAKERGPEVASTFNTLTALVLVLWTAYPILW
IIGTEGAGVVGLGIETLLFMVLDVTAKVGFGFILLRSEAILGDTEAPEPS
AGAD.

SEQ ID NOs: 13-18 are set forth in FIG. 12, and include: Arch-7 (SEQ ID NO: 13); QuasAr-I#3 (SEQ ID NO: 14); QuasAr-I#7 (SEQ ID NO: 15); QuasAr-I#14 (SEQ ID NO: 16); QuasAr-I#16 (SEQ ID NO: 17); and QuasAr-I#22 (SEQ ID NO: 18).

SEQ ID NO: 19 is the DNA sequence of the 'ss' signal sequence from truncated MHC class I antigen:
gtcccgtgcacgctgctcctgctgttggcagccgccctggctccgactca
gacgcgggcc.

SEQ ID NO: 20 is the amino acid sequence of the 'ss' signal sequence from truncated MHC class I antigen:
MVPCTLLLLLAAALAPTQTRA.

SEQ ID NO: 21 is the DNA sequence of the ER export sequence (also referred to herein as ER2":
ttctgctacgagaatgaagtg.

SEQ ID NO: 22 is the amino acid sequence of the ER export sequence (also referred to herein as "ER2":
FCYENEV.

-continued

Brief Description of Certain of the Sequences

SEQ ID NO: 23 is the DNA sequence of KGC, which is
a C terminal export sequence from the potassium
channel Kir2.1:
aaatccagaattacttctgaaggggagtatatccctctggatcaaataga
catcaatgtt.

SEQ ID NO: 24 is the amino acid sequence of KGC,
which is a C terminal export sequence from the
potassium channel Kir2.1:
KSRITSEGEYIPLDQIDINV.

SEQ ID NO: 25 is the DNA sequence of a prolactin
signal sequence (also referred to herein as "Prl":
gacagcaaaggttcgtcgcagaaagggtcccgcctgctcctgctgaggtg
gtgtcaaatctactcttgtgccagggtgtggtctccacccccgtc.

SEQ ID NO: 26 is the amino acid sequence of a
prolactin signal sequence (also referred to
herein as "PrI":
MDSKGSSQKGSRLLLLLVVSNLLLCQVVS.

SEQ ID NO: 27 is an amino acid sequence of a
prolactin signal sequence:
DSKGSSQKGSRLLLLLVVSNLLLCQGVVSTPV.

DETAILED DESCRIPTION

The invention in some aspects relates to voltage reporter molecules that can be used in methods to detect voltage levels and changes in voltage levels across membranes. Voltage reporter polypeptides of the invention display voltage-sensitive fluorescence and thus, the fluorescence of a voltage reporter polypeptide of the invention can be assessed to determine a level or change in level of voltage across a cell membrane. In a non-limiting example, voltage sensor polypeptides of the invention can be used for high-speed optical imaging of neural activity with single cell resolution in intact brain circuits. Voltage sensor polypeptides of the invention can be used in cell culture, in vitro preparations and well as in in vivo settings. Some aspects of the invention include use of the voltage reporter molecules for high speed optical imaging of voltage and voltage changes in cells. Embodiments of methods of the invention can be used to image neural activity with single cell resolution in intact brain circuits.

Voltage reporter polypeptides of the invention have characteristics that distinguish them from prior detection molecules. One such characteristic is the high level of photostability of voltage reporter polypeptides of the invention. For example, though not intended to be limiting, a voltage reporter polypeptide of the invention, referred to herein as Archon1, exhibits almost no photobleaching over timescales relevant to a diversity of behavioral and physiological experiments, whereas prior sensors capable of reporting neuronal activity at single cell resolution, exhibited significant photobleaching. Archon1 was determined to retain 95±16% of its baseline fluorescence versus all other voltage sensors only retained ~50% or less, over continuation illumination of several minutes, see FIG. 29A-B.

Another distinguishing characteristic of voltage reporter molecules of the invention, versus prior reporter molecules, is their ability to detect subthreshold events with single spike resolution. For example, though not intended to be limiting, Archon1 can be used to detect subthreshold events with single spike resolution in an intact brain circuit, which has not been achieved by any other voltage sensors to date. Yet another characteristic of voltage reporter molecules of the invention that distinguishes them from prior reporters is their compatibility for use with optogenetic tools. For example, though not intended to be limiting, Archon1 has demonstrated all-optical electrophysiology, incorporation of neuronal activity control via optogenetic tools and optical imaging of the activity via Archon voltage reporter. This high level of compatibility with other optogenetic tools is due, in part, to the negligible spectral overlap between optogenetic tools and Archon reporter molecules of the invention.

Voltage reporter molecules of the invention include genetically encoded voltage reporter molecules, which, when expressed in a membrane, alter their own fluorescence intensity in proportion to alternations in transmembrane potential of the membrane. In certain embodiments of the invention, Archon1 and other voltage reporter polypeptides of the invention can be used in methods that provide a direct way to observe millisecond-timescale dynamics of neuronal activity in defined cells or at defined points within cells such as neurons or other cells. Non-limiting means to express voltage reporter polypeptides of the invention in cells are via virus injection, electroporation of plasmid DNA, and micro injection of plasmid DNA into embryos, wherein the DNA comprises DNA encoding the voltage reporter polypeptide of the invention.

Methods to prepare and express a voltage reporter polypeptide of the invention in a cell, and in a subject, are described herein and also may include art-known methods to deliver and express genetically encoded fluorescent indicator molecules. Additionally, methods to select and apply a suitable wavelength of light to a cell in which a voltage reporter polypeptide of the invention is expressed, and means of monitoring fluorescence emission by a voltage reporter polypeptide expressed in a cell are provided herein and may also include art-known methods of illumination and imaging/monitoring. As used herein, the terms "signal" and "signaling", used in reference to a voltage reporter polypeptide of the invention is the fluorescent emission of the voltage reporter polypeptide. In certain aspects of the invention wavelengths of light may be applied to a cell or cells in which one or more independently selected voltage reporter polypeptides of the invention are expressed thereby permitting monitoring fluorescence of the different voltage reporter polypeptides of the invention. In certain embodiments of the invention, one voltage reporter polypeptide of the invention may require a different wavelength of light than another voltage reporter polypeptide of the invention. Methods of determining illumination variables and of delivering illumination to cells, tissues, and in subjects are well-known in the art and representative methods can be found in publications such as: Maclaurin, D. et al., (2013) PNAS, vol. 110, no. 15:5939-5944; Hochbaum, D. R. et al., (2014) Nature Methods 11, 825-833; Flytzanis, N.C., et al., (2014) Nature Communications 5:4894, the content of each of which is incorporated herein by reference in its entirety.

Archon1, Archon2, and other voltage reporter polypeptides of the invention have been developed using a directed molecular evolution approach based on microscopy-guided robotic cell picking so that different characteristics and properties, such as those described herein, could be simultaneously optimized for a single fluorescent voltage reporter. The opsin-based fluorescent voltage reporter Archon1 has now been shown to exhibit good localization in neurons of multiple species as compared to previous opsin-based reporters. Embodiments of voltage reporter polypeptides of the invention have been demonstrated as having several fold improvements in voltage sensitivity and photobleaching as compared to prior GFP-based reporters. Certain embodiments of voltage reporter polypeptides of the invention have demonstrated an increased compatibility with optogenetic control, versus that of prior sensor molecules. Activity and characteristics of embodiments of voltage reporter polypeptides of the invention, including, but not limited to Archon1, have been demonstrated using methods such as imaging spiking and millivolt-scale subthreshold and synaptic activity in various cell types and animal models, including but not limited to: imaging subthreshold (e.g., ~5 mV) synaptic activity in mouse cortical brain slices, high speed spiking and subthreshold activity in the larval zebrafish brain, and neural responses synaptically downstream of optogenetically controlled neurons in C. elegans.

To develop a fluorescent voltage reporter for use in multiple voltage detection contexts, a directed molecular evolution approach was developed that enabled multiple properties of a fluorescent voltage reporter to be simultaneously optimized. In particular, robotic cell picking was adapted and used for the isolation of single mammalian cells expressing individual members of a large library of fluorescent voltage reporter candidates, based upon three parameters—brightness, localization, and voltage sensitivity. Resulting fluorescent voltage reporters of the invention, a non-limiting example of which is Archon1, have been shown to exhibit good performance along multiple dimensions of parameters desired in a fluorescent voltage reporter—good localization, high signal-to-noise ratio, large and linear fluorescent changes, high speed of response, reduced photobleaching, and full compatibility with optogenetic control. Embodiments of voltage reporter polypeptides of the invention are also several-fold brighter than previous opsin-based fluorescent voltage reporters. The voltage reporter polypeptide, Archon1, and other voltage reporter polypeptides of the invention are practical voltage reporters suitable for use in a wide range of applications. The terms "sensor" and "reporter" are used interchangeably herein in reference to molecules of the invention, which may be referred to as voltage reporter molecules or voltage sensor molecules herein.

Embodiments of voltage reporting polypeptides of the invention may be expressed in a membrane of a cell, for example in the plasma membrane of the cell. A voltage reporting polypeptide of the invention can be expressed in a cell as an integral membrane protein and can be used to detect voltage and voltage changes across the membrane. A voltage reporter polypeptide of the invention emits endogenous fluorescence that is modulated by voltage levels across a membrane in which the reporter polypeptide of the invention is expressed. In certain embodiments of the invention, a voltage reporter polypeptide of the invention can be expressed in a cell membrane and its fluorescence monitored to assess changes in membrane voltage through individual neurons, through two or more neurons in one or more of physical and chemical communication with each other, and also throughout a population of neurons.

Examples of voltage reporter molecules that have now been identified are: Archon1, Archon2, Variant #3, Variant #4, Variant #5, Variant #6, and Variant #7, which are set forth herein as SEQ ID NOs: 1-7, respectively. Certain embodiments of voltage reporter polypeptides of the invention are functional variants of one or more of Archon1 and Archon 2. In some embodiments of the invention, a voltage reporter polypeptide is a functional variant of one or more of SEQ ID NOs: 3-7. The invention in some aspects relates to novel voltage reporter polypeptides and nucleic acid sequences that encode the polypeptides. In addition, the invention includes methods of using voltage reporter molecules of the invention for one or more of monitoring, detecting, measuring, and assessing a voltage in a cell and one or more changes in voltage in a cell. Some aspects of the invention include methods of incorporating one or more voltage reporter polypeptide of the invention into at least one target cell membrane, the voltage reporter polypeptide functioning to assess voltage across the cell membrane and/or transmembrane passage of ions in the cell.

The invention comprises methods for expressing the voltage reporter polypeptides in one or more genetically targeted cells, which permits detection of millisecond-timescale voltage changes and currents in the one or more cells. The voltage reporter polypeptides of the invention can be genetically expressed in specific cells (e.g., using a virus, vector, or other means for delivery) and then used to assess voltages changes in cells in intact organisms (including humans) as well as cells in vitro. Voltage reporter polypeptides of the invention can be expressed in cell membranes of specific cells, tissues, and/or organisms and the voltage-sensitive fluorescence of the reporter polypeptides can be determined as a measure of one or more of: a voltage state of a cell, a voltage change in a cell, ion flux across the cell membrane, proton flux across the cell membrane, and excitation in the cell in which the voltage reporter of the invention is expressed. In some aspects of the invention, the voltage reporter polypeptide comprises the sequence set forth as SEQ ID NO: 1 or a functional variant thereof. In certain aspects of the invention, the voltage reporter polypeptide comprises the sequence set forth as SEQ ID NO: 2 or a functional variant thereof. In certain aspects of the invention two or more different voltage reporter polypeptides of the invention are expressed in a cell, tissue, or organism.

Molecules, Expression, and Functions

Voltage reporter polypeptides of the invention comprise a voltage-sensitive portion and a fluorophore. As used herein, the fluorophore is also referred to as the "fluorescent component" or "fluorescent portion" of the voltage reporter molecule. The voltage sensitivity permits use of a voltage reporter polypeptide to determine voltage change or conductance across a membrane in which the polypeptide is expressed. A change in voltage across a membrane in which a voltage reporter polypeptide of the invention is expressed modulates absorption in the voltage reporter polypeptide. This modulation alters the fluorescence emission of the voltage reporter polypeptide. Thus, determination of fluorescence emission of the voltage reporter polypeptide identifies the status of, and changes in, voltage across the membrane. When a voltage reporter polypeptide of the invention is expressed in a cell membrane, a modulation of voltage across the membrane alters the fluorescence emitted by the reporter. This alteration permits use of voltage reporter polypeptides of the invention to be used to indicate the voltage state of a cell, a change in voltage across a cell membrane, the lack of change across a cell membrane, etc. As used herein the term: "voltage state" when used in reference to a cell, can mean one of more of: depolarization of the cell, hyperpolarization of the cell, a voltage level in the cell, etc.

Depolarization and hyperpolarization of a cell in which a voltage reporter polypeptide of the invention is expressed, each result in a change in the fluorescence emission of the voltage reporter polypeptide and the fluorescence emission changes indicate the voltage state of the cell. The invention includes, in part, methods comprising expressing a voltage reporter polypeptide in a cell, determining one or more changes in fluorescence of the expressed voltage reporter polypeptide, and assessing one or more characteristics of a voltage change in the cell based on the determined change in fluorescence. Non-limiting examples of characteristics of voltage changes in a cell that can be assessed using methods of the invention are: the type of voltage change, speed of voltage change, direction (increase or decrease) of voltage change, size or amplitude of voltage change, and duration of the voltage change in the cell.

Conduction of ions and/or protons across a membrane of a cell in which a voltage reporter polypeptide of the invention is expressed may also be referred to herein as one or more of the conductivity of the membrane and voltage across the membrane. As used herein, a change in conductivity of the membrane and/or a change in voltage across a membrane may be an increase or decrease in conductivity or voltage, respectively. In certain aspects, voltage reporter polypeptides of the invention can be used for one or more of determining, measuring, assessing, quantifying alternations or changes in one or more of the conductivity of the membrane and the voltage across the membrane in which the voltage reporter polypeptide is expressed. The terms "conductance" and "conductivity" may be used interchangeably herein in reference to the movement of one or more of "charge", protons, and ions across a membrane.

A voltage reporter polypeptide of the invention can be used to assess ion conductance, depolarization, and hyperpolarization in a cell in which it is expressed. As will be understood by those in the art the term "depolarized" used in the context of a cell means an upward change in the voltage in the cell. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold, an action potential (e.g. a spike) results. It will be understood by those in the art that the term: "hyperpolarized" used in the context a cell means a downward change in the cell's membrane potential and voltage such that it becomes more negative, which is the opposite of the depolarization characteristics in a cell. Hyperpolarization of a cell inhibits the occurrence of action potentials in the cell by increasing the stimulus that is necessary to move the membrane potential up to the action potential threshold.

Expression of Voltage Reporter Molecules

In certain aspects of the invention, a voltage reporter polypeptide can be expressed in a cell in methods to determine a baseline voltage level or characteristic of the voltage state and subsequent determinations of fluorescence of the voltage reporter polypeptide in the cell can be compared and/or used to assess an effect of one or more changes to a cell and/or its environment. For example, assessing changes to a cell may include contacting a first cell comprising the voltage reporter polypeptide, or contacting a second cell that is in communication with the first cell, with one or more test agents. As used herein a test agent can be: an electrical stimulation, a candidate compound, a pharmaceutical compound, etc. As used herein, the term "communication with" used in reference to a cell expressing a voltage reporter polypeptide of the invention, includes cells, for example that influence the cell comprising the voltage reporter polypeptide, via neurotransmitter means, electrical means, etc. Communication can be direct communication from a cell immediately (directly) upstream from the cell that expresses the voltage reporter polypeptide, or can be indirect communication, such as the result of activity of a cell further (indirectly) upstream that impacts voltage in the cell in which the voltage reporter polypeptide is expressed. Stimulation of one or more of a cell directly upstream and a cell indirectly upstream may result in a voltage change in the cell expressing the voltage reporter polypeptide and such changes can be assessed using methods of the invention.

Methods and voltage reporter molecules of the invention can be used to assess one or more changes in: (1) an internal environment of a cell, (2) an external environment of a cell, (3) an internal environment of an upstream cell, and (4) an external environment of an upstream cell. Non-limiting examples of events and situations that may change in a cell's internal or external environment include, a disease or injury condition in the cell or subject comprising the cell, contact of the cell with a test agent or compound, contact of the cell with a pharmaceutical agent or compound, a surgical procedure in the subject, contact of the cell with radiation, light, electric stimulation, etc. Other types of events and actions that alter the internal or external environment of a cell are known in the art, and can also be assessed using methods and voltage reporter molecules of the invention.

Voltage reporter polypeptides of the invention can be used to detect and assess depolarization in excitable cells in which one or more voltage reporter polypeptides of the invention are expressed. In some embodiments, a voltage reporter polypeptide of the invention, is expressed in a sub-population of cells in a cell population that also includes one or more additional subpopulations of cells in which a different voltage reporter polypeptide is expressed. The two voltage reporter polypeptides may have the same or different characteristics, non-limiting examples of which are: sensitivity to voltage changes, speed of reaction to voltage changes, brightness levels, photobleaching levels, etc. The expression of voltage reporter polypeptides having one or more different characteristics in distinct, separate, subpopulations in a cell population can permit multiple determinations of changes in voltage in cells in the population by assessing the different characteristics of the expressed voltage reporter polypeptides. Thus, some embodiments of the invention include methods of using two or more different, independently selected voltage reporter polypeptides of the invention to assess voltage changes in a mixed population of cells. In a non-limiting example of a combined expression strategy, an Archon1 polypeptide can be expressed in a set of cells in a tissue, culture, or subject and an Archon2 voltage reporter polypeptide can be expressed in another set of cells in the tissue, culture, or subject. Different characteristics of Archon1 and Archon2 can permit determination of effects of environmental changes on cells in the tissue, culture, or subject. For example, though not intended to be limiting, fluorescence emission by an Archon1 polypeptide expressed in a cell may change in response to a smaller amplitude voltage change in the cell in which it is expressed, than the amplitude of voltage change necessary to alter fluorescence emission of an Archon2 polypeptide expressed in a cell. This difference, and other different characteristics of voltage reporter polypeptides of the invention, may be used to assess voltage in different cells, and in sub-populations of cells in the same tissue, culture, subject, and/or system.

Voltage reporter polypeptides of the invention are well suited for targeting cells, expression in cell membranes, and for use to detect and assess voltage-associated cell activities. In some embodiments, a voltage reporter polypeptide of the invention can be utilized to detect one or more of ion flux and proton flux across cell membranes, thus for assessment of endogenous signaling pathways (such as calcium dependent signaling, etc.), and then putative modulatory compounds can be applied to the cell in which the voltage reporter is expressed, or to a cell upstream of that cell, and monitoring the voltage reporter can be used to determine the effect on voltage in the cell(s). Thus, certain aspects of the invention include methods of using voltage reporter polypeptides of the invention to screen putative therapeutic agents, known therapeutic agents, combinations of two or more independently selected known and putative therapeutic agents. One or more voltage reporter polypeptides of the invention can also be used in methods to assess the effect of internal cellular conditions, environmental conditions external to the cell, and to assess the result diseases, injuries, treatments, etc. on cell voltage and voltage changes.

Molecules and Compounds

The present invention, in part, includes novel voltage reporter polypeptides, their expression in cell membranes, and their use to determine alterations in one or more of: ion flux across the membrane, proton flux across the membrane, and voltage change in the cell in which they are expressed. Embodiments of the invention include voltage reporter polypeptides set forth as SEQ ID NO: 1-7 and their encoding polynucleotides, functional variants of SEQ ID NOs: 1-7 and their encoding polynucleotides, compositions comprising the voltage reporter molecules or functional variants thereof, and methods of using the voltage reporter molecules and/or functional variants to determine one or more voltage states in a cell. Non-limiting examples of voltage reporter polypeptides of the invention are set forth as: Archon1 (SEQ ID NO: 1) and Archon2 (SEQ ID NO: 2). Additional examples of voltage reporter polypeptides of the invention are provided herein as: Var #3 (SEQ ID NO: 3), Var #4 (SEQ ID NO: 4), Var #5 (SEQ ID NO: 5), Var #6 (SEQ ID NO: 6), and Var #7 (SEQ ID NO: 7). Aspects of the invention also include additional functional variants of SEQ ID NOs: 1 and 2, their encoding polynucleotides, compositions comprising the functional variants, and methods of using the functional variants to determine one or more voltage states in a cell.

Certain embodiments of sequences of polypeptides and polynucleotides of the invention are described herein. It is understood that the terms: voltage reporter molecules, voltage reporter polypeptides, and voltage reporter polynucleotides encompass molecules, polypeptides, and polynucleotides, respectively, described herein, as well as functional variants thereof. The invention also includes compounds and compositions that comprise one or more voltage reporter molecules of the invention. A compound or composition that comprises a voltage reporter molecule of the invention may include only the voltage reporter molecule or may include one, two, three, four, five, six, or more additional elements. Non-limiting examples of additional elements are: a vector, a promoter, a detectable label sequence, a trafficking sequence, a delivery molecule sequence, an additional voltage reporter molecule sequence, an additional sequence, etc. The term "voltage reporter molecule" is used herein in reference to voltage reporter polypeptides and/or encoding voltage reporter polynucleotides.

Some embodiments of the invention include functional variants of one of more of Archon1, Archon2, and Variant #3, Variant #4, Variant #5, Variant #6, and Variant #7. For example, one or more positions in a voltage reporter polypeptide sequence of the invention such as one of SEQ ID NOs: 1-7 may be modified to prepare a functional variant. Some aspects of the invention include methods of preparing and using polynucleotide molecules (which may also be referred to herein as "genes") having nucleic acid sequences that encode a voltage reporter polypeptide of the invention.

The invention, in part, also includes nucleic acid sequences that encode voltage reporter polypeptides of the invention, vectors, and constructs comprising the encoding nucleic acid sequences. A construct of the invention may also include nucleic acid sequences that encode one or more of a trafficking molecule, a fluorescent molecule, or other label or desired molecule.

A functional variant of a voltage reporter polypeptide of the invention comprises a modified sequence of the voltage reporter polypeptide of the invention from which it is derived. As used herein the term "modified" or "modification" in reference to a polypeptide sequence refers to a change of one, two, three, four, five, six, or more amino acids in the sequence as compared to the sequence from which it was derived. For example, the amino acid sequence of a functional variant of an Archon1 polypeptide may be identical to the amino acid sequence set forth as SEQ ID NO: 1, except the functional variant has one, two, three, four, five, or more amino acid substitutions, deletions, insertions, or combinations thereof.

It will be understood that sequences of a functional variant of a voltage reporter polypeptide of the invention may be considered to be derived from more than one of SEQ ID NOs: 1-7 set forth here, due to sequence similarity between one or more of SEQ ID NOs: 1, 2, 3, 4, 5, 6, and 7 as set forth herein. For example, a functional variant that has 96% sequence identity to the sequence of Archon1 (SEQ ID NO: 1), may have at least 90%, 95%, 96%, 97%, 98%, 99%, or 100% sequence identity to the amino acid sequence of one or more of Archon2, Var #3, Var #4, Var #5, Var #6, and Var #7, as set forth herein. Using standard sequence alignment methods one of ordinary skill in the art can align sequences for Archon1, Archon2, and Var #3-Var #7 provided herein to determine correspondence of one or more amino acid residues of one sequence with the one or more residues in an aligned sequence. Thus, as a non-limiting example, one skilled in the art can ascertain that residue position 118, which is an "I" in the Archon2 sequence set forth as SEQ ID NO: 2, corresponds to position 118, which is also an "I" in the Var #3 sequence set forth as SEQ ID NO: 3, and corresponds to position 118, which is a "T" in the Archon1 sequence set forth herein as SEQ ID NO: 1.

Routine sequence alignment methods and techniques can be used to align two or more voltage reporter polypeptide sequences, including but not limited to sequences specifically disclosed herein, sequences described herein, and modified sequences derived from such sequences, thus providing a means by which a corresponding location of a modification made in one voltage reporter polypeptide can be identified in another voltage reporter polypeptide sequence. Amino acid sequences of voltage reporter polypeptides of the invention can be aligned with amino acid sequences of one or more other candidate voltage reporter polypeptides, to aid in identifying corresponding positions for sequence modifications such as substitutions, additions, deletions, etc., that can be based, at least in part, on the sequence alignments.

In some embodiments of the invention, certain substituted voltage reporter polypeptides and their encoding polynucleotides are excluded as voltage reporter molecules of the invention. For example, known polypeptides: Ar2, which is set forth herein as SEQ ID NO: 8; Arch, which is set forth herein as SEQ ID NO: 9; Archer1, which is set forth herein as SEQ ID NO: 10; QuasAr1, which is set forth herein as SEQ ID NO: 11; QuasAR2, which is set forth as SEQ ID NO: 12; and Arch-7, which is set forth as SEQ ID NO: 13. In some aspects of the invention, a voltage reporter polypeptide does not have at least 96%, 97%, 98%, 99%, or 100% amino acid sequence identity to one or more of the sequences set forth herein as SEQ ID NOs: 8-13.

In certain embodiments of the invention, amino acids at particular positions (in reference to corresponding to residue positions of the sequence from which they are derived) are not modified from that of the amino acid sequence from which they are derived, which may also be referred to herein as the "parent sequence". In some aspects of the invention, an amino acid present in a position corresponding to a residue position in Archon1 (SEQ ID NO: 1) is not modified and is the same residue as that in the corresponding position in SEQ ID NO: 1. In some aspects of the invention, 1, 2, 3, 4, 5, 6, 7, 8, 9, 10, or 11 of the 97W, 129M, 133G, 149W, 152S, 153T, 156M, 193W, 196Y, 197P, and 227K residue position numbers and amino acids that are present in Archon1 (SEQ ID NO: 1), are the same in the corresponding residue position in another voltage reporter polypeptide of the invention. In certain embodiments of the invention all of the amino acids and residue positions: 97W, 129M, 133G, 149W, 152S, 153T, 156M, 193W, 196Y, 197P, and 227K are the same in the residue positions in a voltage reporter polypeptide that correspond to these positions in SEQ ID NO: 1. In some aspects of the invention, 1, 2, 3, or 4 of the amino acids and residue positions: 94Y, 198I, 200W, 223D are the same in the residue positions in a voltage reporter polypeptide that correspond to these positions in SEQ ID NO: 1.

In some aspects of the invention, an amino acid present in a position corresponding to a residue position in Archon1 (SEQ ID NO: 1) is modified and is not the same residue as that in the corresponding position in SEQ ID NO: 1. For example, a voltage reporter polypeptide of the invention may include "I" in the position corresponding to residue 118 in Archon1, which is T118 in Archon1, as set forth in SEQ ID NO: 1. Non-limiting examples of positions and modifications that that can be made in the sequence of Archon1, and that result in the derived sequence retaining a level of function as a voltage reporter polypeptide of the invention, are indicated in the alignment of SEQ ID NOs: 1-7, as shown in FIG. 14.

Certain embodiments of the invention include polynucleotides comprising nucleic acid sequences that encode a voltage reporter polypeptide of the invention, and some aspects of the invention comprise methods of delivering and/or using such polynucleotides in cells, tissues, and/or organisms. Voltage reporter polynucleotide sequences and amino acid sequences used in aspects and methods of the invention may be "isolated" sequences. As used herein, the term "isolated" used in reference to a polynucleotide, nucleic acid sequence, polypeptide, or amino acid sequence means a polynucleotide, nucleic acid sequence, polypeptide, or amino acid sequence, respectively, that is separate from its native environment and present in sufficient quantity to permit its identification or use. Thus, a nucleic acid or amino acid sequence that makes up a voltage reporter polynucleotide or polypeptide molecule that is present in one or more of a vector, a cell, a tissue, an organism, etc., may be considered to be an isolated sequence if it is not naturally present in that cell, tissue, or organism, and/or did not originate in that cell, tissue, or organism.

As used herein the term "host" used in reference to a membrane, cell, or organism means a membrane, cell, or organism, respectively, in which a voltage reporter polypeptide of the invention is expressed. Examples of a host membrane, cell, tissue, or organism include, but are not limited to vertebrate membranes, invertebrate membranes, mammalian (including but not limited to non-human primate, human, dog, cat, horse, mouse, rat, etc.), insect (including but not limited to *Drosophila*, etc.), fish, worms, nematodes, and avian membranes, cells, tissues, and organisms. In certain embodiments of the invention a membrane may be a plant membrane.

Additional voltage reporter polypeptides of the invention are envisioned based on sequence similarity to the sequence of Archon1, Archon2, and/or one or more of Var #3, Var #4, Var #5, Var #6, and Var #7 set forth herein, and the characteristics or the voltage reporter polypeptides described herein. The presence and/or level of functions/characteristics such as, but not limited to, sensitivity, reaction speed, minimal bleaching, effective and optimal localization to membrane, etc. can be determined using methods described herein and art-known methods. It is understood that that the level of sequence identity with a functional variant of a voltage reporter polypeptide of the invention set forth herein plus functionality with respect to reporter characteristics can be used to identify additional voltage reporter molecules of the invention using standard procedures for sequence alignment, comparisons, and assays for voltage reporter characteristics and activity. Additional voltage reporter polypeptides that have one or more substitutions or other modifications to the sequence of one more sequences set forth herein as SEQ ID NOs: 1-7 can be identified and tested for characteristics including, but not limited to: expression, membrane localization, bleaching, longevity, sensitivity to voltage changes, brightness, maintenance of brightness, etc. using methods and sequences disclosed herein in conjunction with art-known methods.

In some embodiments of the invention, the amino acid sequence of voltage reporter polypeptide of the invention that is a functional variant of one or more of the sequence set forth herein as SEQ ID NOs: 1-7 has at least 90%, 91%, 92%, 93%, 94%, 95%, 96%, 97% 98%, or 99% amino acid sequence identity to the amino acid sequence corresponding to one or more of SEQ ID NOs: 1-7. In certain embodiments of the invention, a voltage reporter polypeptide of the invention that is a functional variant of one or more of SEQ ID NOs: 1-7 has at least 90%, 91%, 92%, 93%, 94%, 95%, 96%, 97%, 98%, 99% identity to the polypeptide sequence of the voltage reporter polypeptide sequence from which it was derived. As a non-limiting example, a functional variant of Archon1 (SEQ ID NO: 1), may have at 97% amino acid sequence identity to the sequence from which it was derived, in this example, the sequence set forth as SEQ ID NO: 1.

Additional amino acid substitutions, deletions, and/or insertions in the sequence of a voltage reporter polypeptide of the invention set forth herein as SEQ ID NOs: 1-7, that result in a functional variant may be constrained with respect to the extent of permissible modifications from the amino acid sequence of the voltage reporter polypeptide from which it is derived in order to permit the functional variant polypeptide to have all, greater than, or at least a portion of the level of function or characteristic of the voltage reporter polypeptide from which is was derived, when the variant is expressed in a cell and a voltage change occurs in the cell under suitable conditions to determine a change in voltage across a membrane of the cell. In certain aspects of the invention determination of a level that is "greater than" or a "portion of" the level of a function or a characteristic is based on the presence or absence of the function or a percentage change, for example, though not intended to be limiting, Archon1 has been shown to have essentially zero photobleaching under 800 mW/mm$^2$ 637 nm illumination during 8 minutes of continuous excitation, thus a voltage reporter polypeptide of the invention that is derived from Archon1, may, under similar test conditions demonstrate a greater level of photobleaching than zero, and it may be described as decreasing no more than: 1%, 2%, 3%, 4%, 5%, 6%, 7%, 8%, 9%, 10%, 11%, 12% 13%, 14%, 15%, 16%, 17%, 18%, 19%, 20%, 21%, 22%, 23%, 24%, 25%, 26%, 27%, 28%, 29%, 30%, 35%, 40%, 45%, or 50% from the initial level of fluorescence emission of the derived voltage reporter polypeptide. Thus, in a non-limiting example, a voltage reporter polypeptide derived from Archon1 may show 3% photobleaching compared to essentially 0% photobleaching of Archon1 when the two are tested under similar conditions.

In certain aspects of the invention, determination of a level that is "greater than" or a "portion of" the level of a function or a characteristic of a parent voltage reporter polypeptide is based on a percentage of the function or characteristic identified under certain conditions. The functional variant polypeptide is then tested under similar conditions and one or more differences are determined. For example, a function or characteristic of a functional variant of a voltage reporter polypeptide of the invention may be at least 80%, 85%, 90%, 95%, 96%, 97%, 98%, 99%, 100%, 105%, 110%, 115%, 120%, 130%, 140%, 150%, 160%, 170%, 180%, 190%, 200%, 300%, 400%, or 500% of the level of the function or the characteristic of the parent voltage reporter polypeptide of the invention from which the functional variant is derived. In a non-limiting example, it has been demonstrated that Archon1 has a level of functionality that permits imaging of subthreshold (e.g., ~5 mV) synaptic activity in neurons. An embodiment of a voltage reporter polypeptide of the invention that is a functional variant of SEQ ID NO: 1 (Archon1) when tested under similar conditions to those used to assess Archon1 sensitivity, may also show sensitivity to imaging subthreshold synaptic activity that is 100% of the sensitivity of Archon1 under the same conditions (which would be sensitivity to ~5 mV), or may show 95% of the sensitivity of Archon1 under the same conditions (indicating it is slightly less sensitive than Archon1), or may show 105% of the sensitivity of Archon1 under the same conditions (indicating it is slightly more sensitive than Archon1). One of skill in the art will be able to determine and compare functional levels and characteristics of voltage reporter polypeptides of the invention and will understand how to compare functions and characteristics when modifying an amino acid sequence in one or more of the sequences set forth herein as SEQ ID NOs: 1-7. Characteristics include, but are not limited to those set forth in FIG. 29A-B, such as responding speed, photostability, and photocurrent.

As used herein, the term "identity" with respect to sequences of voltage reporter polypeptides of the invention refers to the degree of relatedness or similarity between two or more polypeptide sequences (or polynucleotide sequences). Sequence identity can be determined using art-known means that may comprise the alignment and match between the sequences. A percentage of identity or similarity may be the percentage of identical amino acids in two or more sequences, when taking account of gaps and other sequence features. The identity between polypeptide sequences can be determined by means of art-known procedures and numerous algorithms and programs are available and routinely used by those in the art to determine identity between polypeptide sequences and to determine identity between nucleic acid sequences. Non-limiting examples of programs and algorithms include BLASTP, BLASTN and FASTA (Altschul et al., NCB NLM NIH Bethesda Md. 20894; Altschul et al., 1990). Online BLAST programs from the National Library of Medicine are available, for example, at blast.ncbi.nlm.nih.gov/Blast.cgi.

A voltage reporter polypeptide of the invention that is a functional variant of at least one of SEQ ID NOs: 1-7 may be shorter or longer than its parent voltage reporter polypeptide from which it was derived, and in certain aspects of the invention, the percentage identity between two sequences is based on the percent identity of the corresponding sequence regions when the two sequences are aligned. In some aspects of the invention, a voltage reporter polypeptide that is a functional variant of one or more of SEQ ID NOs: 1-7, is a full-length functional variant of its parent sequence, and in some embodiments of the invention, it may be a functional fragment of the sequence from which it was derived.

Sequence modifications can be one or more of substitutions, insertions, and deletions and any combination thereof. Sequence modifications may be prepared using methods described herein, by site-specific mutagenesis of nucleic acids in the DNA encoding a voltage reporter polypeptide of the invention, using cassette or PCR mutagenesis, or other techniques known in the art, to produce DNA encoding a voltage reporter polypeptide that comprises sequence modified from its parent sequence, and expressing the DNA in an in vivo cell, tissue, subject, or in an in vitro cell, for use and/or for testing. Amino acid sequence variants may be characterized by the predetermined nature of the sequence modification. Voltage reporter polypeptides of the invention that are functional variants of one or more voltage reporter polypeptides set forth as SEQ ID NOs: 1-7, can be identified and tested for levels of function and characteristics including, but not limited to: expression, membrane localization, sensitivity to voltage, photobleaching levels, duration of brightness, response time to voltage change, duration of adequate fluorescence emission, etc. using methods disclosed herein and additional art-known methods. In some aspects of the invention, a voltage reporter polypeptide of the invention that is a functional variant of one or more of SEQ ID NOs: 1-7, exhibits the same qualitative level of one or more functions and characteristics, or combination thereof, as the polypeptide from which it is derived. In certain aspects of the invention, a voltage reporter polypeptide of the invention that is a functional variant of one or more of SEQ ID NOs: 1-7, can be prepare and selected on that basis that it exhibits a different qualitative level of one or more functions and characteristics, or combination thereof, as the polypeptide from which it is derived.

A site or region for introducing an amino acid sequence modification in one or more of SEQ ID NOs: 1-7 may be predetermined, and the mutation per se need not be predetermined. For example, to prepare a voltage reporter polypeptide that is a functional variant of one or more of SEQ ID NOs: 1-7, there are regions corresponding to the sequence set forth as SEQ ID NO: 1, that are more tolerant and less tolerant of modification. Non-limiting examples of regions that may be tolerant to sequence modifications include: AA 1-18, AA 21-37, AA 48-55, AA 225-254, with the amino acid numbers corresponding to the residue numbers in SEQ ID NO: 1. Although not wishing to be bound to any theory, regions that may be involved in, and/or important for, functions or characteristics of voltage reporter polypeptides of the invention, include, but are not limited to: AA 21-37 and AA 200-225 (brightness); AA 200-225 (reduced photobleaching); and AA 1-18, AA 21-37, AA 48-55, AA 141-161, and AA 225-254 (localization in plasma membrane), with the amino acid numbers corresponding to residue numbers in SEQ ID NO: 1. It will be understood that by aligning a second amino acid sequence with SEQ ID NO: 1, the corresponding residue numbers and regions in the second amino acid sequence can be determined. Methods to identify and select amino acids to modify include those described elsewhere herein as well as additional art-known methods.

A level of function of a voltage reporter polypeptide of the invention can be tested using methods described herein as can characteristics of voltage reporter polypeptides, including, but not limited to: expression, cell localization, sensitivity, level of photobleaching, duration of fluorescence, speed of reaction to voltage and voltage changes, recovery following voltage changes, brightness, etc. using methods disclosed herein. Types of sequence modifications that may be included in voltage reporter polypeptide of the invention, that is a functional variant of one or more of a voltage reporter polypeptide set forth herein as SEQ ID NOs: 1-7 may include, but are not limited to conservative amino acid substitutions, which will produce molecules having functional characteristics similar to those of the parent polypeptide. Conservative amino acid substitutions are substitutions that do not result in a significant change in the activity or tertiary structure of a selected polypeptide. Such substitutions typically involve replacing a selected amino acid residue with a different residue having similar physico-chemical properties. For example, substitution of Glu for Asp is considered a conservative substitution because both are similarly sized, negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) [see, e.g., Creighton, Proteins (1984)].

In some embodiments, a voltage reporter polypeptide of the invention may include one or more unnatural amino acids as well as natural amino acids. An unnatural amino acid can be included in a certain voltage reporter polypeptide of the invention to enhance a characteristic such as localization, stability, response speed, brightness, or lower toxicity, etc.

Amino acid substitutions may made to 1, 2, 3, 4, 5, 6, 7, 8, 9, 10, 11, 12, 13, 14, 15, or more single residues and amino acid insertions may be on the order of from 1, 2, 3, 4, 5, 6, 7, 8, 9, 10, 11, 12, 13, 14, 15, or more amino acids, though larger numbers of substitutions and insertions may be tolerated. Amino acid deletions may range from 1, 2, 3, 4, 5, 6, 7, 8, 9, 10, 11, 12, 13, 14, 15, or more. Substitutions, deletions, insertions or any combination thereof may be used to arrive at a voltage reporter polypeptide retains all, or a significant portion of one, some, or all of the level of function and characteristics of a voltage reporter polypeptide of the invention as set forth herein. In certain embodiments of the invention, these changes are made on a few amino acids to minimize the alteration of the molecule. However, larger changes may be tolerated in certain circumstances.

Voltage reporter polypeptides derived from one or more of SEQ ID NOs: 1-7 set forth herein, may exhibit the same qualitative function and/or characteristics of the voltage reporter polypeptide from which it is derived, and/or may show one or more increased or decreased level of a function or characteristic of its parent voltage reporter polypeptide. In some embodiments of the invention one, some (for example 2, 3, 4, 5, 6, or 7), or all of the function and characteristics of a voltage reporter polypeptide derived from a voltage reporter polypeptide set forth herein as one of SEQ ID NO: 1-7 are within 1%, 2%, 3%, 4%, 5%, 6%, 7%, 8%, 9%, 10%, 11%, 12%, 13%, 14% 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% of the level of the function or characteristic determined for a voltage reporter polypeptide set forth herein as Archon1 or Archon2. It will be understood that the level of a function or characteristic of a voltage reporter polypeptide derived from one or SEQ ID NOs: 1-7 may be higher than, essentially the same as, or lower than that function or characteristic in Archon1 or Archon2 under similar circumstances. As a non-limiting example, the sequence of Archon1 may modified with one or more independently selected substitutions, insertions or deletions such that the resulting functional variant of Archon1 has an increased sensitivity to voltage change, better localization, faster response to voltage, slower response to voltage, less bright, brighter, etc. than in Archon1, the voltage reporter polypeptide from which it was derived. As non-limiting example, the characteristic of brightness in a voltage reporter polypeptide that is a functional variant of Archon1 may be essentially the same as the brightness of Archon1, 5% brighter than the brightness of Archon1, or 7% less bright than the brightness of Archon1. Routine methods can be used to determine the level of characteristics and functions of voltage reporter polypeptides of the invention and such determinations can be compared in different putative and confirmed voltage reporter polypeptides of the invention.

Specific amino acid locations and/or residues for substitution in a sequence set forth herein as SEQ ID NO: 1 or SEQ ID NO: 2 have now been identified that alone, or in combination with one or more addition substitutions have been demonstrated to be effective to prepare a voltage reporter polypeptide of the invention. Examples, though not intended to be limiting are shown herein in SEQ ID NOs: 3-7.

Another aspect of the invention provides nucleic acid sequences that encode voltage reporter molecules of the invention, including those encoding functional variants of the voltage reporter polypeptides disclosed herein. It will be understood by skilled artisans that the voltage reporter polypeptides can be encoded by various nucleic acids. Each amino acid in the protein is represented by one or more sets of 3 nucleic acids (codons). Because many amino acids are represented by more than one codon, there is not a unique nucleic acid sequence that codes for a given protein. It will be understood by those of skill in the art how to prepare a nucleic acid that encodes a voltage reporter polypeptide of the invention based on knowledge of the amino acid sequence of the polypeptide. A nucleic acid sequence that codes for a polypeptide or protein is the "gene" of that polypeptide or protein. A gene can be RNA, DNA, or other nucleic acid than will code for the polypeptide or protein. The terms, "protein", "polypeptides", and "peptides" are used interchangeably herein.

It is understood in the art that the codon systems in different organisms can be slightly different, and that therefore where the expression of a given protein from a given organism is desired, the nucleic acid sequence can be modified for expression within that organism. Thus, in some embodiments, a polynucleotide that encodes a voltage reporter polypeptide of the invention comprises a mammalian-codon-optimized nucleic acid sequence, which may in some embodiments be a human-codon optimized nucleic acid sequence. In certain aspects of the invention, a polynucleotide that encodes a voltage reporter polypeptide comprises a zebrafish-codon-optimized nucleic acid sequence or sequence with codon optimization for another organism. Codon-optimized sequences can be prepared using routine methods.

Delivery of Voltage Detector Molecules

Delivery of a voltage reporter polypeptide or polynucleotide of the invention to a cell and/or expression of a voltage reporter polypeptide or of the invention in a cell can be done using art-known delivery means. [see for example, Chow et al. Nature 2010 Jan. 7; 463(7277):98-102; and for Adeno-associated virus injection: Betley, J. N. & Sternson, S. M. (2011) Hum. Gene Ther. 22, 669-677; for In utero electroporation: Saito, T. & Nakatsuji, N. (2001) Dev. Biol. 240, 237-46; for microinjection into zebrafish embryos: Rosen J. N. et al., (2009) J. Vis. Exp. (25), e1115, doi:10.3791/1115; and for DNA transfection for neuronal culture: Zeitelhofer, M. et al., (2007) Nature Protocols 2, 1692-1704, the content of each of which is incorporated by reference herein in its entirety].

In some embodiments of the invention a voltage reporter polypeptide of the invention is included in a fusion protein. It is well known in the art how to encode, prepare, and utilize fusion proteins that comprise a polypeptide sequence. In certain embodiments of the invention, a vector that encodes a fusion protein can be used to deliver a voltage reporter polypeptide, and optionally one more additional polypeptides, to a cell and can also in some embodiments be used to target delivery of a voltage reporter polypeptide of the invention to specific cells, cell types, tissues, or regions in a subject. Suitable targeting sequences useful to deliver a voltage reporter molecule of the invention to a cell, tissue, region of interest are known in the art. Delivery of a voltage reporter molecule of the invention to a cell, tissue, or region in a subject can be performed using art-known procedures. A fusion protein of the invention can be delivered to a cell by delivery of a vector encoding a fusion protein. The delivered fusion protein is then expressed in a specific cell type, tissue type, organ type, and/or region in a subject, or in vitro, for example in culture, in a slice preparation, etc. Preparation, delivery, and use of a fusion protein and its encoding nucleic acid sequences are well known in the art. Routine methods can be used in conjunction with teaching herein to express one or more voltage reporter polypeptides and optionally additional polypeptides, in a desired cell, tissue, or region in vitro or in a subject.

In certain aspects of the invention, a voltage reporter polypeptide of the invention that is non-toxic or substantially non-toxic to the cell into which it is delivered and/or expressed. In the absence of excitation light, a voltage reporter molecule of the invention does not significantly alter cell health or ongoing electrical activity in the cell in which it is expressed. In some embodiments of the invention, a voltage reporter molecule of the invention is genetically introduced into a cellular membrane, and reagents and methods are provided for genetically targeted expression of voltage reporter polypeptides. Genetic targeting can be used to deliver one or more voltage reporter polypeptides of the invention to specific cell types, to specific cell subtypes, to specific spatial regions within an organism, and to subcellular regions within a cell. In some embodiments of the invention, genetic targeting can be used to control of the amount of a voltage reporter polypeptide of the invention that is expressed and the timing of the expression. A fusion protein of the invention can be expressed in a specific cell type, tissue type, organ type, and/or region in a subject, or in vitro, for example in culture, in a slice preparation, etc. Preparation, delivery, and use of a fusion protein and its encoding nucleic acid sequences are well known in the art. Routine methods can be used in conjunction with teaching herein to express one or more voltage reporter polypeptides and optionally additional polypeptides, in a desired cell, tissue, or region in vitro or in a subject.

In some embodiments, a voltage reporter polypeptide of the invention is genetically introduced into a cellular membrane, and reagents and methods are provided herein for genetically targeted expression of voltage reporter polypeptides of the invention. Genetic targeting using trafficking or delivery polypeptides can be used to deliver a voltage reporter polypeptide of the invention to specific cell types, to specific cell subtypes, and to specific spatial regions within an organism. Routine genetic procedures can also be used to control parameters of expression, such as but not limited to: the amount of a voltage reporter polypeptide of the invention that is expressed, the timing of the expression, etc.

Vectors and Molecules

Some embodiments of the invention include a reagent for genetically targeted expression of a voltage reporter polypeptide, wherein the reagent comprises a vector that contains the gene for the voltage reporter polypeptide. As used herein, the term "vector" refers to a nucleic acid molecule capable of transporting between different genetic environments another nucleic acid to which it has been operatively linked. The term "vector" may also refer to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a voltage reporter polypeptide of the invention into dividing and non-dividing cells and can insert a voltage reporter polypeptide of the invention into an in vivo, in vitro, or ex vivo cell.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. In certain embodiments of the invention, a vector may be a lentivirus comprising the gene for a voltage reporter polypeptide of the invention. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a voltage reporter polypeptide in a wide variety of cell types—thus a promoter for a gene that is widely expressed in a variety of cell types, for example a "housekeeping gene" can be used to express a voltage reporter polypeptide of the invention in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, or tamoxifen-inducible Cre-ER.

In some embodiments of the invention a reagent for genetically targeted expression of a voltage reporter polypeptide of the invention is a vector that comprises a gene encoding a voltage reporter polypeptide of the invention, and optionally a gene encoding one or more additional polypeptides. Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding a voltage reporter polypeptide of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein. Other vectors that may be used in certain embodiments of the invention are provided in the Examples section herein.

Promoters that may be used in methods and vectors of the invention include, but are not limited to, cell-specific promoters or general promoters. A non-limiting examples promoters that can be used in vectors of the invention are: ubiquitous promoters, such as, but not limited to: CMV, CAG, CBA, and EF1a promoters; and tissue-specific promoters, such as but not limited to: Synapsin, CamKIIa, GFAP, RPE, ALB, TBG, MBP, MCK, TNT, and aMHC promoters. Methods to select and use ubiquitous promoters and tissue-specific promoters are well known in the art. A non-limiting example of a tissue-specific promoter that can be used to express a voltage reporter polypeptide of the invention in a cell such as a neuron is a synapsin promoter, which can be used to express a voltage reporter polypeptide in certain embodiments of methods of the invention. Additional tissue-specific promoters and general promoters are well known in the art and, in addition to those provided herein, may be suitable for use in compositions and methods of the invention. Other non-limiting examples of promoters that may be used in certain embodiments of methods of the invention are provided in the Examples section. Molecules that can be administered and delivered to a cell, include, but are not limited to: opsin polypeptides, detectable label polypeptides, fluorescent polypeptides, additional trafficking polypeptides, etc.

Non-limiting examples of detectable label polypeptides that may be included in a composition comprising a voltage reporter polypeptide of the invention are: green fluorescent protein (GFP); enhanced green fluorescent protein (EGFP), red fluorescent protein (RFP); yellow fluorescent protein (YFP), dtTomato, mCardinal, mCherry, DsRed, cyan fluorescent protein (CFP); far red fluorescent proteins, etc. Numerous fluorescent proteins and their encoding nucleic acid sequences are known in the art and routine methods can be used to include such sequences in fusion proteins and vectors, respectively, of the invention.

Additional sequences that may be included in a fusion protein comprising a voltage reporter polypeptide of the invention are trafficking sequences, including, but not limited to: Kir2.1 sequences and functional variants thereof, KGC sequences, ER2 sequences, etc. Examples of trafficking polypeptides, which may also be referred to herein as "export" polypeptides, that may be used in certain embodiments of the invention include, but are not limited to: SEQ ID NOs: 20, 22, 24, 26, and 27. Examples of nucleic acid sequences that encode trafficking polypeptides that may be used in some embodiments of the invention include, but are not limited to: SEQ ID NOs: 19, 21, 23, and 25. Additional trafficking polypeptides and their encoding nucleic acid sequences are known in the art and routine methods can be used to include and use such sequences in fusion proteins and vectors, respectively, of the invention. In addition to trafficking motifs as KGC and ER2 sequences, the fluorescent protein tag may influence proper membranal localization of the opsin in cells. A non-limiting example comprises use of monomeric GFP-like fluorescent proteins with fluorescence spectrum complementary to that of Archon, i.e. fluorescent protein with emission wavelength shorter than 650 nm. A non-limiting example of a tag that may be used in certain embodiments of the invention are phiLOV2.1 and UnaG proteins, which are shorter than GFP-like fluorescence protein, and therefore save space in AAV vectors.

Imaging and Monitoring

According to principles of this invention, alterations in voltage in a cell can be detected and assessed by monitoring fluorescence emissions of a voltage reporter polypeptide of the invention that is expressed in the cell. Excitation of a fluorescent component of a voltage reporter polypeptide can be performed using methods described herein and other art-known methods. Monitoring emission of the fluorescent component of a voltage reporter polypeptide of the invention including identifying stability, increases, decreases, etc. can be done with routine methods known in the art and routinely used to detect fluorescent emission from fluorescent molecules, opsins, etc. In addition to methods provided herein, additional methods suitable to excite a fluorescent component of a voltage reporter polypeptide of the invention and for imaging fluorescent emissions of voltage reporter polypeptides of the invention are available in Light sheet see for example: Keller, P. J. et al., (2015) Nature Methods 12, 27-29; and two photon see for example: Yang et al, (2016) Cell, //dx.doi.org/10.1016/j.cell.2016.05.031, each of which is incorporated herein by reference in its entirety.

Certain aspects of the invention include use of imaging methods to monitor one or more characteristics of a cell, such as, but not limited to: electrical activity in a cell and ion flux across a cell membrane. Compositions and methods of the invention can be used in a cell and/or a subject as a means with which to image and/or monitor changes in voltage in a cell, changes in ion flux across a membrane of a cell, changes resulting from a disease or condition in a cell or subject, efficacy of a candidate agent to alter voltage in a cell, etc. In some aspects of the invention, methods and compounds are provided that can be used to image and detect an alteration or modulation in voltage. Methods for imaging and/or detecting fluorescence emissions in cells, tissues, and subjects are disclosed herein and are known in the art. Such methods are suitable for use in embodiments of the invention for imaging, determining, detecting, measuring, and comparing fluorescent emission of one or more voltage reporter polypeptides of the invention expressed in a cell and/or a subject. Additional non-limiting examples of imaging equipment and means that may be used in methods of the invention are provided in the Examples section herein.

Cells and Subjects

Some aspects of the invention include cells used in conjunction with one or more voltage reporter polypeptides of the invention and/or their encoding polynucleotides. Cells in which one or more voltage reporter polypeptides of the invention may be expressed, and that can be used in methods of the invention, include prokaryotic and eukaryotic cells. In certain embodiments of the invention, useful cells may be mammalian cells; including but not limited to cells of humans, non-human primates, dogs, cats, horses, fish, rodents, etc. In some embodiments of the invention, useful cells may be non-mammalian cells; including but not limited to insect cells, avian cells, fish cells, plant cells, etc. Cells in which a voltage reporter polypeptide of the invention may be expressed are non-excitable cells and excitable cells, the latter of which includes cells able to produce and respond to electrical signals. Examples of excitable cell types include, but are not limited, to neurons, muscles, visual system cells, sensory cells, auditory cells, cardiac cells, and secretory cells (such as pancreatic cells, adrenal medulla cells, pituitary cells, etc.).

Non-limiting examples of cells that may be used in methods of the invention include: neuronal cells, nervous system cells, cardiac cells, circulatory system cells, visual system cells, auditory system cells, secretory cells, endocrine cells, and muscle cells. In some embodiments, a cell used in conjunction with methods and voltage reporter molecules of the invention is a healthy normal cell, which is not known to have a disease, disorder, or abnormal condition. In some embodiments of the invention, a cell used in conjunction with methods and voltage reporter molecules of the invention may be a normal cell or an abnormal cell, for example, (1) a cell that has a disorder, disease, or condition; (2) a cell obtained from a subject that has, had, or is suspected of having disorder, disease, or condition; (3) a cell known to be or suspected of being involved in a disorder, disease, or condition; (4) a cell that is a model for a disorder, disease, or condition, etc. Non-limiting examples of such cells are: a degenerative cell, a neurological disease-bearing cell, a cell model of a disease or condition, an injured cell, a cell downstream from a disease-bearing or injured cell, etc. In some embodiments of the invention, a cell may be a control cell. A cell that is directly or indirectly upstream from a cell in which a voltage reporter polypeptide is expressed may be a normal cell, or an abnormal cell.

One or more voltage reporter polypeptides of the invention may be expressed in cells from or in culture, cells in solution, cells obtained from subjects, and/or cells in a subject (in vivo cells). One or more voltage reporter polypeptides of the invention may be expressed and monitored in cultured cells, cultured tissues (e.g., brain slice preparations, etc.), and in living subjects, etc. As used herein, a the term "subject" may refer to a human, non-human primate, cow, horse, pig, sheep, goat, dog, cat, bird, rodent, fish, insect, or other vertebrate or invertebrate organism. In certain embodiments, a subject is a mammal and in certain embodiments a subject is a human. Additional non-limiting examples of cell types that may be used in certain methods of the invention are provided in the Examples section, as are non-limiting examples of organisms that may subjected to certain methods of the invention.

A cell in which a voltage reporter polypeptide of the invention is expressed may be a single cell, an isolated cell, a cell in culture, an in vitro cell, an in vivo cell, an ex vivo cell, a cell in a tissue, a cell in a subject, a cell in an organ, a cell in a cultured tissue, a cell in a neural network, a cell in a brain slice, a neuron, a cell that is one of a plurality of cells, a cell that is one in a network of two or more interconnected cells, a cell in communication with another cell, a cell that is one of two or more cells that are in physical contact with each other, etc.

Controls

Voltage reporter polypeptides of the invention and methods of using such voltage reporter polypeptides can be utilized to assess changes in cells, tissues, and subjects in which they are expressed. Some embodiments of the invention include use of voltage reporter polypeptides of the invention to identify effects of candidate compounds on cells, tissues, and subjects. Results of testing a voltage reporter polypeptide of the invention can be advantageously compared to a control. In some embodiments of the invention one or more voltage reporter polypeptides of the invention, may be expressed in a cell population and used to test the effect of candidate compounds on the cells. A "test" cell, membrane, tissue, or organism may be a cell, tissue, or organism in which activity of a voltage reporter polypeptide of the invention can be tested or assayed. Results obtained using assays and tests of a test cell, membrane, tissue, or organism may be compared results obtained from the assays and tests performed in other test cells, membranes, tissues or organisms or assays and tests performed in control cells, membranes, tissues, or organisms.

As used herein a control value may be a predetermined value, which can take a variety of forms. It can be a single cut-off value, such as a median or mean. It can be established based upon comparative groups, such as cells or tissues that include the voltage reporter polypeptides that is under essentially the same conditions of test cells but are not contacted with a candidate compound. Another non-limiting example of a comparative group includes cells or tissues that have a disorder or condition and groups without the disorder or condition. Another non-limiting example of comparative group includes cells or tissues in which a voltage reporter polypeptides that is not a voltage reporter polypeptide of the invention (for example Arch, Archer1, Archer2, etc.) is expressed. In some embodiments of the invention, a control may be characteristics such as brightness, speed of response, photobleaching level, etc. that are determined in reporter polypeptide such as Arch, Archer1, Archer2, Arch-7, QuasAr1, and QuasAr2, QuasAr-I #3, QuasAr-I #7, QuasAr-I #14, QuasAr-I #16, and QuasAr-I #22. Another non-limiting example of comparative group includes cells from a subject or subjects with a family history of a disease or condition and cells from a subject or subjects without such a family history. A predetermined value can be arranged, for example, where a tested population is divided equally (or unequally) into groups based on results of testing. Those skilled in the art are able to select appropriate control groups and values for use in comparative methods of the invention.

Administration Means

Administration of a voltage reporter molecule of the invention may include, but are not limited to: administering to a cell or subject a composition that includes a vector comprising a polynucleotide sequence that encodes a voltage reporter polypeptide, administering to a cell or subject a composition comprising a voltage reporter polypeptide, and administering to a subject a cell in which a voltage reporter molecule is expressed. A composition of the invention optionally includes a carrier, which may be a pharmaceutically acceptable carrier.

A voltage reporter molecule (polypeptide or encoding polynucleotide) of the invention may be administered to a cell and/or subject in a formulation, which may be administered in pharmaceutically acceptable solutions, which may routinely contain pharmaceutically acceptable concentrations of salt, buffering agents, preservatives, compatible carriers, adjuvants, and optionally additional ingredients. In some aspects, a pharmaceutical composition comprises a voltage reporter molecule of the invention and a pharmaceutically-acceptable carrier. Pharmaceutically acceptable carriers are well known to the skilled artisan and may be selected and utilized using routine methods. As used herein, a pharmaceutically acceptable carrier means a non-toxic material that does not interfere with the effectiveness of the biological activity of the active ingredients. Pharmaceutically acceptable carriers may include diluents, fillers, salts, buffers, stabilizers, solubilizers, and other materials that are well-known in the art. Exemplary pharmaceutically acceptable carriers are described in U.S. Pat. No. 5,211,657 and others are known by those in the art.

An effective amount of a voltage reporter molecule of the invention is an amount that increases the level of the voltage reporter polypeptide expressed in a cell, tissue, or subject to a level that is suitable for use in a method of the invention. The amount of active voltage reporter molecule of the invention may be varied, for example, by increasing or decreasing the amount of the voltage reporter molecule that is administered, by changing the delivery composition in which the voltage reporter molecule is administered, by changing the route of administration, by changing the amount delivered, by changing elements that control timing of expression, and so on. The amount of a voltage reporter molecule administered will vary with the particular cell environment, location of the cell in which the voltage reporter molecule is to be expressed, the administration of other voltage reporter molecules of the invention, the nature of the testing parameters, the specific route of administration, and other factors within the knowledge and expertise of the practitioner. For example, the amount administered may depend upon the location and number of cells in the tissue and/or subject in which the voltage reporter polypeptide is to be expressed. An amount administered may also depend on the location of the tissue in which expression is to take place. Compositions used to deliver voltage reporter molecule of the invention may be administered alone, in combination with each other, and/or in combination with other agents and compositions. A composition used in an embodiment of the invention, may result in delivery of an amount of a voltage reporter molecule of the invention for use in a desired method.

The terms "administrate" and "administer" when used herein to describe an action that results in a voltage reporter polypeptide of the invention being present in a cell, is intended to encompass delivery of a voltage reporter polypeptide of the invention into the cell (for example, though not intended to be limiting, in the form of a fusion protein), and delivery of a polynucleotide sequence that encodes a voltage reporter polypeptide of the invention, which is subsequently expressed in the cell. A voltage reporter polypeptide of the invention may be administered using art-known methods. In some embodiments a polynucleotide that encodes a voltage reporter polypeptide of the invention is administered to a cell and/or subject and in certain embodiments a voltage reporter polypeptide is administered to a cell and/or a subject. The manner and amount of a voltage reporter molecule of the invention that is administered to a cell and/or subject may be adjusted by the individual practitioner. The absolute amount administered will depend upon a variety of factors, including the material selected for administration, whether the administration is in a single delivery or multiple deliveries, and individual subject parameters including age, physical condition, size, weight, and the stage of a disease or condition, test parameters to be followed, etc. These factors can be addressed with no more than routine experimentation.

The amount of a composition that is administered to a cell or subject to increase the level of a voltage reporter polypeptide of the invention to a cell and/or a subject can be chosen in accordance with different parameters such as the desired period of monitoring, the number of events to be monitored, etc. In the event that the amount administered to a cell or subject is insufficient at the initial amount administered, higher amounts (or effectively higher amounts by a different, more localized delivery route) may be employed to the extent that cell and subject tolerance permits. The amount and timing of expression and excitation of a voltage reporter polypeptide of the invention (e.g., by adjusting light wavelength, length of light contact, promoters, trafficking polypeptides, etc.) that has been administered to a cell and/or subject can also be adjusted based on the ability to perform desired monitoring methods in a particular cell type or subject. Parameters for illumination and excitation of a voltage reporter polypeptide of the invention that has been administered to a subject can be determined using art-known methods and without requiring undue experimentation.

Various modes of administration will be known to one of ordinary skill in the art that can be used to effectively deliver a composition to increase the level of a voltage reporter polypeptide of the invention in a desired cell, tissue, cell of a subject, organ of a subject, or region of a subject. Methods for administering a composition comprising a voltage reporter molecule of the invention may include, but is not limited to: injection, microinjection, perfusion, electroporation, or other suitable means. The invention is not limited by the particular modes of administration disclosed herein and additional art-known delivery means may be suitable for administration of voltage reporter molecules of the invention.

Other protocols suitable for administration of a voltage reporter molecule of the invention are known to those in the art. Embodiments of methods of the invention to administer a cell or vector to increase a level of a voltage reporter molecule of the invention in an animal other than a human; and administration and use of a voltage reporter molecule of the invention for testing purposes or veterinary purposes, are substantially the same as described above. It will be understood by a skilled artisan that this invention is applicable to both human and animals.

Assessment Methods

Disorders, conditions, and events that may be assessed using methods of the invention to express a voltage reporter polypeptide of the invention in a cell, tissue, and/or subject may include, but are not limited to: injury, brain damage, spinal cord injury, epilepsy, metabolic disorders, cardiac dysfunction, vision loss, blindness, deafness, hearing loss, and neurological conditions (e.g., Parkinson's disease, Alzheimer's disease, seizure), degenerative neurological conditions, drug contact, toxins, etc. In some embodiments of the invention, a disorder or condition may be monitored by expressing a voltage reporter polypeptide of the invention in at least one cell and contacting the at least one cell with a wavelength of light suitable to excite the fluorescent portion of the reporter, and monitoring for changes in the fluorescent emission of the reporter. In some embodiments of the invention, such methods can be used in methods such as, but not limited to, assessing therapeutic agents and treatments, assessing putative therapeutic agents and treatments, expanding understanding of connectivity between cells, and exploring voltage activity patterns in a cell or cells.

A voltage reporter polypeptide of the invention may be targeted to cells and membranes, and to monitor voltage-associated cell activities. Some embodiments of the invention comprise expressing a voltage reporter polypeptide in a cell and monitoring fluorescence emitted from the voltage reporter polypeptide to assess changes in voltage, action potential initiation, and synaptic transmission, etc.

The present invention in some aspects, includes one or more of preparing nucleic acid sequences that encode voltage reporter polypeptide of the invention, expressing in cells and membranes voltage reporter polypeptides encoded by the prepared nucleic acid sequences; illuminating the cells and/or membranes with suitable light to excite the voltage reporter polypeptide, and monitoring changes in voltage in the cell by assessing changes in fluorescence emission from the voltage reporter polypeptide. The ability to specifically, consistently, reproducibly, and sensitively monitor changes in voltage across membranes, in cells, and in subjects has been demonstrated. The present invention enables monitoring of voltage changes in in vivo, ex vivo, and in vitro, and the voltage reporter polypeptides of the invention and their use, have broad-ranging applications for drug screening, disease assessment, treatment assessment, and research applications, some of which are describe herein.

EXAMPLES

Example 1

Methods

Molecular cloning and mutagenesis. The Ace2N-4aa-mNeon, Archer1-KGC-EGFP-ER2 and Quasar2-mOrange-KGC-ER2 genes were synthesized de novo by GenScript, based on the sequences reported in the original publications [Hochbaum, D. R. et al. (2014) Nat. Methods 1-34 doi: 10.1038/nmeth.3000; Flytzanis, N. C. et al. (2014) Nat. Commun. 5, 4894; and Gong, Y. et al. (2015) Scienc express 350, 1-11]. Plasmids encoding mIFP, iRFP670, iRFP682, iRFP702, iRFP and iRFP720 were acquired from Addgene. The RpBphP1/PAS-GAF domains and QuasAr2-ER2 genes were synthesized de novo (Genscript) with mammalian codon optimization and subcloned into pN1 vector (Clontech) using AgeI/NotI sites. Synthetic DNA oligonucleotides used for cloning were purchased from Integrated DNA Technologies. PrimeStar Max mastermix (Clontech) was used for high-fidelity PCR amplifications. Restriction endonucleases were purchased from New England BioLabs and used according to the manufacturer's protocols. Ligations were performed using T4 DNA ligase (Fermentas) or InFusion HD kit (Clontech). Small-scale isolation of plasmid DNA was performed with Mini-Prep kit (Qiagen); large-scale DNA plasmid purification was done with GenElute™ HP Endotoxin-Free Plasmid Maxiprep Kit (Sigma-Aldrich). Random mutagenesis was performed with a GeneMorph II Random Mutagenesis Kit (Stratagene), using conditions that resulted in the mutation frequency of up to 15 mutations per 1,000 base pairs. The QuasAr2 random library with mutation frequency of 10-15 mutations per 1,000 base pairs was prepared by GenScript. Site-directed focused library of the Arch mutants were synthesized de novo as a gBlock (EpochLifescience), amplified with corresponding primers using PCR and subcloned into the pN1 vector. Obtained gene libraries in expression vectors were electroporated into the NEB10-beta E. coli host cells (New England BioLabs). Serial dilutions ($10^{-4}$ and $10^{-5}$) of the electroporated cells were plated on LB/agar medium supplemented with 100 mg·mL−1 of kanamycin to estimate the electroporation efficiency. The remainder of cells was grown overnight in LB medium supplemented with 100 mg/mL of kanamycin for subsequent plasmid DNA isolation.

To express voltage sensors in primary hippocampal neurons, the corresponding genes were PCR amplified and swapped with the ArchT-GFP gene in pAAV-CaMKIIα-ArchT-GFP plasmid (Addgene plasmid #37807) using BamHI and EcoRI sites. For in vivo expression in mouse brain the Archon1/2-KGC-EGFP-ER2 constructs were cloned into pCAG-WPRE vector using KpnI and BsrGI sites. For transient expression in zebrafish larvae, expression vector were designed by cloning the 4 non-repetitive upstream activating sequences (4nrUAS) as previously described [Subedi, A. et al. (2014) Methods 66, 433-440] together with a beta actin core minimal promoter followed by the 1.2 kb long 3'UTR sequence of Danio rerio synaptotagmin IIa (syt2a). The expression cassette was flanked by Tol2 transposon ends. The Archon-KGC-EGFP-ER2 and miRFP genes were codon-optimized for expression in zebrafish using the online resource at www.bioinformatics.org/, synthesized de novo and cloned into the designed pTol2-4nrUAS vector using SpeI and AscI sites. For expression in C. elegans codon-optimized fusion of Archon1 to EGFP (codon optimization was done using the online resource at www.bioinformatics.org/) was subcloned into a pSM vector backbone using KpnI and SacI, and the rig-3 promoter was inserted upstream using FseI and AscI sites.

Protein characterization in vitro. Protein expression and purification were performed as described previously [Piatkevich, K. D., et al., (2013) Nature Communications, 4, [2153]. doi:10.1038/ncomms3153] with few modifications. The pBAD/HisB vectors (Life Technologies/Invitrogen) encoding iRFP670, iRFP682, iRFP702, iRFP, iRFP720 and miRFP were co-transformed with pWA23h plasmid, encoding heme oxygenase1 from Bradyrhizobium ORS278 (hmuO) under the rhamnose promoter, into BW25113 E. coli strain (CGSC #7636 in The Coli Genetic Stock Center). Bacterial cells were grown in RM medium supplemented with ampicillin, kanamycin, 0.002% arabinose, 0.02% rhamnose for 15-18 h at 37° C. and then for 24 h at 18° C. Proteins were purified using TALON Metal Affinity Resin (Clontech) according to the manufacturer's protocol with one minor modification: in the wash buffer, 100 mM EDTA was used instead of 400 mM imidazole. The fluorescence spectra were measured using a Fluorolog 3 spectrofluorometer (Jobin Yvon) and a plate reader SpectraMax-M5 (Molecular Devices). For absorbance measurements, a Lambda 35 UV/Vis spectrometer (Perkin Elmer) was used. Background light scattering was removed by subtracting a fitted $\lambda$-4 curve from the measured spectrum. For determination of quantum yield, fluorescence signal of purified proteins was compared with that of the equally absorbing iRFP. To determine the extinction coefficient, the absorbance value for the protein at the main peak centered in red part of the spectrum was compared with the absorbance value of short wavelength peak centered at 370-390 nm assuming the latter to have the extinction coefficient of the free biliverdin IXα, which is 39,900 $M^{-1}cm^{-1}$ [Filonov, G. S. et al. (2011) Nat. Biotechnol. 29, 757-761]. pH titrations were done using a series of commercially available pH buffers (HYDRION).

Size exclusion chromatography was performed by GenScript on Superdex 200 10/300 GL column (GE Healthcare Life Sciences) using a gel filtration standard (#1511901; BIO-RAD). Two-photon absorption (2PA) spectra and cross sections of the proteins were measured in PBS buffer, pH=7.4 at concentrations ~1-5·10-5 M in 1 mm glass spectroscopy cuvettes (Starna cells) using femtosecond fluorescence, similar to that described in: Tsai, P. S. et al. (2002) In: *In Vivo Optical Imaging of Brain Function*, Chapter: 6, Publisher: CRC Press, Editors: Ron D. Frostig, pp. 113-171. In particular, two-photon excitation (TPE) spectra were collected using an MOM Sutter Instrument two-photon fluorescent microscope coupled with an Insight DeepSee (Newport) femtosecond laser tunable from 680 to 1300 nm. A Plan NeoFluar 2.5×/0.075 Zeiss objective was used to excite and collect fluorescence which was passed through a HQ705/100 filter (Chroma) before reaching the PMT. To correct the TPE spectra for the wavelength-to-wavelength variations of laser properties (pulse duration and beam shape), Styryl 9M (Aldrich) in chloroform was used as a reference standard [Makarov, N. S., et al., (2008) Opt. Express 16, 4029-4047]. The TPE fluorescence had quadratic dependence on excitation power in the whole spectral range presented in FIG. 11. Absolute 2PA cross section was obtained with relative method, using Styryl 9M (Aldrich) in chloroform as a standard [Makarov, N. S., et al., (2008) Opt. Express 16, 4029-4047]. Fluorescence intensity, F, excited at 900 nm, was measured as a function of excitation power, P, for both the sample and the reference in the same conditions through a ET675/20 filter (Chroma), with the transmission center at 667 nm in the MOM setup (18° incidence angle). From the fit of these dependences to a quadratic function $F=aP^2$, factors a values were obtained and then normalized [Makarov, N. S., et al., (2008) Opt. Express 16, 4029-4047] to the concentrations (obtained spectrophotometrically, BioMate™ S3 spectrophotometer) and to the differential quantum efficiencies at 667 nm (obtained with a spectrofluorimeter, PC1 ISS). In FIG. 11, the two-photon action spectrum ($\sigma2\ \phi$) for miRFP is presented and compare to that of EGFP (measured before [Drobizhev, M., M et al., (2011) Nat Methods 8, 393-399]).

Gene library transfection. Conventional calcium phosphate transfection was modified to deliver a small number of plasmids per single cell to enable efficient single cell phenotyping and genotyping (see Results). HEK293FT cells were selected as an expression host due to the several reasons: i) they are suitable for calcium phosphate transfection; ii) they are widely regarded as high expressors for a variety of protein payloads; iii) they are known to have the lowest mutation rate among commonly used mammalian cell lines towards exogenous DNA [Lebkowski, J. S., et al., (1984) Mol. Cell. Biol. 4, 1951-1960]; iv) they are robust and easy to work with. Cells were authenticated by the manufacturer and tested for mycoplasma contamination to their standard levels of stringency and were here used because they are common cell lines for testing new tools. The expression vector used was the commercially available pN1 plasmid (Clontech) which can be replicated in HEK293FT cells due to the SV40 ori of replication [Mahon, M. J. (2011) Biotechniques 51, 119-126]. The replication of plasmids enables a higher level of protein expression upon single copy plasmid delivery, facilitating optical detection of recombinant protein. The CMV promoter was used to drive expression of target genes because it is known to be the strongest promoter among those commonly used in HEK293 cells [Qin, J. Y. et al. (2010) PloS One, 5, 3-6 doi.org/10.1371/journal.pone.0010611]. HEK293FT cells (Invitrogen) were maintained between 10% and 70% confluence at 37° C. with 5% $CO_2$ in DMEM medium (Cellgro) supplemented with 10% heat inactivated FBS (Corning), 1% penicillin/streptomycin (Cellgro), and 1% sodium pyruvate (BioWhittaker). Transfection of HEK293FT cells with gene libraries was performed using a commercially available calcium phosphate transfection kit (LifeTechnologies) according to the manufacturer's protocol with minor modifications as follows. HEK293FT cells from the exponential growth phase were seeded at a density to be approximately 70% confluent on the day of transfection. Culture medium was replaced with fresh medium ~30-60 minutes before adding DNA-CaPhos co-precipitate to make medium of pH~7.4. 2×$CaCl_2$/DNA solution was added quickly to an equal volume of 2×HBS solution at room temperature, mixed gently for 20-30 sec by pipetting up and down, and added dropwise to cell culture. Culture medium was carefully replaced with fresh medium 24 hours after transfection. The "empty" pUC19 plasmid was used as "dummy" DNA to keep the total amount of DNA constant for all transfection conditions to avoid variations in DNA-CaPhos co-precipitate formation [Chen, C. & Okayama, H. (1987) Molecular and Cellular Biology, 7, 2745-2752; Okazaki, M., et al., (2001) Biomaterials vol. 22, Issue 18:2459-2464].

FACS screening. To sort the gene library transfected HEK293FT cells using flow cytometry, cells were harvested from a culture dish ~48 h after gene library transfection by applying trypsin for 5-10 mins (Cellgro) and washed twice by centrifuging the cell suspension for 5 minutes at 500 rpm and re-suspending cells in PBS (Cellgro). The washed cells were then re-suspended in PBS supplemented with 4% FBS (Corning) and 10 mM EDTA at density 1-2·$10^6$ cells/ml and filtered through a 30 μm filter (Falcon) to prevent clogging on the FACS machine. The filtered cells were sorted by FACSAria (BD Biosciences) running BDFACS Diva software and equipped with standard 405, 488, 561 and 640 nm solid-state lasers. Debris, dead cells and cell aggregates were gated out before desired fluorescence signals were detected. For screening RpBphP1/PAS-GAF libraries, excitation at 640 nm and emission at 670/30 nm and 710/50 nm were used; for QuasAr2 libraries excitation was at 640 nm and emission was at 710/50 nm (see Table 1 for details). Approximately 1.5 times more cells than the size of each library were screened per FACS sorting session and 10-100 k cells exhibiting higher fluorescent intensity than that of positive control (HEK293FT cells transfected with a plasmid encoding template protein) were collected in a 5 ml tube. Collected cells were plated on a 3 cm cell culture dish coated with Matrigel (BD Biosciences) for further screening and sorting using the custom cell picker (as described below).

TABLE 1

Screening conditions for monomeric near-infrared FPs and Arch-based voltage sensors

| Template protein | Mutagenesis | Library size (independent clones) | FACS enrichment[a] Channel 1 | Channel 2 | Imaging conditions |
|---|---|---|---|---|---|
| RpBphP1 | Site-directed | $1.29 \cdot 10^6$ | Ex: 640 nm; Em: 670/30BP | Ex: 640 nm; Em: 710/50BP | 10x 0.3NA; Ex: 628/31BP; Em: 716/40BP |
|  | Random | $1.26 \cdot 10^6$ |  |  | 10x 0.3NA; Ex: 628/31BP; Em: 716/40BP |
|  | Random | $4.32 \cdot 10^6$ |  |  | 10x 0.3NA; Ex: 628/31BP; Em: 664LP |
| QuasAr2 | Random | $1.6 \cdot 10^6$ | Ex: 640 nm; Em: 670/30BP | Ex: 640 nm; Em: 710/50BP | 10x 0.3NA/40x 0.75NA[b]; Ex: 628/31BP; Em: 664LP |
|  | Site-directed | $8.1 \cdot 10^6$ |  |  | 10x 0.3NA/40x 0.75NA[b]; Ex: 628/31BP; Em: 664LP |

Figure 1A:
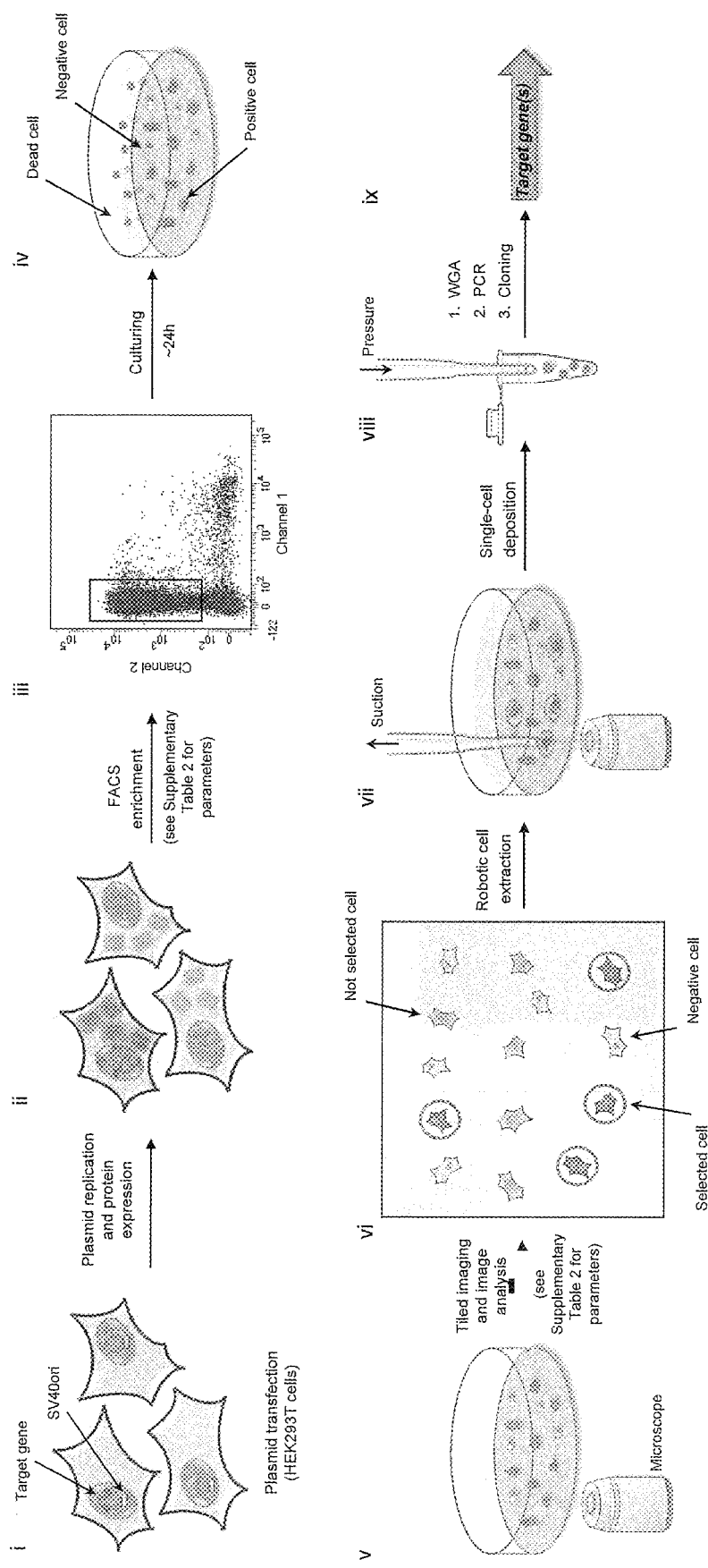
FIG. 1A-J shows an embodiment of multi-parameter directed evolution of proteins in mammalian cells via robotic cell picking.
Figure 1B:
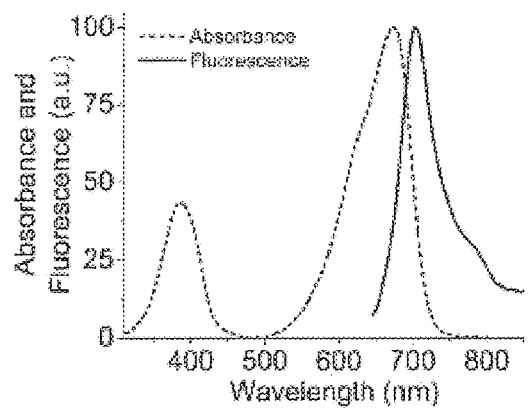

[a]Cells showing positive signals in the indicated channels were collected, see FIG. 1A for details.
[b]Objective lens used for protein localization screening.
Ex—excitation wavelength; Em—emission wavelength, BP—bandpass; LP—longpass.

Multi parameter screening and single cell isolation using cell picker. After 24 hour incubation of collected cells in a culture dish, the cell medium was gently replaced with fresh media to remove non-attached cells. Attached cells in the dish were then subjected to microscope-guided cell screening using our single cell manipulation system (CellSorter, CellSorter INC), controlled by CellSorter4.0 software [Környei, Z. et al. (2013) Sci. Rep. 3, 1088]. The cell sorter consisted of a pulled glass micropipette with an opening of 50 µm in diameter, a motorized micromanipulator (Marzhauser SM 3.25), and a pressure controller that manipulates the pressure inside the micropipette. Both the micromanipulator and pressure controller were operated by the CellSorter4.0 software. The cell sorter was installed on an inverted microscope (Nikon Eclipse Ti equipped with 10× NA 0.3, 20× and 40× objective lenses, a SPECTRA-X light engine (Lumencor) with 390/22 nm, 438/24 nm, 475/28 nm, 510/25 nm, 585/29 nm, and 631/28 nm exciters (Semrock), a 5.5 Zyla camera (Andor), and automated stage (Ludl), controlled by NIS-Elements AR software to obtain fluorescent images of entire population of cells in culture dish. To isolate cells with desired properties (e.g. high fluorescence intensity, exclusive plasma membrane localization) from a petri dish, the workflow of cell picking described in FIG. 6 was followed. Briefly, (1) fluorescent images of cells in a culture dish were acquired using the microscope; (2) 10-50 cells exhibiting desired properties (e.g., high fluorescence intensity, exclusive plasma membrane localization) were selected per dish (10-20 k cells per 3 cm dish); (3) the coordinates of selected cells were compiled and fed to the CellSorter software; (4) the cellSorter software ordered the micromanipulator to position the tip of the micropipette 5-10 µm above a first target cell; (5) negative pressure was applied through the micropipette to detach and pick up the target cell from the dish; (6) the micropipette moved the cell to a rack where PCR tubes were placed and released it into a designated PCR tube pre-filled with PBS, by applying positive pressure. Single mode (isolation of single cell per single run) or multi-mode (isolation of every desired cells in a dish per single run) cell picking was performed.

Target gene recovery. Cells individually collected in PCR tubes by the cell picker were subjected to whole genome amplification using a commercially available whole genomic amplification kit (WGA, New England BioLabs) followed by PCR amplification using corresponding primers. Amplicons with a size corresponding to that of the target gene were purified by agarose gel electrophoresis and cloned into an expression vector, and the purified plasmids were individually transfected and expressed in HEK cells for assessing desired characteristics of each gene.

Figure 1C:
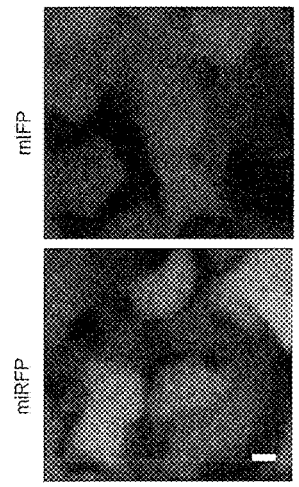
Figure 1D:
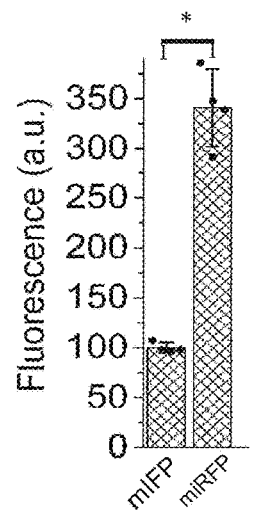
Figure 1E:
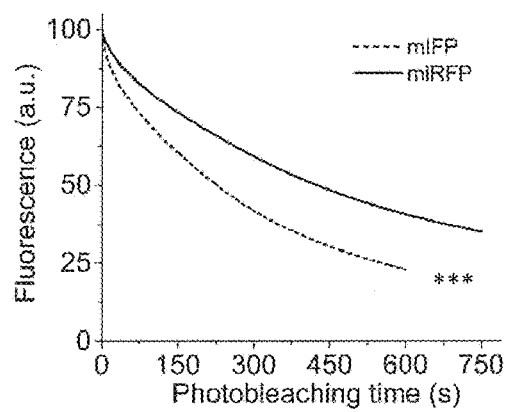
Figure 1F:
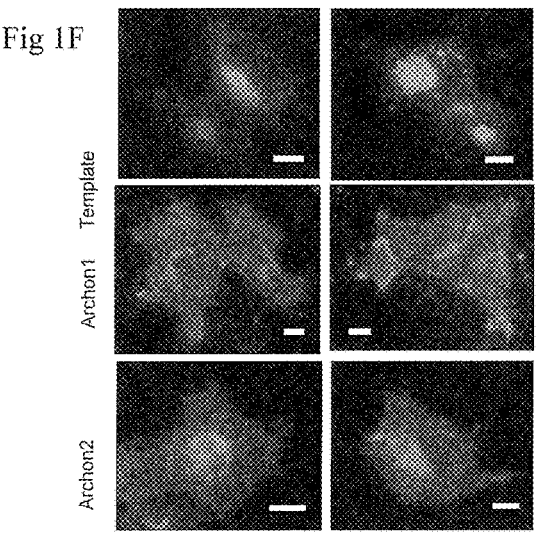
Figure 1H:
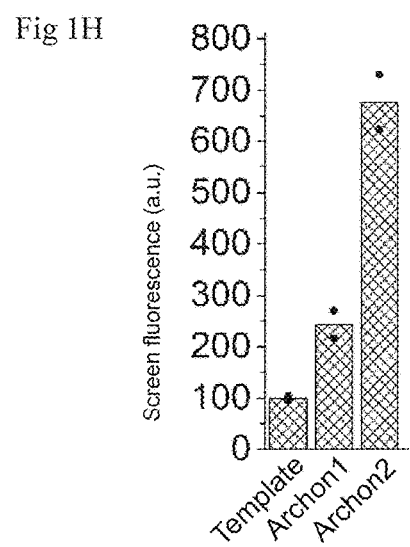

Protein characterization in mammalian cells. HEK293FT (Invitrogen) and HeLa (ATCC CCL-2) cells were maintained between 10% and 70% confluence at 37° C. with 5% $CO_2$ in DMEM medium (Cellgro) supplemented with 10% heat inactivated FBS (Corning), 1% penicillin/streptomycin (Cellgro), and 1% sodium pyruvate (BioWhittaker). Cells were authenticated by the manufacturer and tested for mycoplasma contamination to their standard levels of stringency and were used because they are common cell lines for testing new tools. HeLa cells were used simply as a testbed for protein expression, and not for any reasons of investigating the properties of HeLa cells in their own right. HEK293FT and HeLa cells were transiently transfected using TransIT-X2 (Minis Bio LLC) according to the manufacturer's protocol and analyzed 48 h after transfection. Cells were imaged using a Nikon Eclipse Ti inverted microscope equipped with a SPECTRA X light engine (Lumencor) with 475/28 nm and 631/28 nm exciters (Semrock), a 5.5 Zyla camera (Andor), controlled by NIS-Elements AR software using 10× NA 0.3 (FIG. 1D, FIG. 7B) and 40× NA 1.15NA (FIG. 1C, E, F, G, FIG. 5, FIG. 8B-C and FIG. 7C) objective lenses. To compare brightness of mIFP, miRFP and RpBphP1 intermediate mutants the mean near-infrared fluorescence intensity of ~100% confluent HEK293FT cell cultures expressing corresponding proteins was calculated (FIG. 1D, FIG. 7B). For plasma membrane localization analysis, voltage reporter variants were co-transfected with membrane-anchored YFP (FIG. 1G, FIG. 13B). To quantify protein localization, MATLAB code was written that automatically detected cells in each image and calculated the degree of similarity (i.e., co-localization) between the normalized images acquired in the green and red channels by averaging the difference between the green channel intensity profile and the red channel intensity profile (so that a mean value closer to zero represents better co-localization). For FIG. 1E, raw photobleaching curves were normalized to the spectrum of the red LED of SPECTRA X light engine, the transmission profile of the excitation filter and dichroic mirror, and the absorbance spectrum of respective FP. For flow cytometry analysis HEK293T cells were stained with SYTOX Green (Life Technologies) and analyzed using 488 and 640 nm laser lines and the respective 515/20BP and 710/50BP emission filters on a BD LSR II analyzer (FIG. 1H and FIG. 13A).

Induced transmembrane voltage (ITV) in HEK cells. To screen for voltage sensitivity, HEK293FT cells expressing mutants selected with the cell picker were subjected to a reproducible electric field between two platinum electrodes as described previously [Hochbaum, D. R. et al. (2014) Nat. Methods 1-34 doi:10.1038/nmeth.3000; Pucihar, G., et al., (2009) J. Vis. Exp. 88, 4-6]. In brief, HEK293FT cells were plated on 24 well plates and transfected with 500 ng of target plasmid DNA per well using TransIT-X2 (Minis Bio LLC) following the manufacturer's protocol. Cell imaging was performed on the inverted Eclipse Ti-E (Nikon) equipped with a CMOS camera (Zyla5.5, Andor), LEDs (Spectra, Lumencor), a 637 nm Laser (637 LX, OBIS) focused on the back focal plane of 40×NA 1.15 objective (Nikon), and filter set with 664 nm LP (emission) and 650 nm (dichroic) (Semrock). The pair of platinum electrodes, with a gap of 4 mm, and mounted on an automated micromanipulator, was sequentially placed in the wells, and trains of electrical pulses (80V/cm, 50 ms, 2 Hz) generated by a DG2041A Arbitrary Waveform Function Generator (RIGOL) and amplified with a high voltage amplifier (Model 2205, Trek) were applied across the cell culture to induce changes in the membrane voltage. Fluorescent images were recorded at 200 Hz frame rate in 2×2 binning mode for 20s.

Whole-cell electrophysiology and fluorescence recording in HEK cells. Voltage sensitive variants selected from the ITV screening were subjected to whole-cell electrophysiology in HEK293FT cells. To evaluate voltage reporter candidates, HEK293FT cells were transfected with 100 ng of target plasmid DNA using the calcium phosphate protocol described above. 24 hours post transfection, HEK293FT cells were re-plated on round coverslips (0.15 mm thick, 25 mm in diameter, coated with 2% growth factor reduced Matrigel in DMEM for 1 h at 37° C.) at a density of 20,000 cells per well in a 24-well plate and incubated for a day at 37° C. Whole-cell patch clamp recording was performed between 48 and 72 h post transfection in artificial extracellular solution (Tyrode's solution) consisting of (in mM) 125 NaCl, 2 KCl, 3 $CaCl_2$, 1 $MgCl_2$, 10 HEPES, 30 glucose, pH7.3 (NaOH adjusted) at 320 mOsm; the intracellular solution consisting of (in mM) 135 K-gluconate, 8 NaCl, 10 HEPES, 4 Mg-ATP, 0.4 Na-GTP, 0.6 $MgCl_2$, 0.1 $CaCl_2$, pH 7.25 (KOH adjusted) at 295 mOsm. A gap junction blocker, 2-aminoethoxydiphenyl borate (50 µM, Sigma), was added to eliminate electrical coupling between cells. All-trans-retinal was not supplemented for any HEK cell recordings. Borosilicate glass pipettes (WPI) with an outer diameter 1 mm and a wall thickness of 0.2 mm were pulled using a Flaming/Brown micropipette puller (P-97, Sutter Instrument) to obtain a tip resistance of 3-10 MΩ. Pipettes were positioned by a Sutter MP285 manipulator during whole-cell patching. To ensure accurate measurements, data was acquired from HEK293FT cells with access resistance <15 MΩ, having reversal potentials between −10 and −40 mV, membrane resistance >0.3 GΩ, and holding current within ±100 pA. For FIG. 1I-J and FIG. 13, patch-clamp recordings were acquired via an Axopatch 700B amplifier (Molecular Devices) and Digidata 1440 digitizer (Molecular Devices) in Tyrode's solution maintained at 32° C. during experiments using a warmed holding platform (64-1663D, Warner Instruments) controlled by a temperature controller (TC-324B, Warner Instruments). Fluorescence imaging was performed on the inverted fluorescence microscope (Nikon Ti), equipped with a red laser (637 nm, 100 mW, Coherent, OBIS 637LX, pigtailed) expanded by a beam expander (Thorlabs) and focused on to the back focal plane of the 40×NA 1.15 objective lens (Nikon). Images were taken by an EMCCD camera (iXon, Andor) at 500 Hz frame rate in 2×2 binning mode for 2 s. Voltage sensitivity of fluorescence was recorded in voltage-clamp mode with a holding potential of −70 mV for is and then applying voltage steps from −70 mV to +30 mV for 100 ms. For FIG. 2O and FIG. 18, photocurrents were recorded at room temperature in voltage-clamp mode with a holding potential of −70 mV in response to 500 ms light pulses using Multiclamp 700B and Digidata 1550A digitizer (Molecular Devices), and a PC running pClamp10 (Molecular Devices).

Primary neuron culture and transfection. All procedures involving animals at MIT were conducted in accordance with the US National Institutes of Health Guide for the Care and Use of Laboratory Animals and approved by the Massachusetts Institute of Technology Committee on Animal Care. Hippocampal neurons were prepared from postnatal day 0 or 1 Swiss Webster (Taconic) mice (both male and female mice were used) as previously described [Klapoetke, N. C. et al. (2014) Nat. Methods 11, 338-46; Chow, B. Y. et al. (2010) Nature 463, 98-102] with the following modifications: dissected hippocampal tissue was digested with 50 units of papain (Worthington Biochem) for 6-8 min, and the digestion was stopped with ovomucoid trypsin inhibitor (Worthington Biochem). Cells were plated at a density of 20,000-30,000 per glass coverslip coated with Matrigel (BD Biosciences). Neurons were seeded in 100 µl plating medium containing MEM (Life Technologies), glucose (33 mM, Sigma), transferrin (0.01%, Sigma), Hepes (10 mM, Sigma), Glutagro (2 mM, Corning), Insulin (0.13%, Millipore), B27 supplement (2%, Gibco), heat inactivated FBS (7.5%, Corning). After cell adhesion, additional plating medium was added. AraC (0.002 mM, Sigma) was added when glia density was 50-70% of confluent. Neurons were grown at 37° C. and 5% $CO_2$ in a humidified atmosphere.

Cultured neurons were transfected at 4-5 days in vitro (DIV) with a commercial calcium phosphate transfection kit (Life Technologies) as previously described [Klapoetke, N. C. et al. (2014) Nat. Methods 11, 338-46]. Briefly, 500 ng of plasmid DNA per well was used for transfection followed by an additional washing with acidic MEM buffer (pH 6.7-6.8) after 30-60 min of calcium phosphate precipitate incubation to remove residual precipitates [Jiang, M. & Chen, G. (2006) Nat Protoc 1: 695-700]. All measurements on neurons were taken between DIV 14 and 18 DIV (9-14 d post transfection) to allow for sodium channel maturation. No all-trans-retinal was supplemented for any cultured neuron recordings.

Fluorescence microscopy of primary neurons. Fluorescent imaging of voltage sensors expressed in cultured hippocampal neurons for FIGS. 2B, C, N, P, Q, FIG. 15, and FIG. 17H, I was performed using a Nikon Eclipse Ti inverted microscope equipped with a 40×1.15 NA water immersion objective (Nikon), a 637 nm Laser (637 LX, OBIS) focused on the back focal plane of the objective, a SPECTRA X light engine (Lumencor) with 475/28 nm, 585/29 nm, and 631/28 nm exciters (Semrock), 470 nm LED (ThorLabs) and a 5.5 Zyla camera (Andor), controlled by NIS-Elements AR software.

Electrophysiology in primary hippocampal neurons. Whole-cell patch clamp recordings of cultured neurons for FIG. 2D-M and FIG. 17A-G were acquired via an Axopatch 700B amplifier (Molecular Devices) and Digidata 1440 digitizer (Molecular Devices). Neurons were patched between DIV14 and DIV18. Neurons were bathed in Tyrode's solution [125 NaCl, 2 KCl, 3 $CaCl_2$, 1 $MgCl_2$, 10 HEPES, 30 glucose, pH7.3 (NaOH adjusted)] at 32° C. during measurements. Borosilicate glass pipettes with an outer diameter 1 mm and a wall thickness of 0.2 mm with resistance of 3-10 MΩ were filled with internal solution containing 135 K-gluconate, 8 NaCl, 10 HEPES, 4 Mg-ATP, 0.4 Na-GTP, 0.6 $MgCl_2$, 0.1 $CaCl_2$, pH 7.25 (KOH adjusted) at 295 mOsm. Measurements from primary neuron cultures were performed on the electrophysiology setup described in the "Whole-cell electrophysiology and fluorescence recording in HEK cells" section herein. Patch-clamp data was acquired only if the resting potential was below −45 mV and access resistance was <25MΩ. Access resistance was compensated 30-70%. Fluorescence imaging was performed on an inverted fluorescence microscope (Nikon Ti), equipped with a red laser (637 nm, 100 mV, Coherent, OBIS 637LX, Pigtailed) expanded by a beam expander (Thorlabs) and focused on to the back focal plane of the 40×NA 1.15 objective lens (Nikon). Synaptic blockers (NBQX, 10 µM; d(−)-2-amino-5-phosphonovaleric acid, 25 µM; gabazine, 20 µM; Tocris) were added to the imaging medium for measurements of single-cell electrophysiology. For voltage sensor kinetics studies presented in FIG. 2D, FIG. 17A and FIG. 29A images were acquired with an EMCCD camera (iXon, Andor) at a 3.2 kHz frame rate using an optical mask (Optomask, Andor). For the rest of concurrent imaging and electrophysiology recordings the acquisition rate was reduced to 2.3 kHz to achieve longer recording times without camera overheating and to reduce data storage.

In utero electroporation. Embryonic day (E) 15.5 timed-pregnant female C57BL/6 and CD1 (Charles River; for FIG. 3, FIGS. 20, 21, 22, 23, and 24A-I) or Swiss Webster (Taconic; FIG. 11E) mice were deeply anesthetized with 2% isoflurane. Uterine horns were exposed and periodically rinsed with warm PBS. A plasmid encoding Archon1, Archon2 or miRFP (pCAG-Archon1/2-KGC-EGFP-ER2-WPRE, pAAV-Syn-miRFP; 1 µg/µl) diluted with PBS was injected into the lateral ventricle of one cerebral hemisphere. Five voltage pulses (50 V, 50 ms duration, 1 Hz) were delivered using round plate electrodes (CUY21 electroporator, NEPA GENE, Japan; ECM™ 830 electroporator, Harvard Apparatus). Injected embryos were placed back into the dam, and allowed to mature to delivery. All experimental manipulations were performed in accordance with protocols approved by the Harvard Standing Committee on Animal Care or Massachusetts Institute of Technology Committee on Animal Care (according to location of the respective experiments), following guidelines described in the US National Institutes of Health Guide for the Care and Use of Laboratory Animals.

Acute brain slice preparation. Acute brain sections were obtained from C57BL/6 and CD1 (Charles River) mice at P20-P30, using standard techniques. Mice were used without regard for sex. No statistical methods were used to estimate sample size for animal studies throughout. No randomization or blinding were used for animal studies throughout. Mice were anaesthetized by isoflurane inhalation and perfused transcardially with ice-cold artificial cerebrospinal fluid (ACSF) containing (in mM) 125 NaCl, 2.5 KCl, 25 $NaHCO_3$, 2 $CaCl_2$, 1 $MgCl_2$, 1.25 $NaH_2PO_4$ and 11 glucose (295 mOsm/kg). Cerebral hemispheres were removed, placed in cold choline-based cutting solution (consisting of (in mM): 110 choline chloride, 25 $NaHCO_3$, 2.5 KCl, 7 $MgCl_2$, 0.5 $CaCl_2$, 1.25 $NaH_2PO_4$, 25 glucose, 11.6 ascorbic acid, and 3.1 pyruvic acid), blocked and transferred into a slicing chamber containing ice-cold choline-based cutting solution. Coronal slices (300 µm thick) were cut with a Leica VT1000 s vibratome, transferred to a holding chamber containing ACSF, and recovered for 30 min at 34° C., followed by another 30 min at room temperature. Slices were subsequently maintained at room temperature until use. Both cutting solution and ACSF were constantly bubbled with 95% $O_2$/5% $CO_2$.

Electrophysiology and voltage imaging in acute brain slice Individual slices were transferred to a recording chamber mounted on an upright microscope (Olympus BX51WI, see below herein) and continuously superfused (2-3 ml/min) with ACSF warmed to ~32° C. by passing it through a feedback-controlled in-line heater (SH-27B; Warner Instruments). Cells were visualized through a 60× water-immersion objective with either infrared differential interference contrast (DIC) optics, or epifluorescence to identify GFP-positive cells. Whole-cell voltage- and current-clamp recordings were obtained from GFP-positive pyramidal neurons in layer 2/3 of motor cortex, using patch pipettes (tip resistance 2.2-3.5 MΩ) pulled from borosilicate glass (G150E-3, Warner Instruments). For current-clamp recordings the pipette solution consisted of in (mM): 130 K-gluconate, 10 KCl, 4 NaCl, 10 HEPES, 4 $Mg_2$-ATP, 0.3 Tris-GTP, 14 Tris-phosphocreatine (290 mOsm/1; pH 7.28 adjusted with KOH), and for voltage-clamp recordings a cesium-based pipette solution was used (135 $CsMeSO_3$, 1 EGTA(CsOH), 10 HEPES, 3.3 QX-314(Cl—), 4 Mgt-ATP, 0.3 Na-GTP, $Na_2$-phosphocreatine; 295 mOsm/l; pH 7.35 adjusted with CsOH). For 2-photon imaging of recorded cells 20 µM AlexaFluor594 was added to the respective internal solution. Voltage-clamp recordings were performed in the presence of tetrodotoxin (TTX, 0.5 µM) and cadmium (50 µM). EPSPs were evoked by positioning a tungsten bipolar electrode (FHC) in layer 5, and delivering a train of 5 pulses (0.1 ms, 1 Hz). Individual trials were separated by >30 s. Stimulation strength was adjusted to evoke subthreshold EPSPs, and only cells in which clean, short-latency EPSPs could be evoked were used for voltage imaging.

Archon fluorescence was excited via a red laser (637 nm, 140 mW, Coherent Obis 637-140 LX), which was focused onto the back focal plane of the objective (Olympus LUMFL N 60×/1.10 W). Neutral density filters were used such that the power recorded after the objective was ~7 mW. The laser spot was ~25 µm in diameter at the sample plane; the resulting intensity was ~15 W/$mm^2$. Fluorescence was collected through the same objective, passed through a 705/100 nm emission filter, and imaged onto an EMCCD camera (Andor iXON Ultra 888) at 1000 frames/s. In order to acquire images at this frame rate, the EMCCD region of interest was restricted to a 99×300 pixel window (binned 3×3), and individual sweeps were no longer than 30 s. Membrane currents and potentials were amplified and low-pass filtered at 3 kHz using a Multiclamp 700B amplifier (Molecular Devices), digitized at 10 kHz and acquired using National Instruments acquisition boards and a custom version of ScanImage written in MATLAB (Mathworks) (github.com/bernardosabatinilab/
SabalabSoftware_Nov2009.git). For two-photon images presented in FIG. 21, individual neurons expressing Archon1 were filled through a recording pipette with an internal solution containing Alexa Fluor 594 (20 µM), and both Alexa Fluor 594 and GFP fluorescence were visualized using a Ti-Sapphire laser (Coherent) tuned to 850 nm.

Visualization of Archon expression in fixed brain tissue. Deeply anesthetized mice were perfused transcardially with 4% paraformaldehyde in 0.1 M phosphate buffer (pH 7.3) and brains were postfixed for 4 h at 4° C. 50 µm sections were cut on a vibratome, stained with fluorescent Nissl stain (NeuroTrace 640/660; Molecular Probes), and mounted in ProLong Antifade Diamond reagent (Invitrogen). Images were taken first with a slide-scanning wide-field microscope (VS120, Olympus), and high-resolution images of regions of interest were subsequently acquired with a Leica LS8 confocal microscope (Harvard NeuroDiscovery Center). Confocal images represent maximum intensity projections of 15 to 40 µm image stacks.

Transient expression in zebrafish embryos. All experiments were conducted in accordance with MIT Committee on Animal Care and Janelia Farm IACUC protocols (as appropriate for the respective locations of specific experiments). Zebrafish were raised and bred at 28° C. according to standard methods. DNA plasmids encoding zArchon1-KGC-GFP-ER2 or miRFP were co-injected with Tol2 transposase mRNA into embryos of the pan-neuronal expressing Gal4 line, tg(elavl3:GAL4-VP16)nns6 [Kimura, Y., et al., (2008) Development 135, 3001-3005]. The embryos used in the study were homozygous nacre. Briefly, DNA and Tol2 transposase mRNA, synthesized using pCR2FA as a template [Kwan, K. M. et al. (2007) Dev. Dyn. 236, 3088-3099] (mMESSAGE mMACHINE® SP6 Transcription Kit, Thermofisher), were diluted to a final concentration of 25 ng/µl in 0.4 mM KCl solution containing 0.05% phenol red solution (Sigma Aldrich) to monitor the injection quality. The mixture was kept on ice to minimize degradation of mRNA during the injection. The mixture was injected into embryos at 1-4 cell stages as described previously [Fisher, S. et al. (2006) Nat. Protoc. 1, 1297-1305]. Larvae were screened for green fluorescence in the brain and spinal cord at 2-3 days post fertilization (dpf; animals were used without regard to sex) and subsequently imaged at 3-4 dpf.

Voltage imaging in zebrafish embryos. Zebrafish larvae at 3-4 dpf were used to image neurons expressing zArchon1. To prevent motion artifacts during imaging, larvae were paralyzed by applying a paralytic agent, pancronium bromide, at a final concentration of 0.20 mg/ml (Sigma Aldrich), to stop muscle motion [Panier, T. et al. (2013) Front. Neural Circuits 7, 65]. Larvae were placed in a dish with the paralytic agent until they stopped moving, taking about one minute on average. Paralyzed larvae were immobilized in 1.5% ultra-low-melting agarose (Sigma Aldrich) prepared in E3 medium following standard protocols [Renaud, O., et al., (2011) Nat. Protoc. 6, 1897-904]. The embedded larvae were mounted on an inverted epifluorescent microscope (Nikon Eclipse Ti) for voltage imaging. The fluorescence of zArchons was excited by a red laser (OBIS 637 LX) focused onto the back focal plane of a 40×1.15NA water-immersion objective (Nikon). Illumination intensities of 1.1-2.2 W/mm2 were used for voltage imaging recorded using a sCMOS camera (Zyla 5.5, Andor) with image acquisition rates of 250-500 Hz. No chemical or physical stimuli were applied before or during recording of spontaneous activity.

Lightsheet zebrafish imaging. Lightsheet imaging for FIG. 11 was performed on a Zeiss Z.1 lightsheet microscope. The fixed sample was embedded in 1% agarose in a capillary and mounted on the freely rotating stage of the Z.1 lightsheet microscope. For image acquisition, the sample with the surrounding agarose gel was extruded from the glass capillary. Lightsheets were generated by two illumination objectives (10×, NA 0.2), and the fluorescence signal detected by a 20× water immersion objective (NA 1.0). Both lightsheets were used for data collection. The laser line used for excitation was 488 nm. Optical filters used to separate and clean the fluorescence response included a Chroma T560lpxr as a dichroic, and a Chroma 59001m for GFP. Tiled datasets were taken with the Zeiss ZEN Software, and subsequently merged and processed with FIJI, and Arivis Vision4D.

Voltage imaging in C. elegans. The Archon1-KGC-EGFP-ER2 gene was codon-optimized for expression in C. elegans using the online resource at www.bioinformatics.org/. Worms were maintained and grown following standard protocols [Brenner, S. (1974) Genetics 77, 71-94]. SWF4 (flvEx3[rig-3::wArchon1-KGC-EGFP-ER2, sra-6::ChR2-GFP, elt-2::nGFP]) and SWF5 (flvEx4[rig-3::wArchon1-KGC-EGFP-ER2, sra-6::ChR2-GFP), elt-2::nGFP]) were two independent lines generated by injecting the indicated plasmids into N2 background worms and picking those with strongest expression of the wArchon1-GFP fusion. Results from these two lines were indistinguishable. SWF7 (flvEx5[rig-3::wArchon1-KGC-EGFP-ER2, elt-2::nGFP]), generated by injecting the indicated plasmid into N2 background worms, was used for control experiments examining the action of wArchon1 in the absence of channelrhodopsin-2.

Transgenic worms (used without regard to sex) at L4 stage of development were put onto NGM plates with OP50 lawns supplemented with 100 µM all-trans-retinal (Sigma-Aldrich, USA) no less than 16 hours prior to experiments. Worms were mounted on 5% agarose pads on microscope slides, immobilized with 5 mM tetramisol and imaged using a Nikon Eclipse Ti inverted microscope equipped with a 40×1.15 NA water immersion objective (Nikon), a 637 nm Laser (637 LX, OBIS) focused on the back focal plane of the objective, a SPECTRA X light engine (Lumencor) with 475/28 nm excitation filter (Semrock), and a 5.5 Zyla camera (Andor), controlled by NIS-Elements AR software. Fluorescence of wArchon1 was imaged with 635 nm excitation at 800 mW/mm$^2$ and 664 nm LP emission filter (Semrock); GFP fluorescence was imaged with 475/34BP excitation filter and 527/50BP emission filter (Semrock). Optogenetic stimulation was performed with 475/34 nm illumination at 0.2 mW/mm$^2$.

Data analysis and statistics. Data were analyzed offline using NIS-Elements Advance Research software, Origin (OriginLab), FlowJo v10, Excel (Microsoft), ImageJ, Igor Pro (Wavemetrics), BoxPlotR and MATLAB. Analysis of all presented fluorescence traces was performed as following: cells and a neighboring cell-free region were selected manually and fluorescence measurements were performed for each region of interest (ROI), and then fluorescence from an Archon-free region was subtracted from cell fluorescence to correct for background; except FIG. 3 and FIG. 22, in which Archon fluorescence was extracted by a maximum-likelihood pixel-weighting algorithm described previously [Kralj, J. M., et al., (2012) Nat Methods 9, 90-95]. In addition, for FIG. 3 and FIG. 17D Archon fluorescence traces were corrected for photobleaching by subtracting baseline fluorescence traces that were low-pass filtered and fit to a double exponential or an exponential function, respectively. All fluorescent traces were presented without noise filtering except for the zoomed-in trace in FIG. 4B (bottom), which was filtered for noise using a moving average window. Fluorescence changes to voltage steps were calculated as $\Delta F/F=(Fss-Fbl)/Fbl$, where Fss (steady-state fluorescence) is the mean fluorescence intensity averaged over 50-70 ms during a voltage step after the fluorescence signal reaches its plateau, Fbl (baseline fluorescence) is the mean fluorescence intensity averaged over 100 ms before the voltage step. Fluorescence changes during the action potential (AP) were calculated as $\Delta F/F=(Fpeak-Fbl)/Fbl$, where Fpeak (peak fluorescence) is the max fluorescence intensity during an AP, Fbl (baseline fluorescence) is the mean fluorescence intensity averaged over the 100 to 200 ms before an AP. The SNR for an AP was calculated by dividing the peak fluorescence of an AP by the standard deviation of baseline fluorescence over a 100 to 200 ms window preceding the AP. These SNRs were averaged to determine the AP SNR for a given cell. AP width was calculated at 50% of peak AP fluorescence by linearly interpolating the average AP fluorescence for a cell. This width was compared to the electrical AP waveform width after the electrical signal was down-sampled to the frame rate of the camera.

For kinetics analysis (FIG. 2D, FIG. 17A, and FIG. 29A), fluorescent traces were averaged across cells and the fluorescence rise segment and fluorescence decay segment were extracted from the averaged trace in MATLAB, by inspection. Only the first 50 ms in the fluorescence rise and fluorescence decay segments were used in the downstream bi-exponential fitting. Next, the fluorescence rise (inverted for convenience of using the single equation below for both rise and decay) or decay segment, F(t), was fitted to the following bi-exponential function in MATLAB: $F(t)=A\times(C\times exp(-t/t1)+(1-C)\times exp(-t/t2))$, where t1 was time constant of the fast component and t2 was time constant of the slow component. The percentage of the fast component (% t1) was defined as "C" above. For FIG. 3C and FIG. 24, to measure the time constant of actual voltage change in voltage-clamp experiments, a series of hyperpolarizing voltage steps (6 repetitions of −5 mV) were applied immediately before the voltage imaging protocol (without capacitance and series resistance compensation), and the decay constant of the first transient of each step was analyzed in the same way as described above.

For FIG. 19E-F, ROIs for the Archon2 signal were identified using a novel algorithmic approach utilizing non-negative matrix factorization (NMF) [Lee, D. D. & Seung, H. S. (1999) Nature 401, 788-91] on the power spectral density of each pixel's time history Intuitively, pixels that do not represent Archon2 activity will have a time history that is a mix of noise and camera artifacts, whereas pixels that do capture Archon2 activity will have a distinct signature in the frequency domain that captures the Archon2 dynamics. To automatically separate both the spatial and time history of these two types of pixels, a rank-2 NMF is calculated on the 3D dataset (X, Y and frequency), reshaped as a 2D matrix (space and frequency). What is required from a human is to specify one pixel that is known to be demonstrating Archon2 signal. For all other pixels, the algorithm compares the weight of the NMF component known to correspond to noise versus the NMF component known to correspond to Archon2 activity. For robustness, this algorithm is applied to overlapping partitions of the data, and then each pixel receives a set of votes as either noise or Archon2 signal. The result of this voting system is a mask that can be applied to the entire dataset, removing 98% of the pixels. The remaining data is then spatially clustered via connected components and available for existing time-domain interrogations. The code is available as a MATLAB script at github.com/dgoodwin208/nmfroi.

All statistics were performed in JMP (SAS), except that Wilcoxon rank sum tests were performed in MATLAB (MathWorks). A power analysis was not performed because the goal was to create a new technology; as noted in Dell, R. B., et al., (2002) ILAR J. 43, 207-13, and recommended by the NIH, "In experiments based on the success or failure of a desired goal, the number of animals required is difficult to estimate . . . " As noted in the aforementioned paper, "The number of animals required is usually estimated by experience instead of by any formal statistical calculation, although the procedures will be terminated [when the goal is achieved]." These numbers reflect our past experience in developing neurotechnologies.

Results

In order to achieve the multidimensional screening capability needed to assess large numbers of mutant genes along multiple parameters, microscopy (with its capacity to measure many parameters exhibited in an image at once) was combined with robotic cell picking (FIG. 1A), so that cells expressing members of a library of mutant genes could be phenotyped and then captured for mutant gene isolation. Cell picking was done using an adapted computer-vision-guided automated micropipette capable of controlled suction and positive pressure, and thus the isolation and ejection of single cells [Kornyei, Z. et al. (2013) Sci. Rep. 3, 1088]. The microscopy based cell-picking strategy has throughput sufficient to screen 300,000 cells in ~4 hours. To increase throughput, robotic cell picking was preceded [FIG. 1A(v)-1A(viii) with FACS sorting (FIG. 1A(i)-1A(iv)]. In brief, a gene library was transfected into HEK293T cells so that transfected cells would receive from one to four plasmids per cell (details of characterization in Results section), sorted the cells [FIG. 1A(ii-iv), performed multiple rounds of imaging to examine multiple parameters (e.g., brightness, localization), and extraction by suction FIG. 1A(vii) for target gene recovery] [FIG. 1A(viii); see FIG. 6 for detailed flowchart].

As a test case for the hierarchical robotic screen strategy, a monomeric near-infrared fluorescent protein (FP) was developed. A library of mutants of the RpBphP1 bacteriophytochrome [Giraud, E. et al. (2002) Nature 417, 202-205], was created, reasoning based on the crystal structure of RpBphP1 [Bellini, D. & Papiz, M. Z. (2012) Structure 20, 1436-1446] that this protein could serve as a viable backbone for engineering monomeric near-infrared FPs because of a lack of dimerization at its PAS-GAF domains (unique amongst bacteriophytochrome crystal structures), and did three rounds of robotic cell-picking with microscopy image-based criteria of brightness (all three rounds) and photostability (in the first round) (see Table 1, top row, for screening parameters; screening progress is described in FIG. 7). The selected mutant exhibited absorbance and emission maxima at 674 nm and 703 nm, respectively (FIG. 1B, with comparisons to other BphP-derived FPs in Table 2), and had 12 amino acid substitutions in comparison to the parental protein (see full sequences in FIG. 8). Size-exclusion chromatography demonstrated that the mutant was 96% monomeric at a high concentration (4 mg/ml; data in FIG. 9A, B). The protein was named monomeric iRFP, or miRFP for short. Indeed, fusions of miRFP to α-tubulin, β-actin, vimentin and H2B [as used in Ai, H.-W., et al., (2014) Nat. Protoc. 9, 910-28] localized properly in live mammalian cells (images in FIG. 10), demonstrating its usefulness as a monomeric fusion tag. Molecular brightness (the product of molar extinction coefficient and quantum yield) of miRFP purified from *E. coli* was higher than that of any spectrally similar bacteriophytochrome-based FP reported to date including dimers (Table 2). The fluorescence of miRFP was stable in pH 5-9 with a pKa value of 4.3 (FIG. 9C, Table 2). The fluorescence signal of miRFP-expressing HEK cells was 3.4× higher than that of cells expressing mIFP, an earlier monomeric near-infrared FP [Yu, D. et al. (2015) Nat. Methods 12, 1-6] (FIG. 1C-D), with twice higher photostability than that of mIFP (FIG. 1E). When expressed without heme oxygenase-1, which is required to enable mIFP fluorescence in vivo [Yu, D. et al. (2015) Nat. Methods 12, 1-6], miRFP functioned well in cultured neurons, zebrafish larvae, and mouse brain, and even could be co-excited with EGFP in two photon mode using standard Ti-Sapphire laser (FIG. 11).

TABLE 2

Properties of bacteriophytochrome-derived FPs

| Protein | BphP template | Abs. (nm)[a] | Em. (nm)[a] | Extinction coefficient (M$^{-1}$cm$^{-1}$)[a] | Quantum yield (%)[a] | Molecular brightness[b] vs. iRFP (%) | pK$_a$ | Photostability, t$_{1/2}$ (s) | Oligomeric state |
|---|---|---|---|---|---|---|---|---|---|
| iRFP670 | RpBphP6 | 651 | 670 | 59,000 | 13.2 | 154 | 4.5 | ND | Dimer |
| iRFP682 | RpBphP2 | 670 | 682 | 69,000 | 11.3 | 155 | 4.6 | ND | Dimer |
| iRFP702 | RpBphP6 | 673 | 702[c] | 85,000 | 8.2[c] | 138 | 4.5[c] | ND | Dimer |
| iRFP | RpBphP2 | 692 | 713 | 80,000 | 6.3[c] | 100 | 4.5[c] | ND | Dimer |
| iRFP720 | RpBphP2 | 700 | 720[c] | 70,000 | 6.0[c] | 83 | 4.5[c] | ND | Dimer |
| mIFP[d] | BrBphP | 683 | 703 | 82,000 | 8.4 | 137 | 3.5[e] | 227 | Monomer |
| miRFP670[f] | RpBphP1 | 642 | 670 | 87,400 | 14 | 243 | 4.5 | ND | Monomer |
| miRFP703[f] | RpBphP1 | 674 | 703 | 90,900 | 8.6 | 155 | 4.5 | ND | Monomer |
| miRFP709[f] | RpBphP1 | 683 | 709 | 78,400 | 5.4 | 84 | 4.5 | ND | Monomer |
| miRFP | RpBphP1 | 674 | 703 | 92,400 | 9.7 | 178 | 4.3 | 432 | Monomer |

[a]Measured on protein purified from *E. coli*.
[b]The product of molar extinction coefficient and quantum yield. All data was collected in this study, except:
[c]data from Shcherbakova, D. M. & Verkhusha, V. V. (2013) Nature Methods, 10(8), 751-754;
[d]this row of data from Yu, D. et al. (2015) Nat. Methods 12, 1-6;
[e]estimated from the plot in Yu, D. et al. (2015) Nat. Methods 12, 1-6;
[f]data from Shcherbakova, D. M. et al. (2016) Nat. Commun. 7, 1-12.
ND—not determined.
Proteins spectrally similar to miRFP were: iRFP702, iRFP, iRFP720, mIFP, miRFP703, miRFP709, and miRFP.

TABLE 3 provides statistical analysis for FIG. 1D, E, G, J; FIG. 2C, I, N; FIG. 3G, H, I; and FIG. 16.

Statistical analysis for FIG. 1D

| Protein | Number of data points for statistics (n) | Mean | Standard error of mean |
|---|---|---|---|
| mIFP | 4 | 29.33 | 0.75 |
| miRFP | 4 | 100.00 | 5.70 |

Wilcoxon rank sum test between mIFP and miRFP

| | |
|---|---|
| P-value | 0.0286 |
| rank sum test statistic | 10 |

Statistical analysis for FIG. 1E

| Protein | Number of data points for statistics (n) | Mean | Standard error of mean |
|---|---|---|---|
| mIFP | 8 | 227.36 | 11.27 |
| miRFP | 8 | 432.74 | 25.45 |

Wilcoxon rank sum test between mIFP and miRFP

| | |
|---|---|
| P-value | 1.5540e-04 |
| rank sum test statistic | 36 |

Statistical analysis for FIG. 1G

| Protein | Number of data points for statistics (n) | Mean | Standard error of mean |
|---|---|---|---|
| Template | 16 | 3.0616 | 0.3247 |
| Archon1 | 15 | 10.3510 | 1.3950 |
| Archon2 | 16 | 7.7443 | 1.0947 |

Kruskal-Wallis Test Rank Sums

| Protein | Count | Score Sum | Expected Score | Score Mean | (Mean-Mean0)/Std0 |
|---|---|---|---|---|---|
| Archon1 | 15 | 510.500 | 360.000 | 34.0333 | 3.423 |
| Archon2 | 16 | 449.500 | 384.000 | 28.0938 | 1.459 |
| Template | 16 | 168.000 | 384.000 | 10.5000 | -4.838 |

1-Way Test, Chi Square Approximation

| ChiSquare | DF | Prob > ChiSq |
|---|---|---|
| 24.9704 | 2 | <.0001 |

Nonparametric Comparisons with Control using Steel's test Control Group: Template

| q* | Alpha |
|---|---|
| 2.21304 | 0.05 |

| Protein1 | Protein2 | Score Mean Difference | Std Err Dif | Z | p-Value |
|---|---|---|---|---|---|
| Archon2 | QuasAr2 | -12.4375 | 3.316625 | -3.75005 | 0.0003 |
| Archon1 | QuasAr2 | -14.9188 | 3.267687 | -4.56554 | <.0001 |

Figure 1I:
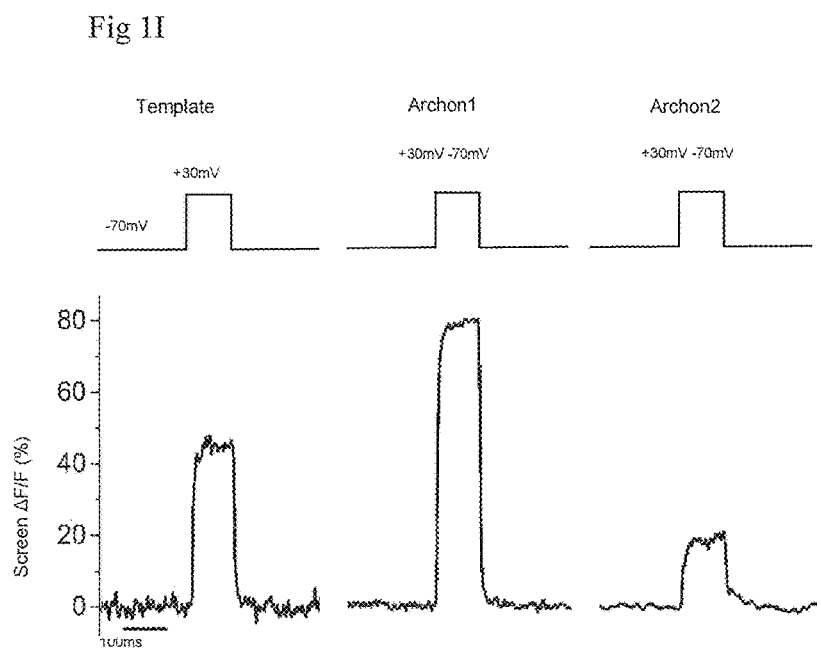
Figure 1J:
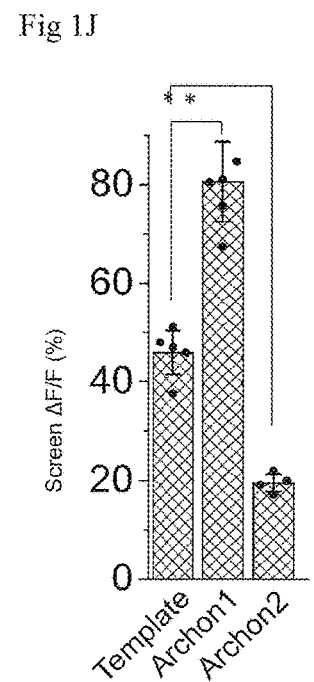

Statistical analysis for FIG. 1J

| Protein | Number of data points for statistics (n) | Mean | Standard error of mean |
|---|---|---|---|
| Template | 5 | 45.9002 | 2.0012 |
| Archon1 | 6 | 80.6349 | 3.3146 |
| Archon2 | 4 | 19.5504 | 0.8723 |

Kruskal-Wallis Test Rank Sums

| Protein | Count | Score Sum | Expected Score | Score Mean | (Mean-Mean0)/Std0 |
|---|---|---|---|---|---|
| Archon1 | 6 | 75.000 | 48.000 | 12.5000 | 3.123 |
| Archon2 | 4 | 10.000 | 32.000 | 2.5000 | -2.807 |
| Template | 5 | 35.000 | 40.000 | 7.0000 | -0.551 |

1-Way Test, ChiSquare Approximation

| ChiSquare | DF | Prob > ChiSq |
|---|---|---|
| 12.3750 | 2 | 0.0021 |

TABLE 3-continued provides statistical analysis for FIG. 1D, E, G, J; FIG. 2C, I, N; FIG. 3G, H, I; and FIG. 16.

Nonparametric Comparisons with Control using Steel's test Control Group: Template

| q* | Alpha |
|---|---|
| 2.21298 | 0.05 |

| Protein1 | Protein2 | Score Mean Difference | Std Err Dif | Z | p-Value |
|---|---|---|---|---|---|
| Archon2 | QuasAr2 | 4.27500 | 1.837117 | 2.32702 | 0.0374 |
| Archon1 | QuasAr2 | −5.31667 | 2.008316 | −2.64733 | 0.0155 |

Statistical analysis for FIG. 2C

| Protein | Number of data points for statistics (n) | Mean | Standard error of mean |
|---|---|---|---|
| Archer1 | 16 | 534.2359 | 66.17127 |
| QuasAr2 | 18 | 519.0741 | 80.68391 |
| Archon1 | 23 | 1440.3283 | 114.8950 |
| Archon2 | 23 | 4160.2174 | 441.5730 |

Kruskal-Wallis Test Rank Sums

| Protein | Count | Score Sum | Expected Score | Score Mean | (Mean-Mean0)/Std0 |
|---|---|---|---|---|---|
| Archer1 | 16 | 304.000 | 648.000 | 19.0000 | −4.132 |
| Archon1 | 23 | 1052.00 | 931.500 | 45.7391 | 1.276 |
| Archon2 | 23 | 1568.00 | 931.500 | 68.1739 | 6.761 |
| QuasAr2 | 18 | 316.000 | 729.000 | 17.5556 | −4.753 |

1-Way Test, ChiSquare Approximation

| ChiSquare | DF | Prob > ChiSq |
|---|---|---|
| 65.0330 | 3 | <.0001 |

Nonparametric Comparisons For All Pairs Using Steel-Dwass test

| q* | Alpha |
|---|---|
| 2.56903 | 0.05 |

| Protein1 | Protein2 | Score Mean Difference | Std Err Dif | Z | p-Value |
|---|---|---|---|---|---|
| Archon2 | Archon1 | 21.3043 | 3.958114 | 5.38245 | <.0001 |
| Archon2 | Archer1 | 19.4470 | 3.711762 | 5.23929 | <.0001 |
| Archon1 | Archer1 | 19.1291 | 3.711762 | 5.15364 | <.0001 |
| QuasAr2 | Archer1 | −2.4201 | 3.421575 | −0.70732 | 0.8942 |
| QuasAr2 | Archon1 | −18.2717 | 3.769795 | −4.84688 | <.0001 |
| QuasAr2 | Archon2 | −20.4505 | 3.769795 | −5.42483 | <.0001 |

Statistical analysis for FIG. 2I
Wilcoxon signed-rank test between electric and optical FMHW of Archon1 in culture.

| P-value | 0.0156* |
|---|---|
| rank sum test statistic | 14 |

Statistical analysis for FIG. 2N
Kruskal-Wallis Test Rank Sums

| Protein | Count | Score Sum | Expected Score | Score Mean | (Mean-Mean0)/Std0 |
|---|---|---|---|---|---|
| Ace | 5 | 52.000 | 80.000 | 10.4000 | −1.477 |
| Archer1 | 5 | 77.000 | 80.000 | 15.4000 | −0.134 |
| Archon1 | 7 | 196.000 | 112.000 | 28.0000 | 3.945 |
| Archon2 | 7 | 143.000 | 112.000 | 20.4286 | 1.441 |
| QuasAr2 | 7 | 28.000 | 112.000 | 4.0000 | −3.945 |

1-Way Test, Chi Square Approximation

| ChiSquare | DF | Prob > ChiSq |
|---|---|---|
| 27.9664 | 4 | <0.0001 |

Nonparametric Comparisons For All Pairs Using Steel-Dwass test

| q* | Alpha |
|---|---|
| 2.72777 | 0.05 |

| Protein1 | Protein2 | Score Mean Difference | Std Err Dif | Z | p-Value |
|---|---|---|---|---|---|
| Archon1 | Ace | 5.82857 | 2.111195 | 2.76079 | 0.0456 |
| Archon1 | Archer1 | 5.82857 | 2.111195 | 2.76079 | 0.0456 |
| Archon2 | Ace | 5.82857 | 2.111195 | 2.76079 | 0.0456 |
| Archon2 | Archer1 | 4.45714 | 2.111195 | 2.11119 | 0.2152 |
| Archer1 | Ace | 4.00000 | 1.914854 | 2.08893 | 0.2248 |
| QuasAr2 | Ace | −5.82857 | 2.111195 | −2.76079 | 0.0456 |
| QuasAr2 | Archer1 | −5.82857 | 2.111195 | −2.76079 | 0.0456 |
| Archon2 | Archon1 | −6.85714 | 2.236068 | −3.06661 | 0.0184 |
| QuasAr2 | Archon1 | −6.85714 | 2.236068 | −3.06661 | 0.0184 |
| QuasAr2 | Archon2 | −6.85714 | 2.236068 | −3.06661 | 0.0184 |

Statistical analysis for FIG. 3G
Wilcoxon signed-rank test between electric and optical FMHW of Archon1 at 1.5 W.

| P-value | 0.002** |
|---|---|
| rank sum test statistic | 27.5 |

Wilcoxon signed-rank test between electric and optical FMHW of Archon1 at 15 W.

| P-value | 0.0002*** |
|---|---|
| rank sum test statistic | 45.5 |

Statistical analysis for FIG. 3H
Wilcoxon signed-rank test of Archon1 df/f per action potential at 1.5 W and at 15 W.

| P-value | 0.375 |
|---|---|
| rank sum test statistic | 9.5 |

Statistical analysis for FIG. 3I
Wilcoxon signed-rank test of Archon1 SNR per action potential at 1.5 W and at 15 W.

| P-value | 0.002** |
|---|---|
| rank sum test statistic | −27.5 |

Statistical analysis for FIG. 16 providing information on (a) membrane resistance, (b) membrane capacitance, and (c) resting potential
(a) Membrane resistance
Kruskal-Wallis Test Rank Sums

| Protein | # of cells | Score Sum | Expected Score | Score Mean | (Mean-Mean0)/Std0 |
|---|---|---|---|---|---|
| Negative | 10 | 384.000 | 355.000 | 38.4000 | 0.478 |
| Archer1 | 8 | 344.000 | 284.000 | 43.0000 | 1.098 |
| QuasAr2 | 10 | 275.000 | 355.000 | 27.5000 | −1.334 |
| Ace2N-4aa-mNeon | 14 | 208.000 | 497.000 | 14.8571 | −4.236 |
| Archon1 | 17 | 719.000 | 603.500 | 42.2941 | 1.575 |
| Archon2 | 11 | 555.000 | 390.500 | 50.4545 | 2.647 |

TABLE 3-continued provides statistical analysis for FIG. 1D, E, G, J; FIG. 2C, I, N; FIG. 3G, H, I; and FIG. 16.

1-Way Test, Chi Square/Approximation

| ChiSquare | DF | Prob > ChiSq |
|---|---|---|
| 25.0740 | 5 | 0.0001 |

Nonparametric Comparisons with Control using Steel's test Control Group: Negative

| q* | Alpha |
|---|---|
| 2.50102 | 0.05 |

| Protein | Score Mean Difference | Std Err Dif | Z | p-Value |
|---|---|---|---|---|
| Archon2 | 4.10455 | 2.711088 | 1.51398 | 0.3990 |
| Archer1 | 1.68750 | 2.530984 | 0.66674 | 0.9394 |
| Archon1 | 1.19118 | 3.163208 | 0.37657 | 0.9947 |
| QuasAr2 | −3.10000 | 2.645751 | −1.17169 | 0.6379 |
| Ace2N-4aa-mNeon | −8.65714 | 2.927700 | −2.95698 | 0.0136 |

(b) Membrane capacitance
Kruskal-Wallis Test Rank Sums

| Protein | # of cells | Score Sum | Expected Score | Score Mean | (Mean-Mean0)/Std0 |
|---|---|---|---|---|---|
| Negative | 10 | 268.000 | 355.000 | 26.8000 | −1.452 |
| Archer1 | 8 | 190.000 | 284.000 | 23.7500 | −1.726 |
| QuasAr2 | 10 | 375.000 | 355.000 | 37.5000 | 0.327 |
| Ace2N-4aa-mNeon | 14 | 762.000 | 497.000 | 54.4286 | 3.884 |
| Archon1 | 17 | 586.500 | 603.500 | 34.5000 | −0.226 |
| Archon2 | 11 | 303.500 | 390.500 | 27.5909 | −1.396 |

1-Way Test, ChiSquare Approximation

| ChiSquare | DF | Prob > ChiSq |
|---|---|---|
| 18.4052 | 5 | 0.0025 |

Nonparametric Comparisons with Control using Steel's test control Group: Negative

| q* | Alpha |
|---|---|
| 2.50102 | 0.05 |

| Protein | Score Mean Difference | Std Err Dif | Z | p-Value |
|---|---|---|---|---|
| Ace2n-4aa-mNeon | 9.17143 | 2.927700 | 3.13264 | 0.0077 |
| QuasAr2 | 3.30000 | 2.645751 | 1.24728 | 0.5825 |
| Archon1 | 2.93824 | 3.163208 | 0.92888 | 0.8077 |
| Archon2 | 0.85909 | 2.711088 | 0.31688 | 0.9976 |
| Archer1 | −1.68750 | 2.530984 | −0.66674 | 0.9394 |

(c) Resting potential
Kruskal-Wallis Test Rank Sums

| Protein | # of cells | Score Sum | Expected Score | Score Mean | (Mean-Mean0)/Std0 |
|---|---|---|---|---|---|
| Negative | 10 | 245.500 | 400.000 | 24.5500 | −2.285 |
| Archer1 | 9 | 453.000 | 360.000 | 50.3333 | 1.436 |
| QuasAr2 | 10 | 520.000 | 400.000 | 52.0000 | 1.773 |
| Ace2N-4aa-mNeon | 17 | 536.000 | 680.000 | 31.5294 | −1.722 |
| Archon1 | 19 | 852.500 | 760.000 | 44.8684 | 1.062 |
| Archon2 | 14 | 553.000 | 560.000 | 39.5000 | −0.084 |

1-Way Test, ChiSquare Approximation

| ChiSquare | DF | Prob > ChiSq |
|---|---|---|
| 12.4210 | 5 | 0.0295 |

Non-parametric Comparisons with Control using Steel's test Control Group: Negative

| q* | Alpha |
|---|---|
| 2.49072 | 0.05 |

| Protein | Score Mean Difference | Std Err Dif | Z | p-Value |
|---|---|---|---|---|
| Archon1 | 7.478947 | 3.297313 | 2.268194 | 0.0870 |
| QuasAr2 | 6.600000 | 2.635786 | 2.503997 | 0.0483 |
| Archer1 | 5.594444 | 2.574207 | 2.173269 | 0.1085 |
| Archon2 | 4.800000 | 2.897632 | 1.656525 | 0.3059 |
| Ace2N-4aa-mNeon | 2.461765 | 3.154021 | 0.780516 | 0.8833 |

Having validated the power of the robotic cell picking microscopy screening strategy, and showing its ability to balance high-content and high-throughput goals, the next studies were directed to multidimensional screening for a high-performance fluorescent voltage sensor. The goal was to have, in the end, a molecule compatible with optogenetic control, so it was determined to begin with a template with red fluorescence (since all optogenetic tools are sensitive to blue light to some extent, meaning that ideally it would result in a voltage reporter that would be illuminated by yellow or red light). The process began with the opsin part of the previously reported voltage sensor QuasAr2, which has fluorescence excitation and emission maxima at 590 nm and 715 nm respectively [Hochbaum, D. R. et al. (2014) Nat. Methods 1-34 doi:10.1038/nmeth.3000], leaving out the mOrange fluorescent protein part of QuasAr2 because the focus was on improvement of the voltage sensitive domain. A library was generated with error-prone PCR, FACS sorted cells for brightness, and then performed one round of robotic cell-picking to optimize brightness and localization, followed by voltage sensitivity screening via electrical stimulation as previously described [Pucihar, G., et al., (2009) J. Vis. Exp. 88, 4-6], resulting in five variants that exhibited improved brightness and localization in HEK cells (see Table 1, bottom row, for screen parameters). Sequence analysis of the mutants revealed four amino acid positions, namely T56, T117, T183 and L198, that were changed in four out of the five variants identified at this stage, and four amino acid mutations were also identified in α-helices (T205, L31V, K47R, and A137T) and two mutations in β-strands (580P and D88N) which were represented at least once in the selected mutants (see FIG. 12 for amino acid alignments). A site-directed library of variants containing mutations identified was generated in the first round of directed evolution, as well as mutations near the Schiff base linkage (some of which had been previously probed for their impact on brightness and voltage sensitivity of Arch [Flytzanis, N. C. et al. (2014) Nat. Commun. 5, 4894; Mclsaac, R. S. et al. (2014) Proc. Natl. Acad. Sci. 105, 6374-9] and underwent a second round of FACS, robotic cell picking, and electrical stimulation to obtain seven final candidates with higher brightness and better membrane localization; for two of the seven voltage sensitivity was improved over the template (see data in FIG. 13), with mutations resulting throughout (sequences in FIG. 14). Prioritizing localization as the key parameter, with brightness and voltage sensitivity as secondary parameters, two molecules were selected— denoted Archon1 and Archon2 (FIGS. 13 and 14) for further investigation. Upon expression in HEK cells, Archon1 and Archon2 localized well on the plasma membrane (FIG. 1F), showing statistically significant several fold higher co-localization with membrane localized YFP vs. parental template, respectively (FIG. 1G; see Methods for details of the analysis). Archon1 and Archon2 had 2.4- and 6.8-fold increased brightness over the parental template, respectively (FIG. 1H). Fluorescence changes ($\Delta F/F$) in HEK cells for Archon1 and Archon2 to voltage steps from −70 to +30 mV were 81±8% and 20±2%, respectively, compared to the 46±4% of template (FIG. 1I-J). Thus, robotic cell picking was able to support multidimensional hierarchical screening to generate improved voltage sensor candidates, with properties optimized along the axes of brightness, localization and voltage sensitivity.

For expression in cultured neurons and in vivo mouse, zebrafish, and C. elegans, Archons were fused with EGFP, and the Golgi export trafficking signal (KGC) and endoplasmic reticulum export (ER) sequences [Gradinaru, V. et al. (2010) Cell 141, 154-165; Chuong, A. S. et al. (2014) Nat. Neurosci. 17, 1123-1129] (FIG. 2A). Archons demonstrated excellent membrane localization in cultured neurons (FIG. 2B; see FIG. 15 for images of neurons expressing other sensors, transfected into neurons under the same CaMKIIα promoter and imaged on the same day post transfection). Focusing on the Arch-derived voltage reporters (QuasAr2-mOrange and Archer1-EGFP, abbreviated as QuasAr2 and Archer1 in FIG. 2), which have similar excitation and emission wavelengths, in neural culture it was found that the improvement in brightness for Archon1 and Archon2 over QuasAr2 and Archer1 was several-fold higher and statistically significant (FIG. 2C), reminiscent of what was seen in HEK cells (FIG. 1H). Archon expression did not alter membrane resistance, membrane capacitance, or resting potential of cultured neurons (FIG. 16).

When expressed Archon2 was expressed in mouse brain slices, lower SNR and slightly worse membrane localization was obtained than with Archon1 (FIGS. 20 and 23). Results indicated that Archon2 has a high brightness and thus it can be used in methods in which that may be desirable. In cultured mouse neurons, it was determined that Archon1 exhibited a $\Delta F/F$ of 43±5% (mean±standard deviation throughout; n=10 cells from 4 cultures; raw trace in FIG. 2d) for a 100 mV deflection, somewhat smaller than found for Archon1 in HEK cells (compare FIG. 1I-J), highlighting the importance of testing constructs in multiple preparations and species. The dependence of fluorescence on voltage was linear (FIG. 2E-F). For comparison, other voltage reporters were found to have similar or smaller voltage sensitivity, and some of them were reported to exhibit nonlinear responses (FIG. 29A). The speed of response of Archon1 was very fast, with a biexponential response to a 100 mV voltage step with time constants of onset of 0.61±0.06 ms (88% of total amplitude) and 8.1±0.5 ms (12% of total amplitude) (n=6 neurons from 2 cultures), and a time constant of inactivation of 1.1±0.2 ms (88% of total amplitude) and 13±3 ms (12% of total amplitude) (FIG. 2D). These kinetics were comparable to or faster than other voltage reporters were tested at the same temperature and acquisition rate as for Archon1 (FIG. 29A). Indeed, Archon1 fluorescence was able to follow high-speed and small changes in voltage in cultured neurons, including the reporting of ~5 mV voltage transients (FIG. 2G), as well as action potentials (FIG. 2G, H, L), with the latter broadening by a few hundred microseconds in waveform duration (FIG. 2H-I). Thus, even high speed fluctuations in membrane potential (e.g., 200 Hz action potential-like voltage swings in FIG. 2M) were accurately followed. For action potentials, Archon1 in cultured neurons presented a $\Delta F/F$ of 30±6% and SNR of 36 (with noise calculated as the standard deviation of the baseline before the spike; FIG. 2J-K; n=7 cells from 5 cultures). Archon2 exhibited much faster kinetics than Archon1 (to the point where action potential broadening was imperceptible), but voltage sensitivity was lower than that of Archon1 by about half (FIG. 17A-G and FIG. 29A). Both Archons demonstrated linear dependence of fluorescence intensity vs. 637 nm excitation light power in the range from 7 to 860 mW/mm$^2$, which suggests that fluorescence was a single-photon process with the voltage-sensitive transition occurring from the ground state (FIG. 17H). Thus, from a voltage sensitivity and kinetics standpoint, Archons met or exceeded the performance of prior reagents, when tested in cultured neurons.

Photobleaching is a problem with prior voltage reporters, making it difficult to do voltage imaging in real experimental contexts, as signals decrease and ultimately blend in with the noise. Tests were performed to assess the photobleaching properties of Archon1, in cultured neurons. Archons were excited with 800 mW/mm$^2$ 637 nm light for 900 seconds, and it was found that Archon1 retained 95±16% of its baseline fluorescence (n=9 cells from 2 cultures). Next studies were performed to assess photobleaching for other reporters, tuning the light power in each case to yield similar action potential SNR (~26 for the hardware used in this experiment; see Methods section) as the Archon1 experiment. Archon2 showed 58±10% retention of initial baseline fluorescence after 900 seconds (n=7 cells from 2 cultures; FIG. 2N), followed by QuasAr2, Archer1 and Ace with 51±11% (n=7 cells from 1 culture), 38±7% (n=7 cells from 1 culture) and 21±4% (after 600 seconds; n=5 cells from 1 culture) retention, respectively (FIG. 2N; summarized in FIG. 29A). Thus, Archon1 exhibited almost no photobleaching over timescales relevant to a diversity of behavioral and physiological experiments, whereas other sensors exhibited significant photobleaching.

As Archons are derived from a light-driven proton pump, which generates photocurrent under visible light stimulation, experiments were performed that characterized their responses to illumination with light powers representative of those used during imaging (470/20 nm at 15 mW/mm$^2$ as used to image EGFP expressing neurons; 637 nm at 800 mW/mm$^2$ as used in this figure for imaging). Under all tested wavelengths, Archons showed no steady state photocurrent (FIG. 2O for Archon1; see FIG. 18 for further data). Under repetitive pulses of blue illumination, as often used for optogenetic control, the first pulse generated a transient photocurrent with value of −8±6 pA for a few milliseconds (n=8 cells from one culture; FIG. 2O) and subsequent pulses generated similar transient photocurrents (FIG. 18). Under repetitive pulses of red illumination, Archon1 showed a brief (<5 ms) transient photocurrent with value of −33±25 pA during initial illumination (FIG. 2O), and subsequent pulses of red light separated by dark recovery periods of a few seconds produced no detectable transient photocurrents (FIG. 18). Thus, Archon1 could be utilized in neural imaging with effectively zero photocurrent by having a brief "pre-pulse" of red light to eliminate the transient photocurrent before voltage imaging begins. Archon2 showed no transient or steady-state photocurrents under all tested conditions (FIG. 18). Thus, it was demonstrated that photocurrents of Archon1 under red and blue illumination were similar to or smaller than those of previously developed opsin-based voltage sensors at the light intensity used to image Archons in culture (i.e., 800 mW/mm$^2$; see FIG. 29A for comparisons). The red-shifted fluorescence spectrum of Arch-based voltage sensors could allow for combination of the sensors with channelrhodopsin actuators and GFP-based reporters. Therefore, blue light crosstalk with Archon fluorescence was characterized. Changes in the red fluorescence of Archons were measured under blue light intensities typically used for optogenetic experiments [Klapoetke, N. C. et al. (2014) Nat. Methods 11, 338-46]; in particular, under blue light at 4.8 mW/mm$^2$ and with red illumination as above, both Archons showed less than 2% increases in fluorescence brightness (FIG. 2P for Archon1 and FIG. 17I for Archon2), comparable to that of QuasAr2 (FIG. 29A). In summary: overall, Archon1 exhibited higher photostability than all other voltage sensors, and was brighter and showed better localization than previously developed Arch-based voltage sensors. Archons produced small transient and zero steady-state photocurrents under visible illumination and showed minimal cross talk under blue light. These photophysical and biochemical properties of Archons allowed for long term voltage imaging in both individual distal neuronal processes and even single spines on a single-trial basis, enabling mapping voltage fluctuations throughout dendritic branches (FIG. 19).

To test the function of Archons in brain tissue, Archon1 (and Archon2) were expressed in cortical pyramidal neurons by in utero electroporation (IUE). It was found that targeting the hippocampus by IUE at E15.5 also resulted in sparse expression in layer (L) 2/3 pyramidal neurons in motor cortex (FIG. 20). Voltage-clamp recordings from L2/3 pyramidal neurons were performed in acute brain slices from 3-4 week old mice, and simultaneously monitored Archon1 fluorescence at the cell body, using an imaging frequency of 1 kHz (FIG. 3A-B). A light intensity of 1.5 W/mm$^2$ yielded excellent imaging of neural membrane potential (FIG. 3E-J). A 10-fold higher light intensity, which did not seem to damage cells as assessed with electrophysiology (FIG. 2L), yielded very high SNRs (FIG. 3I), and resulting in the ability to obtain reliable optical signals from cells during extremely low voltage changes (i.e., 2-3 mV; FIG. 3N). Thus, 1.5 W/mm$^2$ may be useful for recording action potentials, with higher light intensities potentially being useful for recording extremely small voltage changes. Archon1 expressed in vivo was highly enriched at the plasma membrane (FIG. 3B and see FIGS. 20 and 22 for more images).

A series of voltage-steps in voltage-clamp mode was used to test the ability of Archons to report membrane voltage over a physiologically relevant range. Stepping the holding-potential (Vm) from −90 to +10 mV resulted in step-like fluorescent signals for Archon1 (FIG. 3C-D; Archon1: ΔF/F per 100 mV: 23.5±9.3%, n=7 neurons from 2 mice). The on- and off-kinetics of Archons were well described by a double-exponential function, and reached steady state within a few ms (FIG. 3C bottom). These data suggested that Archon1 should be sensitive enough to report sub-threshold voltage events and fast enough to report individual action potentials in acute brain slices. To test this, a series of 2 ms current pulses with increasing amplitudes was injected, while monitoring membrane potential and fluorescent signals. Archon1 allowed reliable detection of voltage transients from both sub-threshold depolarization and action potentials (APs) under 1.5 and 15 W/mm$^2$ of excitation light (FIG. 3E). Overlaying the average AP waveforms with the optical signal demonstrated faithful temporal resolving of individual APs by Archon1, with the optical signal reporting APs with high fidelity regardless of excitation intensity (FIG. 3F). Indeed, Archon1 fluorescence was able to follow action potentials in brain slices (n=10 neurons from 6 mice) without broadening by more than a millisecond in waveform duration (FIG. 3G). These results suggest that Archon1 should be capable of resolving trains of APs at high frequencies, and this was tested by injecting a series of 500 ms current steps with increasing amplitude (FIG. 3J). The reporter faithfully reported all APs, even at the highest frequencies tested (FIG. 3K; 59.5±14.2 Hz, n=22 steps from 5 neurons). Similar recordings were obtained with Archon2, and these recordings revealed similar temporal properties, but reduced ΔF/F and SNR (FIG. 23).

Under 1.5 and 15 W/mm$^2$ of excitation light, optically recorded APs by Archon1 displayed an average ΔF/F of 22.4±9.4% and 22.2±10.2, respectively (FIG. 3H; n=10 cells for 6 animals, with data acquired from paired experiments with individual cells recorded first at 1.5 W/mm$^2$ and then 15 W/mm$^2$). SNRs for single APs increased from 12±5 to 21±11 when the light intensity increased from 1.5 W/mm$^2$ to 15 W/mm$^2$ (FIG. 3I; n=10 cells for 6 animals, with data acquired from paired experiments with individual cells recorded first at 1.5 W/mm$^2$ and then 15 W/mm$^2$). At the higher light intensity, it was possible to obtain clear optical signals even with millivolt scale depolarizations (FIG. 3L-N). To this end, excitatory postsynaptic potentials (EPSPs) were electrically triggered in L5 (FIG. 3A) and selected stimulation intensities that evoked sub-threshold events (2-16 mV) in L2/3 pyramidal neurons (0.1 ms, 5 pulses at 1 Hz) (FIG. 3L, N). Even small synaptic events could be detected in single trials (FIG. 3M, left, with averaged traces included or reference, FIG. 3M, right). Across cells, voltage deflections of ~5 mV were reliably reported with ~2% fluorescence changes (FIG. 3N; n=45 events from 4 neurons from 2 mice). Thus, Archon can be used to report a wide variety of physiologically relevant neuronal signals in intact mammalian brain slices, including EPSPs with voltage changes below 10 mV.

Next the use of Archon1 was explored in multiple in vivo contexts. Zebrafish (*Danio rerio*) is, due to its genetic tractability and transparent nature, a widely used species in the study of the development and operation of the nervous system [Friedrich, R. W., et al., (2010) Curr. Biol. 20, R371-R381; Stewart, A. M., et al., (2014) Trends Neurosci. 37, 264-278; Ahrens, M. B. et al. (2012) Nature 485,471-477; Ahrens, M. B., et al., (2013) Nat Methods 10, 413-420; and Wyart, C. et al. (2009) Nature 461, 407-410]. To perform in vivo voltage imaging of neurons in larval zebrafish a zebrafish codon-optimized version of Archon1 (zArchon1 for short) fused to GFP was transiently expressed in a subset of neurons. A light intensity of 2.2 W/mm$^2$ was used for zArchon1 imaging. zArchon1, expressed in zebrafish larvae, demonstrated excellent membrane localization (see FIG. 24 for images of neurons expressing zArchon1 in a representative larva). In an immobilized larval zebrafish, zArchon1 reported bursts of spontaneous action potentials with large fluorescence changes from baseline to peak (FIG. 4A, B). For spontaneous action potentials, zArchon1 presented an action potential ΔF/F of 33±6% and SNR of 16 (FIG. 4C, D; n=5 neurons in 5 fish, measured at the soma); although no other voltage reporter has reported neuronal activity with single cell resolution in zebrafish to date, the voltage sensitivity and SNR of the voltage reporter are several fold higher than were found for other voltage reporters in other intact neural systems (FIG. 29A-B). The high voltage sensitivity of zArchon1 enabled detection of subthreshold events (FIG. 25), as well as voltage recording from neuronal processes (FIG. 4F-G).

Assessing photobleaching of voltage reporters in the context of use is important to ensure robustness of fluorescence signals over behaviorally relevant time periods in experimental settings. Thus, the photobleaching properties of zArchon1 in zebrafish larvae were assessed by applying the same illumination condition used for voltage imaging (637 nm at 2.2 W/mm$^2$). The fluorescence of zArchon1 declined to 84±8% of baseline fluorescence over 300 seconds (n=9 neurons in 5 fish; FIG. 4E; see FIG. 26 for a zArchon1 fluorescence trace reporting spontaneous responses over 300 seconds), or 0.05%/s in zebrafish in vivo (vs. 0.01%/s in cultured mouse neurons). Thus, the high performance of zArchon1 in zebrafish larvae could persist over extended time periods under practical imaging conditions.

The usage of Archon1 was examined in the nematode C. elegans, whose compact nervous system and genetic tractability have long made it a preferred model organism for neuroscience. The rig-3 promoter was used to drive expression of codon-optimized Archon1 (wArchon1 for short) fused to EGFP in AVA interneurons, involved in backward locomotion (FIG. 5A). wArchon1 demonstrated good membrane localization both at the soma and in individual axons of AVA neurons (FIG. 5B; see FIG. 27 for more images), as well as essentially zero photobleaching under 800 mW/mm$^2$ 637 nm illumination during 8 minutes of continuous excitation (FIG. 5C), thus enabling recordings of neural activity over behaviorally relevant time scales. The AVA neurons, when imaged at points at the soma or along the axon, exhibited long-lasting (tens of seconds to several minutes) high and low states similar to those previously reported in AVA calcium recordings24 (FIG. 5D), with changes in fluorescence intensity relative to baseline of magnitude ~20-25% and SNR ~25-35 (although the diversity of these fluctuations (FIG. 5D-F), in contrast to the stereotyped action potentials of vertebrate neurons, makes it difficult to arrive at a single number; n=10 worms). Blue light illumination (three pulses of 6 sec duration each) did not affect wArchon1 fluorescence in either high or low voltage states (FIG. 5E-G). The absence of blue light crosstalk allows for combining voltage imaging using wArchon1 with optogenetic control using opsins. To demonstrate compatibility of wArchon1 with optogenetic control, synaptic transmission between the polymodal nociceptor ASH neuron and the downstream wArchon1-expressing AVA interneuron was probed, by targeting the former with ChR2-GFP under control of the sra-6 promoter (FIG. 5H-I). Transgenic worms expressing ChR2 and wArchon1 without blue light illumination showed spontaneous activity of AVA neurons, similar to that observed for transgenics expressing only wArchon1 in AVA neurons (FIG. 5J-K; with ~18-23% of ΔF/F, ~22-32 SNR, for these high states; n=20 worms). However, 51 out of 60 blue light pulses resulted in sustained elevation of wArchon1 fluorescence in AVA neurons lasting for 38±13 seconds (FIG. 5L-N; ΔF/F of ~16-21%, ~20-28 SNR; n=20 worms). Thus Archon1 may be of widespread use for all-optical electrophysiology in C. elegans.

Additional Results

Optimization of gene library expression in mammalian cells. For expression of gene libraries in mammalian cells a way of transfecting single genes into cultured cells was created, so that high-content imaging and subsequent genotyping of individual cells would be meaningful. Electroporation [Heiser, W. C. (2000) Methods Mol Biol. Vol. 130: pp 117-134; Reid, L. H., et al., (1991) Mol. Cell Biol. 11, 2769-2777]; and transduction [Kutner, R. H., et al., (2009) Nat. Protoc. 4, 495-505; Wang, L. & Tsien, R. Y. (2006) Nat. Protoc. 1, 1346-1350] have been used to deliver single genes into single cells in bulk, but studies were performed to determine whether commonly used chemical means might offer greater degrees of simplicity and scalability. Calcium phosphate transfection was examined due to the flexibility of adjusting the amount of DNA delivered across many orders of magnitude, in comparison to other chemical means [Jordan, M., et al., (1996) Nucleic Acids Research, 24, 596-601; Jordan, M. & Wurm, F. (2004) Methods 33, 136-143]. To validate the potential for single gene-per-cell transfection, an equimolar mixture of plasmids encoding green (EGFP) and red (mCardinal) fluorescent proteins (FPs) were delivered to cultured HEK293T cells, diluted by varying amounts of empty pUC19 plasmid, using commercially available calcium phosphate transfection kit according to a slightly modified manufacture protocol (see Methods section herein). As an expression vector, commercially available pN1 plasmid (Clontech) was used, which can be replicated in HEK293T cells due to the SV40 origin of replication, thus enhancing expression of target genes [Mahon, M. J. (2011) Biotechniques 51, 119-126]. The cells were analyzed via flow cytometry to access the fraction of the cells that expressed only one of the two transfected FPs (FIG. 28A). With dilution factors of 100, 1,000, and 10,000, respectively, cells with just one of the fluorophores were ~2×, ~8×, and ~23× more common than dual expressors, with roughly 4.4±0.8%, 0.35±0.8 and 0.07±0.02% (all numbers mean±standard deviation (S.D.); n=6 experiments on 2 different days) of transfection efficiency as defined by the fraction of cells expressing either or both of the two fluorophores. Accordingly, a 100× dilution was used throughout various experiments, to balance the single cell transfection ratio and efficiency for all screens. In order to evaluate optimal duration of gene library expression for screening, kinetics of EGFP expression in HEK293T cells upon transfection with 100-fold plasmid dilution was compared to that without the dilution. Peak of protein expression for 100-fold diluted pEGFP-N1 plasmid was reached in 100-110 h after transfection, which is about 40 h slower than that for the non-diluted plasmid (FIG. 28B). Therefore, all further library enrichments by FACS were performed at least in 48 h post transfection.

To determine the impact of single-copy dilution transfection on actual library screening efficacy, a test case was selected to create a library of mutants of the RpBphP1 bacteriophytochrome (BphP) [Giraud, E. et al. (2002) Nature 417, 202-205]. The PAS-GAF domains were mutated at amino acid positions 201, 202, 257 and 282 to NNS (N, any nucleotide; S, T or C; see FIG. 8 for amino acid alignments), based on previous studies on enabling fluorescence in BphPs [Piatkevich, K. D., et al., (2013) Chem. Soc. Rev. 42, 3441-52]. The resulting site-directed library was transfected into HEK293T cells, the cells exhibiting fluorescence upon excitation with 640 nm laser were FACS sorted (reducing the cell count from ~50M to ~60 k), and then robotically cell picked based upon brightness (reducing the cell count from ~25-35 k to 45).

To evaluate the RpBphP1 mutants expressed in the 45 picked cells, the genes recovered from the pool of extracted cells were cloned into expression vectors and 184 clones were randomly selected for further characterization. Only 85 out of 184 selected clones (all with unique nucleotide sequences, corrected for duplications) exhibited near-infrared fluorescence upon expression in HEK cells. To find out why over half of the clones were non-functional, all selected clones were sequenced. Sequence analysis revealed multiple point mutations scattered throughout the entire gene with on average ~2.3 nucleotide mutations per gene in addition to the intended mutations at amino acid positions 201, 202, 257 and 282. Only about 12% of recovered genes had no nucleotide mutations beyond those at these 4 intended sites, while about ~66% contained 1 to 3 nucleotide mutations at sites beyond the 4 intended sites (FIG. 28C). That implies that HEK293T cells introduced 2.4.10-3 nucleotide mutations per base pair of exogenous DNA. Indeed, HEK293T cells have been reported to mutate plasmids delivered by calcium phosphate transfection [Lebkowski, J. S., et al., (1984) Mol. Cell. Biol. 4, 1951-1960].

To estimate the exact number of plasmids delivered per single positive cells, sequence analysis of the intended mutation regions was performed. The robot cell picking was repeated for the same gene library and eight cells were extracted that exhibited bright near-infrared fluorescence. Each of eight extracted cells was placed into a separate PCR tube for gene recovery. For each cell, 24 colonies were selected randomly for further characterization. For four of the cells, all of the recovered clones had a single common set of nucleotides at the 12 bases that were mutated intentionally, suggesting a single plasmid was transfected [although the 24 colonies yielded, due to the aforementioned HEK mutation effect, an average of 22±1 (mean±S.D.) different clones per cell]. For the other four cells, the clones that emerged from each cell contained 3-4 unique sets of nucleotides at the intended mutated codons, implying triple or quadruple transfection (the 24 colonies yielded 21±2 unique clones per cell). Among the entire set of recovered genes, 41% exhibited any near-infrared fluorescence upon expression in HEK cells. Thus, the mutagenic activity of HEK293T cells can inactivate protein function. Also, since multiple plasmids end up in a given cell, perhaps 4-5 (or more) recovered genes should be phenotyped per extracted cell to ensure identification of positive clones.

Additional Discussion

Experiments have been performed to prepare, test, and utilize opsin-based fluorescent voltage reporter Archon1, that exhibits good localization in neurons of multiple species (mouse, C. elegans, zebrafish), several fold improved brightness over previous opsin-based reporters, several fold improvements in voltage sensitivity to single APs and in photobleaching over GFP-based reporters, and compatibility with optogenetic control (which can also permit simultaneous imaging of voltage in conjunction with green reporters of calcium and other physiological signals). The utility of Archon1 has been demonstrated by imaging single spikes and millivolt-scale subthreshold or synaptic activity in acute mouse brain slices and larval zebrafish in vivo, as well as postsynaptic responses downstream of optogenetic control in C. elegans. The ability to survey neural activity in such well-defined systems, e.g., brain circuits from the mouse, or entire transparent organisms, may be used in synergy with new technologies that allow for mapping of physiological data onto fine wiring and connectivity.

Imaging of Archon1 requires excitation light intensity much higher than required for GFP-based fluorescent reporters. However, Archon1 supported imaging with about an order of magnitude lower light intensity in comparison to the best performing Arch-based voltage sensor (i.e. 0.080-0.8 $W/mm^2$ for Archon1 vs. 3-8 $W/mm^2$ for QuasAr2 in cultured neurons; 1.5 $W/mm^2$ for Archon1 in acute brain slice vs. 12 $W/mm^2$ for QuasAr2 in organotypic brain slices). To achieve light intensity above 0.1 $W/mm^2$, commercially available red laser diodes were used, with pricing comparable to LED setups, and it was found that they provided sufficient light power to image Archon1 in a variety of neural systems as explored in experiments presented herein. Thus, in price, such setups might be comparable to blue LED setups used for imaging GCaMP under 1-photon microscopy.

To develop Archon1, a novel directed molecular evolution approach based on robotic cell picking under microscopy guidance was designed and implemented, so that different properties could be simultaneously optimized for a single fluorescent voltage reporter, in mammalian cells. Archon1 and other voltage reporter molecules of the invention represent new tools that may be of broad utility in neuroscience, and the robotic cell picking strategy for directed molecular evolution in mammalian cells may be of broad utility in the development of a variety of novel molecular tools for neuroscience and biology.

Imaging of neuronal activity using voltage reporters opens up the exciting possibility for simultaneous recordings of large populations of neurons with single cell single spike resolution in vivo. Several ongoing trends, as they mature, will help make voltage imaging even more accessible. Currently available scientific-grade cameras can perform fast imaging (500-1000 Hz) over pixel counts smaller by an order magnitude than those commonly used for calcium imaging (at 10-20 Hz); new cameras capable of fast imaging at cellular resolution over broader fields of view will continue to enhance the power of voltage imaging. Use of optics capable of large volume imaging with precise optical sectioning (e.g., through light-sheet scanning [Ahrens, M. B., et al., (2013) Nat Methods 10, 413-420; Bouchard, M. B. et al. (2015) Nat. Photonics 9, 113-119], or through computational optical sectioning [Prevedel, R. et al. (2014) Nat. Methods 11, 727-30] are used. Densely labeled neurons may be imaged in populations because reporter expression can be restricted to the somata, so that the light emitting sources are made sparser.

Example 2

Experiments are performed as described herein in Example 1 that include expressing voltage reporters of the invention (for example though not limited to: Archon1, Archon2, Variant #3, Variant #4, Variant #5, Variant #6, and Variant #7) in cells and subjects, including vertebrate and/or mammalian cells. In certain studies human cells are used in the experiments. Experiments are performed in vitro, ex vivo, and in vivo. In some experiments a voltage reporter is delivered to a subject in a cell that includes the voltage reporter. In some experiments a voltage reporter of the invention is delivered to a cell and/or a subject in the form of a vector encoding the voltage reporter, or is delivered to a cell and/or a subject in the form of a fusion protein that includes the voltage reporter of the invention.

Experiments are performed that include voltage imaging and/or and lightsheet imaging and other methods as described in Example 1 herein. Expression and function of the voltage reporters are observed. Results demonstrate use of voltage reporters of the invention in vertebrate cells and organisms, mammalian cells and organisms, which in some experiments include human cells and subjects. In some experiments the cell is one or more of a neuronal cell, a nervous system cell, a cardiac cell, a circulatory system cell, a visual system cell, and an auditory system cell.

It is to be understood that the methods, compositions, and apparatus which have been described above are merely illustrative applications of the principles of the invention.

Numerous modifications may be made by those skilled in the art without departing from the scope of the invention. Although the invention has been described in detail for the purpose of illustration, it is understood that such detail is solely for that purpose and variations can be made by those skilled in the art without departing from the spirit and scope of the invention which is defined by the following claims. The contents of all references, patents and published patent applications cited throughout this application are incorporated herein by reference in their entirety.

We claim:

1. A voltage reporter polypeptide, comprising an amino acid sequence set forth as SEQ ID NO: 1 or a functional variant thereof, wherein the functional variant has at least 97% amino acid sequence identity to SEQ ID NO: 1 and the amino acid sequence of the functional variant is not a sequence set forth as SEQ ID NO: 8, 9, 10, 11, 12, or 13, and wherein the functional variant comprises one or more amino acid substitutions, deletions, and insertions to the amino acid sequence set forth as SEQ ID NO: 1.

2. The voltage reporter polypeptide of claim, wherein the functional variant has at least 98%, 99%, or 100% amino acid sequence identity to the corresponding region of SEQ ID NO: 1.

3. The voltage reporter polypeptide of claim 1, wherein the functional variant comprises the amino acid sequence of SEQ ID NO: 1 having one or more modifications, wherein the SEQ ID NO: 1 amino acid sequence is not modified at 1 or more of SEQ ID NO: 1 amino acid positions: 20, 41, 44, 60, 80, 88, 96, 107, 137, 162, 184, 199, and 242.

4. The voltage reporter polypeptide of claim 1, wherein the functional variant comprises the amino acid sequence of SEQ ID NO: 1 having one or more modifications, wherein the amino acid sequence of SEQ ID NO: 1 is not modified at 1 or more of SEQ ID NO: 1 amino acid positions: 97, 129, 133, 149, 152, 153, 156, 193, 196, 197, 200, 223, and 227.

5. The voltage reporter polypeptide of claim 1, wherein the amino acid sequence of the functional variant comprises the amino acid sequence set forth as SEQ ID NO: 2; SEQ ID NO: 3; SEQ ID NO: 4; SEQ ID NO: 5; SEQ ID NO: 6; or SEQ ID NO: 7.

6. A membrane comprising the voltage reporter polypeptide of claim 1.

7. A fusion protein comprising the voltage reporter polypeptide of claim 1.

8. A method of determining voltage in a cell, the method comprising,
   a) monitoring a detectable signal of a voltage reporter polypeptide comprising an amino acid sequence set forth as SEQ ID NO: 1 or a functional variant thereof, wherein the functional variant has at least 97% amino acid sequence identity to SEQ ID NO: 1 and the amino acid sequence of the functional variant is not a sequence set forth as SEQ ID NO: 8, 9, 10, 11, 12, or 13, and wherein the functional variant comprises one or more amino acid substitutions, deletions, and insertions to the amino acid sequence set forth as SEQ ID NO: 1 expressed in a cell; and
   b) determining a voltage characteristic in the cell by detecting a detectable signal of the reporter molecule of the expressed voltage reporter polypeptide, where the detectable signal indicates a voltage characteristic in the cell.

9. A method of identifying an effect of a test agent on a voltage in a cell, the method comprising,
   (a) contacting a first cell comprising the voltage reporter polypeptide comprising an amino acid sequence set forth as SEQ ID NO: 1 or a functional variant thereof, wherein the functional variant has at least 97% amino acid sequence identity to SEQ ID NO: 1 and the amino acid sequence of the functional variant is not a sequence set forth as SEQ ID NO: 8, 9, 10, 11, 12, or 13, and wherein the functional variant comprises one or more amino acid substitutions, deletions, and insertions to the amino acid sequence set forth as SEQ ID NO: 1 expressed in a membrane of the first cell, with a stimulus that results in voltage in the cell that is detectable by the voltage reporter polypeptide;
   (b) contacting the first cell or a cell in communication with the first cell with a test agent;
   (c) detecting at least one voltage characteristic in the first cell, by detecting a detectable signal of the reporter molecule of the expressed voltage reporter polypeptide, where the detectable signal indicates voltage in the first cell; and
   (d) comparing the at least one voltage characteristic detected in step (c) to the at least one voltage characteristic detected in a control cell, wherein a difference in the at least one voltage characteristic detected in the first cell compared to the at least one voltage detected in the control cell identifies an effect of the test agent on the voltage in the first cell.

10. A composition comprising one or more of a: voltage reporter polypeptide of claim 1, a fusion protein comprising the voltage reporter.

11. The composition of claim 10, further comprising one or more of: a carrier agent, a delivery agent, and a detectable agent.

12. The composition of claim 10, wherein the composition is a pharmaceutically acceptable composition.

13. A cell comprising the voltage reporter polypeptide of claim 1.

14. The cell of claim 13, wherein the cell is a vertebrate cell, and optionally, is a mammalian cell.

15. A cell comprising the fusion protein of claim 7.

* * * * *